United States Patent
Or et al.

(10) Patent No.: US 9,616,099 B2
(45) Date of Patent: *Apr. 11, 2017

(54) CYCLOSPORIN ANALOGUES FOR PREVENTING OR TREATING HEPATITIS C INFECTION

(71) Applicant: Enanta Pharmaceuticals, Inc., Watertown, MA (US)

(72) Inventors: Yat Sun Or, Watertown, MA (US); Guoqiang Wang, Belmont, MA (US); Jiang Long, Wayland, MA (US); In Jong Kim, Lexington, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/948,876

(22) Filed: Nov. 23, 2015

(65) Prior Publication Data

US 2016/0136233 A1    May 19, 2016

Related U.S. Application Data

(63) Continuation of application No. 14/469,403, filed on Aug. 26, 2014, now Pat. No. 9,221,878.

(60) Provisional application No. 61/870,069, filed on Aug. 26, 2013.

(51) Int. Cl.
| | |
|---|---|
| *A61K 45/06* | (2006.01) |
| *A61K 38/13* | (2006.01) |
| *C07K 7/64* | (2006.01) |
| *A61K 38/21* | (2006.01) |
| *A61K 38/00* | (2006.01) |

(52) U.S. Cl.
CPC .............. *A61K 38/13* (2013.01); *A61K 38/21* (2013.01); *A61K 45/06* (2013.01); *C07K 7/645* (2013.01); *A61K 38/00* (2013.01)

(58) Field of Classification Search
None
See application file for complete search history.

(56) References Cited

PUBLICATIONS

Overview of Viral Infections Infections Merck Manuals Consumer Version (2016) pp. 1-7.*
Ettmayer P. et al. J. Med. Chem. (2004) 47(10), pp. 2393-2404.*
Singh, Yashveer et al, "Recent Trends in Targeted Anticancer Prodrug and Conjugate," DesignCurr Med Chem. 2008 ; 15(18): 1802-1826.*
Muller, Christa E. "Prodrug Approaches for Enhancing the Bioavailability of Drugs with Low Solubility," Chemistry & Biodiversity, vol. 6 (2009), pp. 2071-2083.*
Beaumont, et, al "Design of Ester Prodrugs to Enhance Oral Absorption of Poorly Permeable Compounds: Challenges to the Discovery Scientist," Current Drug Metabolism, 2003, 4, 461-485.*
Han, H.-K.. AAPS Pharmsci. (2000) 2(1), Article 6, pp. 1-11.*
Testa Prodrug research: futile or fertile? Biochemical Pharmacology (2004) 2097-2106.*

* cited by examiner

*Primary Examiner* — Thomas S Heard
(74) *Attorney, Agent, or Firm* — Edgar W. Harlan; Carolyn S. Elmore, Esq.; Elmore Patent Law Group, P.C.

(57) ABSTRACT

The present invention relates to novel cyclosporine analogs having antiviral activity against HCV and useful in the treatment of HCV infections. More particularly, the invention relates to novel cyclosporine analog compounds, compositions containing such compounds and methods for using the same, as well as processes for making such compounds.

7 Claims, No Drawings

CYCLOSPORIN ANALOGUES FOR PREVENTING OR TREATING HEPATITIS C INFECTION

RELATED APPLICATION

This application is a continuation of U.S. application Ser. No. 14/469,403, filed on Aug. 26, 2014, which claims the benefit of U.S. Provisional Application No. 61/870,069, filed on Aug. 26, 2013. The entire teachings of the above applications are incorporated herein by reference.

TECHNICAL FIELD

The present invention relates to novel cyclosporine analogues having antiviral activity against HCV and useful in the treatment of HCV infections. More particularly, the invention relates to novel cyclosporine analogue compounds, compositions containing such compounds and methods for using the same, as well as processes for making such compounds.

BACKGROUND OF THE INVENTION

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Due to the high degree of variability in the viral surface antigens, existence of multiple viral genotypes, and demonstrated specificity of immunity, the development of a successful vaccine in the near future is unlikely. Only two approved therapies for HCV infection are currently available. The original treatment regimen generally involves a 3-12 month course of intravenous interferon-α (IFN-α), while a new approved second-generation treatment involves co-treatment with IFN-α and the general antiviral nucleoside mimics like ribavirin. Both of these treatments suffer from interferon related side effects as well as low efficacy against HCV infections. There exists a need for the development of effective antiviral agents for treatment of HCV infection due to the poor tolerability and disappointing efficacy of existing therapies.

Cyclosporin A (CsA), a neutral cyclic undecapeptide isolated from the fungus *Tolypocladium injlaturn* and currently marketed as Neoral and sandimmunem (Novartis, Basel, Switzerland), has been widely used for the prevention of organ transplant rejection. The molecular basis for the immunosuppressant activity of cyclosporin A and cyclosporin analogues begins with the passive diffusion of the cyclosporin (Cs) molecule into the cell, followed by binding to its intracellular receptor, cyclophilin A (CypA). CypA belongs to a family of proteins that catalyze cis-trans peptidyl-prolyl isomerization, i.e., PPIase, a rate-limiting step in protein folding. CsA and other cyclosporin analogues bind to the active site of CypA. However, immunosuppression is not believed to be due to the inhibition of CypA PPIase activity. The target of the CsA-CypA complex is a $Ca^{2+}$-calmodulin-dependent serine-threonine-specific protein phosphatase, calcineurin. In T-cells responding to antigen presentation, an increase in intracellular $Ca^{2+}$ activates calcineurin, which subsequently dephosphorylates the transcription factor called the nuclear factor of activated T-cells ("NFAT"). Dephosphorylated NFAT undergoes a molecular change, e.g., homodimerization that allows it to cross into the nucleus, and promotes the expression of T-cell activation genes. CsA and other immunosuppressive cyclosporin derivatives inhibit calcineurin which results in the inhibition of expression of cytokine genes, e.g., interleukin-2 (IL-2) that promotes T-cell activation and proliferation, i.e., immunosuppressive activity.

Cyclosporine A and certain derivatives have been reported as having anti-HCV activity, see Watashi et al., Hepatology, 2003, Volume 38, pp 1282-1288, Nakagawa et al., Biochem. Biophys. Res. Commun. 2004, Volume 3 13, pp 42-7, and Shimotohno and K. Watashi, 2004 American Transplant Congress, Abstract No. 648 (American Journal of Transplantation 2004, Volume 4, Issue s8, Pages 1-653). The authors of the Nakagawa et al. paper state that certain chaperone activities, such as those of cyclophilins, may be crucial for the processing and maturation of the viralproteins and for viral replication. Cyclosporine derivatives having HCV activity are known from International Publication No's. WO 2005/021028, WO 2006/039668, WO 2006/038088, WO 2006/039688, WO 2007/112352, WO 2007/112357, WO 2007/112345 and WO 2007/041631.

A subsequent controlled clinical trial showed that a combination of cyclosporin A with interferon α2b is more effective than interferon monotherapy, especially in patients with high viral loads (Inoue et al., "Combined Interferon α2b nd Cyclosporin A in the Treatment of Chronic Hepatitis C: Controlled Trial," *J. Gastroenterol.* 38:567-572 (2003)).

PCT International Patent Publication No. WO 2006/005610 recently described the use of a combination of cyclosporin A and pegylated interferon for treating hepatitis C viral infection. In addition, PCT International Patent Publication No. WO 2005/021028 relates to the use of non-immunosuppressive cyclosporine for treatment of HCV disorders. Also, Paeshuyse et al., "Potent and Selective Inhibition of Hepatitis C Virus Replication by the Non-Immunosuppressive Cyclosporin Analogue DEBIO-025," *Antiviral Research* 65(3):A41 (2005) recently published results for a non-immunosuppressive cyclosporin analogue, DEBIO-025, that exhibited potent and selective inhibition of hepatitis C virus replication. Debio-025 does possess potent binding affinity for cyclophilin A.

SUMMARY OF THE INVENTION

The present invention relates to novel Cyclosporin analogues represented herein below, pharmaceutical compositions comprising such compounds, and methods for the treatment of viral (particularly hepatitis C viral) infection in a subject in need of such therapy with said compounds.

In its principal embodiment, the present invention provides a compound of formula (I);

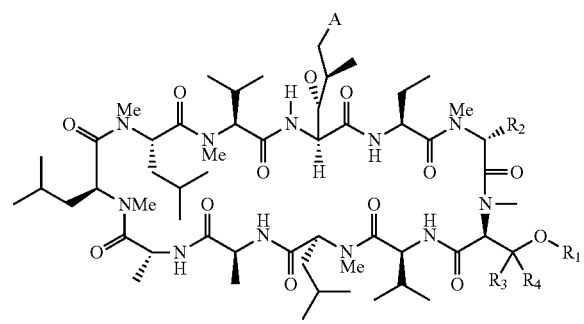

(I)

$R_1$ and A are each independently selected from:
a) $R_{11}$, which is selected from:
1) Hydrogen;
2) Deuterium;
3) $C_1$-$C_8$ alkyl;
4) Substituted $C_1$-$C_8$ alkyl;
5) $C_2$-$C_8$ alkenyl;
6) Substituted $C_2$-$C_8$ alkenyl;
7) $C_2$-$C_8$ alkynyl;
8) Substituted $C_2$-$C_8$ alkynyl;
9) $C_3$-$C_{12}$ cycloalkyl;
10) Substituted $C_3$-$C_{12}$ cycloalkyl;
11) Aryl;
12) Substituted aryl;
13) Heterocycloalkyl;
14) Substituted heterocycloalkyl;
15) Heteroaryl; or
16) Substituted heteroaryl;
b) —C(O)N($R_{12}$)($R_{13}$), where $R_{12}$ and $R_{13}$ are independently selected from $R_{11}$ and $R_{11}$ is as previously defined or $R_{12}$ and $R_{13}$ combined together with the N which attached to is substituted or unsubstituted heterocycloalkyl;
c) $R_{14}$, where $R_{14}$ is selected from:
1) -M-$R_{11}$, where $R_{11}$ is as previously defined and M is selected from:
  i. $C_1$-$C_8$ alkylene;
  ii. Substituted $C_1$-$C_8$ alkylene;
  iii. $C_2$-$C_8$ alkenylene;
  iv. Substituted $C_2$-$C_8$ alkenylene;
  v. $C_2$-$C_8$ alkynylene;
  vi. Substituted $C_2$-$C_8$ alkynylene;
  vii. $C_3$-$C_{12}$ cycloalkylene;
  viii. Substituted $C_3$-$C_{12}$ cycloalkylene;
2) -M-$NR_{15}R_{11}$, where $R_{15}$ is $R_{11}$ or $R_{15}$ and $R_{11}$ combined together with the N which attached to is substituted or unsubstituted heterocycloalkyl, M is as previously defined;
3) -M-$S(O)_mR_{11}$, where m=0, 1, or 2; M and $R_{11}$ are as previously defined;
4) -M-$OR_{11}$, where M and $R_{11}$ are as previously defined;
5) -M-C(O)$R_{16}$, where M is as previously defined and $R_{16}$ is selected from:
  i. $C_1$-$C_8$ alkyl;
  ii. Substituted $C_1$-$C_8$ alkyl;
  iii. $C_2$-$C_8$ alkenyl;
  iv. Substituted $C_2$-$C_8$ alkenyl;
  v. $C_2$-$C_8$ alkynyl;
  vi. Substituted $C_2$-$C_8$ alkynyl;
  vii. $C_3$-$C_{12}$ cycloalkyl; and
  viii. Substituted $C_3$-$C_{12}$ cycloalkyl;
6) -M-OC(O)$R_{16}$, where M and $R_{16}$ are as previously defined;
7) -M-OC(O)O$R_{16}$, where M and $R_{16}$ are as previously defined;
8) -M-$NR_{17}$C(O)$R_{16}$, where $R_{17}$ is $R_{11}$, M and $R_{16}$ are as previously defined;
9) -M$NR_{17}$C(O)O$R_{16}$, where $R_{17}$, M and $R_{16}$ are as previously defined;
10) -M-C(O)$NR_{17}R_{11}$, where $R_{17}$, M and $R_{11}$ are as previously defined;
11) -M-C(O)N($R_{17}$)—O$R_{11}$, where $R_{17}$, M and $R_{11}$ are as previously defined;
12) -M-OC(O)$NR_{17}R_{11}$, where $R_{17}$, M and $R_{11}$ are as previously defined;
13) -M-$NR_{17}$C(O)$NR_{16}R_{11}$, where M, $R_{11}$, $R_{17}$ and $R_{16}$ are as previously defined or $R_{16}$ and $R_{11}$ combined together with the N which attached to is substituted or unsubstituted heterocycloalkyl;
14) -M-C(S)S $R_{11}$, where M and $R_{11}$ are as previously defined;
15) -M-OC(S)S $R_{16}$, where M and $R_{16}$ are as previously defined;
16) -M-$NR_{17}$C(O)S $R_{16}$, where M, $R_{17}$ and $R_{16}$ are as previously defined;
17) -M-SC(O)$NR_{17}R_{11}$, where M, $R_{11}$ and $R_{17}$ are as previously defined or $R_{17}$ and $R_{11}$ combined together with the N which attached to is substituted or unsubstituted heterocycloalkyl;
18) -M-CH=N—O$R_{11}$, where M and $R_{11}$ are as previously defined;
19) -M-CH=N—$NR_{17}R_{11}$, where M, $R_{11}$ and $R_{17}$ are as previously defined or $R_{17}$ and $R_{11}$ are taken together with the nitrogen atom to which they are attached to form a substituted or unsubstituted heterocycloalkyl; provided that A is not

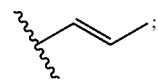 [SMILES: */C=C/C]

and
$R_2$, $R_3$ and $R_4$ are independently selected from hydrogen and methyl.

In a preferred embodiment, $R_2$ is methyl. In another preferred embodiment, one of $R_3$ and $R_4$ is methyl and the other is hydrogen.

In another embodiment, the present invention provides a pharmaceutical composition comprising a therapeutically effective amount of a compound or combination of compounds of the present invention, or a pharmaceutically acceptable salt form, prodrug, salt of a prodrug, stereoisomer, tautomer, solvate, or combination thereof, in combination with a pharmaceutically acceptable carrier or excipient.

In yet another embodiment, the present invention provides a method of inhibiting the replication of an RNA-containing virus comprising contacting said virus with a therapeutically effective amount of a compound or a combination of compounds of the present invention, or a pharmaceutically acceptable salt, prodrug, salt of a pro drug, stereoisomer, tautomer, solvate, or combination thereof. Particularly, this invention is directed to methods of inhibiting the replication of hepatitis C virus.

In still another embodiment, the present invention provides a method of treating or preventing infection caused by an RNA-containing virus comprising administering to a patient in need of such treatment a therapeutically effective amount of a compound or combination of compounds of the present invention, or a pharmaceutically acceptable salt form, prodrug, salt of a prodrug, stereoisomer, or tautomer, solvate, or combination thereof. Particularly, this invention is directed to methods of treating or preventing infection caused by hepatitis C virus.

Yet another embodiment of the present invention provides the use of a compound or combination of compounds of the present invention, or a therapeutically acceptable salt form, prodrug, salt of a prodrug, stereoisomer or tautomer, solvate, or combination thereof, as defined hereinafter, in the preparation of a medicament for the treatment or prevention of infection caused by RNA-containing virus, specifically hepatitis C virus (HCV).

DETAILED DESCRIPTION OF THE INVENTION

In a first embodiment of the present invention is a compound of formula (I) as illustrated above, or a pharmaceutically acceptable salt, ester or prodrug thereof.

Representative subgenera of the present invention are:
Compounds represented by Formula (II);

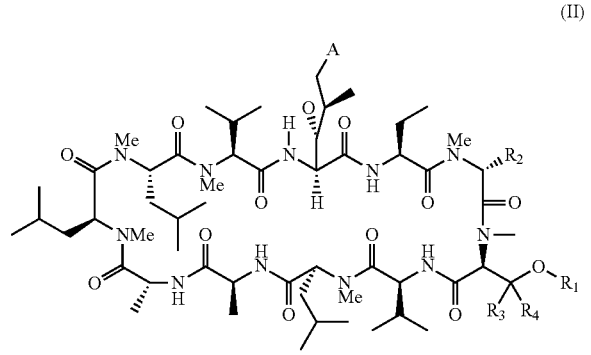

(II)

wherein $R_1$, $R_2$, $R_3$, $R_4$ and A are as defined in Formula (I);
Compounds represented by Formula (III);

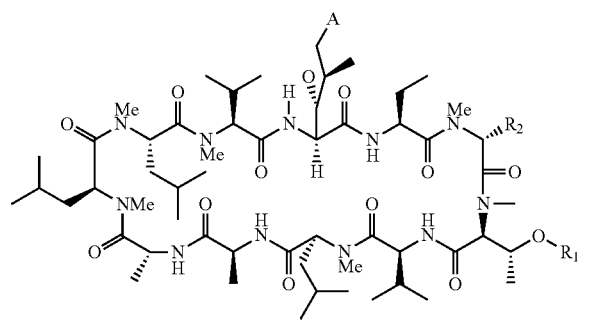

(III)

wherein, $R_1$, $R_2$ and A are as defined in Formula (I).

In a preferred embodiment, A is $C_1$-$C_5$-alkyl-X or $C_2$-$C_5$-alkenyl-X, where X is H, OH, optionally substituted aryl, optionally substituted O-aryl, optionally substituted S-aryl, optionally substituted heteroaryl, optionally substituted O-heteroaryl, optionally substituted S-heteroaryl, —OC(O)NR$_5$R$_6$, —NHC(O)OR$_5$, C(O)OR$_7$, —OC(O)OR$_7$, —CN, —N$_3$, —C(O)NR$_5$R$_6$, —C(O)R$_5$, —OSO$_2$R$_7$, —NHC(O)R$_5$, or —NR$_5$R$_6$.

$R_5$ and $R_6$ are independently H; optionally substituted alkyl, optionally substituted alkenyl, optionally substituted aryl, optionally substituted heteroaryl, optionally substituted arylalkyl or optionally substituted heteroarylalkyl. Alternatively, $R_5$, $R_6$ and the nitrogen atom to which they are attached form an optionally substituted heterocyclic. $R_7$ is optionally substituted alkyl, optionally substituted alkenyl, optionally substituted aryl, optionally substituted heteroaryl, optionally substituted arylalkyl or optionally substituted heteroarylalkyl.

In particularly preferred embodiments, A is $C_1$-$C_4$-alkyl-X or $C_2$-$C_4$-alkenyl-X, where X is H; OH; optionally substituted phenyl; optionally substituted —O-phenyl; optionally substituted —S-phenyl; optionally substituted 5-membered heteroaryl; optionally substituted —O-5-membered heteroaryl; optionally substituted —S-5-membered heteroaryl; —OC(O)NR$_5$R$_6$, —NHC(O)OR$_5$, C(O)OR$_7$, —OC(O)OR$_7$, —CN, —N$_3$, —C(O)NR$_5$R$_6$, —C(O)R$_5$, optionally substituted —OSO$_2$-phenyl, —NHC(O)R$_5$, or —NR$_5$R$_6$. In this embodiment, 5-membered heteroaryl is preferably imidazolyl, triazolyl or tetrazolyl, optionally fused to a benzo ring or a 6-membered nitrogen-containing heteroaryl ring. In this embodiment, A is preferably $C_3$-$C_4$-alkyl-X or $C_3$-$C_4$-alkenyl-X.

In one embodiment, A is selected from the groups shown below.

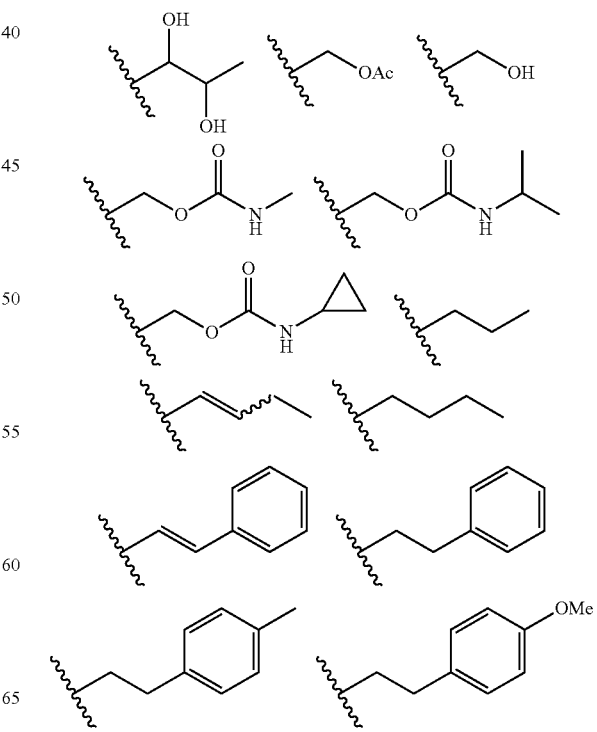

-continued
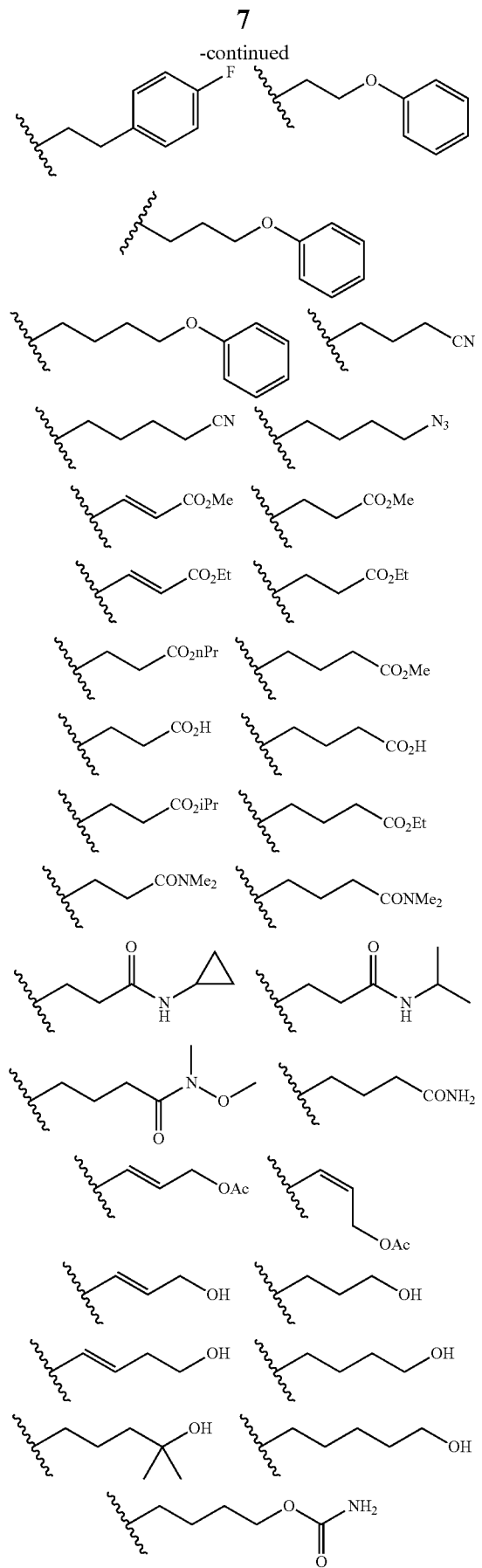
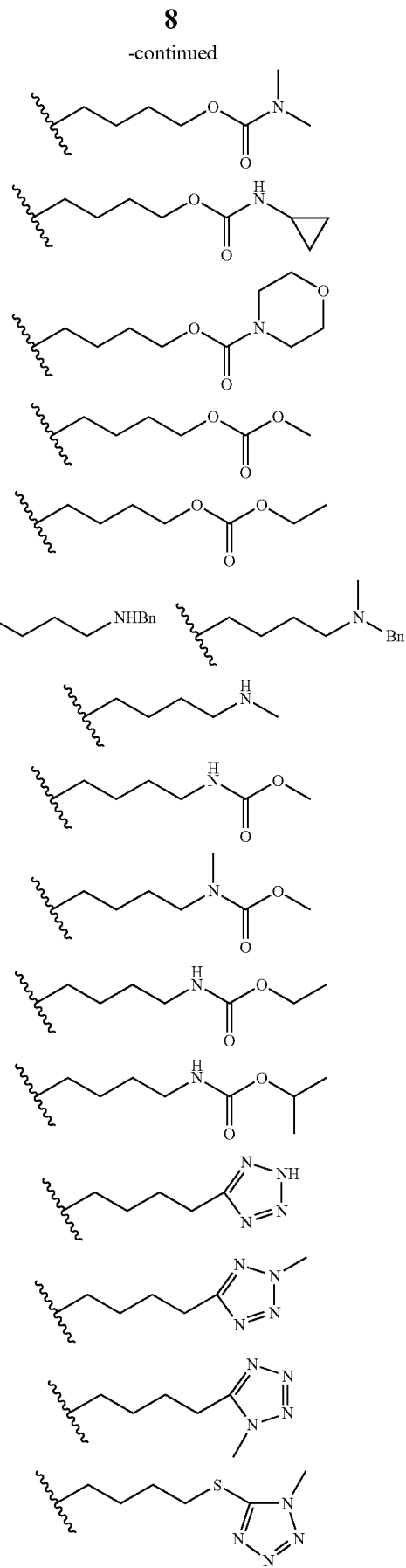

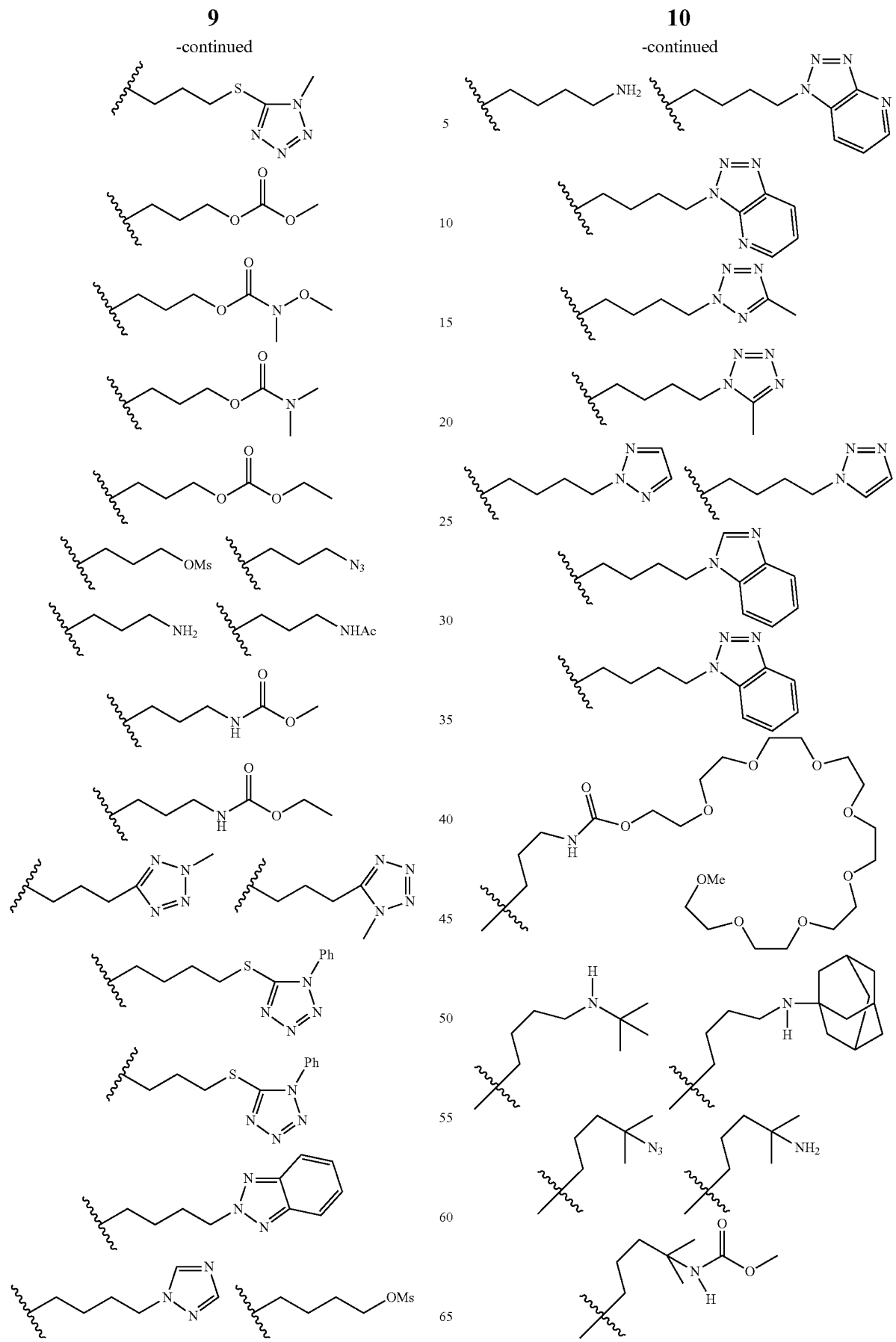

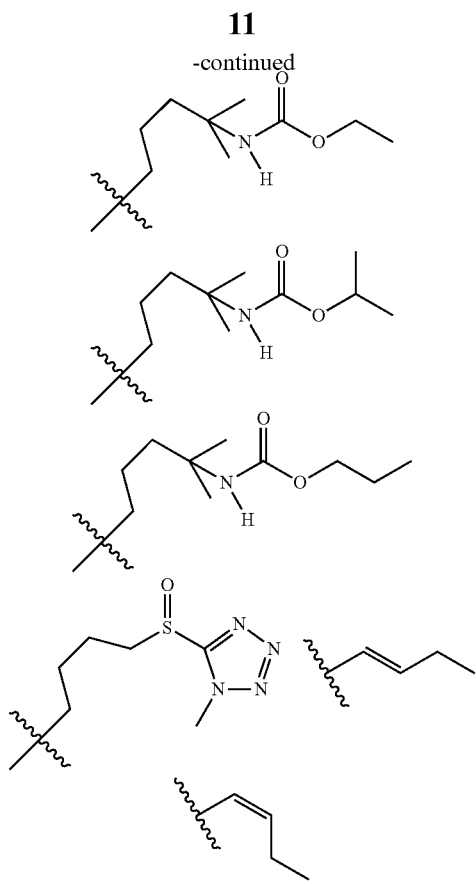

In certain embodiments, $R_1$ is $C_1$-$C_5$-alkyl-Y or $C_2$-$C_5$-alkenyl-Y, where Y is H; optionally substituted aryl, preferably optionally substituted phenyl; optionally substituted heterocyclyl; —OC(O)$R_5$; N$R_5R_6$; OH; —O—(CH$_2$)$_n$—W, where n is 1 to 4 and W is heterocyclyl; —OC(O)N$R_5R_6$; —C(O)H; —CH=NOZ, where Z is H, or alkyl, aryl, arylalkyl, heteroaryl or heteroarylalkyl, each optionally substituted; —CH(O$R_5$)$_2$; —SC(O)$R_5$; —SH; —OSO$_2R_5$; —C(O)OH; —C(O)N($R_8$)OH, where $R_8$ is hydrogen or $C_1$-$C_4$-alkyl; $N_3$; —CN; or halogen, preferably fluorine.

In certain embodiments, $R_1$ is selected from the groups set forth below:

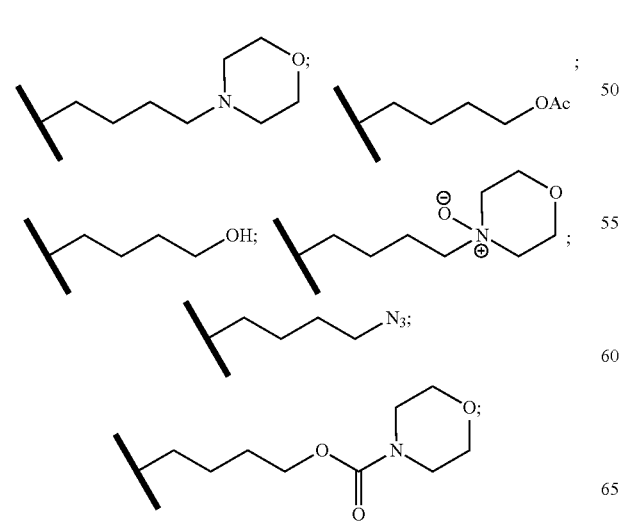

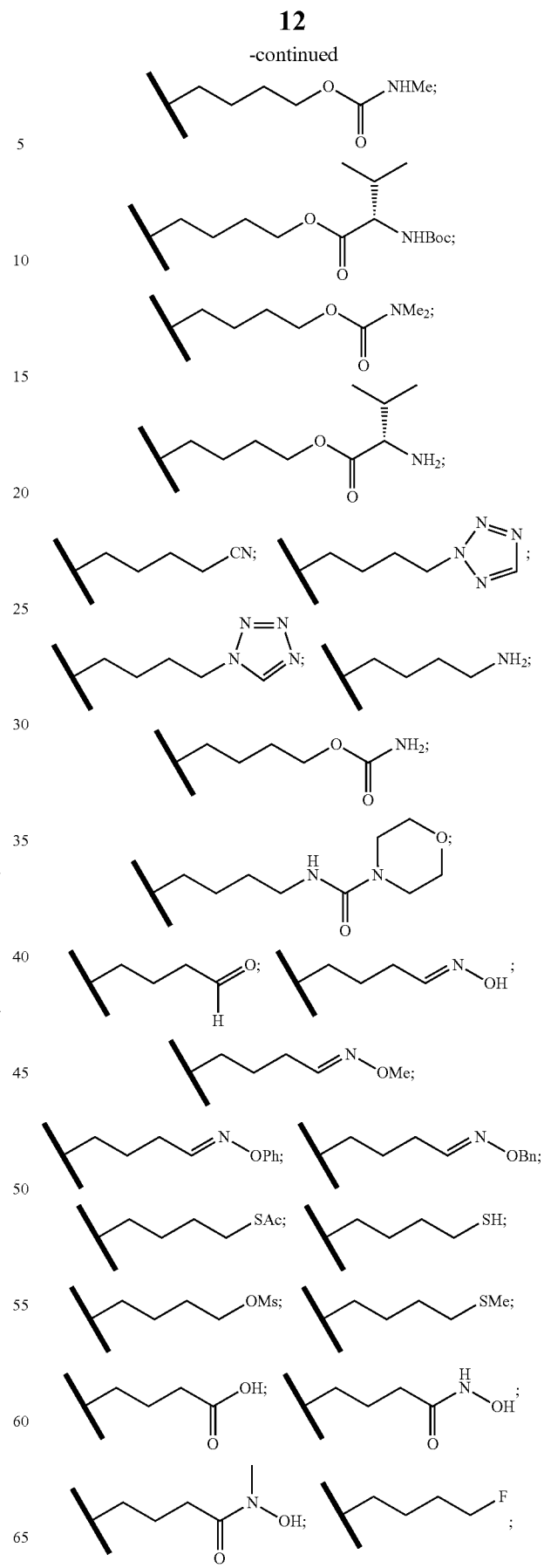

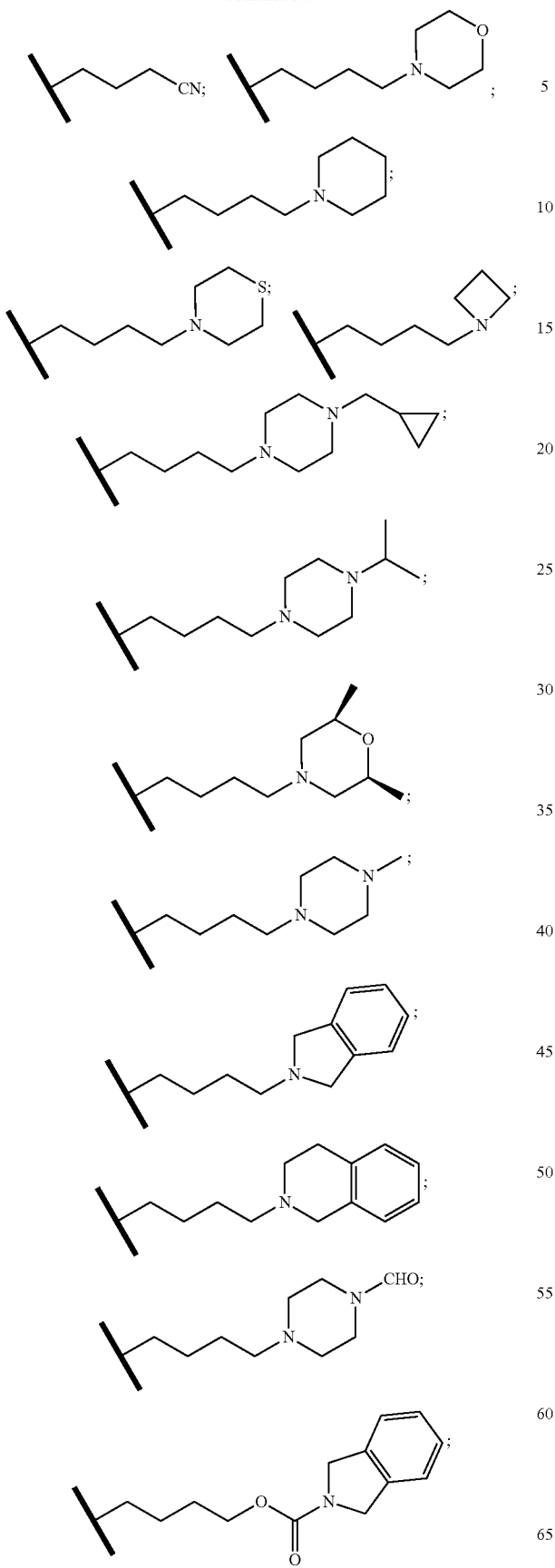
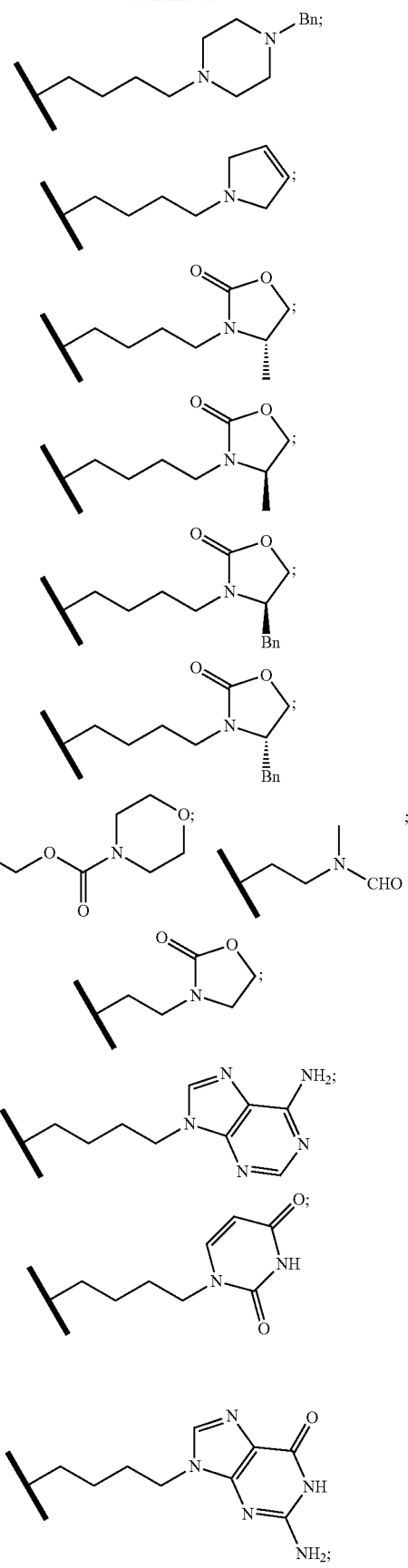

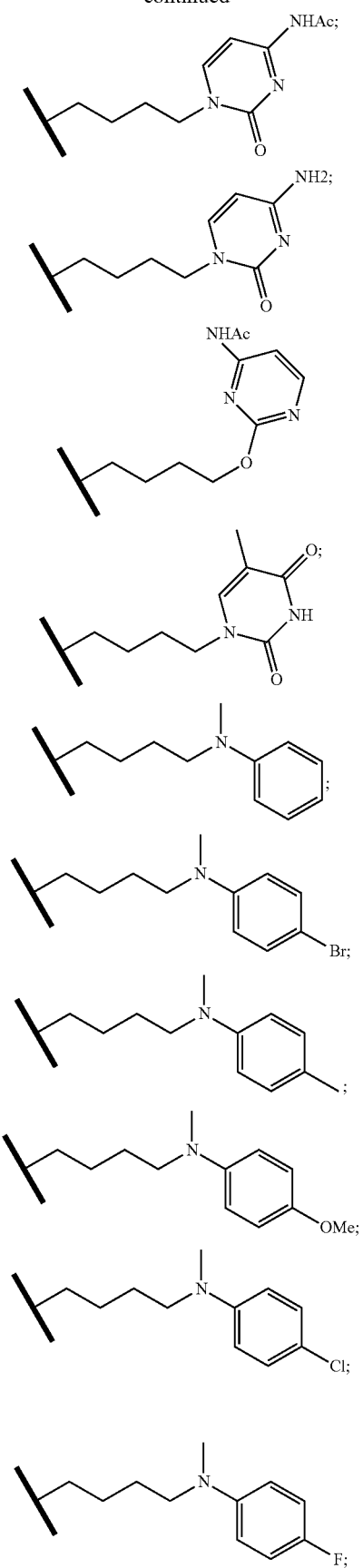
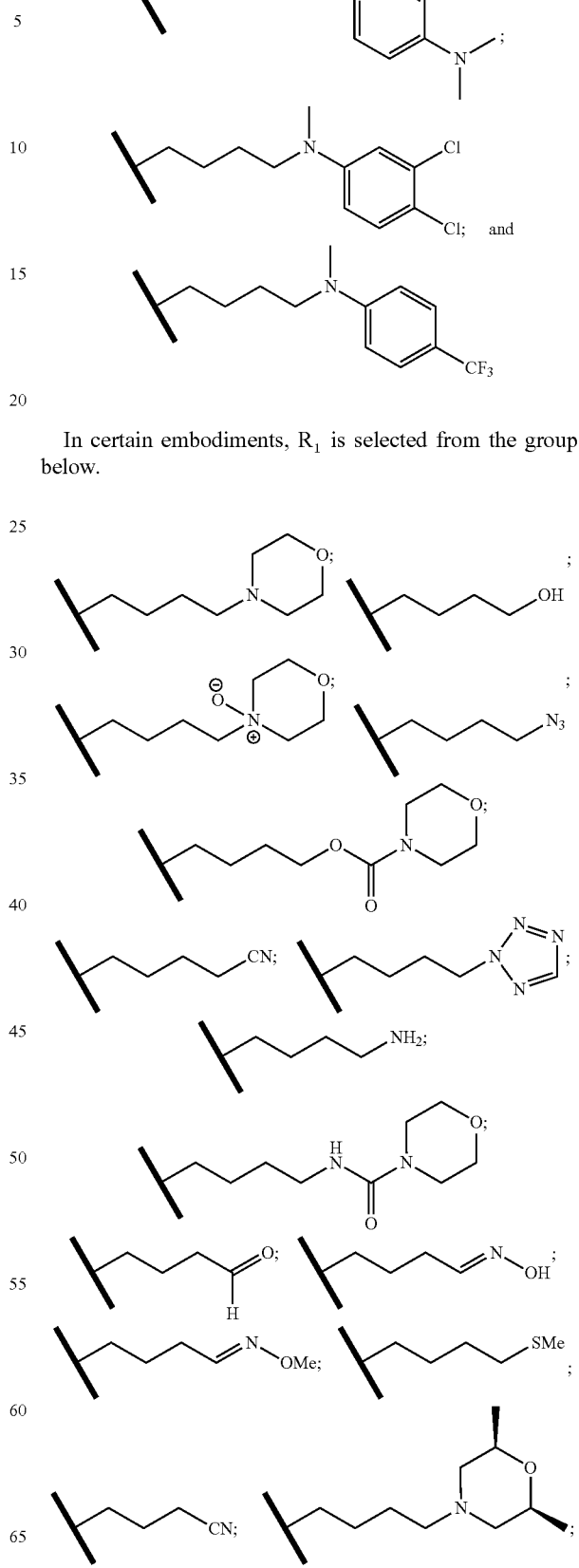
In certain embodiments, $R_1$ is selected from the groups below.

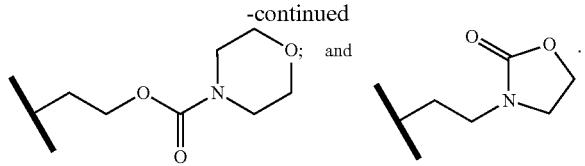
In preferred embodiments, $R_1$ is
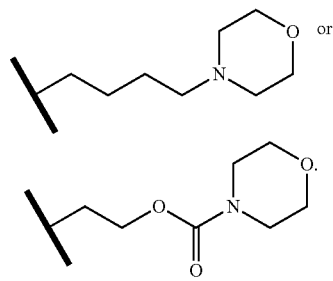
In one embodiment, the compounds of the invention are represented by Formula IV, wherein A is defined as above.
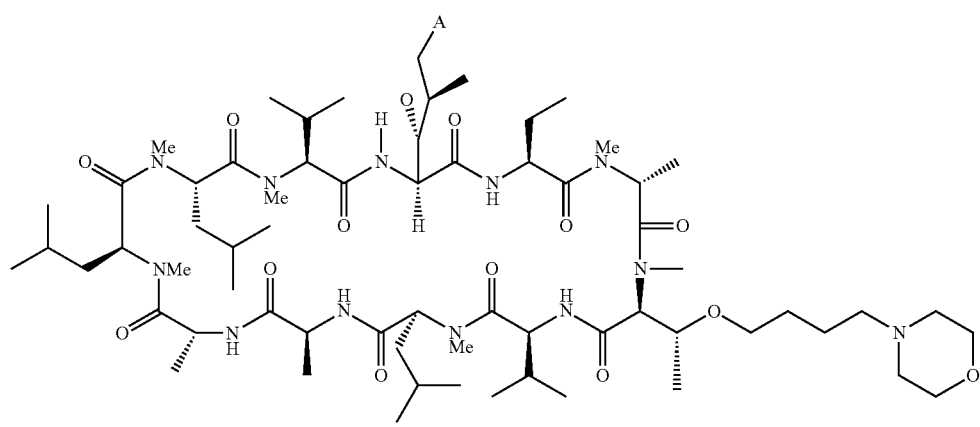
(IV)
Representative compounds of the invention include, but are not limited to, the following compounds illustrated in Table 1 according to Formula (IV), wherein A is delineated for each compound of Table 1.
TABLE 1
| Example | A |
|---------|---|
| 1 | 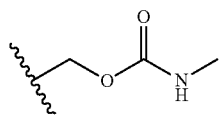 [SMILES: *COC(=O)NC] |
| 2 | 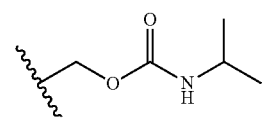 [SMILES: *COC(=O)NC(C)C] |
| 3 | 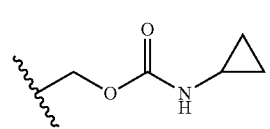 [SMILES: *COC(=O)NC1CC1] |
| 4 |  |
| 5 | 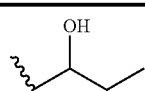 |
| 6 |  |
| 7 | 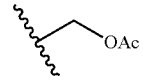 |
| 8 | 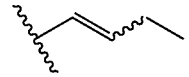 [SMILES: *C=CCC] |
| 9 | 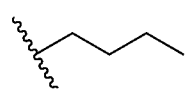 [SMILES: *CCCC] |
| 10 | 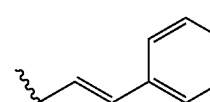 |

TABLE 1-continued
| Example | A |
|---|---|
| 11 | 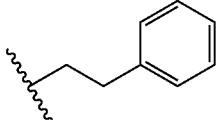 [SMILES: *CCc1ccccc1] |
| 12 | 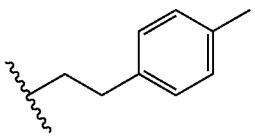 [SMILES: *CCc1ccc(C)cc1] |
| 13 | 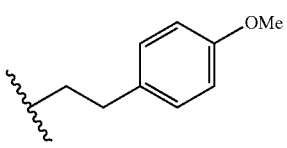 [SMILES: *CCc1ccc(OC)cc1] |
| 14 | 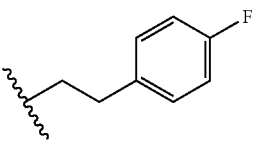 [SMILES: *CCc1ccc(F)cc1] |
| 15 | 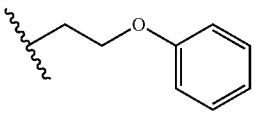 [SMILES: *CCOc1ccccc1] |
| 16 | 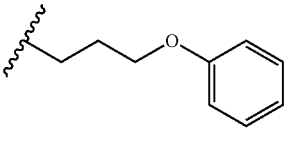 [SMILES: *CCCOc1ccccc1] |
| 17 | 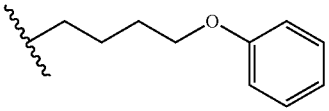 [SMILES: *CCCCOc1ccccc1] |
| 18 | 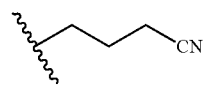 [SMILES: *CCCC#N] |
| 19 | 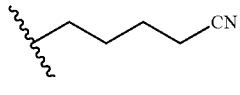 |
| 20 | 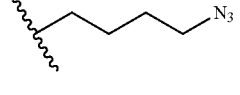 [SMILES: *CCCCN=[N+]=[N-]] |
| 21 | 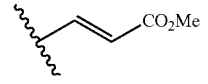 [SMILES: */C=C/C(=O)OC] |
| 22 | 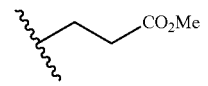 |
| 23 | 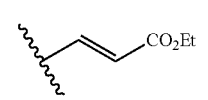 |
| 24 | 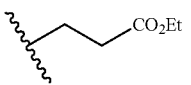 |
| 25 | 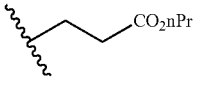 |
| 26 | 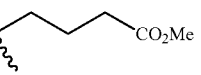 |
| 27 | 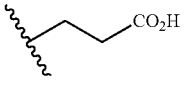 |
| 28 | 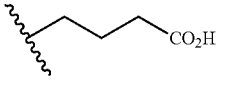 |
| 29 | 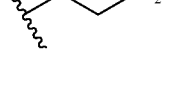 |
| 30 |  |
| 31 |  |
| 32 | 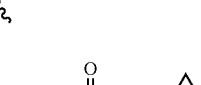 |
| 33 | 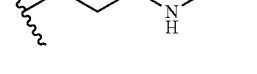 |
| 34 | 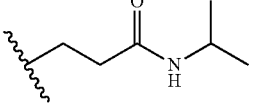 |
| 35 | 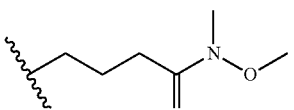 |
| 36 | 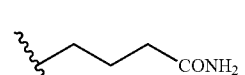 |
| 37 | 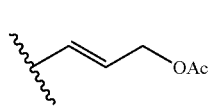 [SMILES: */C=C/COC(C)=O] |

TABLE 1-continued

| Example | A |
|---------|---|
| 38 | (cis-CH2-CH=CH-CH2-OAc) |
| 39 | (trans-CH2-CH=CH-CH2-OH) |
| 40 | (-(CH2)3-OH) |
| 41 | (-CH2-CH=CH-CH2-OH, trans) |
| 42 | (-(CH2)4-OH) |
| 43 | (-(CH2)3-C(CH3)2-OH) |
| 44 | (-(CH2)5-OH) |
| 45 | (-(CH2)4-O-C(O)-NH2) |
| 46 | (-(CH2)4-O-C(O)-N(CH3)2) |
| 47 | (-(CH2)4-O-C(O)-NH-cyclopropyl) |
| 48 | (-(CH2)4-O-C(O)-morpholinyl) |
| 49 | (-(CH2)4-O-C(O)-O-CH3) |
| 50 | (-(CH2)4-O-C(O)-O-CH2CH3) |
| 51 | (-(CH2)4-NHBn) |

TABLE 1-continued

| Example | A |
|---------|---|
| 52 | (-(CH2)4-N(CH3)(Bn)) |
| 53 | (-(CH2)4-NH-CH3) |
| 54 | (-(CH2)4-NH-C(O)-O-CH3) |
| 55 | (-(CH2)4-N(CH3)-C(O)-O-CH3) |
| 56 | (-(CH2)4-NH-C(O)-O-CH2CH3) |
| 57 | (-(CH2)4-NH-C(O)-O-iPr) |
| 58 | (-(CH2)4-tetrazol-5-yl (NH)) |
| 59 | (-(CH2)4-(2-methyltetrazol-5-yl)) |
| 60 | (-(CH2)4-(1-methyltetrazol-5-yl)) |
| 61 | (-(CH2)4-S-(1-methyltetrazol-5-yl)) |
| 62 | (-(CH2)3-S-(1-methyltetrazol-5-yl)) |
| 63 | (-(CH2)3-O-C(O)-O-CH3) |

TABLE 1-continued

| Example | A |
|---------|---|
| 64 | (butyl)-O-C(=O)-O-ethyl |
| 65 | (butyl)-O-C(=O)-N(CH₃)₂ |
| 66 | (butyl)-O-C(=O)-N(OCH₃)(CH₃) |
| 67 | (butyl)-OMs |
| 68 | (butyl)-N₃ |
| 69 | (butyl)-NH₂ |
| 70 | (butyl)-NHAc |
| 71 | (butyl)-NH-C(=O)-O-methyl |
| 72 | (butyl)-NH-C(=O)-O-ethyl |
| 73 | (butyl)-(2H-tetrazol-5-yl) |
| 74 | (butyl)-(1-methyl-1H-tetrazol-5-yl) |
| 75 | (pentyl)-S-(1-phenyl-1H-tetrazol-5-yl) |
| 76 | (butyl)-S-(1-phenyl-1H-tetrazol-5-yl) |
| 77 | (pentyl)-(1H-[1,2,3]triazolo[4,5-b]pyridin-1-yl) |
| 78 | (pentyl)-(3H-[1,2,3]triazolo[4,5-b]pyridin-3-yl) |
| 79 | (pentyl)-(5-methyl-2H-tetrazol-2-yl) |
| 80 | (pentyl)-(5-methyl-1H-tetrazol-1-yl) |
| 81 | (pentyl)-(2H-1,2,3-triazol-2-yl) |
| 82 | (pentyl)-(1H-1,2,3-triazol-1-yl) |
| 83 | (pentyl)-(1H-1,2,4-triazol-1-yl) |
| 84 | (pentyl)-(1H-benzotriazol-1-yl) |
| 85 | (pentyl)-(2H-benzotriazol-2-yl) |

TABLE 1-continued

| Example | A |
|---------|---|
| 86 | 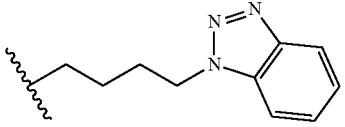 [SMILES: *CCCCn1nnc2ccccc21] |
| 87 | 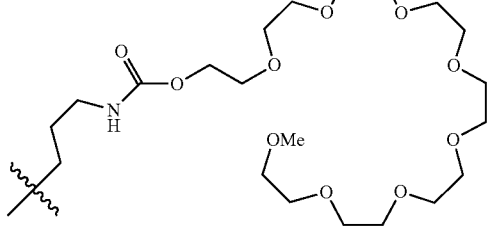 |
| 88 | 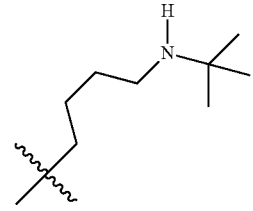 [SMILES: *CCCCNC(C)(C)C] |
| 89 | 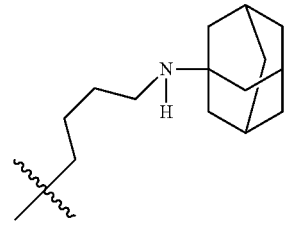 [SMILES: *CCCCNC12CC3CC(CC(C3)C1)C2] |
| 90 | 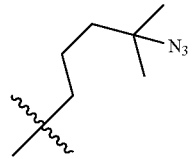 [SMILES: *CCCC(C)(C)N=[N+]=[N-]] |
| 91 | 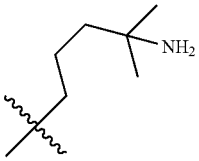 [SMILES: *CCCC(C)(C)N] |
| 92 | 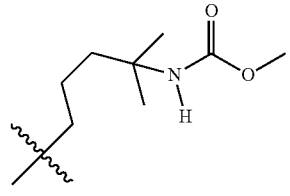 [SMILES: *CCCC(C)(C)NC(=O)OC] |
| 93 | 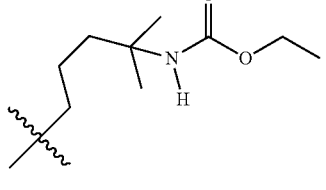 |
| 94 | 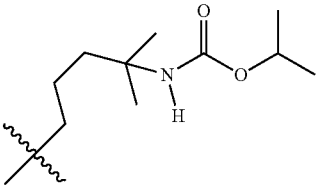 [SMILES: *CCCC(C)(C)NC(=O)OC(C)C] |
| 95 | 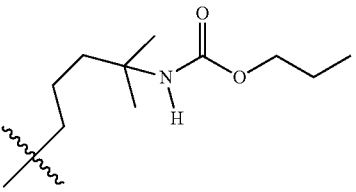 [SMILES: *CCCC(C)(C)NC(=O)OCCC] |
| 96 | 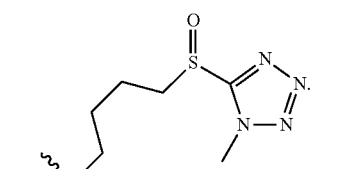 |

A further embodiment of the present invention includes pharmaceutical compositions comprising a compound of the invention, or a pharmaceutically acceptable salt, ester, solvate, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, solvate, or prodrug thereof, with a pharmaceutically acceptable carrier or excipient.

Yet a further embodiment of the present invention is a pharmaceutical composition comprising any single compound delineated herein in combination with one or more anti-HCV compounds known in the art, or a pharmaceutically acceptable salt, ester, solvate, or prodrug thereof, with a pharmaceutically acceptable carrier or excipient.

It will be appreciated that reference herein to therapy and/or treatment includes, but is not limited to prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

It will be further appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It will be further appreciated that the compounds of the invention, or their pharmaceutically acceptable salts, stereoisomers, tautomers, prodrugs or salt of a prodrug thereof, can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), or antiviral compounds that inhibit host cellular functions such as inosine monophosphate dehydrogenase (for example, ribavirin and the like). Also included are cytokines that modulate immune function. Also included are vaccines which comprise HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO 01/90121 (A2), or U.S. Pat. No. 6,348,587B1 or WO 01/60315 or WO 01/32153 or non-nucleoside inhibitors such as, for example, benzimidazole polymerase inhibitors described in EP 1162196A1 or WO 02/04425.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of the invention, or a pharmaceutically acceptable salt, stereoisomer, tautomer, prodrug, salt of a prodrug, or combination thereof. Examples of the host immune modulator include, but are not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

A further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the invention, or a pharmaceutically acceptable salt, stereoisomer, tautomer, prodrug, salt of a prodrug, or combination thereof. Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the invention, or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenofovir, or any combination thereof. An example of the RNA-containing virus includes, but not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the invention, or a pharmaceutically acceptable salt, stereoisomer, tautomer, prodrug, salt of a prodrug, or combination thereof. The agent that treats patients for disease caused by human immunodeficiency virus (HIV) infection may include, but is not limited thereto, ritonavir, lopinavir, indinavir, nelfmavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. An example of the RNA-containing virus includes, but not limited to, hepatitis C virus (HCV). In addition, the present invention provides the use of a compound or a combination of compounds of the invention, or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined herein above, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amount of the compound or combination of compounds of interest, or their pharmaceutically acceptable salt form, prodrugs, or salts of the prodrug, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system including, but not limited to, phenyl, naphthyl, tetrahydronaphthyl, indanyl, idenyl.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl.

In accordance with the invention, any of the aryls, substituted aryls, heteroaryls and substituted heteroaryls described herein, can be any aromatic group. Aromatic groups can be substituted or unsubstituted.

The terms "$C_1$-$C_8$ alkyl," or "$C_1$-$C_{12}$ alkyl," as used herein, refer to saturated, straight- or branched-chain hydrocarbon radicals containing between one and eight, or one and twelve carbon atoms, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals; and examples of $C_1$-$C_{12}$ alkyl radicals include, but are not limited to, ethyl, propyl, isopropyl, n-hexyl, octyl, decyl, dodecyl radicals.

The term "$C_2$-$C_8$ alkenyl," as used herein, refer to straight- or branched-chain hydrocarbon radicals containing from two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The term "$C_2$-$C_8$ alkynyl," as used herein, refer to straight- or branched-chain hydrocarbon radicals containing from two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$-cycloalkyl", or "$C_3$-$C_{12}$-cycloalkyl," as used herein, refers to a monocyclic or polycyclic saturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl.

The term "$C_3$-$C_8$ cycloalkenyl" or "$C_3$-$C_{12}$ cycloalkenyl" as used herein, refers to monocyclic or polycyclic carbocyclic ring compound having at least one carbon-carbon double bond. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$ cycloalkenyl include, but not limited to, cyclopropenyl, cyclobutenyl, cyclopentenyl, cyclohexenyl, cycloheptenyl, cyclooctenyl, and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocyclic groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "substituted" refers to substitution by independent replacement of one, two, or three or more of the hydrogen atoms thereon with substituents including, but not limited to, —F, —Cl, —Br, —I, —OH, protected hydroxy, —$NO_2$, —CN, —$N_3$, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protic solvent' as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2$^{nd}$ Ed. Wiley-VCH (1999); T. W. Greene and P. G. M. Wuts, *Protective Groups in Organic Synthesis,*

3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the Formula described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the invention described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" include but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or anti-microbial and anti-viral agents (e.g. ribavirin and amantidine). The compositions according to the invention may also be used in combination with gene replacement therapy.

Unless otherwise defined, all technical and scientific terms used herein are accorded the meaning commonly known to one of ordinary skill in the art. All publications, patents, published patent applications, and other references mentioned herein are hereby incorporated by reference in their entirety.

ABBREVIATIONS

Abbreviations which may be used in the descriptions of the scheme and the examples that follow are:
Ac for acetyl;
Boc$_2$O for di-tert-butyl-dicarbonate;
Boc for t-butoxycarbonyl;
Bz for benzoyl;
Bn for benzyl;
BocNHOH for tert-butyl N-hydroxycarbamate;
t-BuOK for potassium tert-butoxide;
BOP for (benzotriazol-1-yloxy)tris(dimethylamino)phosphonium Hexafluorophosphate;
Brine for sodium chloride solution in water;
CDI for carbonyldiimidazole;
$CH_2Cl_2$ for dichloromethane;
$CH_3$ for methyl;
$CH_3CN$ for acetonitrile;
$Cs_2CO_3$ for cesium carbonate;
dba for dibenzylidene acetone;
dppb for diphenylphosphino butane;
dppe for diphenylphosphino ethane;
DBU for 1,8-diazabicyclo[5.4.0]undec-7-ene;
DCC for N,N'-dicyclohexylcarbodiimide;
DEAD for diethylazodicarboxylate;
DIAD for diisopropyl azodicarboxylate;
DIPEA or (i-Pr)$_2$EtN for N,N,-diisopropylethyl amine;
Dess-Martin periodinane for 1,1,1-tris(acetyloxy)-1,1-dihydro-1,2-benziodoxol-3-(1H)-one;
DMAP for 4-dimethylaminopyridine;
DME for 1,2-dimethoxyethane;
DMF for N,N-dimethylformamide;
DMSO for dimethyl sulfoxide;
DPPA for diphenylphosphoryl azide;
EDC for N-(3-dimethylaminopropyl)-N'-ethylcarbodiimide;
EDC HCl for N-(3-dimethylaminopropyl)-N'-ethylcarbodiimide hydrochloride;
EtOAc for ethyl acetate;
EtOH for ethanol;
Et$_2$O for diethyl ether;
HATU for O-(7-azabenzotriazol-1-yl)-N,N,N',N',-tetramethyluronium Hexafluorophosphate;
HCl for hydrogen chloride;
HOBT for 1-hydroxybenzotriazole;
$K_2CO_3$ for potassium carbonate;
MeOH for methanol;
Ms for mesyl or —$SO_2$—$CH_3$;
Ms$_2$O for methanesulfonic anhydride or mesyl-anhydride;
$NaHCO_3$ for sodium bicarbonate or sodium hydrogen carbonate;
$Na_2CO_3$ sodium carbonate;
NaOH for sodium hydroxide;
$Na_2SO_4$ for sodium sulfate;
$NaHSO_3$ for sodium bisulfite or sodium hydrogen sulfite;
$Na_2S_2O_3$ for sodium thiosulfate;
$NH_2NH_2$ for hydrazine;
$NH_4HCO_3$ for ammonium bicarbonate;
$NH_4Cl$ for ammonium chloride;
NMMO for N-methylmorpholine N-oxide;
$NaIO_4$ for sodium periodate;
OH for hydroxy;
$OsO_4$ for osmium tetroxide;
TEA or Et$_3$N for triethylamine;
TFA for trifluoroacetic acid;
THF for tetrahydrofuran;
TPP or PPh$_3$ for triphenylphosphine;
Ts for tosyl or —$SO_2$—$C_6H_4CH_3$;
Ts$_2$O for tolylsulfonic anhydride or tosyl-anhydride;
TsOH for p-tolylsulfonic acid;
Pd for palladium;
Ph for phenyl;
Pd$_2$(dba)$_3$ for tris(dibenzylideneacetone) dipalladium (0);
Pd(PPh$_3$)$_4$ for tetrakis(triphenylphosphine)palladium (0);
TBS for tert-butyl dimethylsilyl; or TMS for trimethylsilyl;
TMSCl for trimethylsilyl chloride;
CsA for cyclosporine A.

Synthetic Methods

The compounds and processes of the present invention will be better understood in connection with the following synthetic schemes that illustrate the methods by which the compounds of the invention may be prepared.

The novel cyclosporine analogues of the present invention are derived from cyclosporine A. As shown in Scheme 1, Compound of formula (1-1), which is prepared by replacement of two amino acids in position three and four of cyclosporine according to the procedure described in WO 2010/088573, was converted to the compound of formula (1-2) through an olefin cross metathesis reaction.

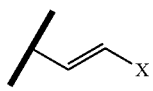

is A, where A is as as previously defined. The double bond of the compound of formula (1-2) was saturated by catalytic hydrogenation or other reduction conditions to give the compound of formula (1-3).

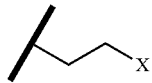

is A, where A is as as previously defined.

A number of account and literature regarding CM reaction are reported; i. e., Chatterjee, A. K.; Choi, T-L; Sanders, D. P.; Grubbs, R. H., *J. Am. Chem. Soc.,* 2003, 125, 11360; Scholl, S; Ding, S.; Lee, C. W.; Grubbs, R. H., *Org. Lett.* 1999, 1, 953; Hoveyda, A. H.; Zhugralin, A. R., *Nature,* 2007, 450, 243. The catalyst used in cross metathesis reactions are, such as but not limited to Grubbs catalyst $1^{st}$ and $2^{nd}$ generation, Hoveyda-Grubbs catalyst $1^{st}$ and $2^{nd}$ generation, Zhan-1A, Zhan-1B and Zhan-1C. The catalysts used in catalytic hydrogenation are such as, but mot limited to, 5% palladium on carbon, 10% palladium on carbon, $PtO_2$, palladium hydroxide.

Scheme 1

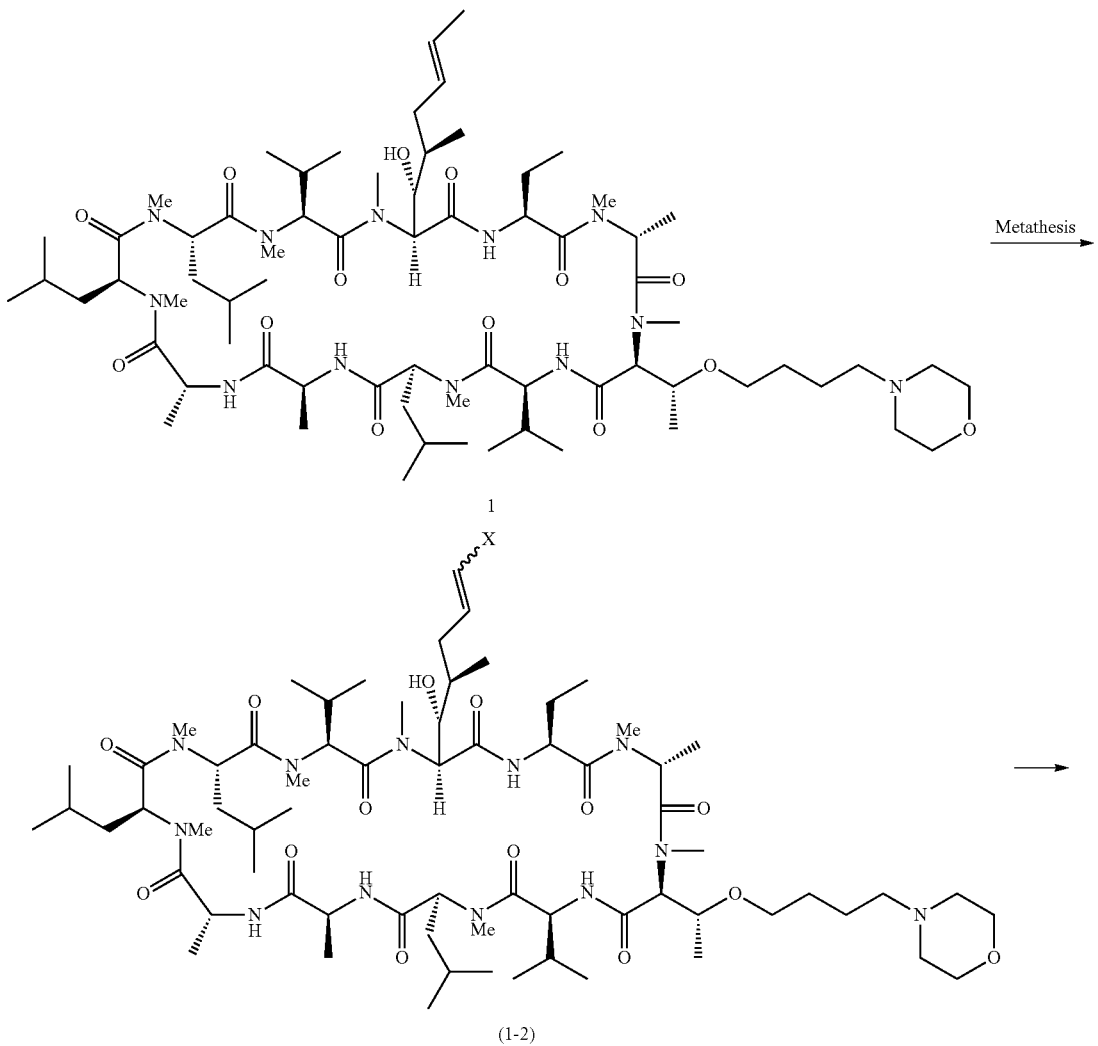

-continued

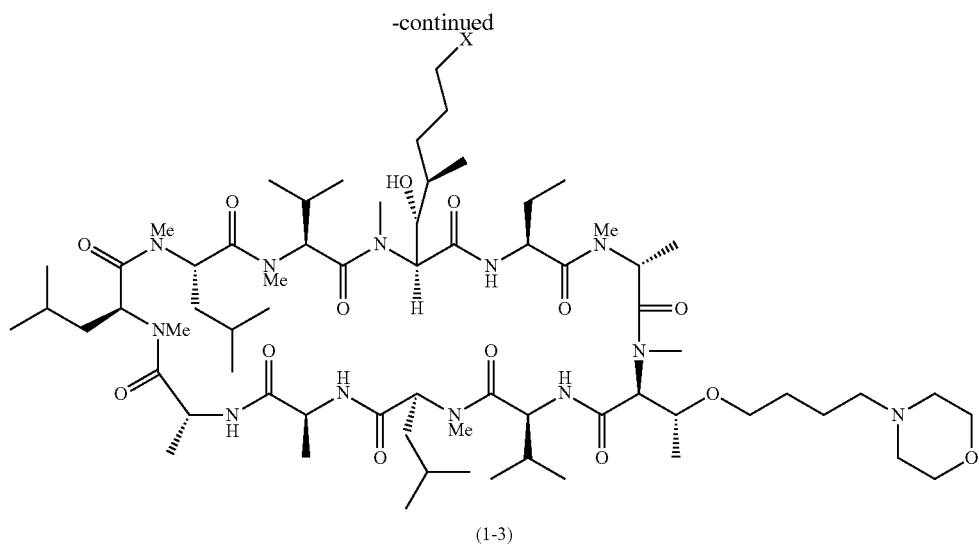

(1-3)

Scheme 2 depicts another process to prepare the novel cyclosporine analogues of the present invention by modification of compound of formula (1-1). Thus, the hydroxy group of the compound of formula (1-1) is protected with the suitable protecting group P, where P can be, but not limited to, TMS, TES, acetyl and chloroacetyl, to afford the compound of formula (2-1). A more thorough discussion of the procedures, reagents and conditions for protecting hydroxyl groups is provided in the literature, for example, by T. W. Greene and P. G. M. Wuts in "*Protective Groups in Organic Synthesis*" $3^{rd}$ ed., John Wiley & Son, Inc., 1999. Then the compound of formula (2-1) is converted to the aldehyde compound of formula (2-2) by oxidative cleavage reaction such as, but not limited to, ozonolysis and osmium teroxide/sodium periodate. Further, the aldehyde compound of formula (2-2) was transformed to the compound of formula (2-3) by different functional group transformation reactions. A thorough discussion of different functional group transformation reactions is described in literature, for example, by Richard C. Larock in "*Comprehensive Organic Transformations*" $2^{rd}$ ed., John Wiley & Son, Inc., 1999.

Scheme 2

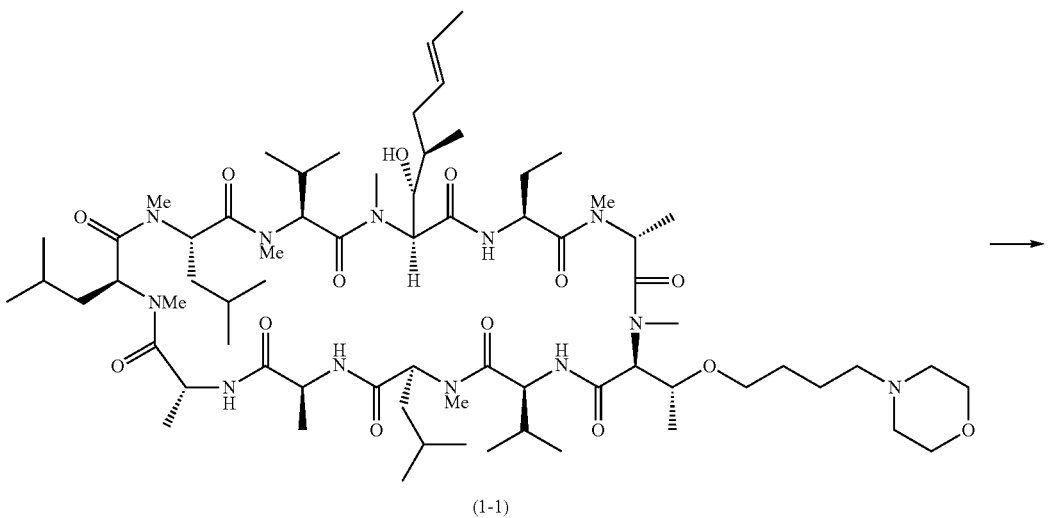

(1-1)

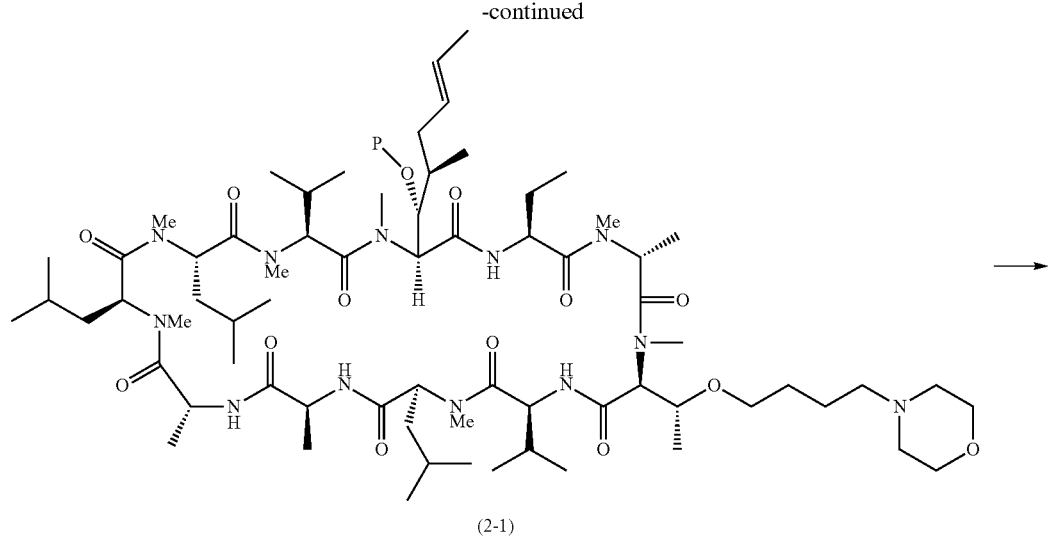
(2-1)
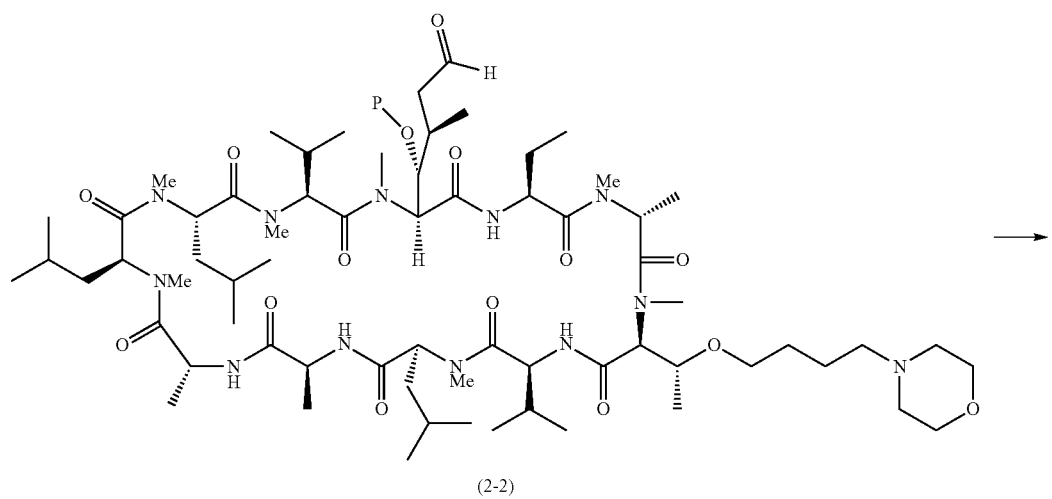
(2-2)
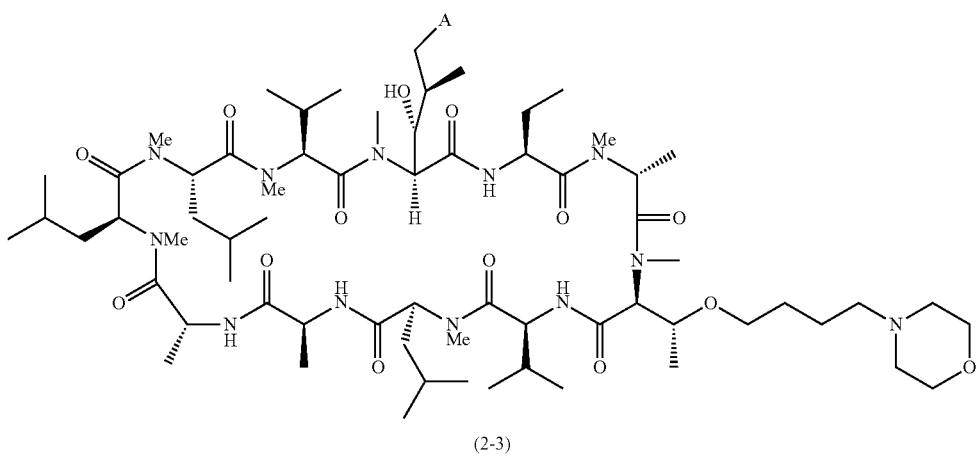
(2-3)

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

To a 25 ml, round-bottomed flask were added compound 1 (1 g, 0.743 mmol), acetone (7.4 mL), $^t$BuOOH (70%, 123 μL), and Et$_4$NOAc (19.5 mg) respectively and the mixture was stirred at room temperature for 10 min. After cooled to 0° C., a OsO$_4$ solution (2% in $^t$BuOH, 200 μL) was added. The reaction mixture was stirred at 0° C. for 25 min. and then at at room temperature for 13 hrs. Another portion of $^t$BuOOH (70%, 250 μL) and OsO$_4$ solution (2% in $^t$BuOH, 200 μL) were added and the mixture was stirred at at room temperature for 4 hrs. The reaction mixture was poured into a mixture of ice and water. Then Saturated Na$_2$S$_2$O$_3$ was added dropwise and the mixture was stirred for 30 min. Extracted with EtOAc and organic layer was separated and washed with water and brine respectively. Dried, filtered, concentrated, purified by Combiflash (MeOH/DCM: 0~10%) to give the compound of example 1 as a white foam (300 mg). MS-ESI (m/z): 1380.15 (M+H)$^+$.

Example 1

Compound of formula IV: A is

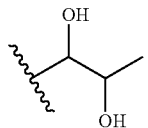

Example 2

Compound of formula IV: A is

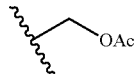 [SMILES: *COC(C)=O]

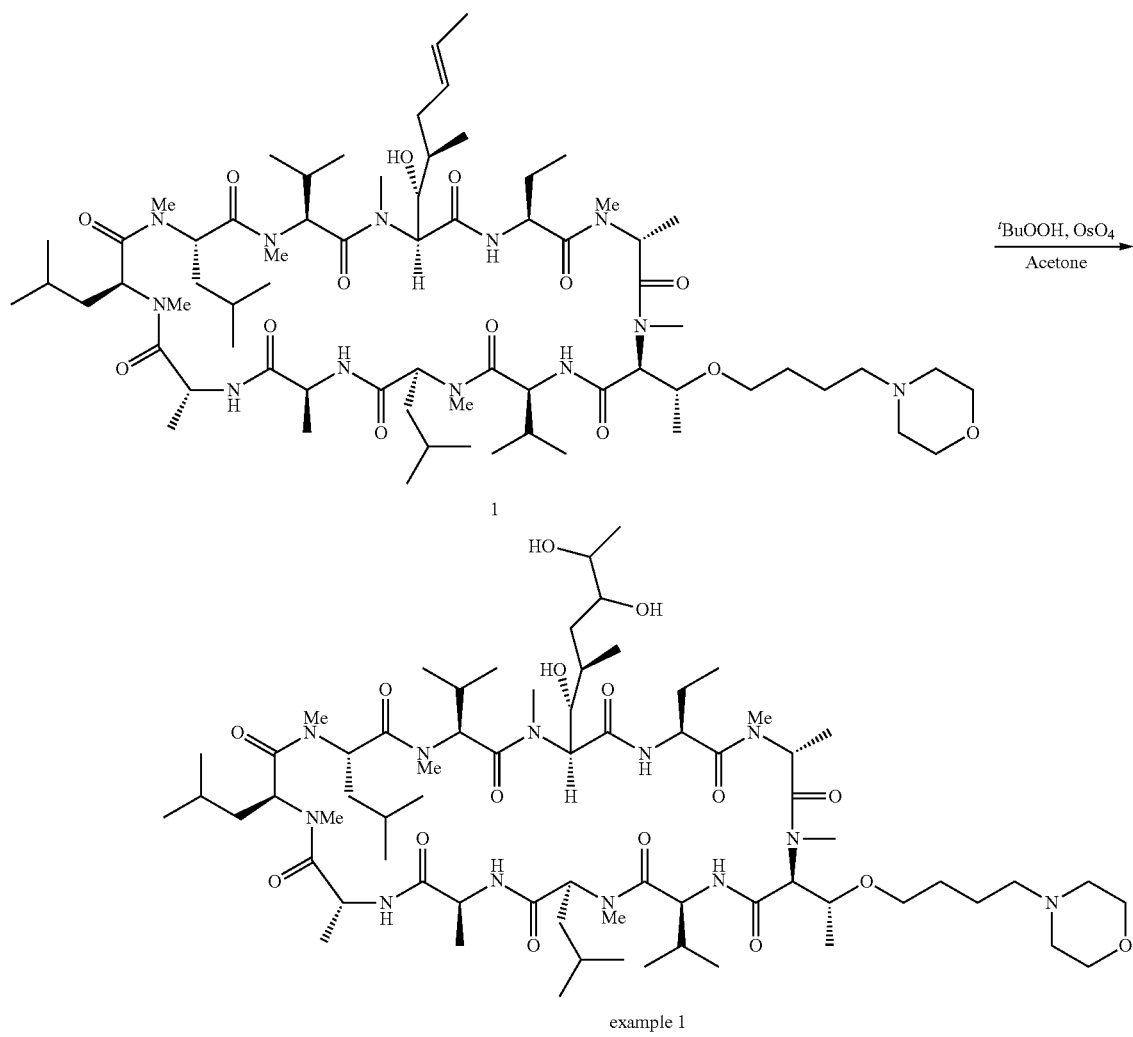

example 1

Step 2a

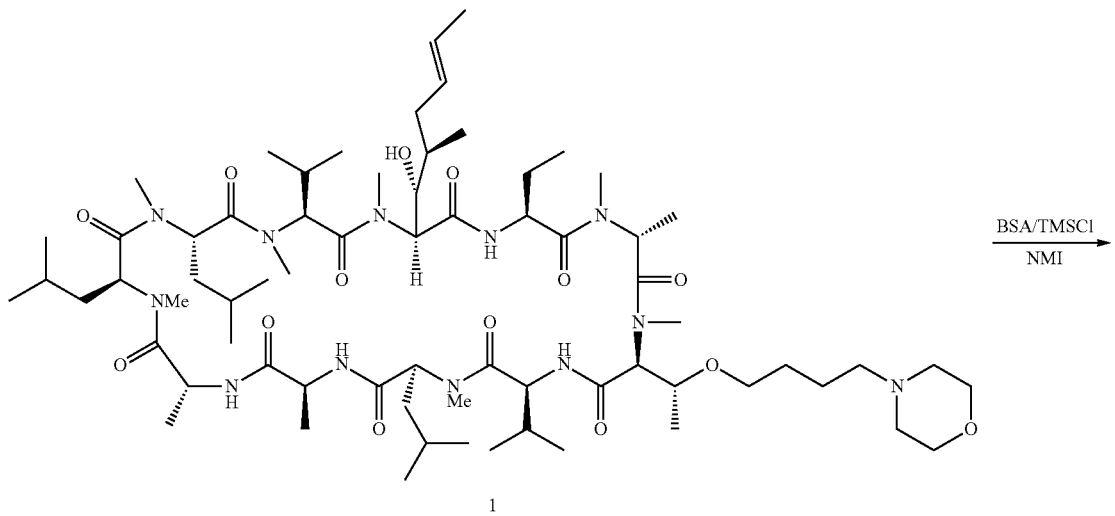

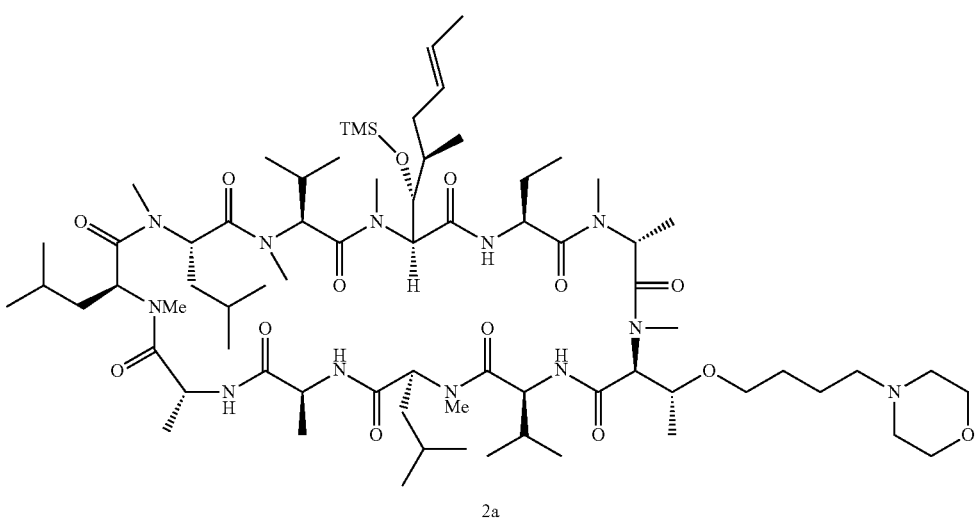

To a mixture of compound 1 (3.668 g, 2.726 mmol) in dichloromethane (27 mL) N-methylimidazole (0.87 mL, 10.9 mmol) and N,O-bis (trimethylsilyl)acetamide (6.7 mL, 27.26 mmol) was slowly added trimethylsilyl chloride (0.348 mL, 2.726 mmol) at 0° C. and stirred for 1.5 hr. Then, dry MeOH (27 mL) was added to the reaction, allowed to warm to room temperature and stirred for 2 hrs. After evaporation, the residue was diluted with MTBE (50 mL) and H2O (30 mL) and separated. The aqueous layer was extracted with MTBE (30 mL). The combined organic layer was washed with brine (30 mL), dried over $Na_2SO_4$, filtered and evaporated to dryness. The residue was dried further on vacuum pump for overnight to give the title compound 2a (3.777 g) as a white foam; MS: (ESI) m/z (M+H) 1418.55 (M+Na) 1440.58.

Step 2b

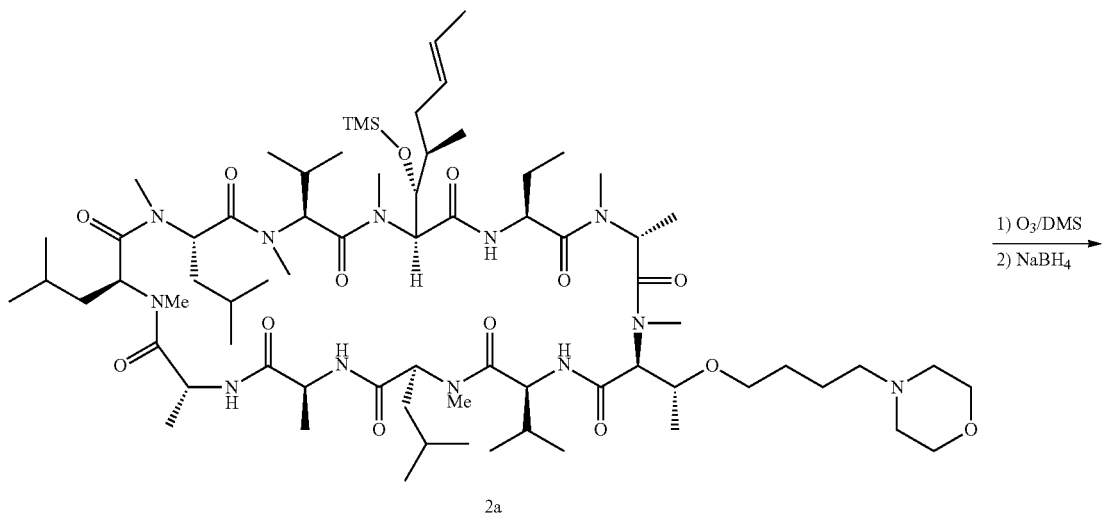

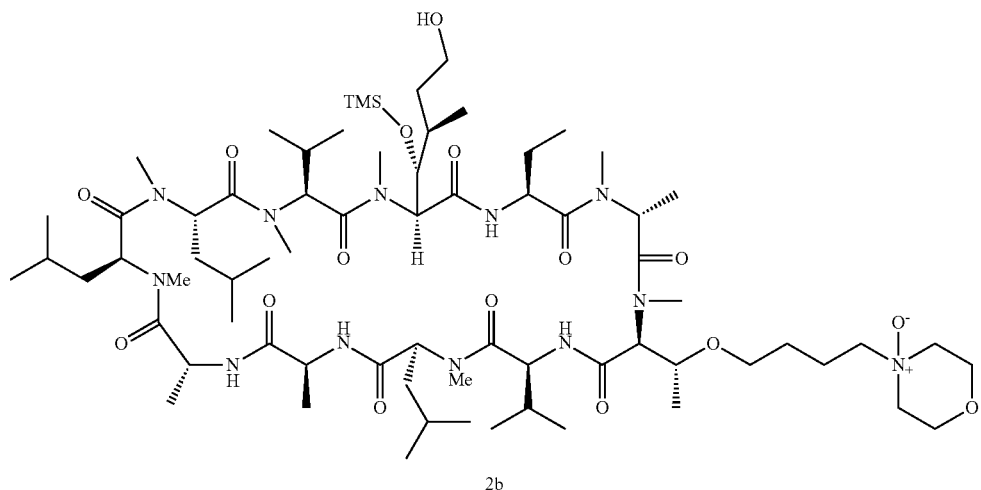

To a mixture of compound 2a (0.3 g, 0.2115 mmol) in dry MeOH (10 mL) was passed ozone at −78° C. until the starting material disappeared. Then, oxygen was passed through the reaction mixture for 15 min and subsequently N₂ was passed through for 20 min. Dimethyl sulfide (0.1 mL, 1.48 mmol) was added to the reaction, allowed to warm to room temperature and stirred for 16 hrs. The reaction mixture was evaporated off, dissolved in tert-BuOH-MeOH (4:1, 3 mL), cooled to 5° C., treated with sodium borohydride (24 mg, 0.630 mmol) and stirred at room temperature for ~1 hr. The reaction mixture was cooled to 5° C., quenched by addition of saturated aqueous NH₄Cl sol'n (0.5 mL), diluted with ethyl acetate (20 mL), washed with H₂O (5 mL) and brine (5 mL), dried over Na₂SO₄, filtered and evaporated to dryness. The residue was dried further on vacuum pump for overnight to give the title compound 2b (276 mg) as a white foam; MS: (ESI) m/z (M+H) 1423.67 (M+Na) 1445.71.

Step 2c
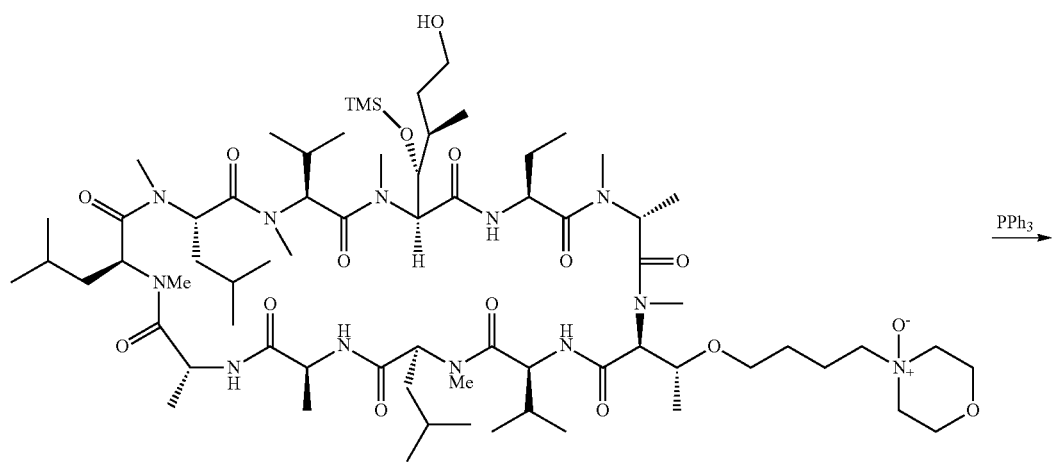
A mixture of 2b (224 mg, 0.158 mmol) and triphenylphospine (124 mg, 0.473 mmol) in dry THF (2.5 mL) was refluxed for 2.5 hrs. The reaction was concentrated and purified by silica gel column chromatography with 0~65% acetone in Hexanes to give the title compound 2c (129 mg) as a white foam; MS: (ESI) m/z (M+H) 1407.73 (M+Na) 1429.74.
Step 2d
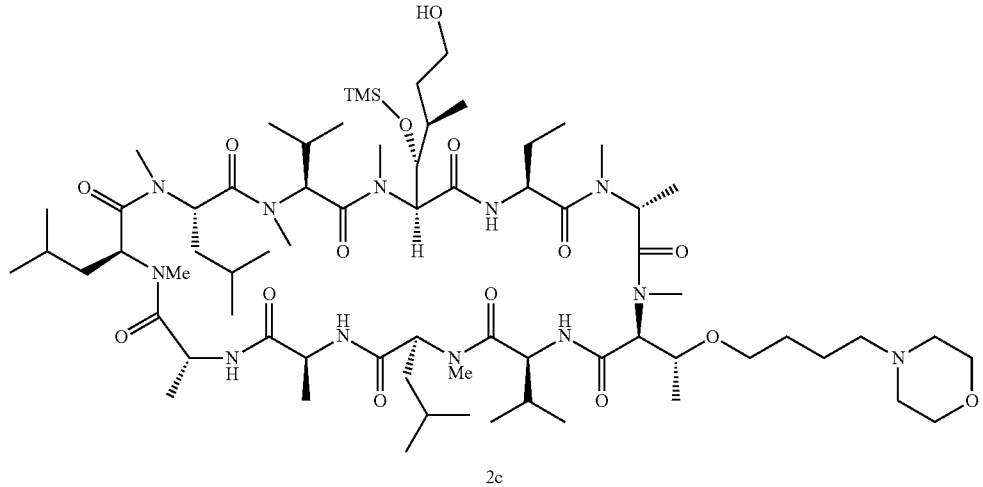
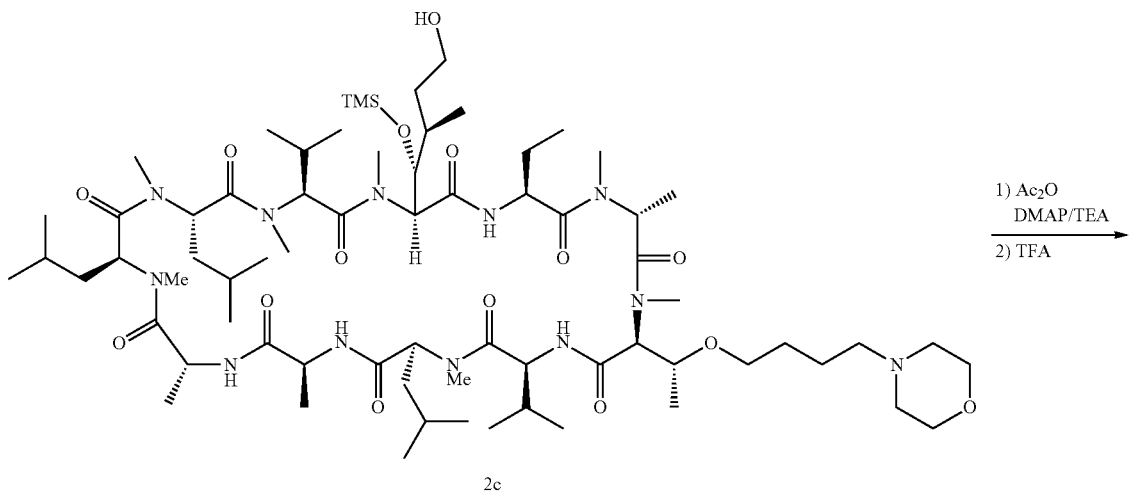

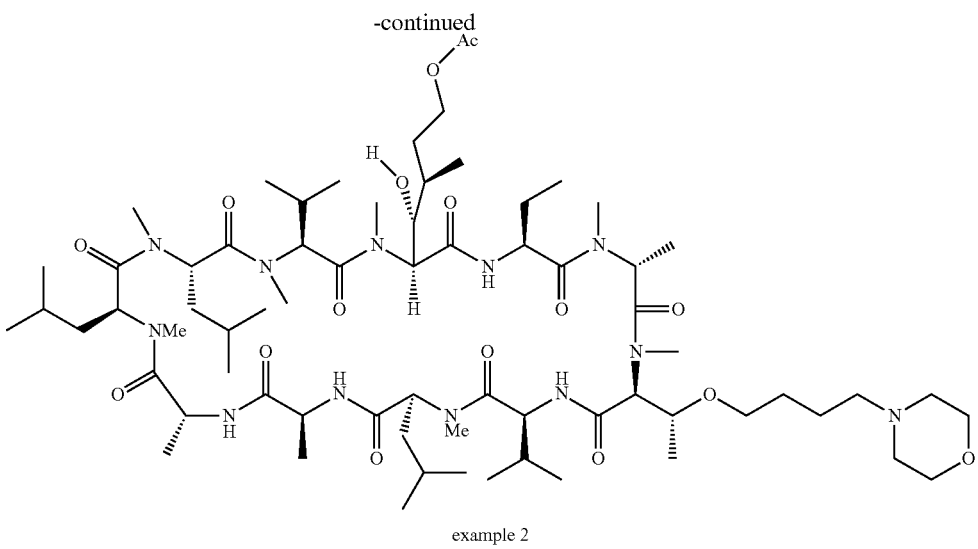

example 2

A mixture of 2c (80 mg, 0.0568 mmol), acetic anhydride (27 μl), DMAP (3.6 mg) and triethylamine (0.016 mL) in 1,2-dichloroethane (0.3 mL) was stirred at room temperature for 16 hrs and the reaction was diluted with dichloromethane (1 mL), cooled to 0° C., treated with trifluoroacetic acid (0.4 mL) and stirred at 0° C. for 2 hrs. The reaction mixture was diluted with dichloromethane (5 mL), poured into cold saturated NaHCO$_3$ sol'n-20% K$_2$CO$_3$ sol'n (5:1, 3 mL) and separated. The organic layer was washed with brine (2 mL), dried over Na$_2$SO$_4$, filtered and evaporated to dryness. The residue was purified by preparative HPLC to give the compound of example 2 (16 mg) as a white foam; MS: (ESI) m/z (M+H) 1377.50, (M+Na) 1399.54.

Example 3

Compound of formula IV: A is

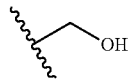

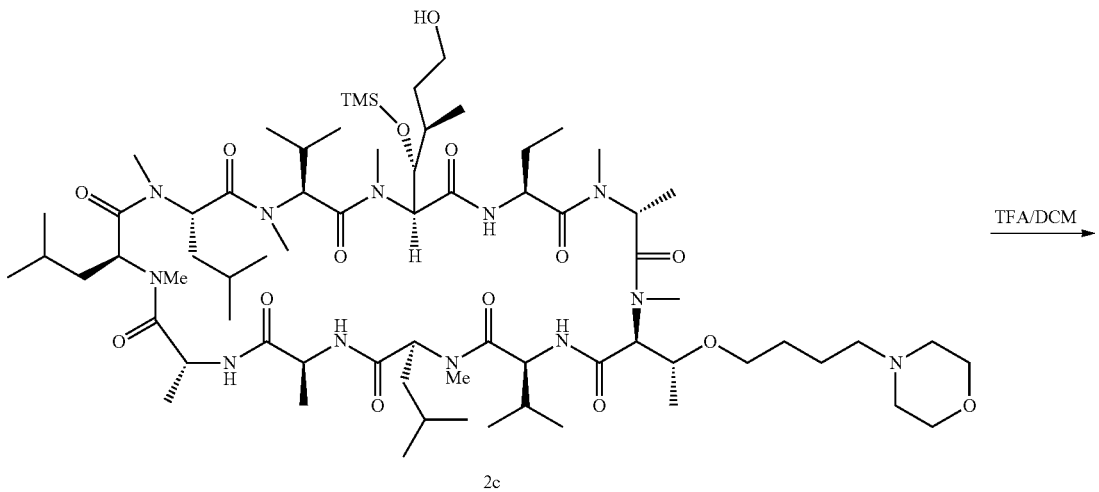

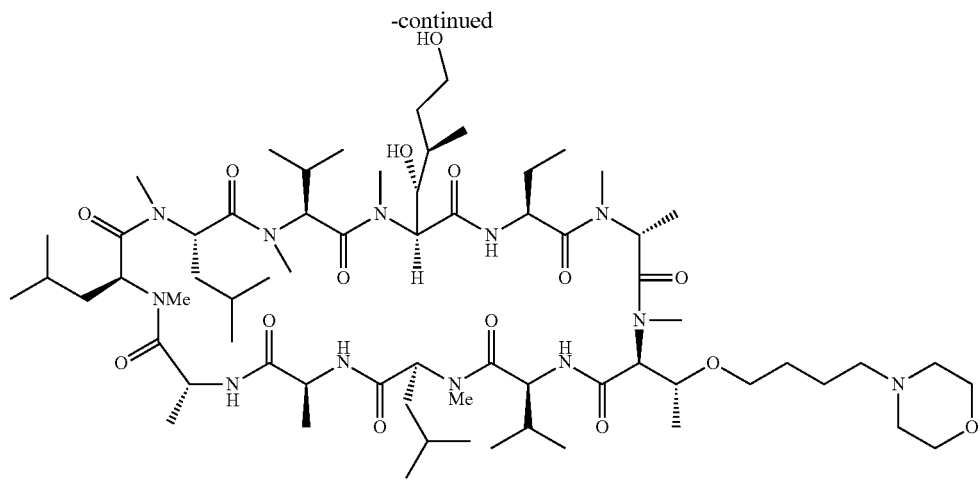

example 3

To a solution of compound 2c (1.4 g) in DCM (25 ml) was added TFA (5 ml) at 0° C. and the mixture was stirred at 0° C. for 2 hrs. The reaction mixture was diluted with dichloromethane (50 mL), poured into cold saturated NaHCO$_3$ solution-20% K$_2$CO$_3$ solution (5:1, 60 mL). The organic layer was separated, washed with brine (40 mL), dried over Na$_2$SO$_4$, filtered and evaporated to dryness. The residue was purified by silica gel column to give the compound of example 3 (1.2) as a white foam; MS: (ESI) m/z (M+H) 1335.60, (M+Na) 1357.64.

Example 4

Compound of formula IV: A is

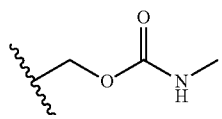 [SMILES: *COC(=O)NC]

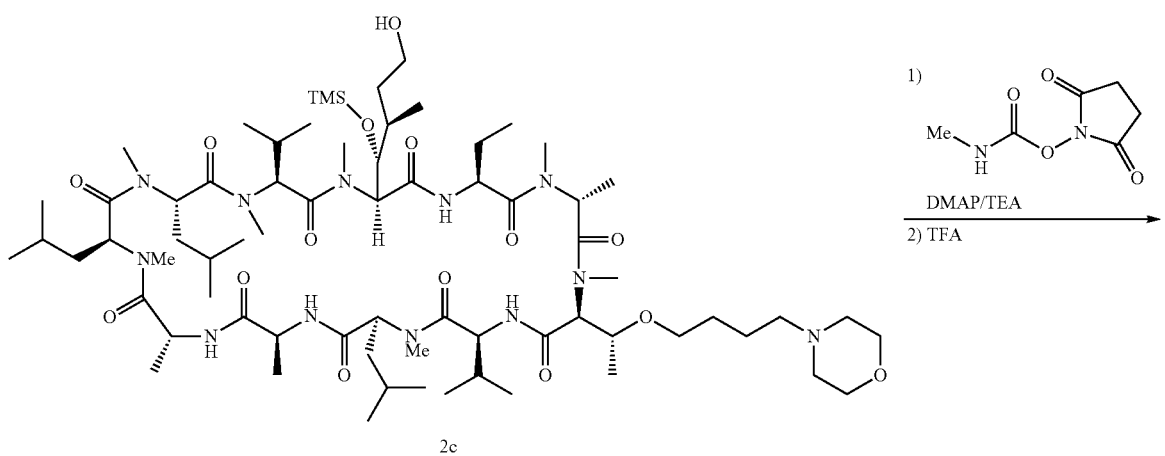

2c

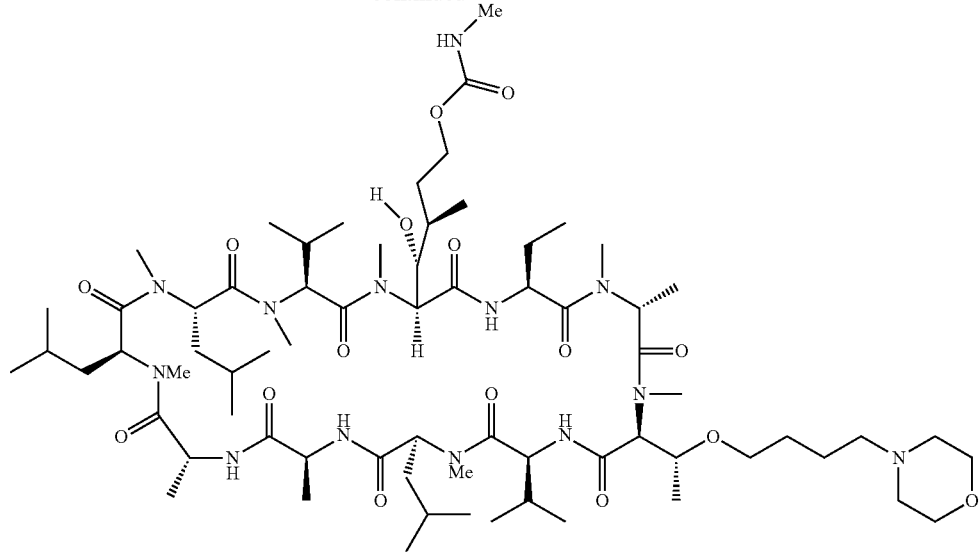

example 4

A mixture of compound 2c (80 mg, 0.0568 mmol), N-succinimidyl N-methylcarbamate (27 mg), DMAP (3.6 mg) and triethylamine (0.016 mL) in 1,2-dichloroethane (0.3 mL) was heated at 80° C. for 70 min. Then, additional N-succinimidyl N-methylcarbamate (50 mg) was added to the reaction and heated at 80° C. for 24 hrs. After cooling to room temperature, the reaction was diluted with dichloromethane (1 mL), cooled to 0° C., treated with trifluoroacetic acid (0.4 mL) and stirred at 0° C. for 2 hrs. The reaction mixture was diluted with dichloromethane (5 mL), poured into cold saturated NaHCO₃ solution –20% K₂CO₃ solution (5:1, 3 mL) and separated. The organic layer was washed with brine (2 mL), dried over Na₂SO₄, filtered and evaporated to dryness. The residue was purified by preparative HPLC (HPLC condition: mobile phase A-20 mM NH₄HCO₃ in H₂O (HPLC grade); mobile phase B-acetonitrile (HPLC grade); Luna column (pre-heated at 55° C.), flow rate: 20 mL/min; 60-95% B for 40 min.) to give the compound of example 4 (6.3 mg) as a white cotton after lyophilization; MS: (ESI) m/z (M+H) 1393.50, (M+Na) 1415.54.

Example 5

Compound of formula IV: A is

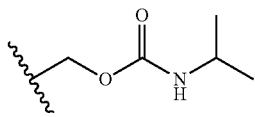 [SMILES: *COC(=O)NC(C)C]

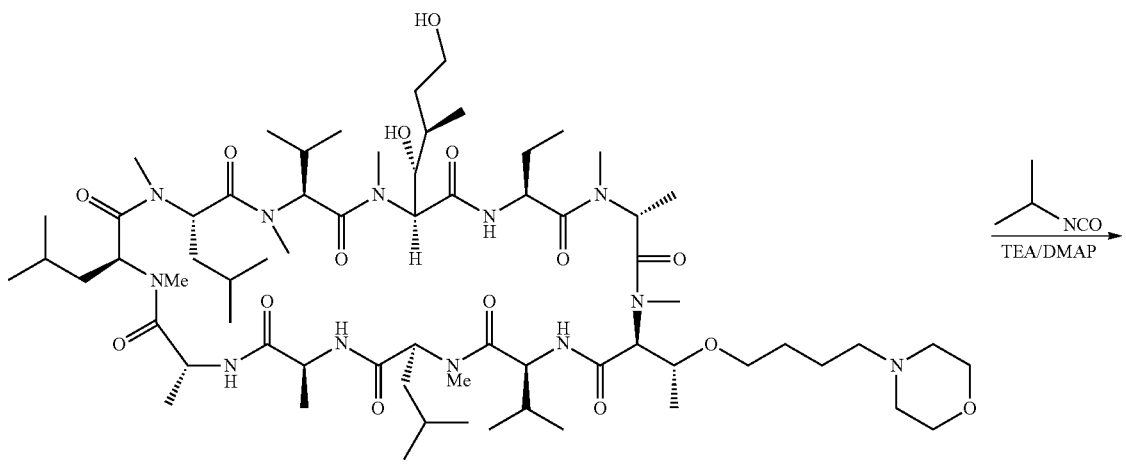

example 2

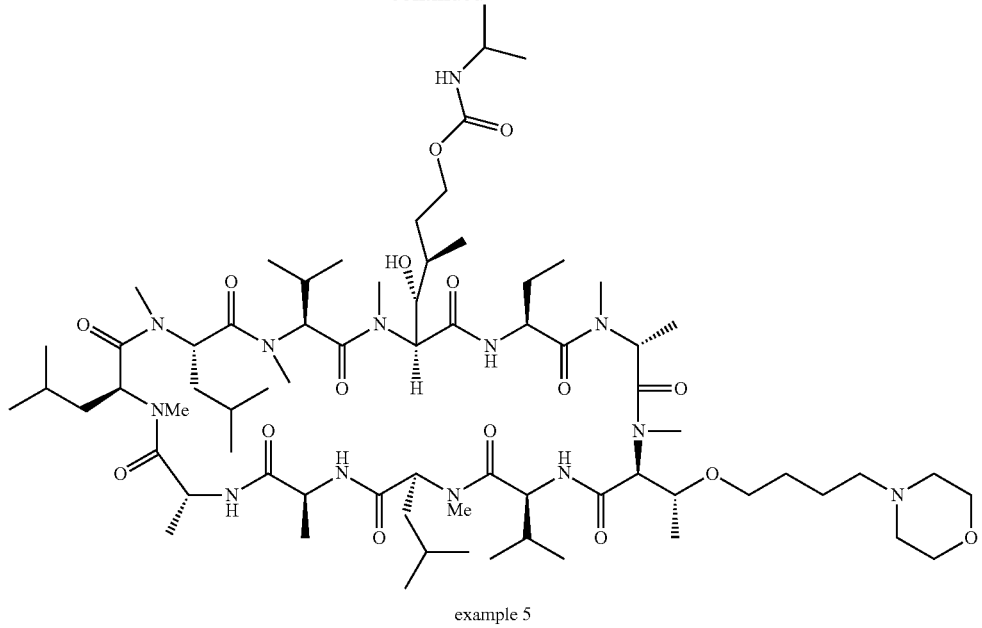

example 5

A mixture of compound of example 2 (65.1 mg, 0.0487 mmol) in dry DMF (0.3 mL) was reacted with isopropyl isocyanate (40 μL) in the presence of DMAP (2.4 mg) and triethylamine (14 μL). After the reaction, it was treated with 2M-methylamine in THF (0.2 mL) for 1 hr and evaporated. The residue was diluted with ethyl acetate (5 mL), washed with H₂O (3×2 mL), brine (2 mL), dried over Na₂SO₄, filtered and evaporated to dryness. The residue was purified by preparative HPLC (HPLC condition: mobile phase A-20 mM NH₄HCO₃ in H₂O (HPLC grade); mobile phase B-acetonitrile (HPLC grade); Luna column (pre-heated at 55° C.), flow rate: 20 mL/min; 60-90% B for 40 min.) to give the compound of example 5 (5.5 mg) as a white cotton after lyophilization; MS: (ESI) m/z (M+H) 1421.53, (M+Na) 1443.53.

Example 6

Compound of formula IV: A is

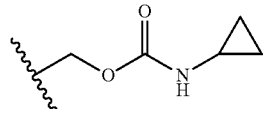 [SMILES: *COC(=O)NC1CC1]

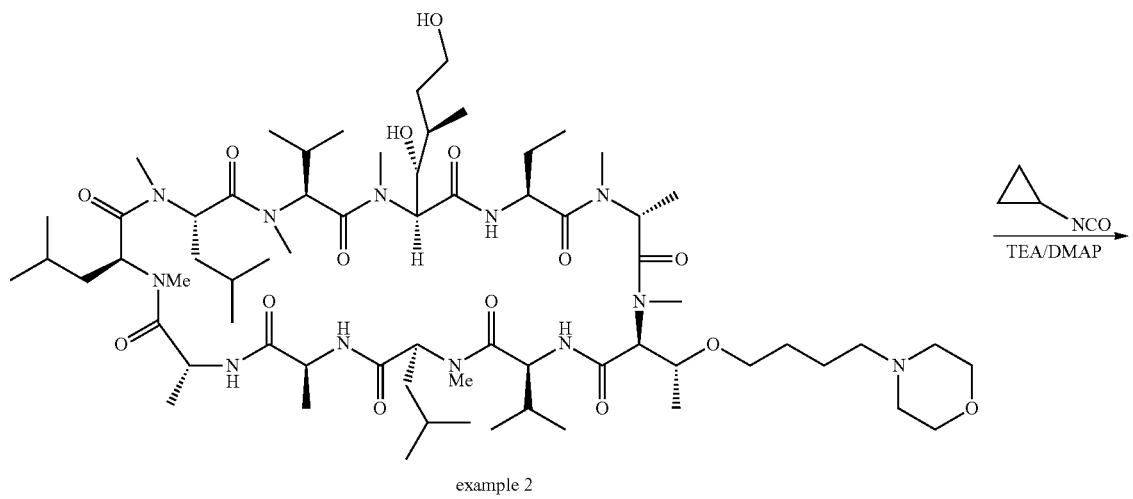

example 2

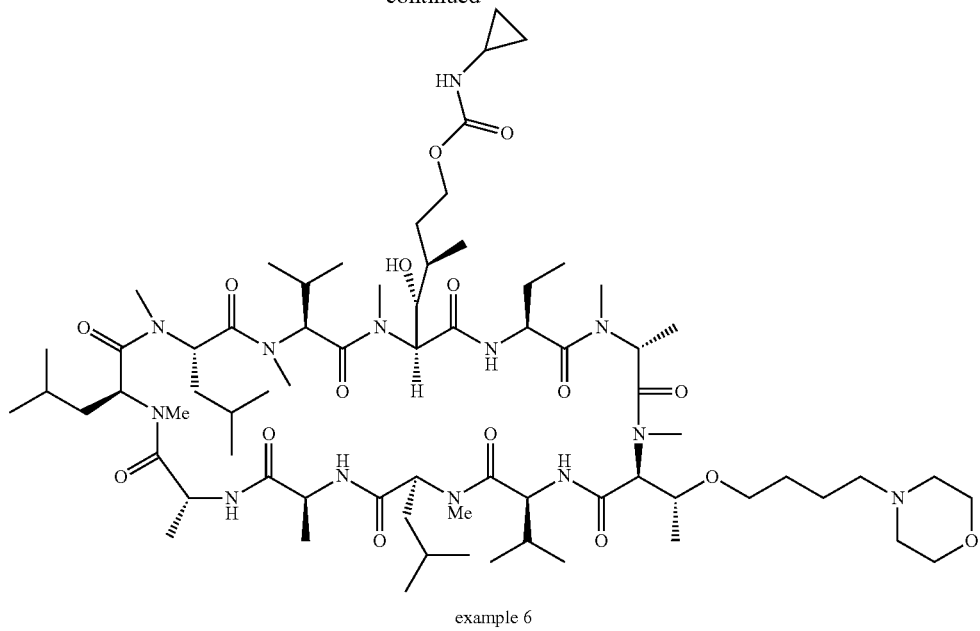
example 6
The compound of example 6 was prepared using the same procedure as described in the preparation of example 5. MS: (ESI) m/z (M+H) 1419.53, (M+Na) 1441.53.
Example 7
Compound of formula IV: A is
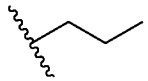 [SMILES: *CCC]
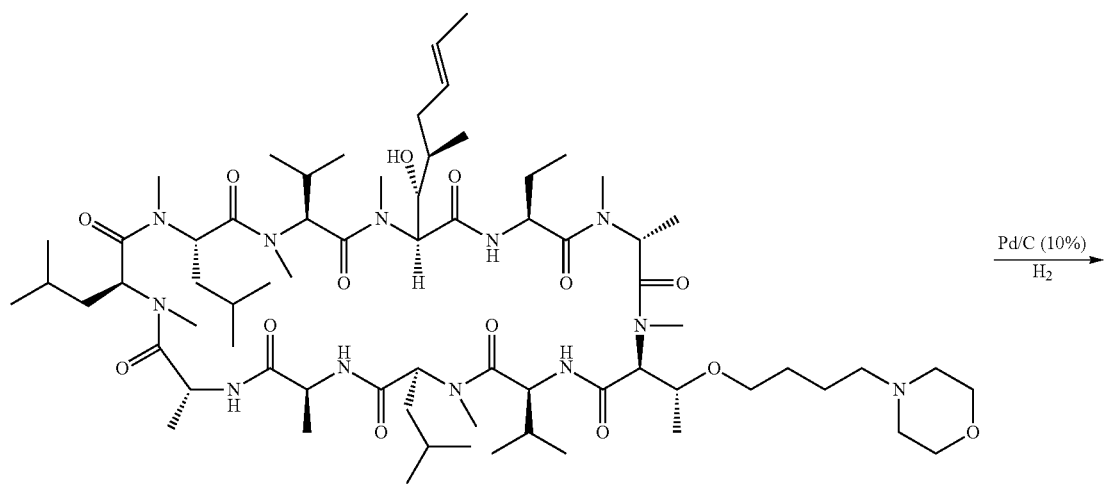

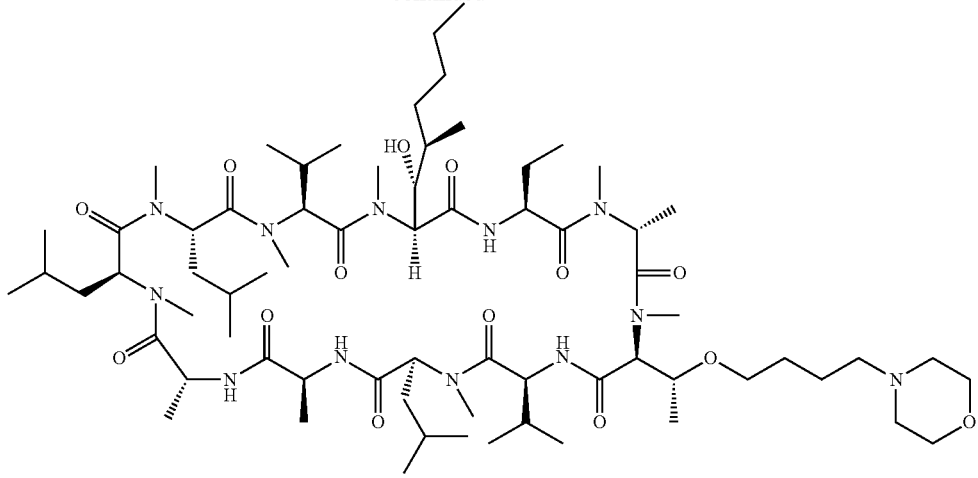

example 7

The compound of 1 (1.0 g, 0.743 mmol) and 10% Pd/C (0.2 g) in ethyl acetate (32 mL) was degassed with H$_2$ for 15 min and then stirred at room temperature overnight under balloon pressure of H$_2$. The reaction mixture was filtrated through a Celite pad and washed with ethyl acetate (30 mL×2). The crude mixture was treated with activated charcoal (80 mg, 5% w/w) by stirring in ethyl acetate at 40° C. for 1 h for decolorizing. The filtrate was collected and the solvent was evaporated to afford crude product as white solid form. The crude product was purified by silica gel column chromatography with 0~100% Acetone in Hexane to afford the compound of example 7 (0.96 g) as a white foam; MS: (ESI) m/z (M+H) 1348.07.

Example 8

Compound of formula IV: A is

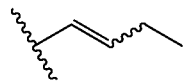 [SMILES: *C=CCC]

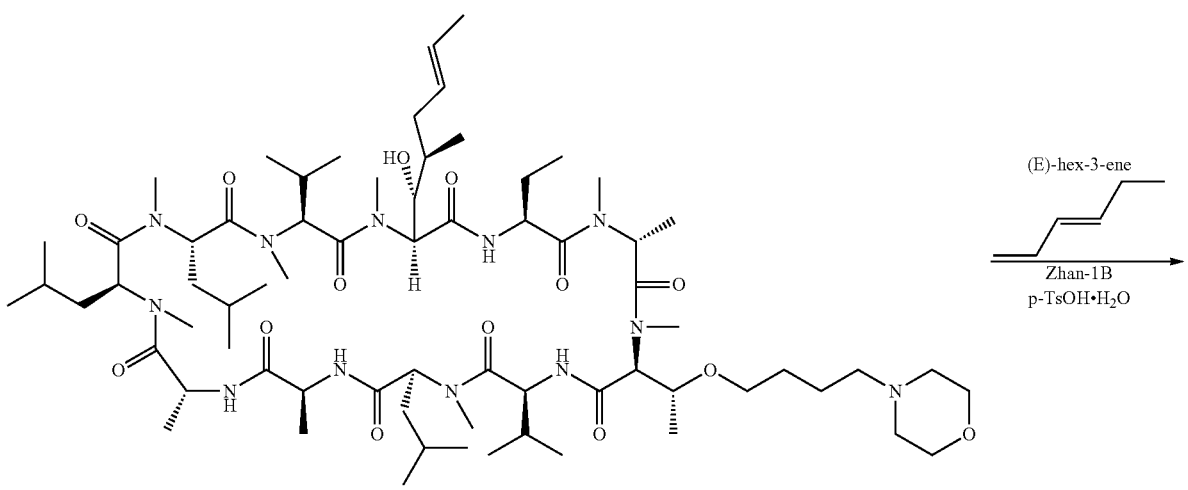

1

-continued

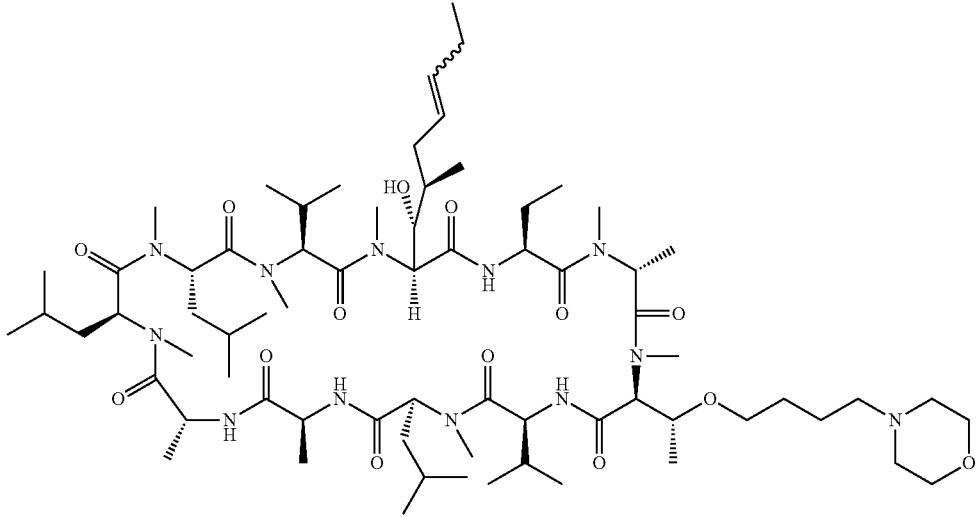

example 8

A mixture of compound 1 (1.0 g, 0.743 mmol) and p-toluenesulfonic acid monohydrate (141 mg, 0.74 mmol) in dry toluene (5 mL) was heated at 60° C. for 30 min. After cooling to <−40° C. (dry-ice/acetone bath) and degassing, (E)-hex-3ene (12 mmol) and Zhan-1B catalyst (55 mg, 0.074 mmol) were added to the reaction, which was degassed and filled with nitrogen. The reaction was heated at 60° C. for 3 h. Then, triethylamine (0.031 mL, 0.223 mmol), 2-mercaptonicotinic acid (24 mg, 0.15 mmol) and were added to the reaction and heated at 60° C. for 30 min. After cooling, the reaction mixture was diluted with ethyl acetate (80 mL), washed with saturated aqueous NaHCO$_3$ solution (2×30 mL), brine (10 mL), dried over Na$_2$SO$_4$, filtered and evaporated to dryness. The residue was purified by silica gel column chromatography with 0~100% acetone in hexane to afford the compound of example 8 (0.9 g) as a white foam; MS: (ESI) m/z (M+H) 1360.05.

Example 9

Compound of formula IV: A is

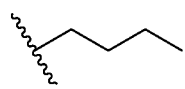 [SMILES: *CCCC]

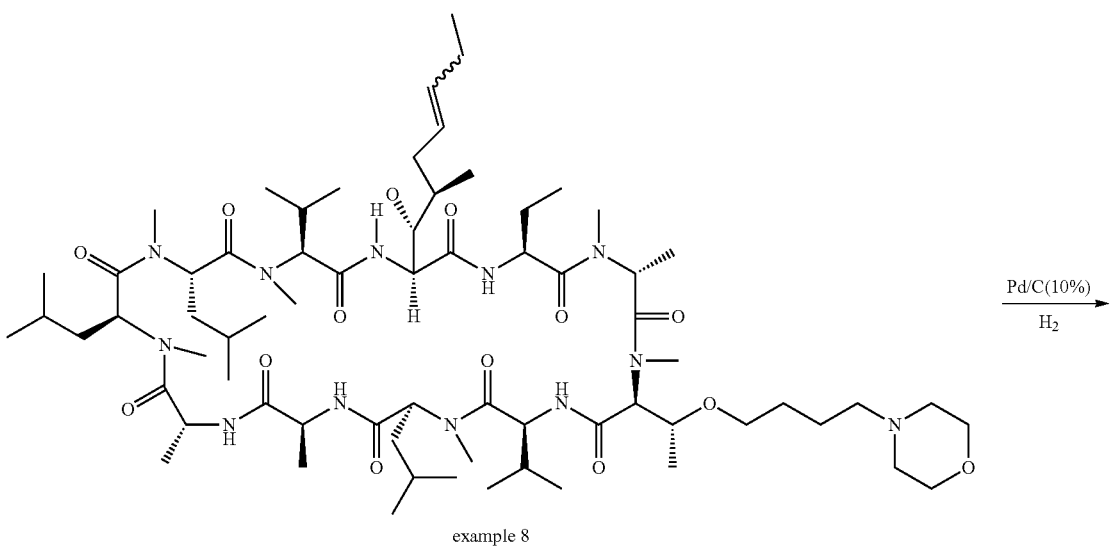

example 8

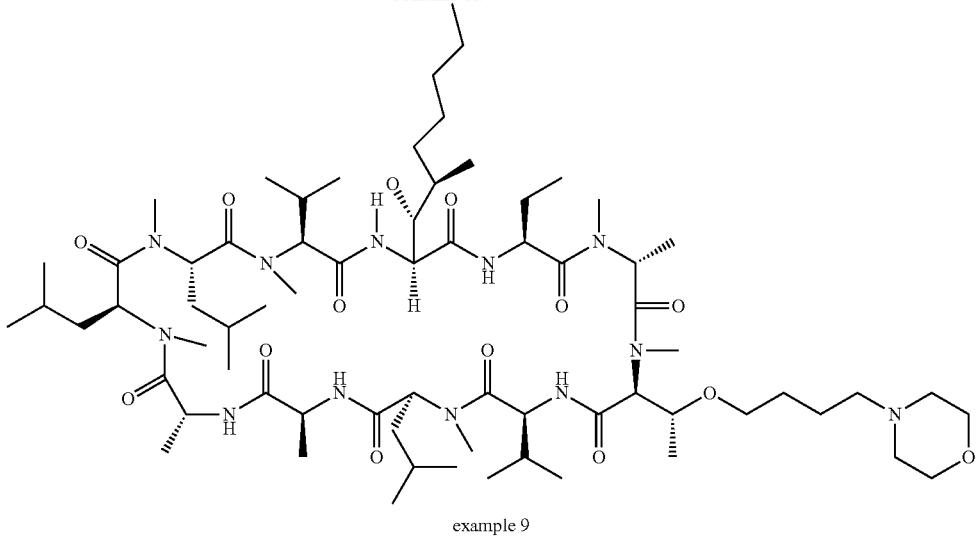

example 9

The compound of example 8 (1.36 g, 1.0 mmol) and 10% Pd/C (0.3 g) in ethyl acetate (32 mL) was degassed with $H_2$ for 15 min and then stirred at room temperature overnight under balloon pressure of $H_2$. The reaction mixture was filtrated through a Celite pad and washed with ethyl acetate (30 mL×2). The crude mixture was treated with activated charcoal (80 mg, 5% w/w) by stirring in ethyl acetate at 40° C. for 1 h for decolorizing. The filtrate was collected and the solvent was evaporated to afford crude product as white solid form. The crude product was purified by silica gel column chromatography with 0~100% Acetone in Hexane to afford the compound of example 9 (1.19 g) as a white foam; MS: (ESI) m/z (M+H) 1362.07.

Example 10

Compound of formula IV: A is

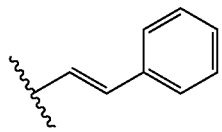 [SMILES: */C=C/c1ccccc1]

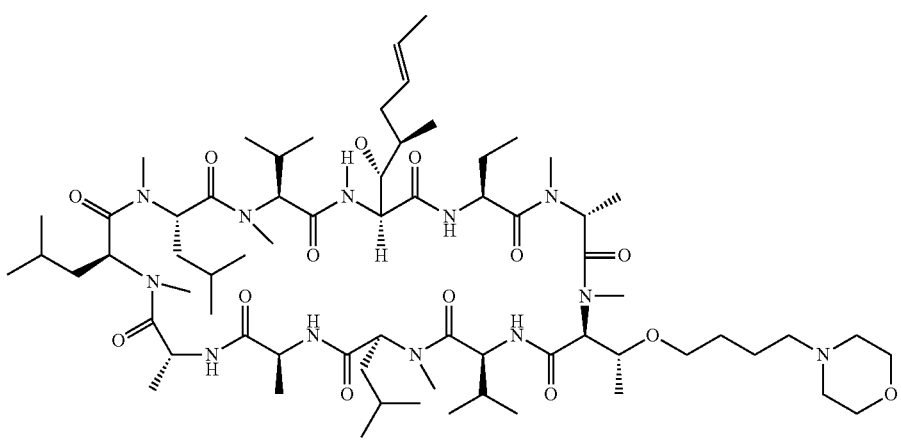

1

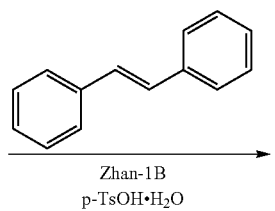

Zhan-1B
p-TsOH•$H_2O$

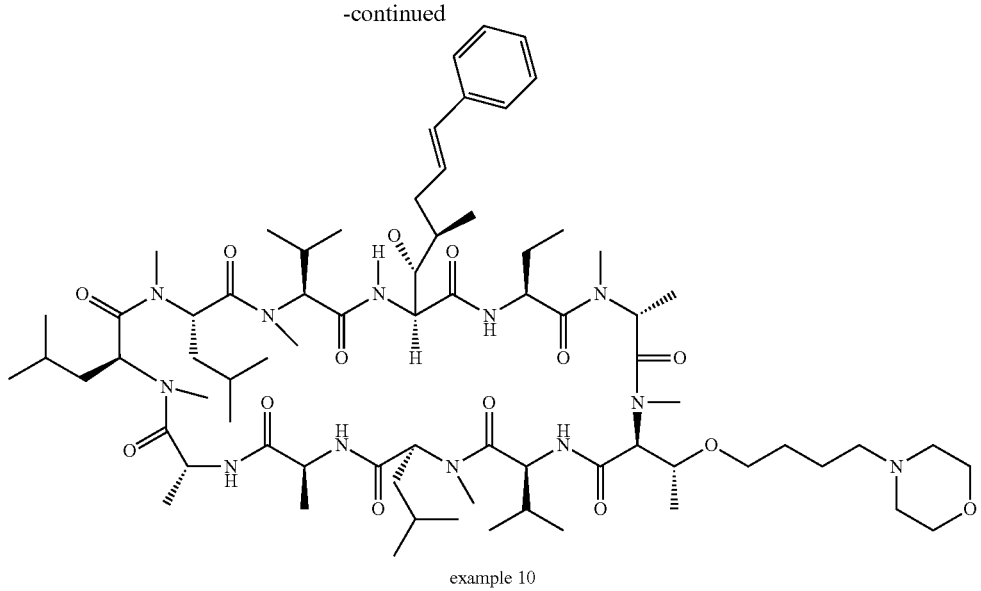
example 10
The compound of example 10 was synthesized from compound 1 and trans-Stilbene using similar procedure described in the synthesis of example 7. MS: (ESI) m/z (M+H) 1408.07.
Example 11
Compound of formula IV: A is
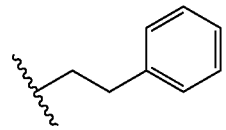 [SMILES: *CCc1ccccc1]
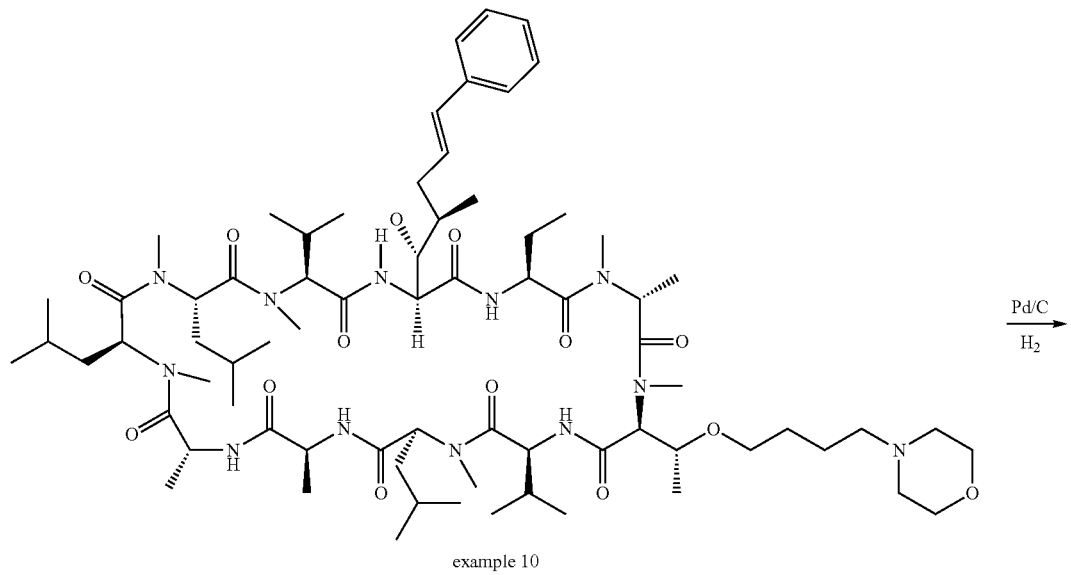
example 10

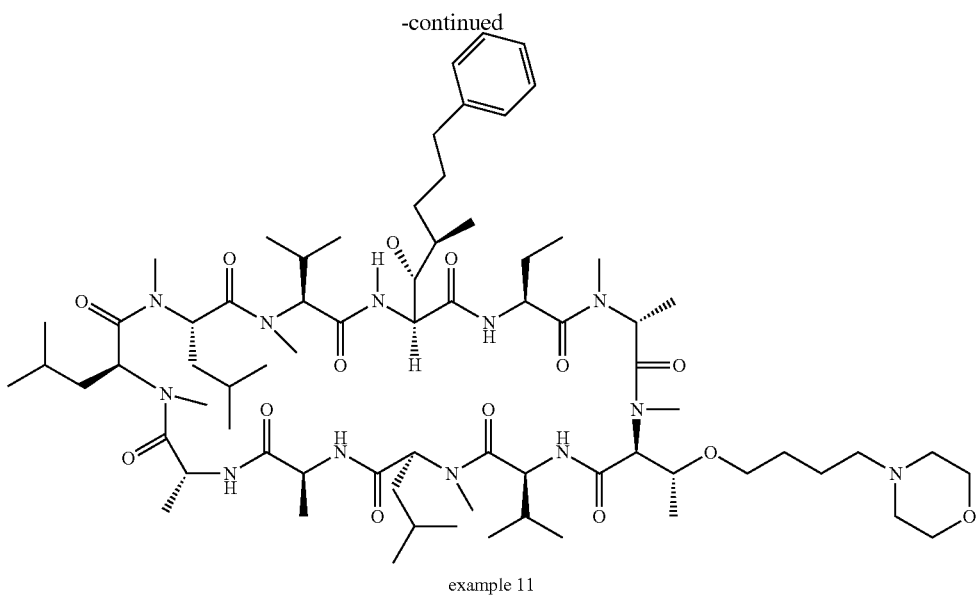
example 11
The compound of example 11 was synthesized from compound of example 10 using similar procedure described in the synthesis of example 8. MS: (ESI) m/z (M+H) 1410.07.
Example 12
Compound of formula IV: A is
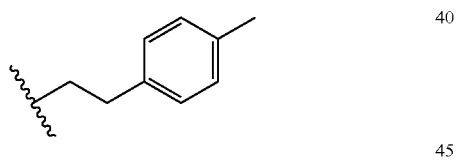
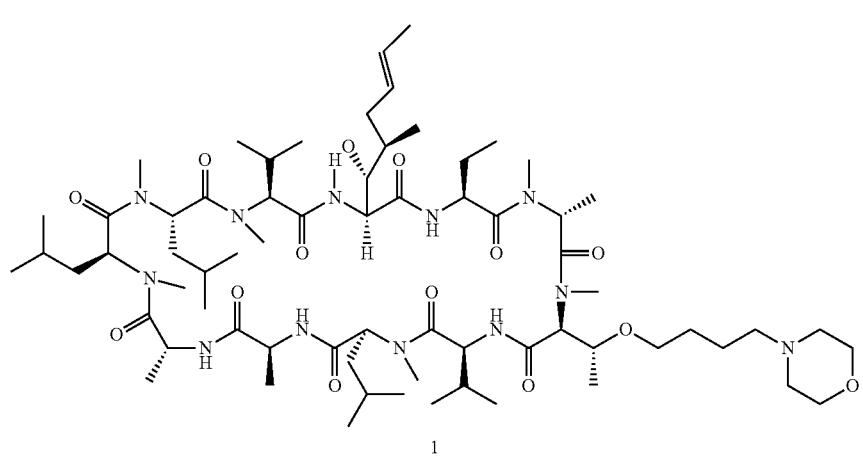
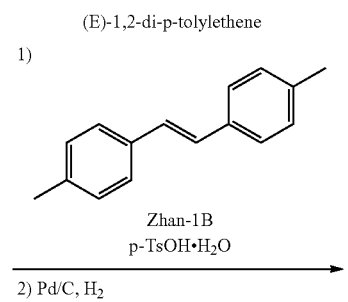
(E)-1,2-di-p-tolylethene
1)
Zhan-1B
p-TsOH•H$_2$O
2) Pd/C, H$_2$

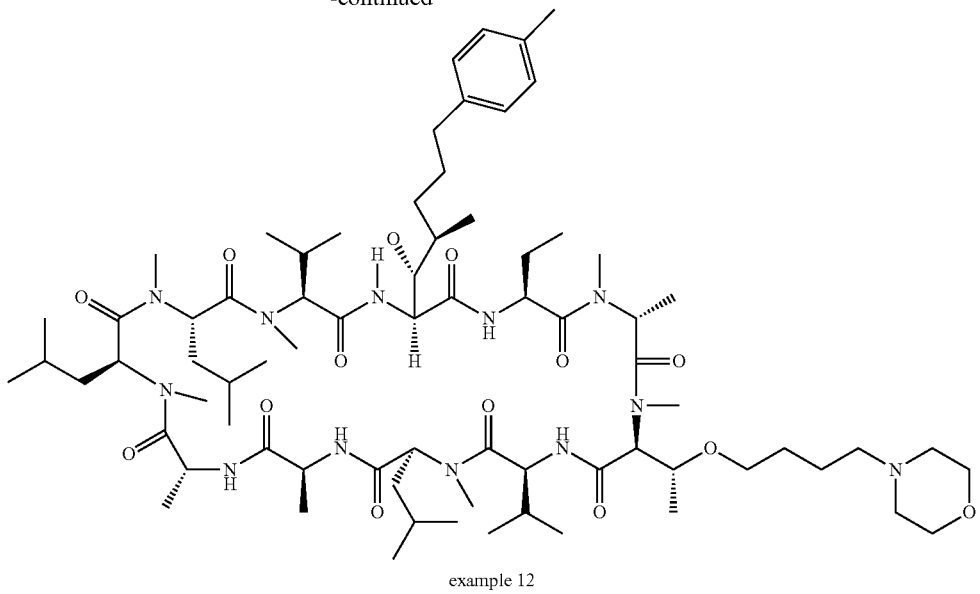
example 12
The compound of example 12 was synthesized from compound 1 and (E)-1,2-di-p-tolylethene using similar procedure described in the synthesis of example 7 and example 8. MS: (ESI) m/z (M+H) 1424.07.
Example 13
Compound of formula IV: A is
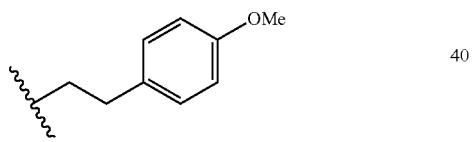
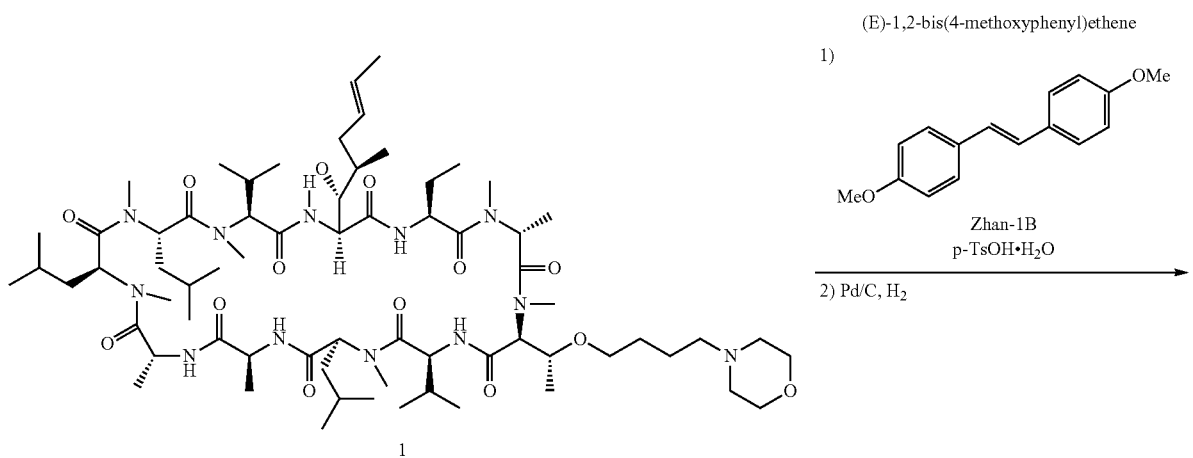

-continued
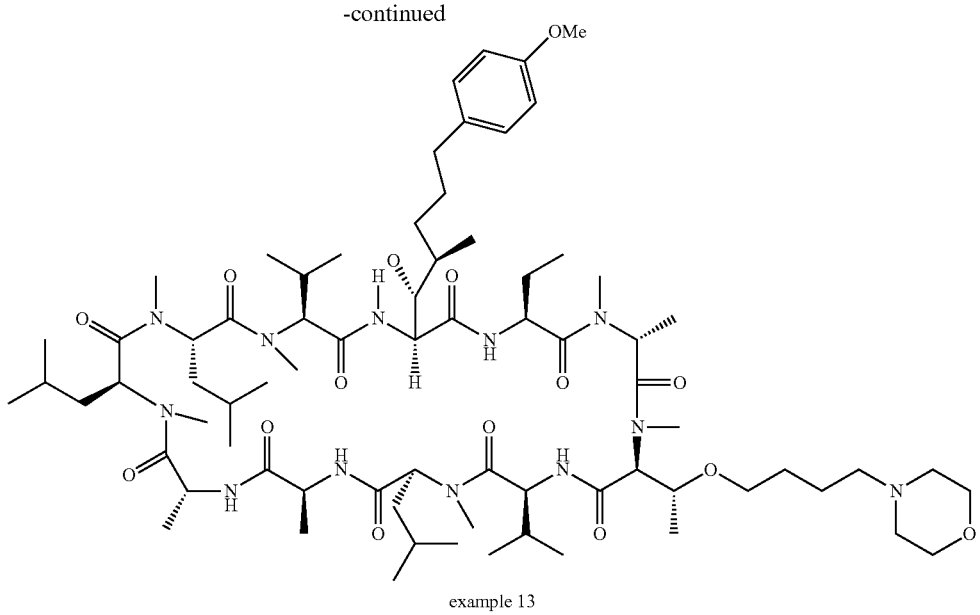
example 13
The compound of example 13 was synthesized from compound 1 and (E)-1,2-bis(4-methyoxyphenyl)ethene using similar procedure described in the synthesis of example 7 and example 8. MS: (ESI) m/z (M+H) 1440.07.
Example 14
Compound of formula IV: A is
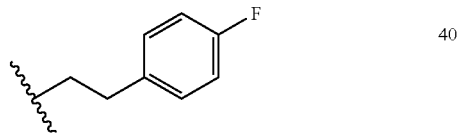
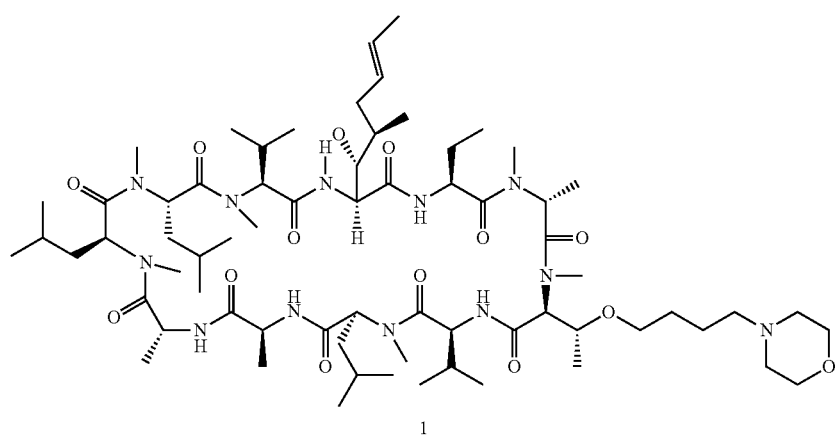
1) (E)-1,2-bis(4-fluorophenyl)ethene
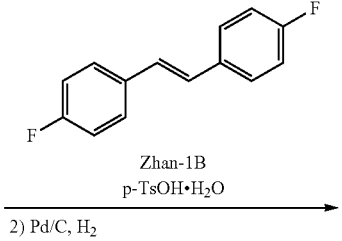
Zhan-1B
p-TsOH•H$_2$O
2) Pd/C, H$_2$ -continued
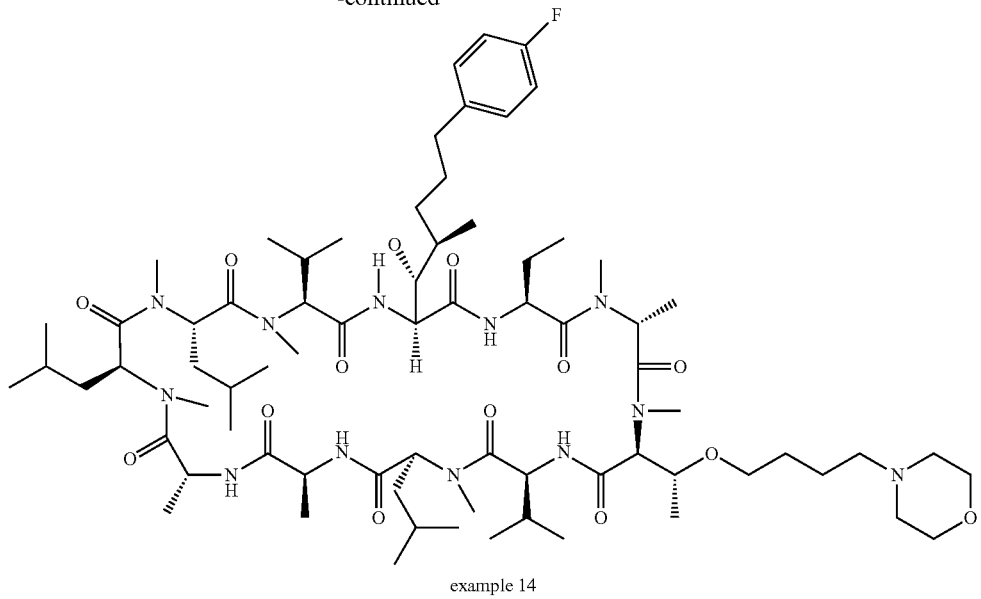
example 14
The compound of example 14 was synthesized from compound 1 and (E)-1,2-bis(4-fluorophenyl)ethene using similar procedure described in the synthesis of example 7 and example 8. MS: (ESI) m/z (M+H) 1428.04.
Example 15
Compound of formula IV: A is
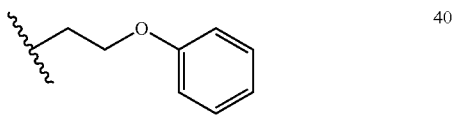
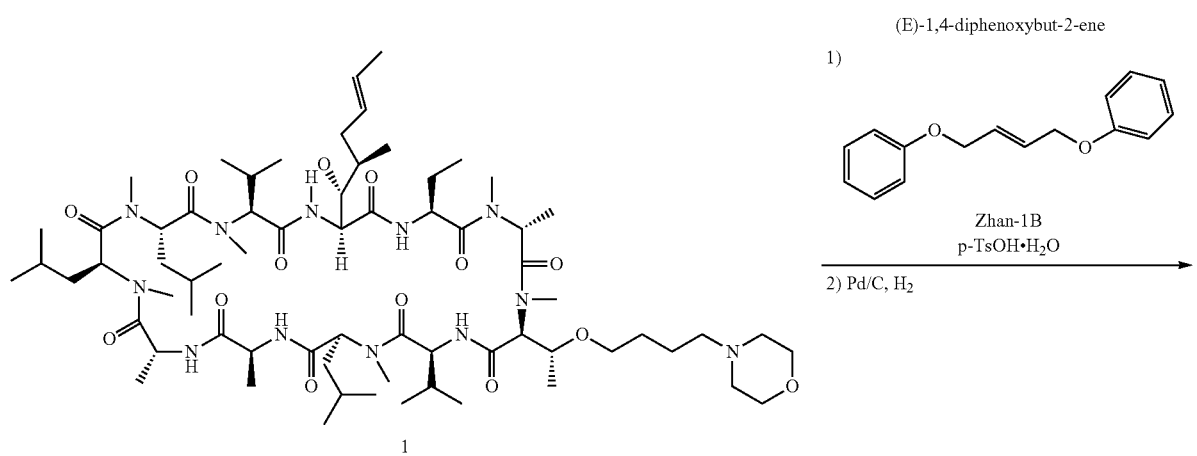

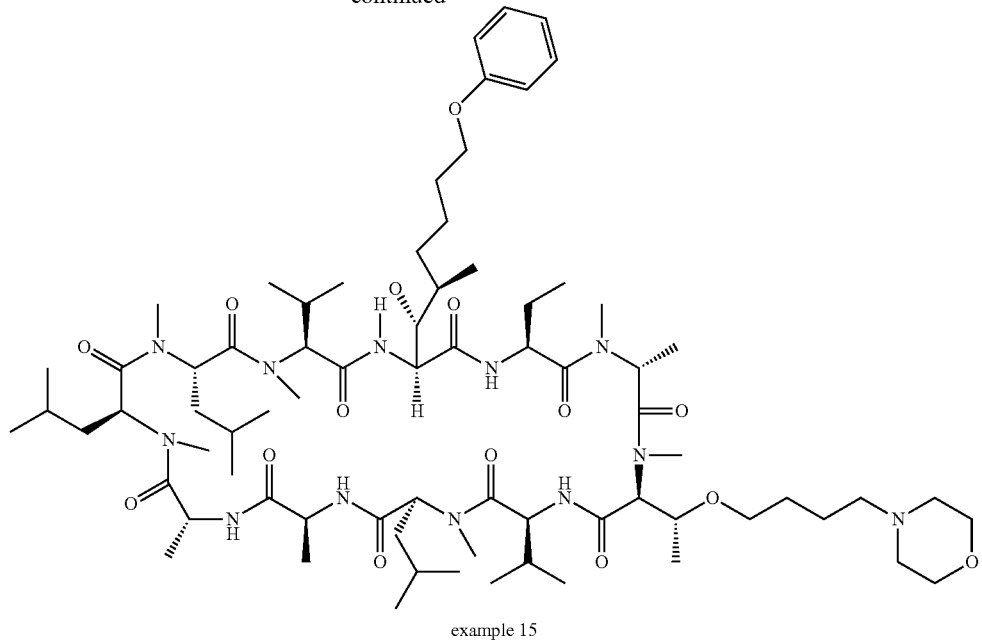

example 15

The compound of example 15 was synthesized from compound 1 and (E)-1,4-diphenoxybut-2-ene using similar procedure described in the synthesis of example 7 and example 8. MS: (ESI) m/z (M+H) 1426.54.

Example 16

Compound of formula IV: A is

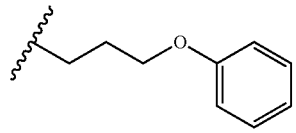 [SMILES: *CCCOc1ccccc1]

The compound of example 16 was synthesized from compound 1 and (E)-1,4-diphenoxybut-2-ene using similar procedure described in the synthesis of example 7 and example 8. MS: (ESI) m/z (M+H) 1440.59.

Example 17

Compound of formula IV: A is

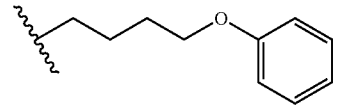 [SMILES: *CCCCOc1ccccc1]

The compound of example 17 was synthesized from compound 1 and (E)-1,4-diphenoxybut-2-ene using similar procedure described in the synthesis of example 7 and example 8. MS: (ESI) m/z (M+H) 1454.50.

Example 18

Compound of formula IV: A is

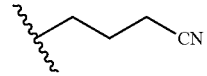

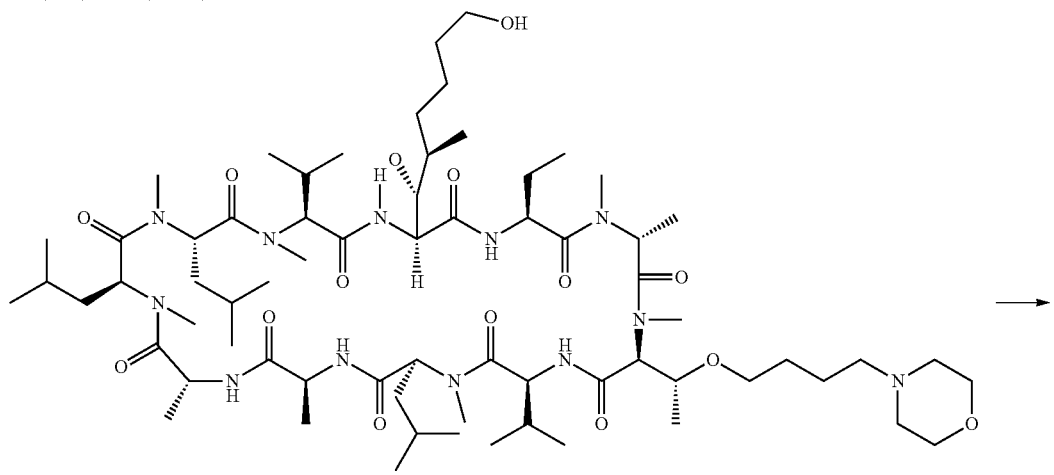

example 40

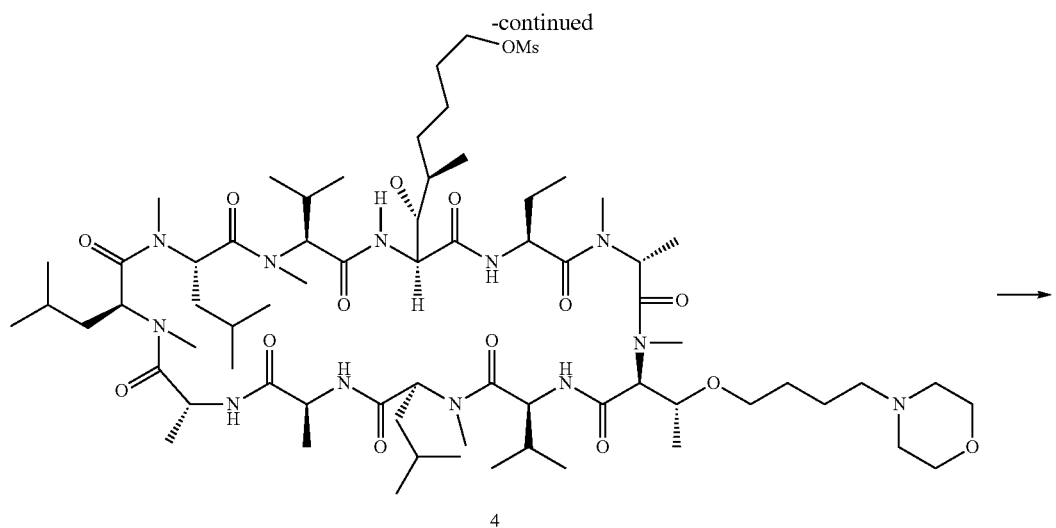

4

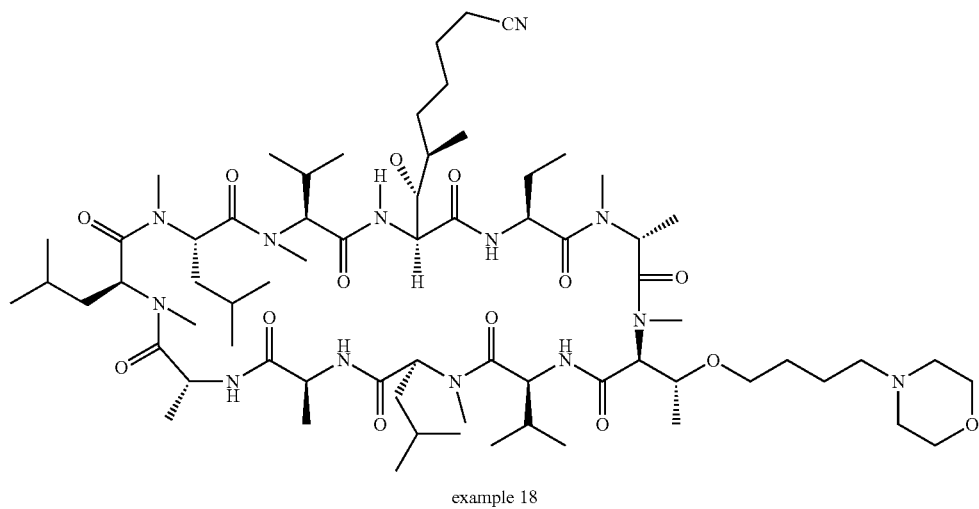

example 18

Step 18a:

To a solution of example 40 (406 mg, 0.2976 mmol) in dry dichloromethane (4 mL) was added triethylamine (0.166 mL, 1.19 mmol) and methanesulfonyl chloride (0.046 mL, 0.60 mmol) at 0° C. and stirred for 50 min. The reaction was diluted with dichloromethane (20 mL), washed with saturated aqueous NaHCO$_3$ solution (5 mL), brine (5 mL), dried over Na$_2$SO$_4$, filtered, evaporated to dryness. The residue was further dried on the vacuum pump to give the intermediate compound 4 as a white foam (442 mg); MS: (ESI) m/z (M+H) 1442.79 (M+Na) 1464.83.

Step 18b:

A mixture of compound 4 (151 mg, 0.1047 mmol) and sodium cyanide (102.6 mg, 2.09 mmol) in dry DMF (0.4 mL) was heated at 60° C. for 2 hrs and 65° C. for 30 min. After cooling to room temperature, the reaction was diluted with ethyl acetate (15 mL), washed with saturated aqueous NaHCO$_3$ sol'n (20 mL), H$_2$O (3×20 mL), brine (20 mL), dried over Na$_2$SO$_4$, filtered, evaporated to dryness. The residue was purified by preparative HPLC [HPLC condition: mobile phase A-20 mM NH$_4$HCO$_3$ in H$_2$O (HPLC grade); mobile phase B-acetonitrile (HPLC grade); Luna column (pre-heated at 55° C.), flow rate: 20 mL/min; 50-95% B for 40 min.] to give the pure title compound of example 18 (119 mg) as a white cotton after lyophilization; MS: (ESI) m/z (M+H) 1389.49, (M+Na) 1411.44.

Example 19

Compound of formula IV: A is

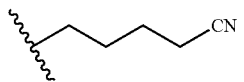 [SMILES: *CCCCC#N]

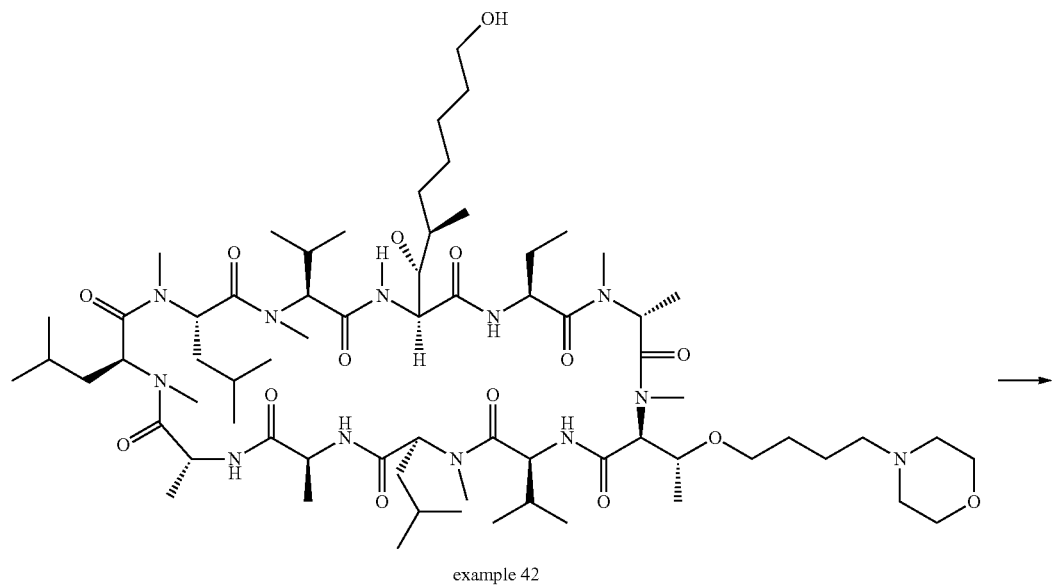
example 42
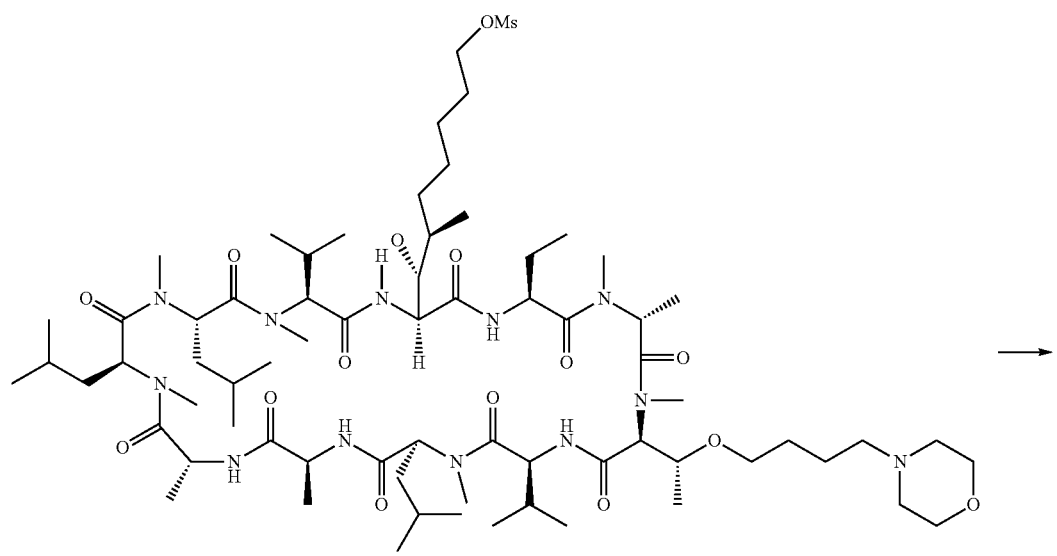
5

-continued

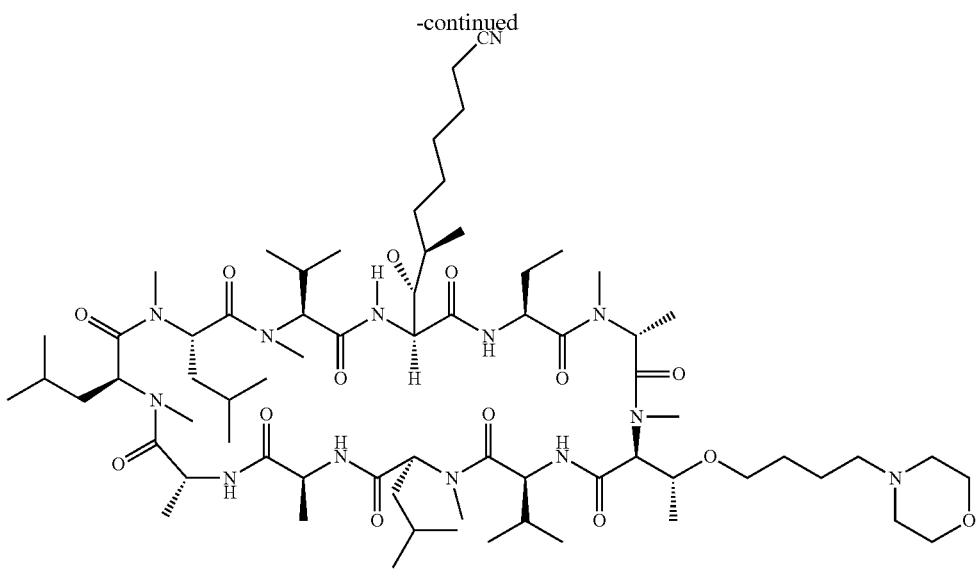

example 19

Step 19a:

A mixture of compound of example 42 (411.7 mg, 0.2988 mmol) and triethylamine (0.17 mL, 1.2 mmol) in dichloromethane (5 mL) was cooled to 0° C., treated with methanesulfonyl chloride (0.046 mL, 0.60 mmol) at 0° C. and stirred for 30 min. The reaction was diluted with dichloromethane (20 mL), washed with saturated aqueous NaHCO$_3$ sol'n (5 mL), brine (5 mL), dried over Na$_2$SO$_4$, filtered, evaporated to dryness. The residue was further dried on the vacuum pump to give the intermediate compound 5 as a white foam (442 mg); MS: (ESI) m/z (M+H) 1456.40, (M+Na) 1478.42.

Step 19b:

The compound of example 19 was prepared from compound 5 using the same procedure described in the synthesis of example 18 step 18b. MS: (ESI) m/z (M+H) 1403.49, (M+Na) 1425.44.

Example 20

Compound of formula IV: A is

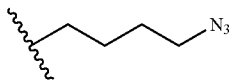 [SMILES: *CCCCN=[N+]=[N-]]

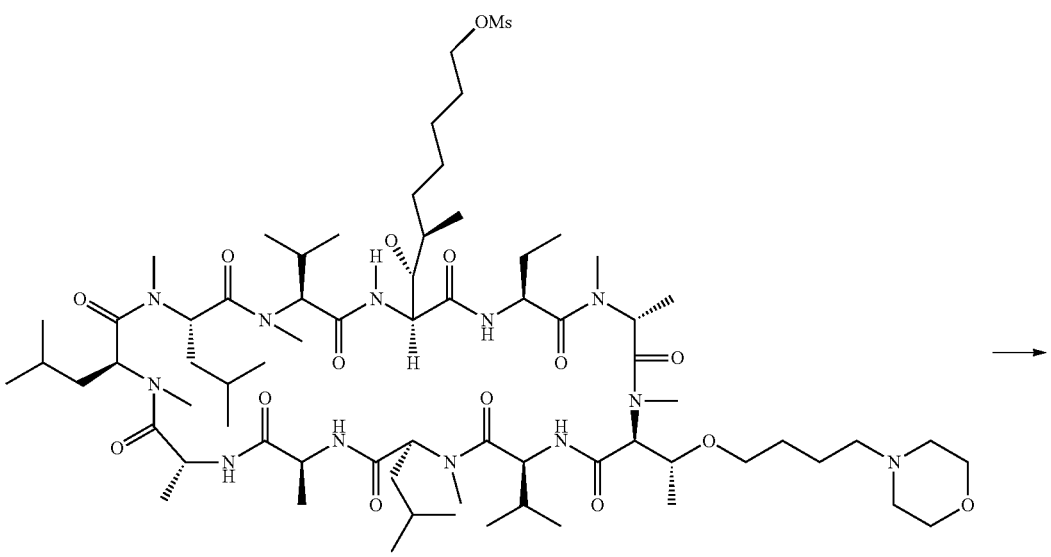

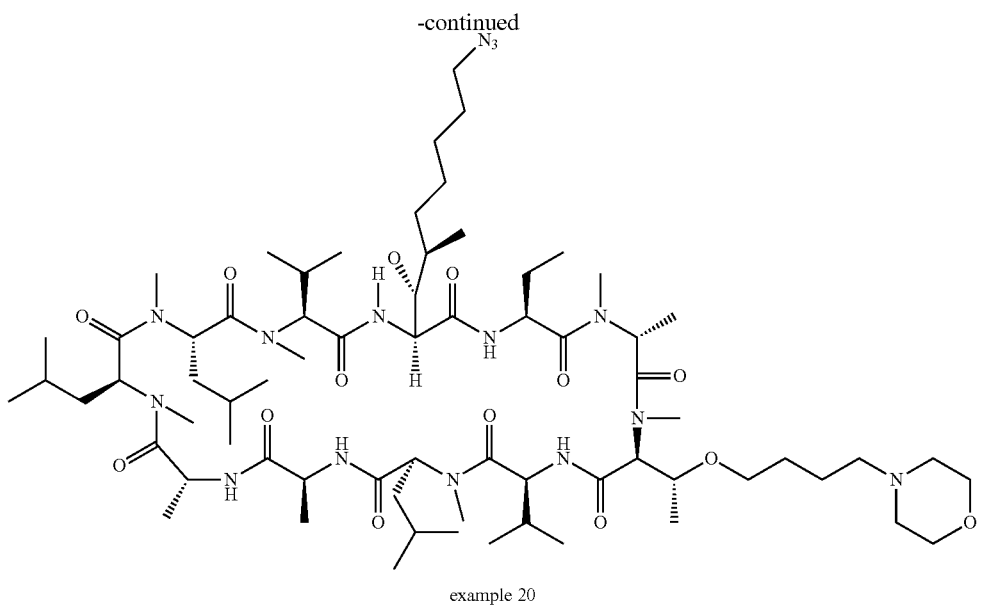
example 20
The compound of example 20 was prepared from compound 5 and sodium azide using the same procedure described in the synthesis of example 18 (step 18b). MS: (ESI) m/z (M+H) 1402.85, (M+Na) 1424.86.
Example 21
Compound of formula IV: A is
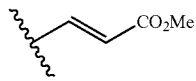
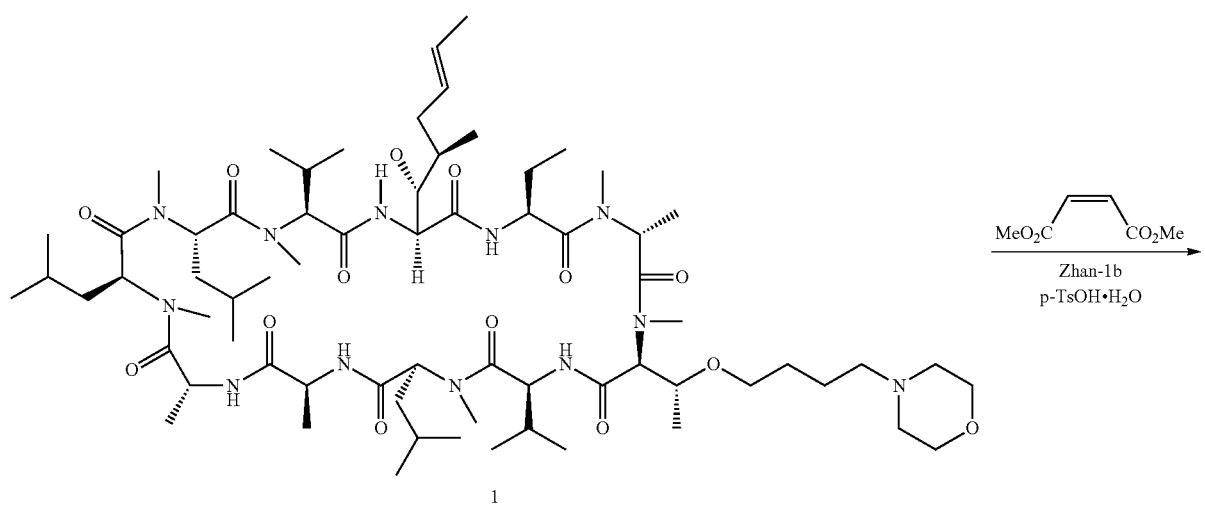

-continued

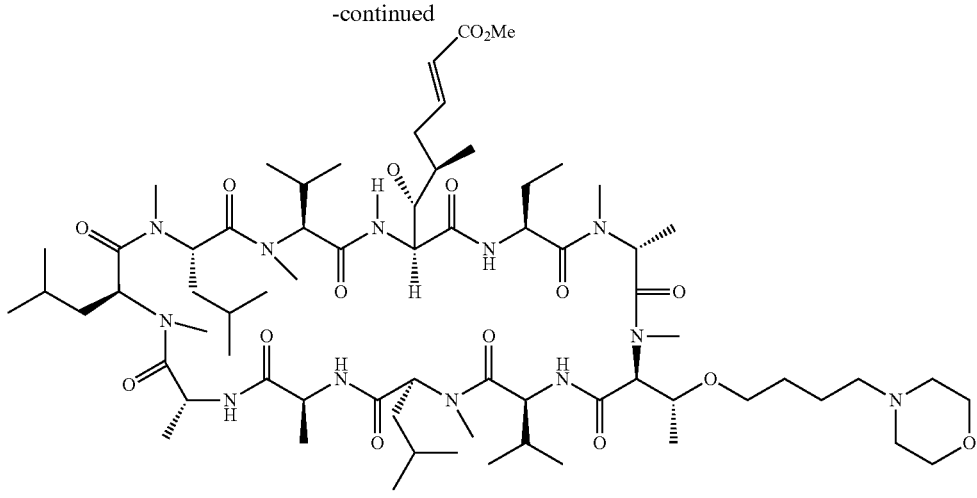

example 21

A mixture of compound 1 (2.0 g, 1.487 mmol) and p-toluenesulfonic acid monohydrate (283 mg, 1.487 mmol) in dry toluene (7 mL) was heated at 60° C. for 30 min. After cooling to <−40° C. (dry-ice/acetone bath) and degassing, dimethyl malonate (2.8 mL, 22.31 mmol) and Zhan-1B catalyst (109 mg, 0.1487 mmol) were added to the reaction, which was degassed and filled with nitrogen. The reaction was heated at 60° C. for 3 h. Then, triethylamine (0.062 mL, 0.446 mmol), 2-mercaptonicotinic acid (47 mg, 0.297 mmol) and were added to the reaction and heated at 60° C. for 30 min. After cooling, the reaction mixture was diluted with ethyl acetate (150 mL), washed with saturated aqueous NaHCO3 solution (2×50 mL), brine (10 mL), dried over Na$_2$SO$_4$, filtered and evaporated to dryness. The residue was purified by silica gel column chromatography with 0~100% acetone in hexane to afford the compound of example 21 (1.98 g) as a white foam; MS: (ESI) m/z (M+H) 1390.05.

Example 22

Compound of formula IV: A is

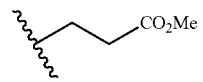

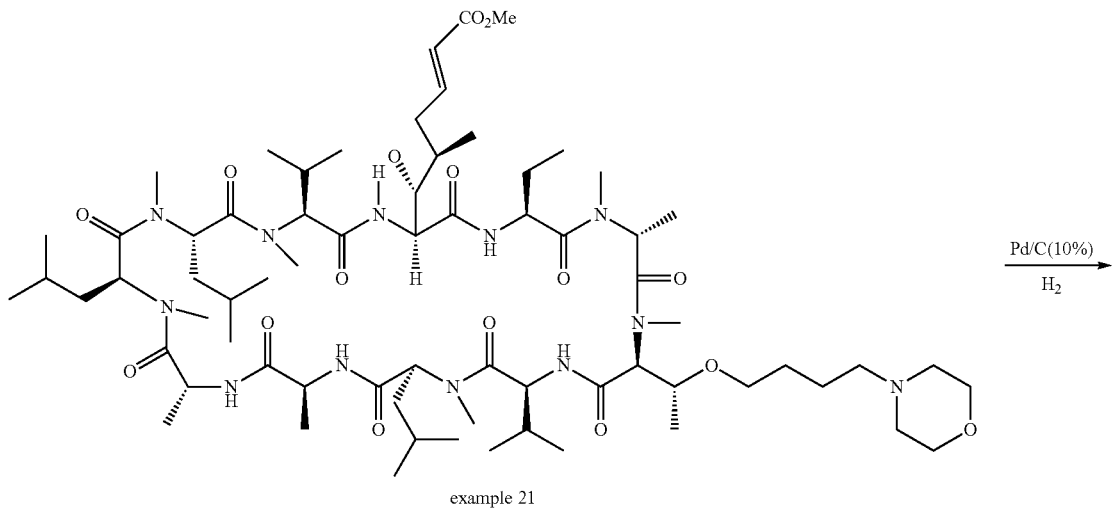

example 21

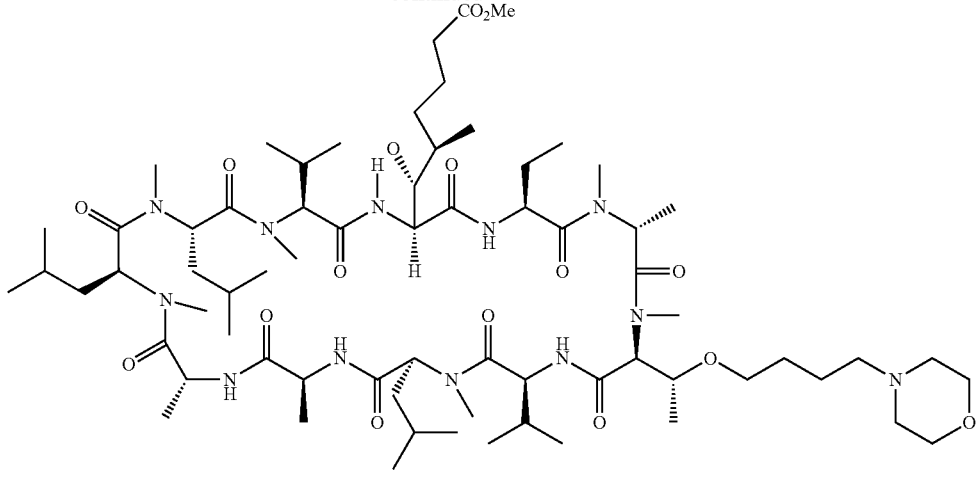

example 22

The compound of example 21 (1.39 g, 1.0 mmol) and 10% Pd/C (0.3 g) in ethyl acetate (32 mL) was degassed with $H_2$ for 15 min and then stirred at room temperature overnight under balloon pressure of $H_2$. The reaction mixture was filtrated through a Celite pad and washed with ethyl acetate (30 mL×2). The crude mixture was treated with activated charcoal (80 mg, 5% w/w) by stirring in ethyl acetate at 40° C. for 1 h for decolorizing. The filtrate was collected and the solvent was evaporated to afford crude product as white solid form. The crude product was purified by silica gel column chromatography with 0~100% Acetone in Hexane to afford the compound of example 22 (1.29 g) as a white foam; MS: (ESI) m/z (M+H) 1392.07.

Example 23

Compound of formula IV: A is

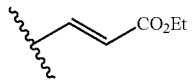

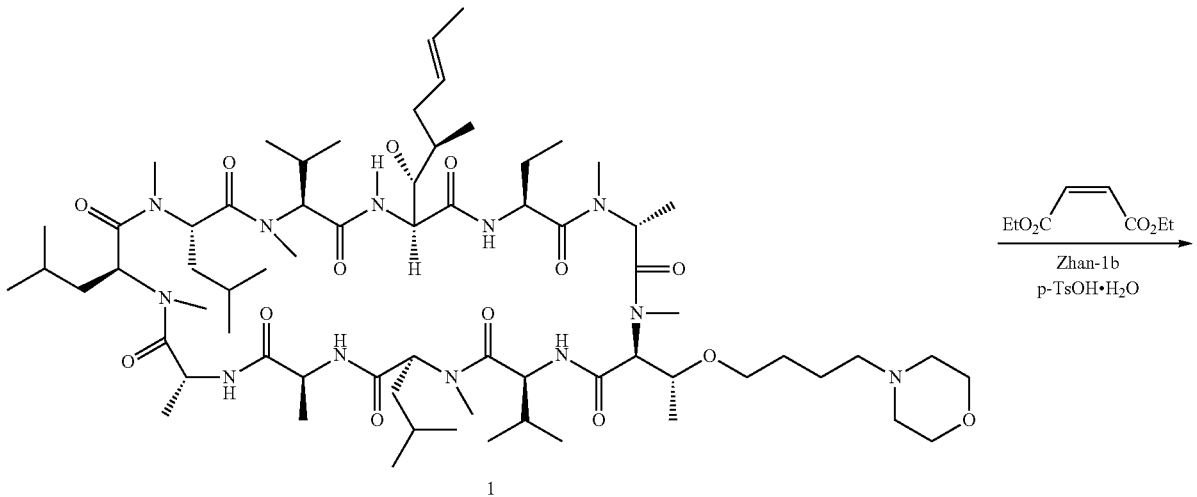

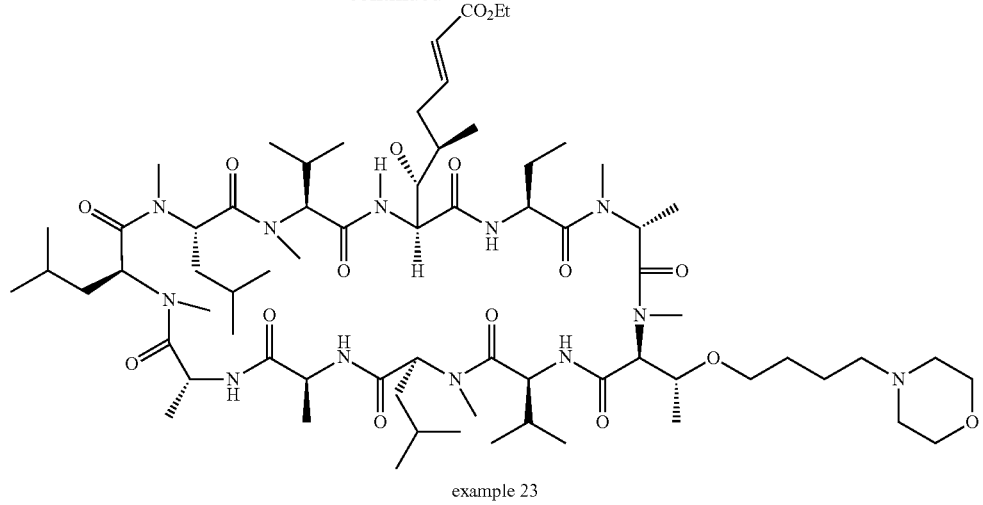
example 23
The compound of example 23 was synthesized from compound 1 and diethyl malonate using similar procedure described in the synthesis of example 21. MS: (ESI) m/z (M+H) 1404.01.
Example 24
Compound of formula IV: A is
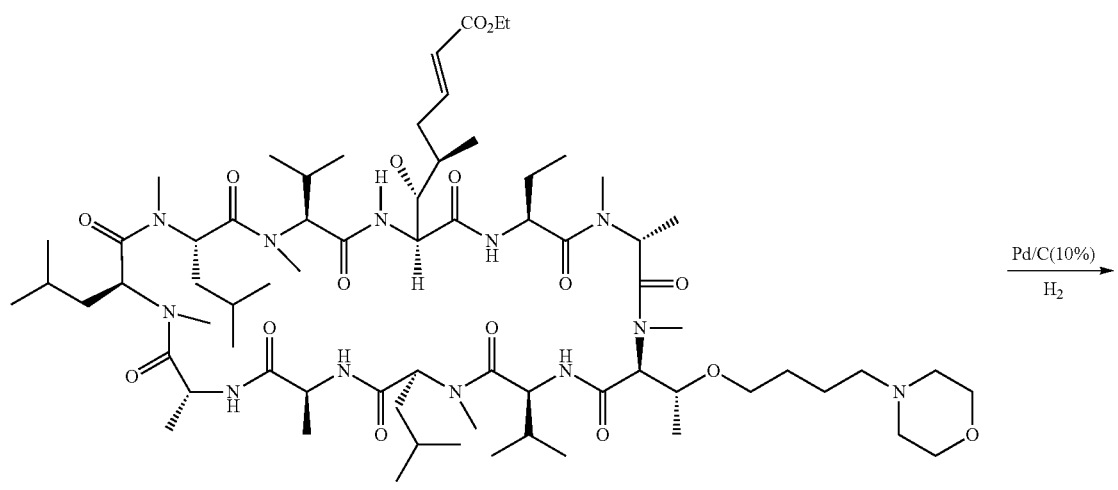
example 23

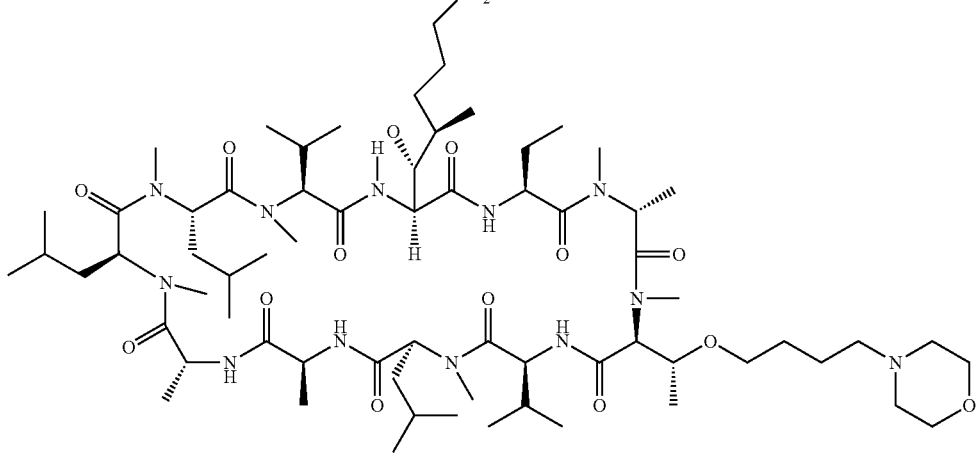
example 24
The compound of example 24 was synthesized from compound of example 23 using similar procedure described in the synthesis of example 22. MS: (ESI) m/z (M+H) 1406.09.
Example 25
Compound of formula IV: A is
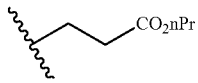
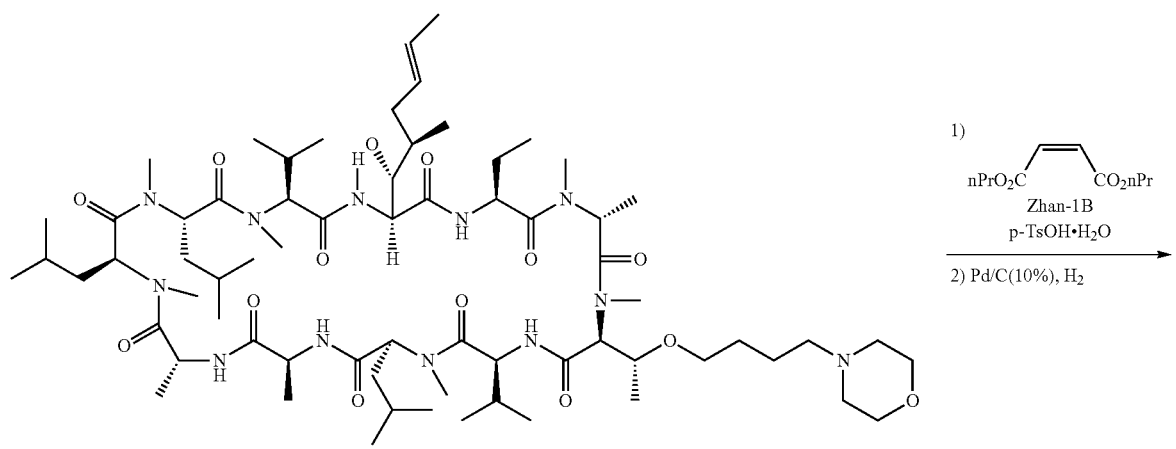

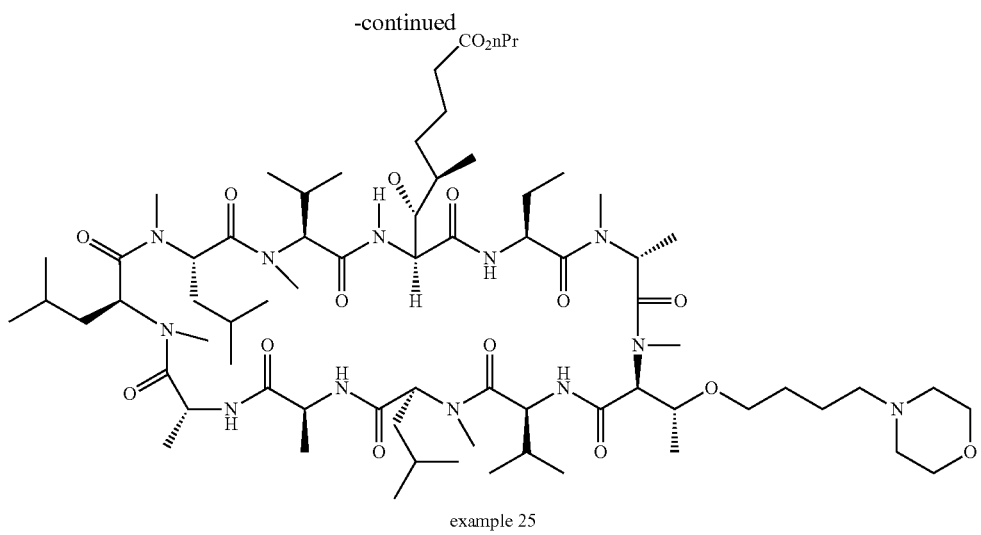
example 25
The compound of example 25 was synthesized from compound 1 and di-n-propyl malonate using similar procedure described in the synthesis of example 21 and example 22. MS: (ESI) m/z (M+H) 1420.19.
Example 26
Compound of formula IV: A is
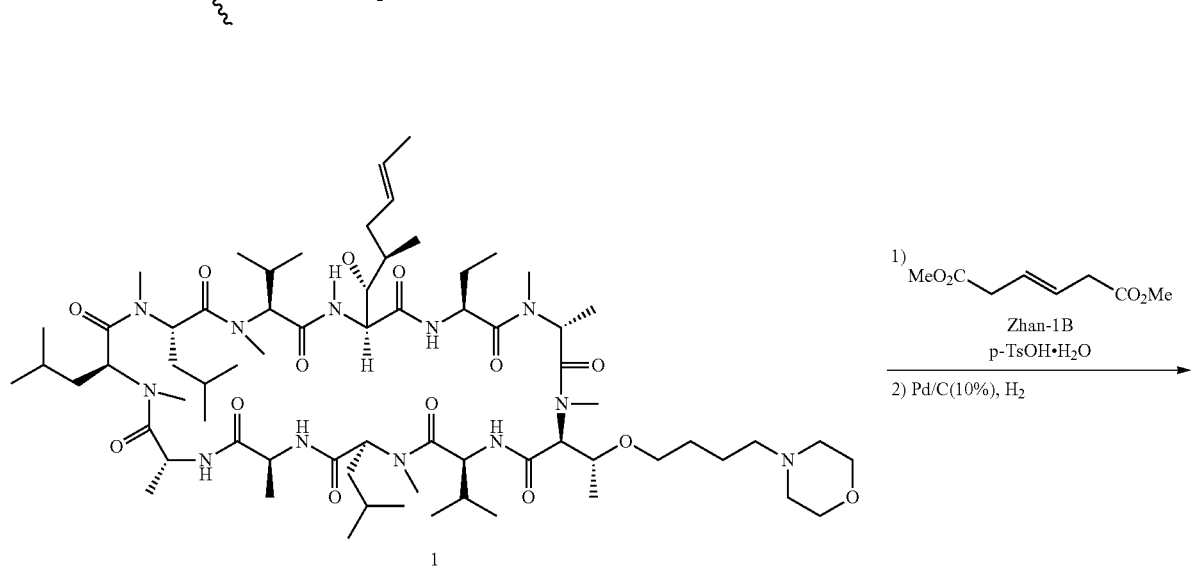

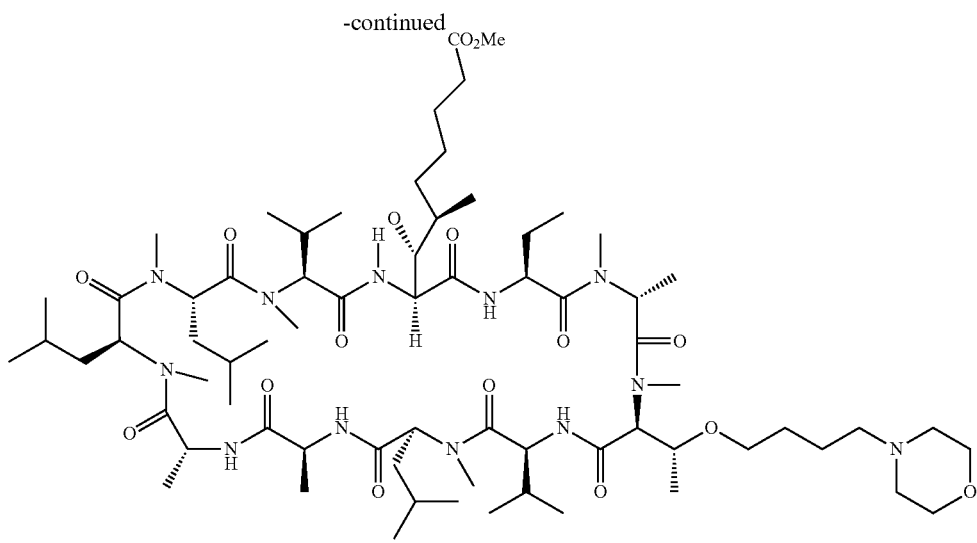
example 26
The compound of example 26 was synthesized from compound 1 and (E)-dimethyl hex-3-enedioate using similar procedure described in the synthesis of example 21 and example 22. MS: (ESI) m/z (M+H) 1406.06.
Example 27
Compound of formula IV: A is
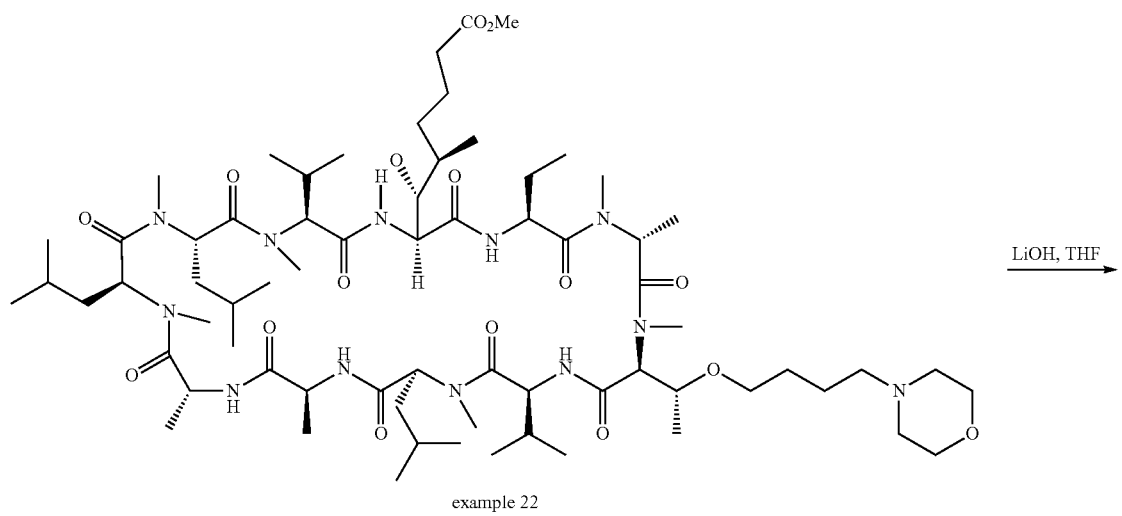
example 22

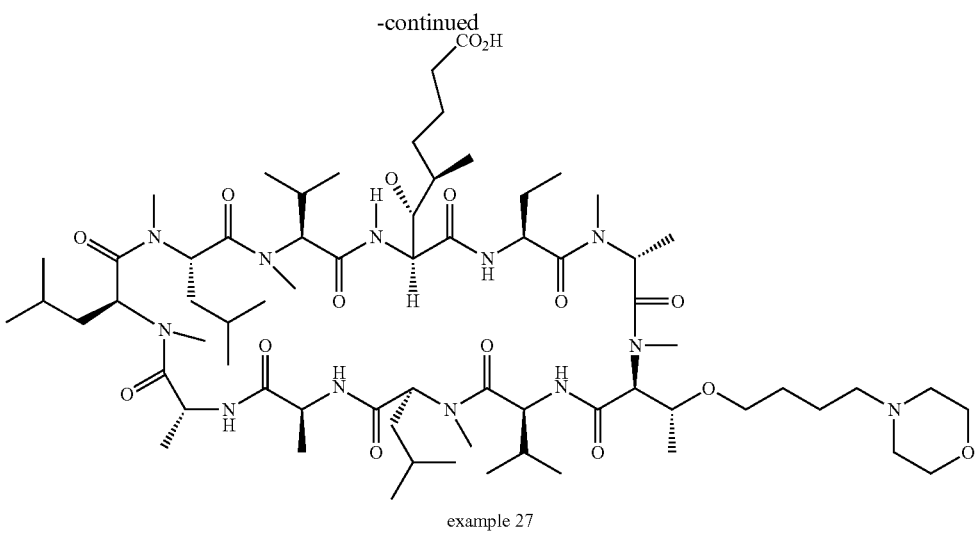

example 27

To a solution of the compound of example 22 (1.4 g, 1 mmol) in THF (20 ml) was added 1 N LiOH (1.1 ml) at 0° C. and the mixture was stirred at room temperature for 3 hrs. The reaction was quenched with 10% HOAc to PH=7 at 0° C. and extracted with ethyl acetate, washed with brine and dried over anhydrous $Na_2SO_4$. The solvent was evaporated and the residue was purified by by silica gel column chromatography to afford the compound of example 27 (1.2 g) as a white foam; MS: (ESI) m/z (M+H) 1377.98.

Example 28

Compound of formula IV: A is

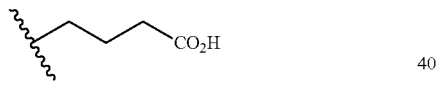

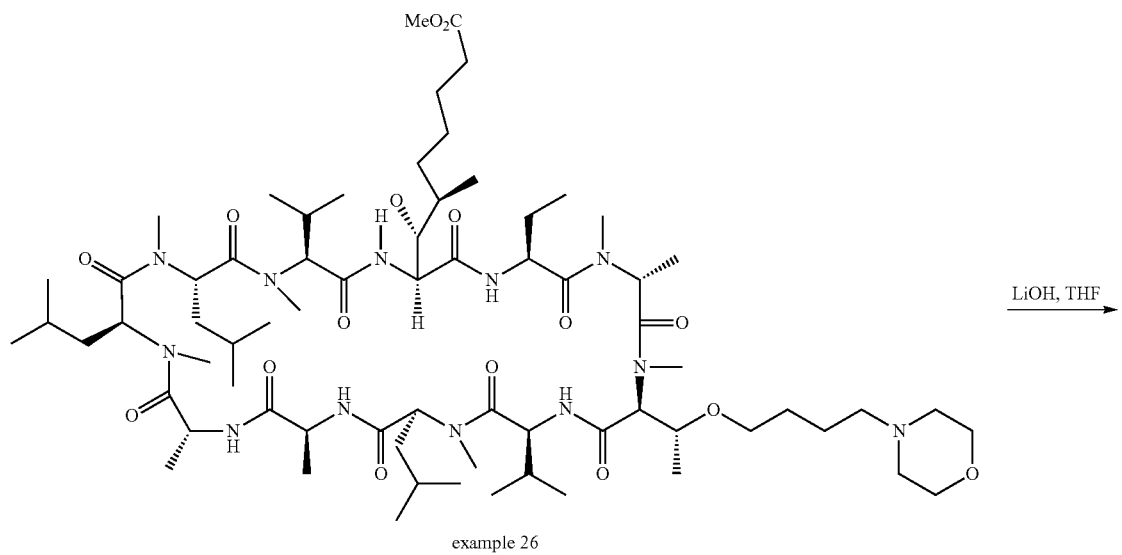

example 26

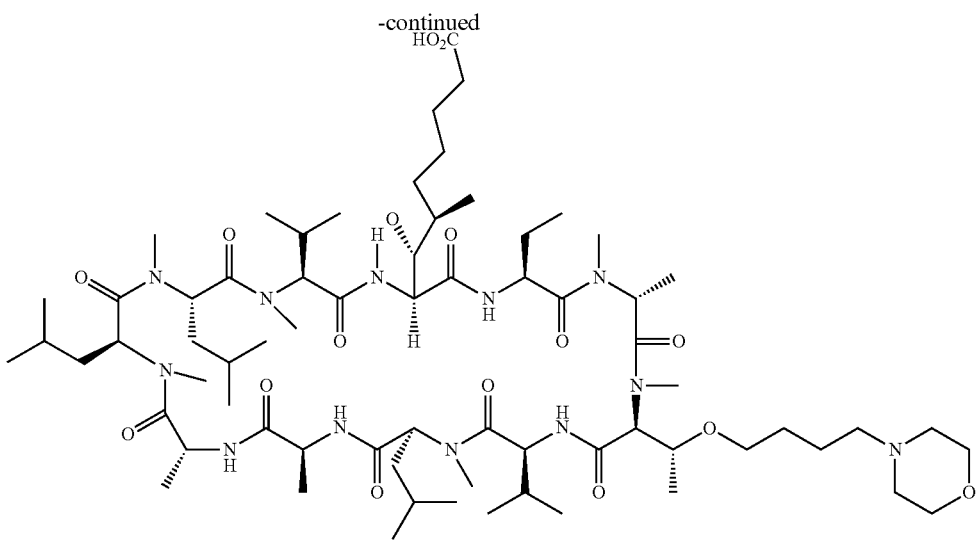
example 28
The compound of example 28 was synthesized from compound of example 26 using similar procedure described in the synthesis of example 27. MS: (ESI) m/z (M+H) 1392.09.
Example 29
Compound of formula IV: A is
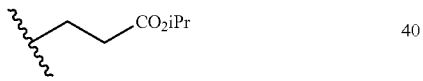
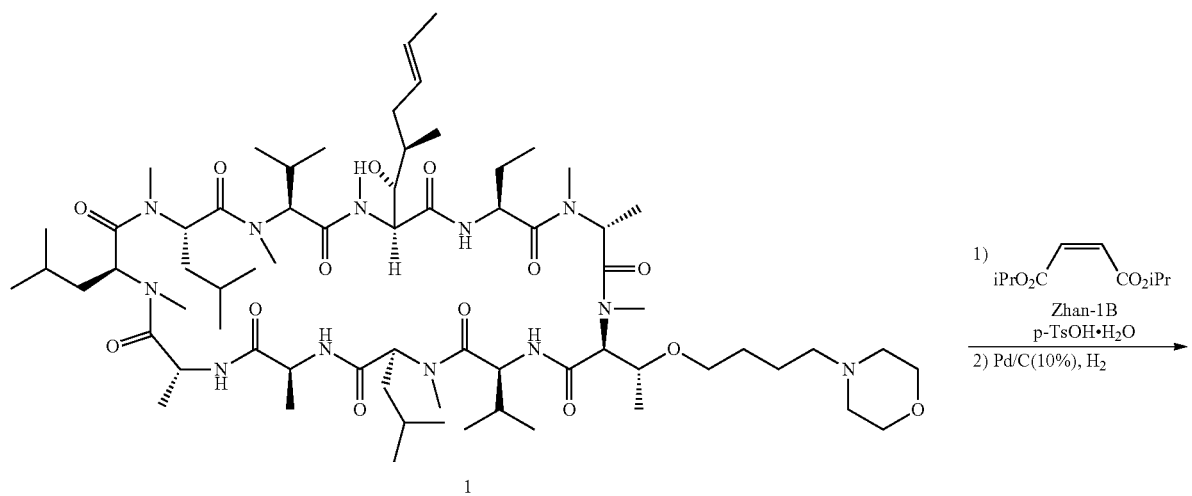

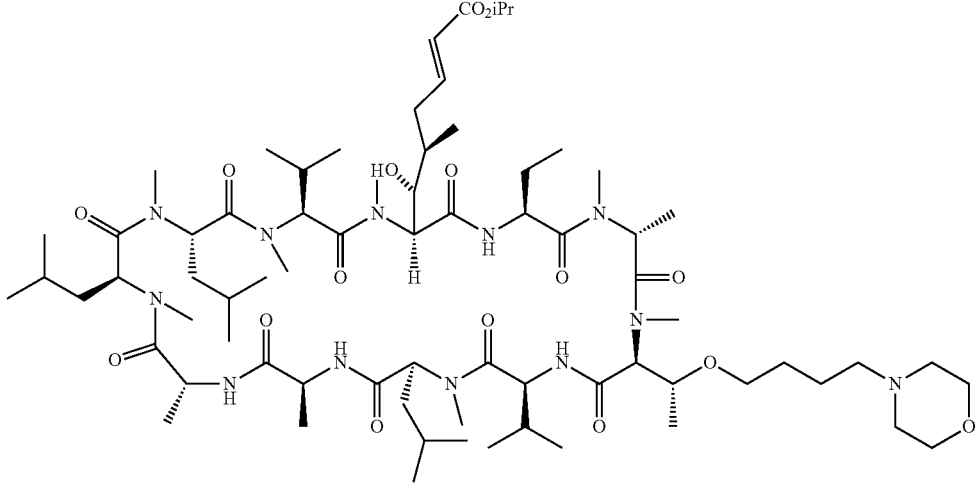
example 29
The compound of example 29 was synthesized from compound 1 and di-isopropyl malonate using similar procedure described in the synthesis of example 21 and example 22. MS: (ESI) m/z (M+H) 1420.09.
Example 30
Compound of formula IV: A is
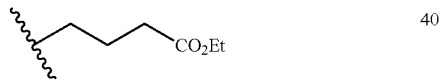
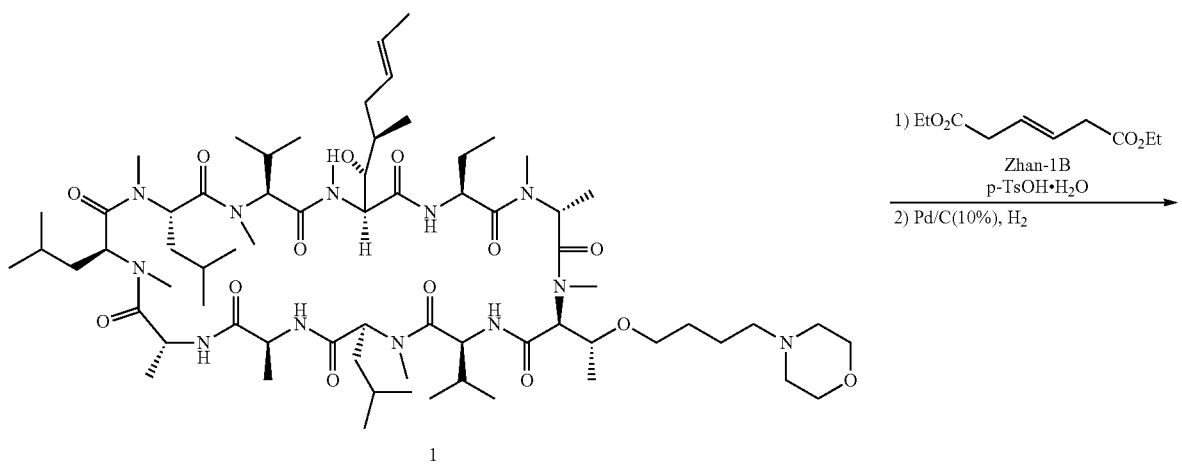

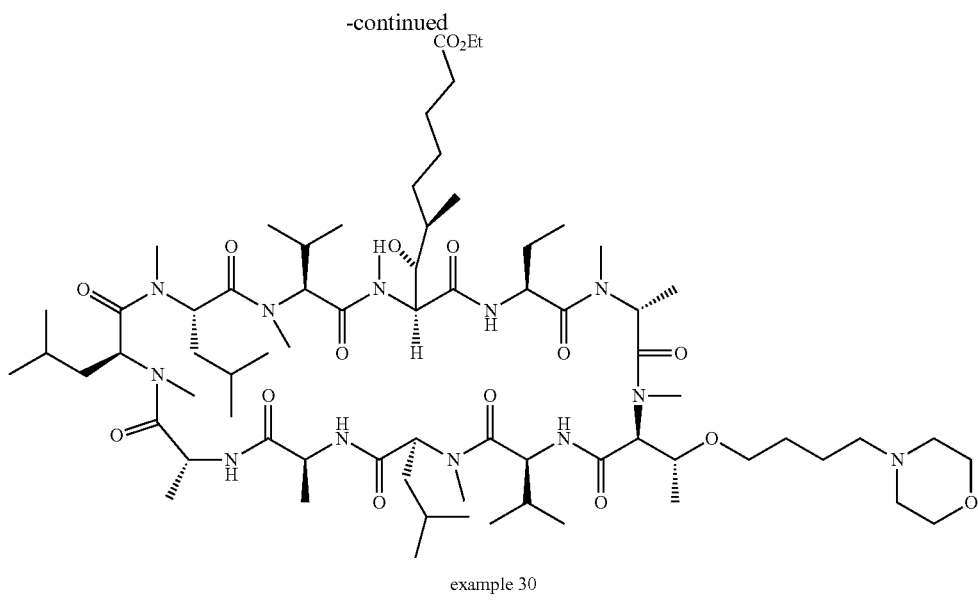
example 30
The compound of example 30 was synthesized from compound 1 and (E)-diethyl hex-3-enedioate using similar procedure described in the synthesis of example 21 and example 22. MS: (ESI) m/z (M+H) 1420.06.
Example 31
Compound of formula IV: A is
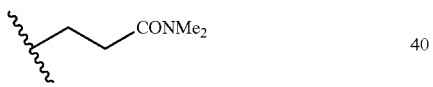
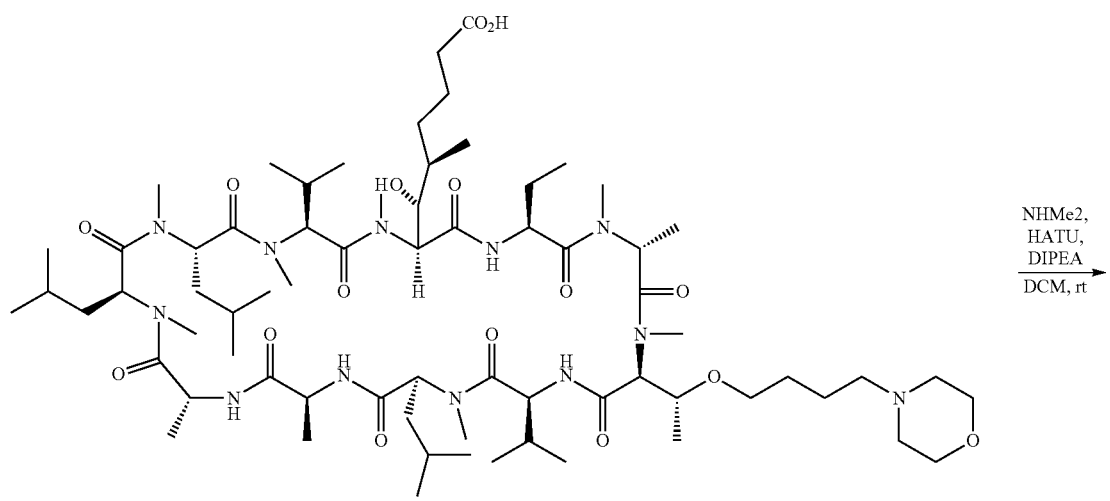
example 27

-continued

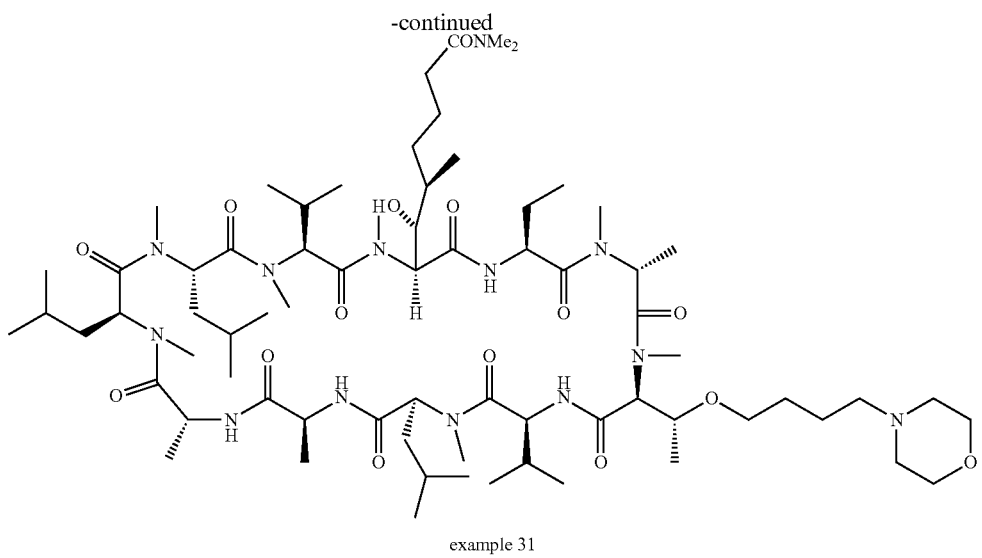

example 31

To a mixture of example 27 (60 mg, 0.0435 mmol) in DCM (1 mL) were added HATU (20 mg, 0.0522), DIPEA (0.013 mL, 0.0871 mmol) and Dimethylamine (2M solution in THF, 0.044 mL, 0.871 mmol). The reaction mixture was stirred at rt for 2 h. The solvent was evaporated and added ethyl acetate (10 mL0 and washed with saturated aqueous NaHCO$_3$ solution (5 mL), brine (5 mL), dried over anhydrous Na$_2$SO$_4$, filtered and evaporated to dryness. The residue was purified by silica gel column chromatography with 0~100% Acetone in Hexane to afford the compound of example 31 as white powder (31 mg). MS: (ESI) m/z, (M+Na) 1405.52.

Example 32

Compound of formula IV: A is

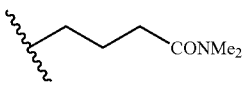

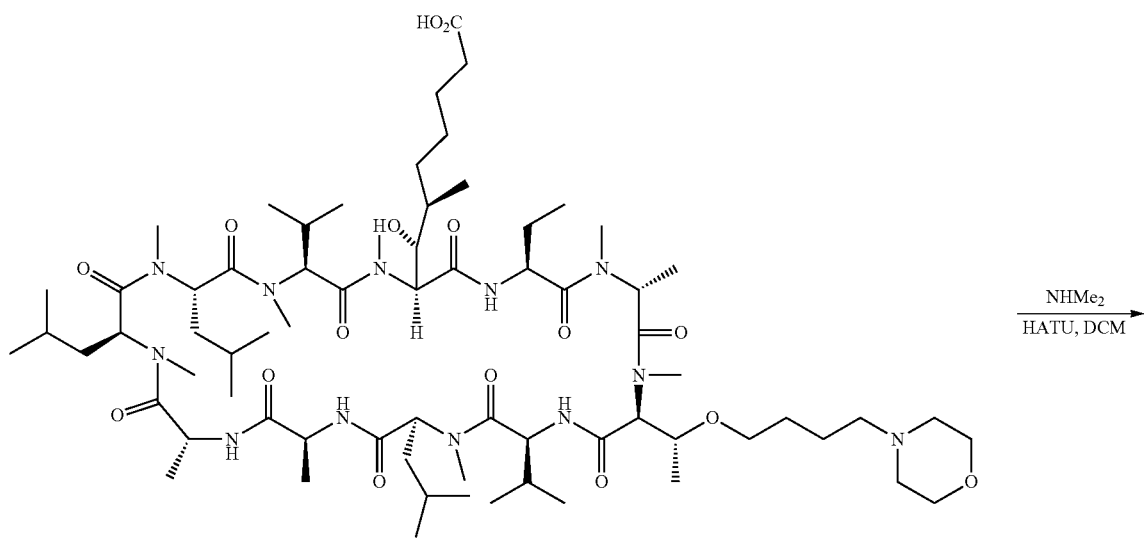

example 28

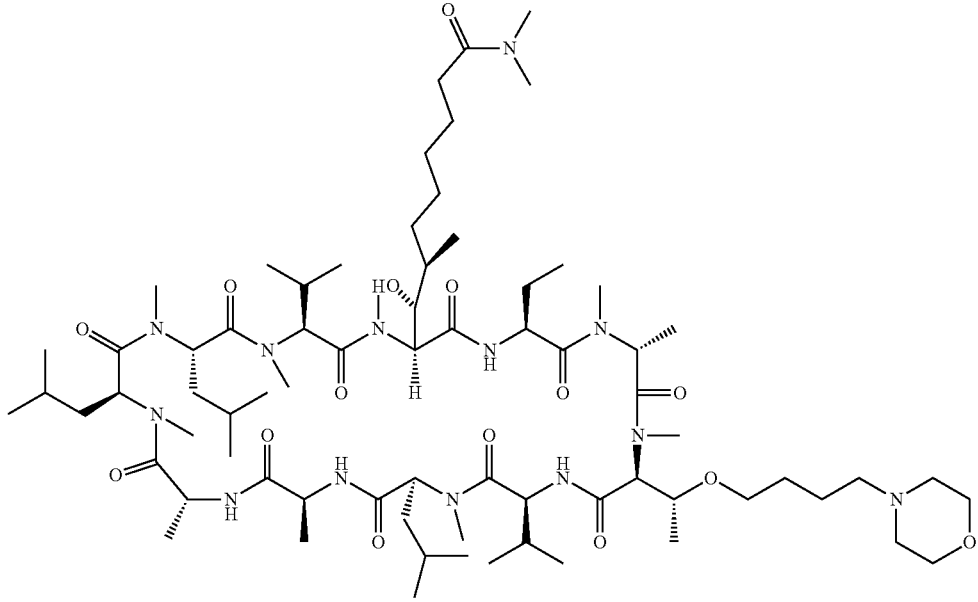
example 32
The compound of example 32 was synthesized from compound of example 28 using similar procedure described in the synthesis of example 31. MS: (ESI) m/z (M+H) 1433.09.
Example 33
Compound of formula IV: A is
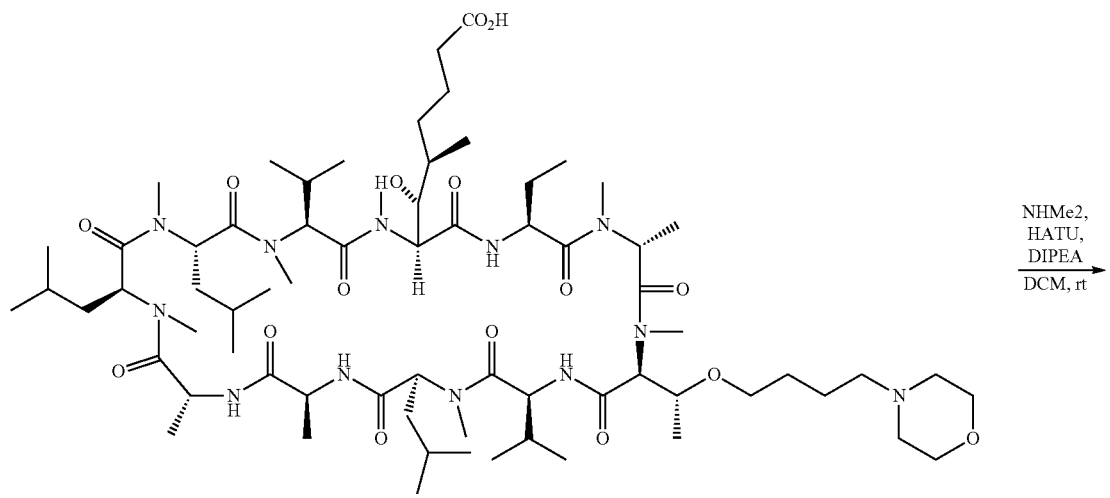
example 27

-continued
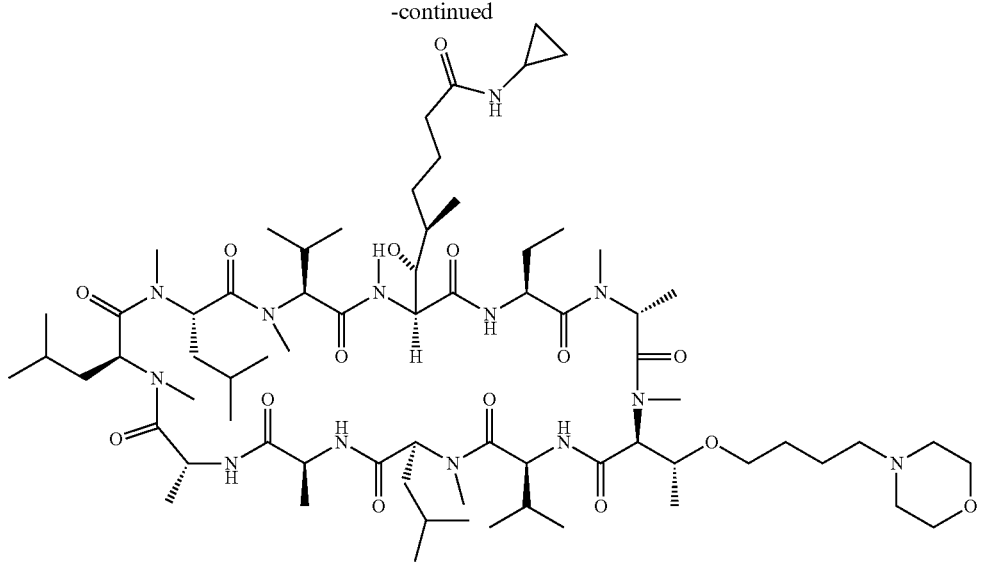
example 33
The compound of example 33 was synthesized from compound of example 27 using similar procedure described in the synthesis of example 31. MS: (ESI) m/z (M+H) 1417.06.
Example 34
Compound of formula IV: A is
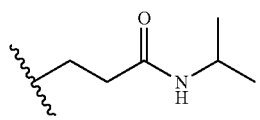 [SMILES: *CCC(=O)NC(C)C]
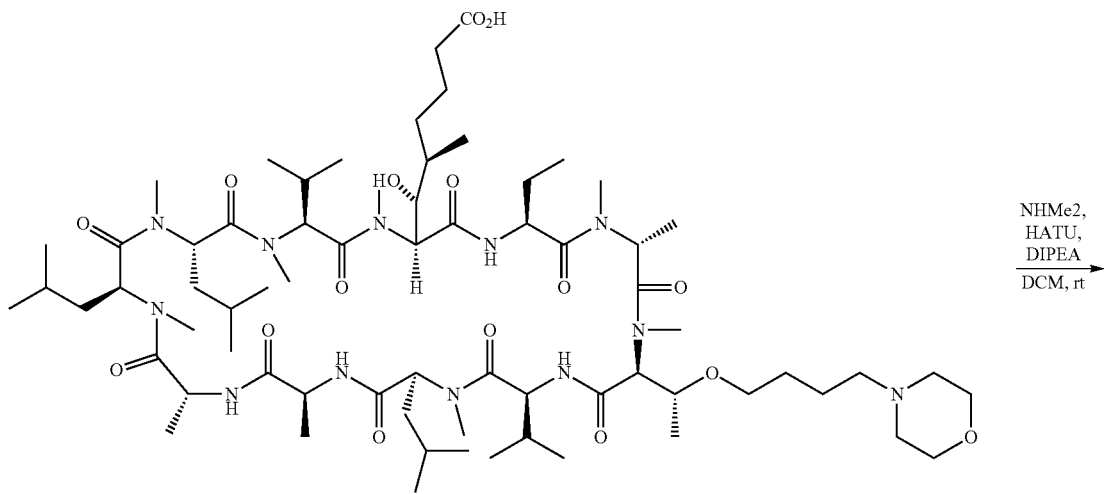
example 27

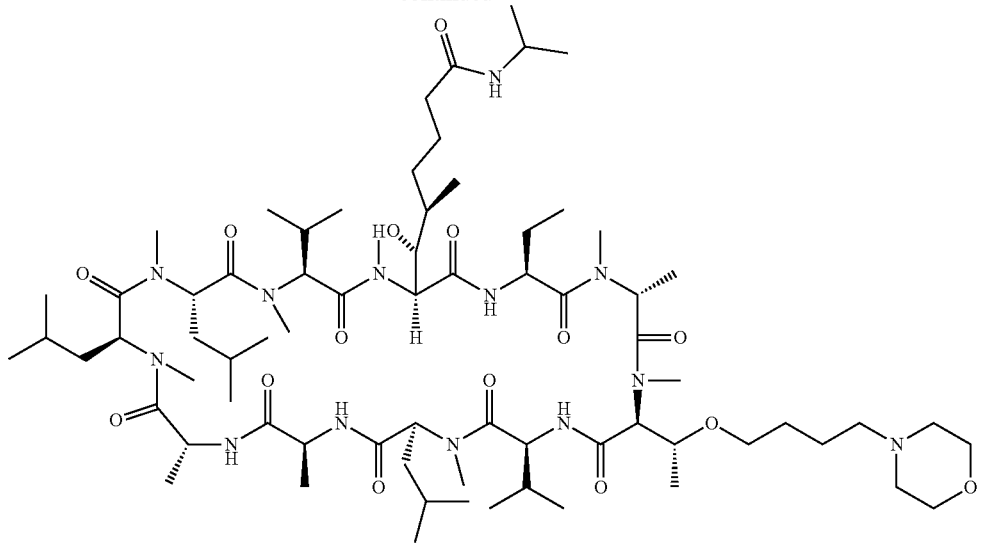
example 34
The compound of example 34 was synthesized from compound of example 27 using similar procedure described in the synthesis of example 31. MS: (ESI) m/z (M+H) 1419.06.
Example 35
Compound of formula IV: A is
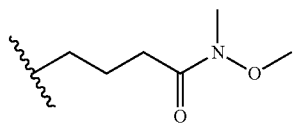 [SMILES: *CCCC(=O)N(C)OC]
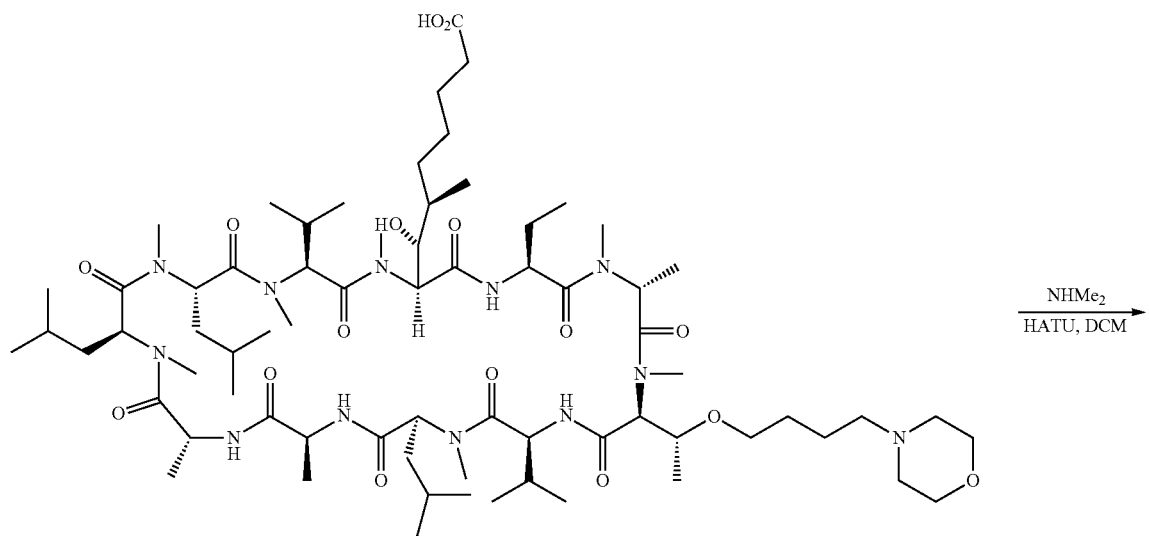
example 28

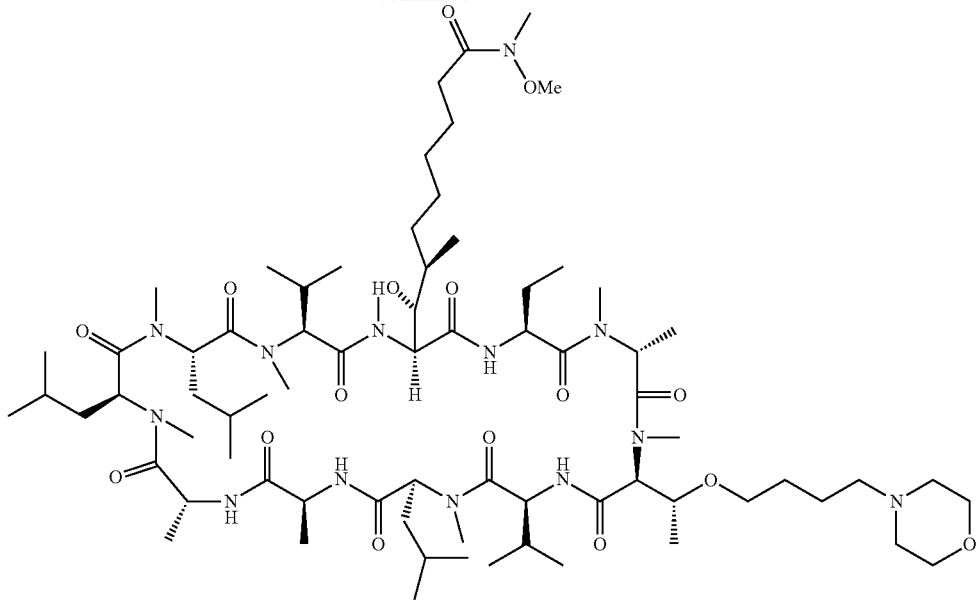
example 35
The compound of example 35 was synthesized from compound of example 28 using similar procedure described in the synthesis of example 31. MS: (ESI) m/z (M+H) 1449.09.
Example 36
Compound of formula IV: A is
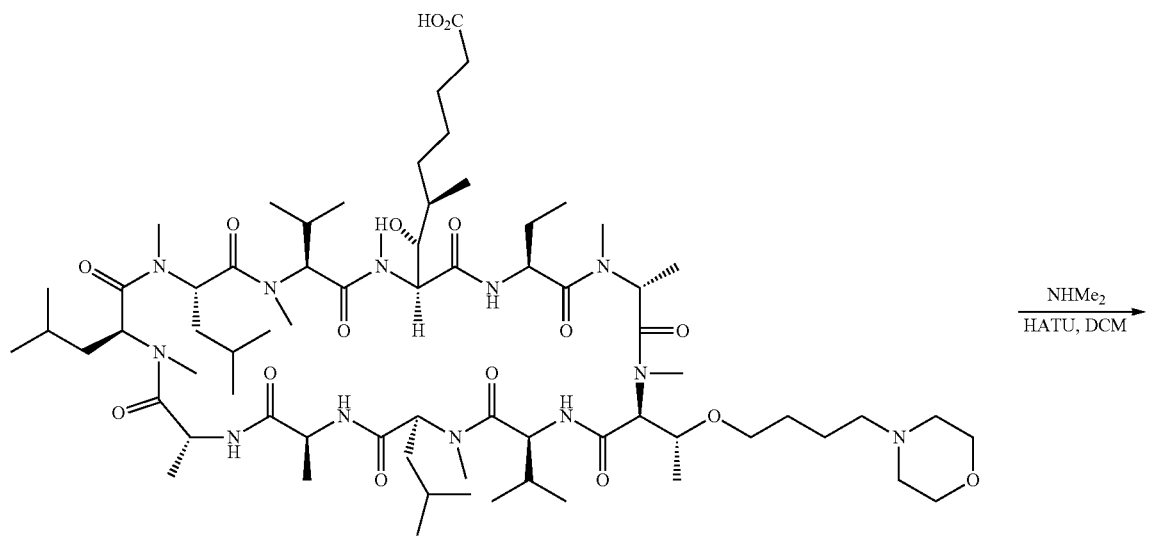
example 28

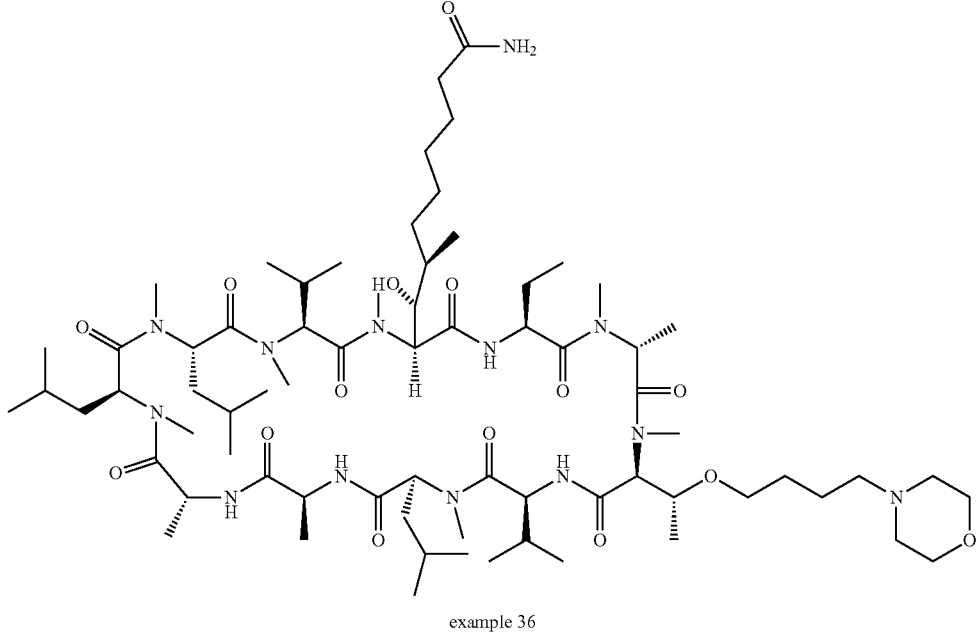
example 36
The compound of example 36 was synthesized from compound of example 28 using similar procedure described in the synthesis of example 31. MS: (ESI) m/z (M+H) 1405.06.
Example 37
Compound of formula IV: A is
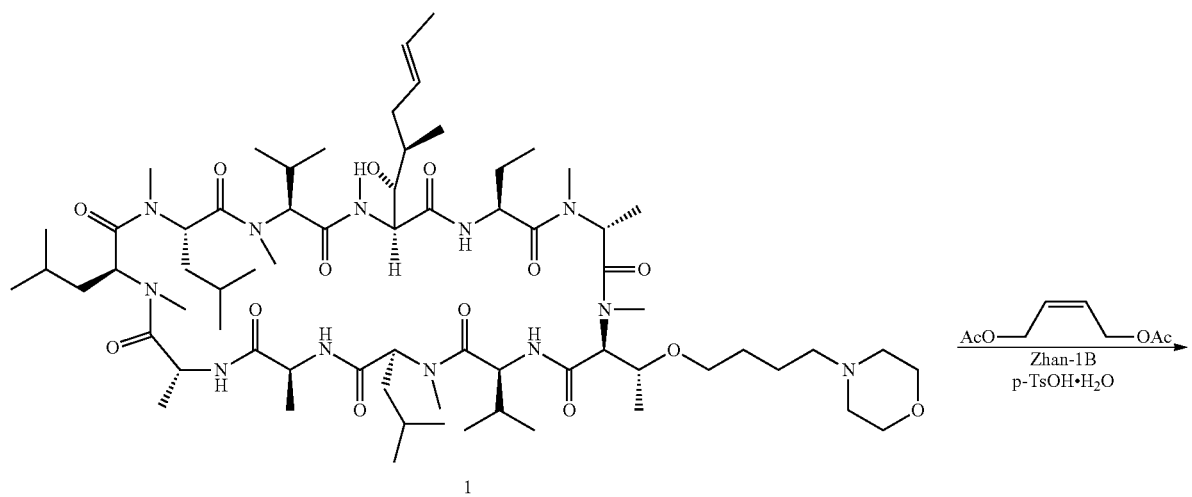

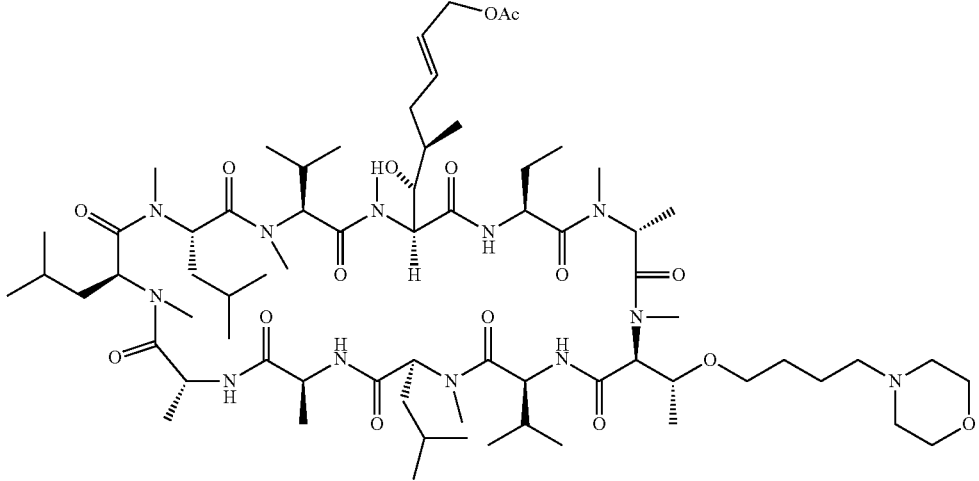

example 37

A mixture of compound (1) (1.03 g, 0.7658 mmol) and p-toluenesulfonic acid monohydrate (145.7 mg, 0.7658 mmol) in dry toluene (7.7 mL) was heated at 60° C. for 20 min. After cooling to −40° C. and degassing, cis-1,4-diacetoxy-2-butene (1.83 mL, 11.487 mmol) and Zhan-1B catalyst (225 mg, 0.3063 mmol) were added to the reaction, which was degassed and filled with nitrogen. The reaction was heated at 60° C. for 3.5 hrs. Then, 2-mercaptonicotinic acid (238 mg, 1.53 mmol) and N,N'-diisopropylethylamine (0.32 mL, 1.84 mmol) were added to the reaction and heated at 60° C. for 30 min. After cooling, the reaction mixture was diluted with ethyl acetate (50 mL), washed with saturated aqueous NaHCO$_3$ sol'n (2×10 mL), brine (10 mL), dried over Na$_2$SO$_4$, filtered and evaporated to dryness. The residue was purified by silica gel column chromatography with 0~7% methanol in dichloromethane to give crude (978 mg) as a white foam with E/Z ratio=2:1. HPLC purification to give compound of example 37 (510 mg); MS: (ESI) m/z (M+H) 1403.87, (M+Na) 1425.92.

Example 38

Compound of formula IV: A is

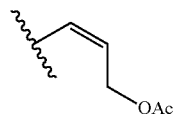

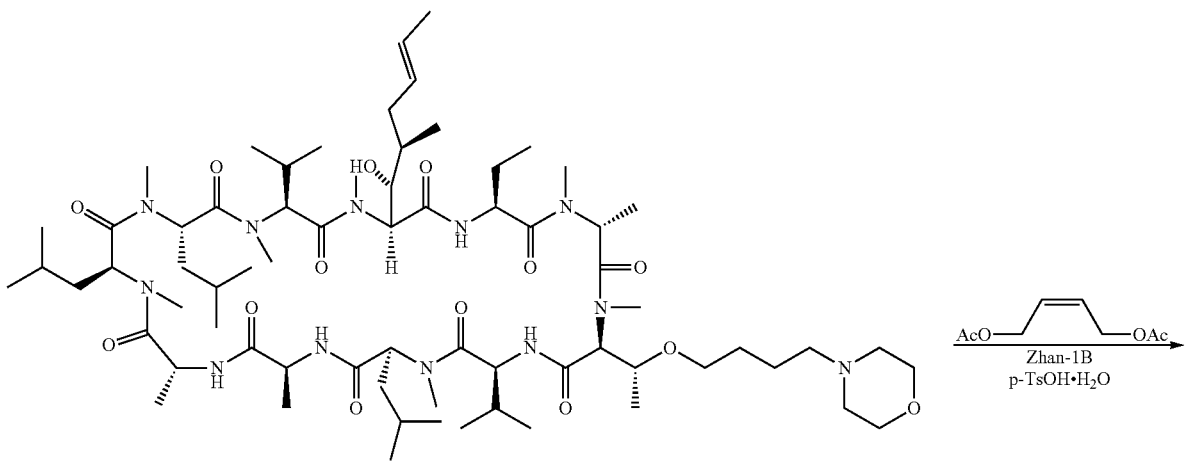

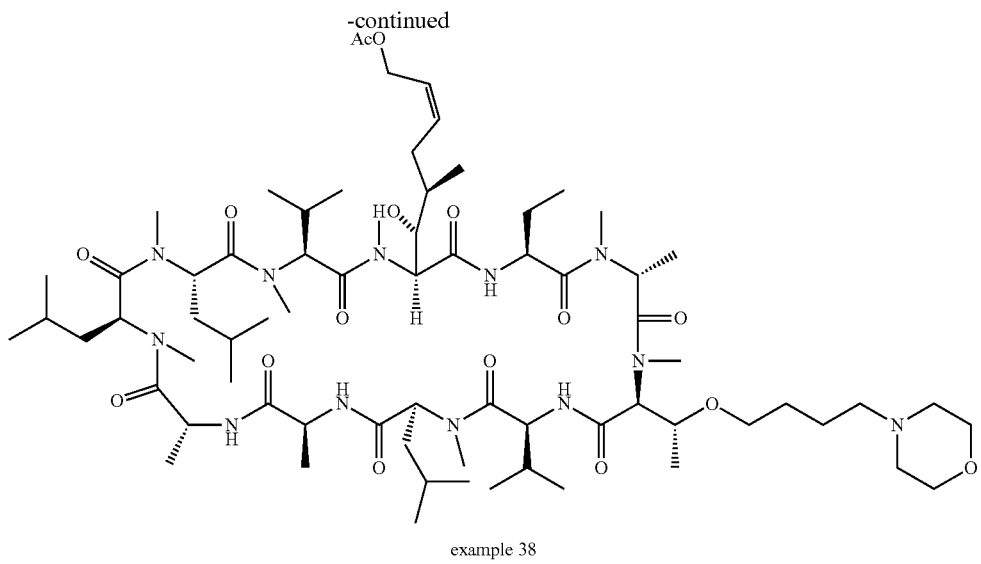

example 38

A mixture of compound (1) (1.03 g, 0.7658 mmol) and p-toluenesulfonic acid monohydrate (145.7 mg, 0.7658 mmol) in dry toluene (7.7 mL) was heated at 60° C. for 20 min. After cooling to −40° C. and degassing, cis-1,4-diacetoxy-2-butene (1.83 mL, 11.487 mmol) and Zhan-1B catalyst (225 mg, 0.3063 mmol) were added to the reaction, which was degassed and filled with nitrogen. The reaction was heated at 60° C. for 3.5 hrs. Then, 2-mercaptonicotinic acid (238 mg, 1.53 mmol) and N,N'-diisopropylethylamine (0.32 mL, 1.84 mmol) were added to the reaction and heated at 60° C. for 30 min. After cooling, the reaction mixture was diluted with ethyl acetate (50 mL), washed with saturated aqueous NaHCO₃ sol'n (2×10 mL), brine (10 mL), dried over Na₂SO₄, filtered and evaporated to dryness. The residue was purified by silica gel column chromatography with 0~7% methanol in dichloromethane to give crude (978 mg) as a white foam with E/Z ratio=2:1. HPLC purification to give compound of example 38 (280 mg); MS: (ESI) m/z (M+H) 1403.87, (M+Na) 1425.92.

Example 39

Compound of formula IV: A is

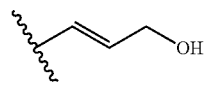 [SMILES: */C=C/CO]

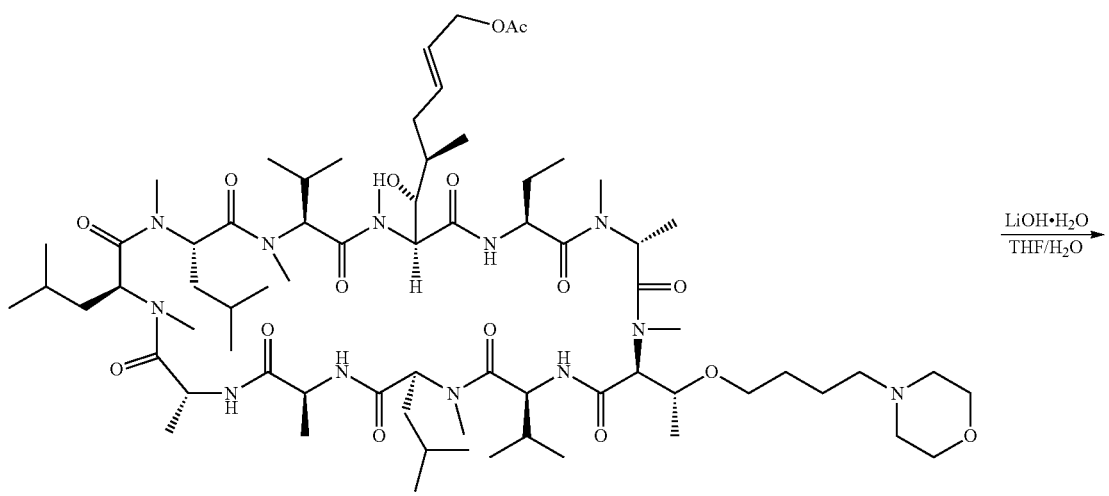

example 37

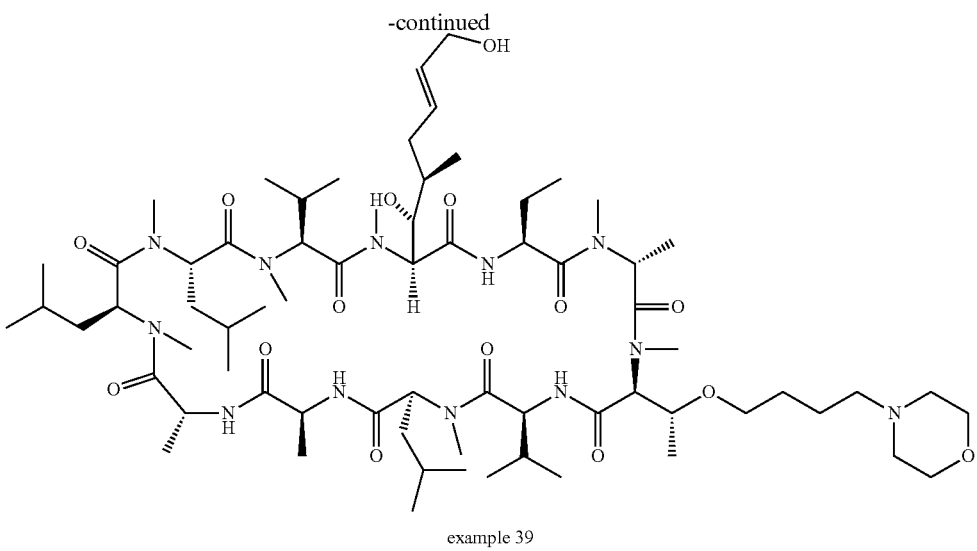

example 39

The compound of example 37 (20 mg, 0.0143 mmol) was treated with LiOH.H$_2$O (8 mg, 0.1716 mmol) in THF (2 mL) and H$_2$O (0.5 mL) at 0° C. for 4 h. The reaction was quenched with 10% HOAc to PH=7 at 0° C. The reaction was extracted with ethyl acetate, washed with brine and dried over anhydrous Na$_2$SO$_4$. The solvent was evaporated and the residue was purified by by silica gel column chromatography with 0~30% Acetone in Hexane to afford the title compound of example 39 (11 mg) as a white foam; MS: (ESI) m/z (M+H) 1361.98.

Example 40

Compound of formula IV: A is

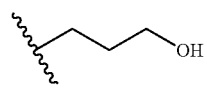 [SMILES: *CCCO]

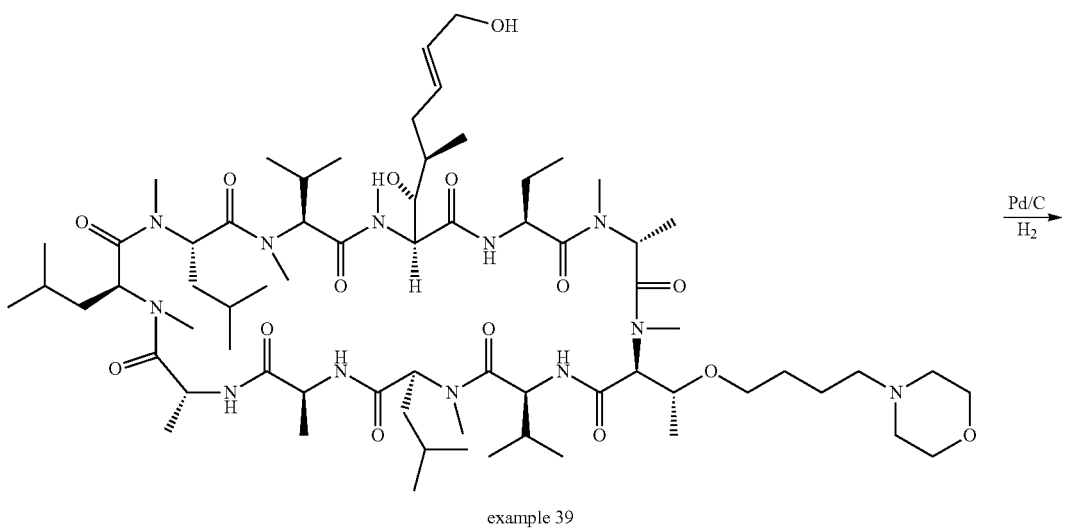

example 39

-continued

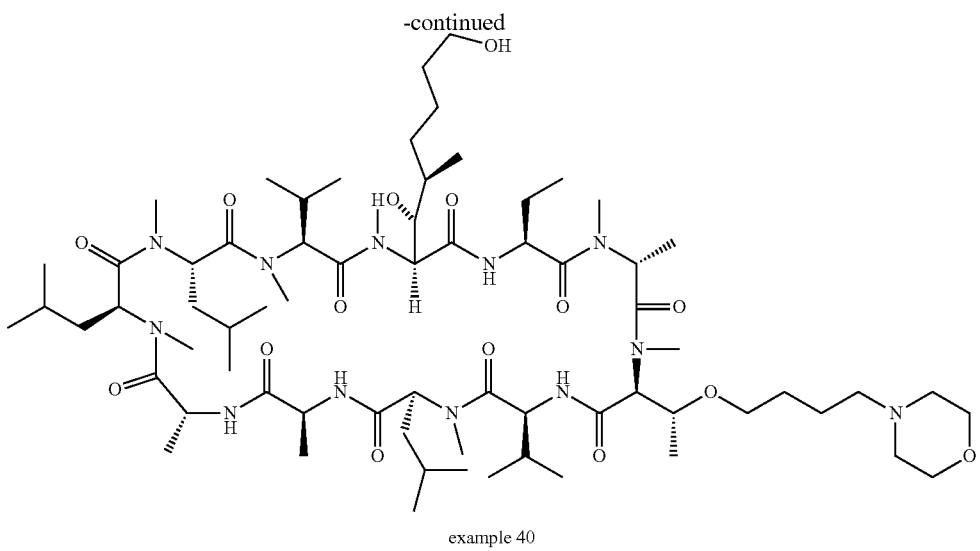

example 40

The compound of example 39 (900 mg) was dissolved in ethyl acetate-ethanol (40 mL, 4:1), treated with 10% Pd—C (300 mg) and degassed at −78° C. and filled with H$_2$. The reaction was vigorously stirred at room temperature for 19 hrs. It was filtered through a pad of celite, washed with ethyl acetate-ethanol mixture and concentrated. The residue was purified by silica gel column chromatography with 0~8.5% methanol in dichloromethane to give the title compound of example 40 (854 mg) as a white foam; MS: (ESI) m/z (M+H) 1364.51 (M+Na) 1386.57.

Example 41

Compound of formula IV: A is

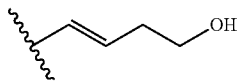 [SMILES: */C=C/CCO]

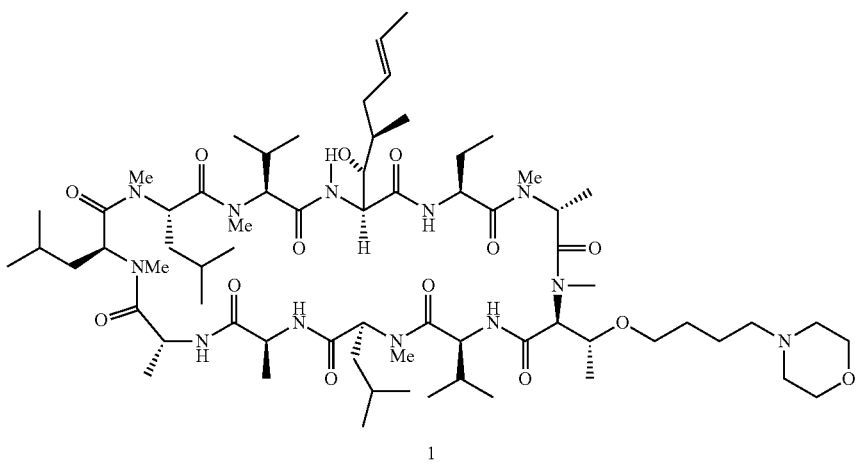

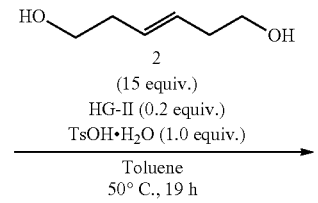

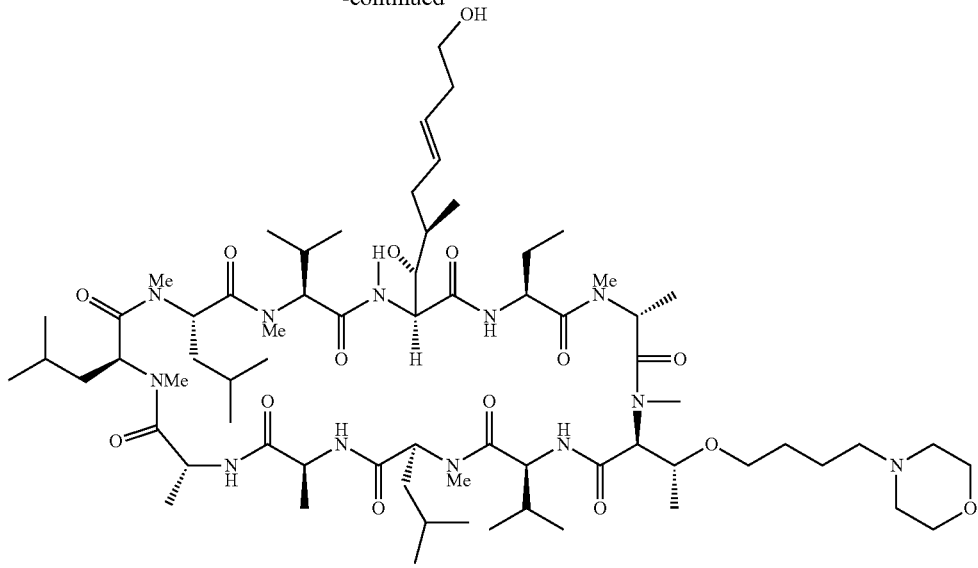

example 40

To a 1-dram vial were added compound 1 (200 mg, 0.15 mmol), Hoveyda-Grubbs II catalyst (18.8 mg, 0.2 equiv.), TsOH.H$_2$O (28.5 mg, 0.15 equiv.), toluene (1 mL), and compound 2 (258 mg, 15 equiv., 2.22 mmol) respectively, and the mixture was degassed and heated at 50° C. for 19 h. Cooled to rt, diluted with EtOAc, washed with Sat. NaHCO$_3$ and brine. Dried, filtered, concentrated, purified by Combiflash (MeOH/DCM: 0~10%) to give a pale yellow foam 140 mg with E/Z=3:1. The crude product mixture was purified by Prep HPLC (Acetonitrile:H$_2$O=40~95% over 30 min; Column temperature: 50° C.) to give the compound of example 40 (82 mg). MS-ESI (m/z): 1375.44 (M+H)$^+$.

Example 42

Compound of formula IV: A is

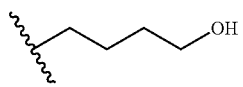

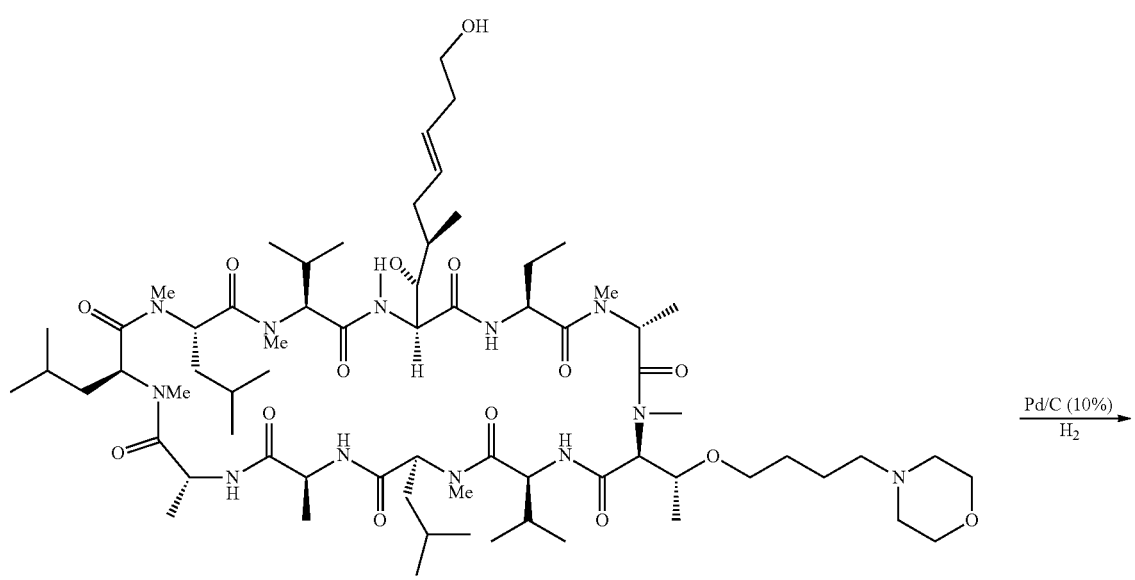

example 40

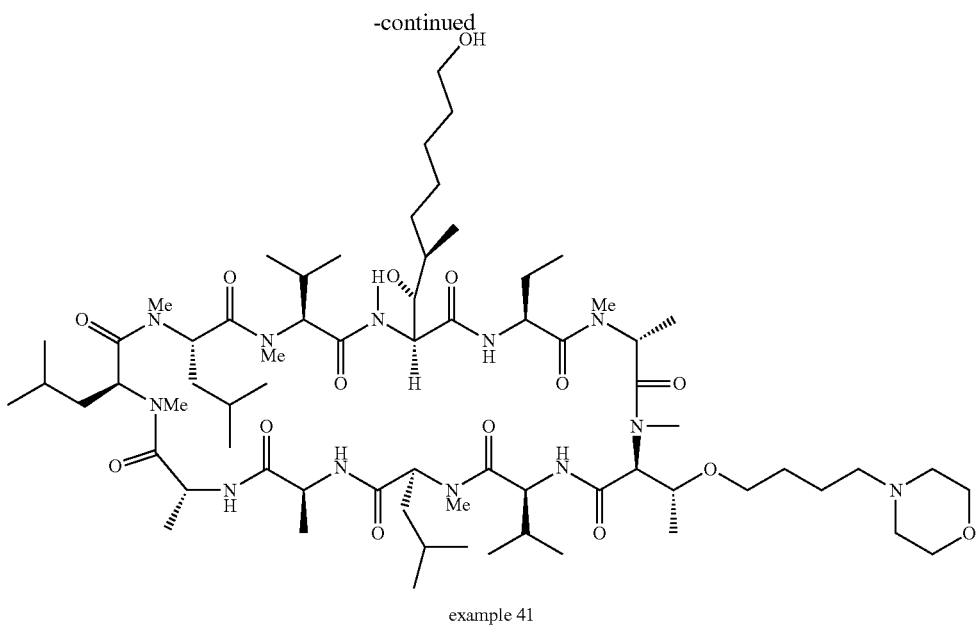
example 41
The compound of example 41 was prepared using the same procedure as described in the preparation of the compound of example 40. MS-ESI (m/z): 1378.12 (M+H)⁺.
Example 43
Compound of formula IV: A is
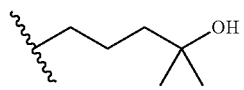 [SMILES: *CCCC(C)(C)O]
Step a:
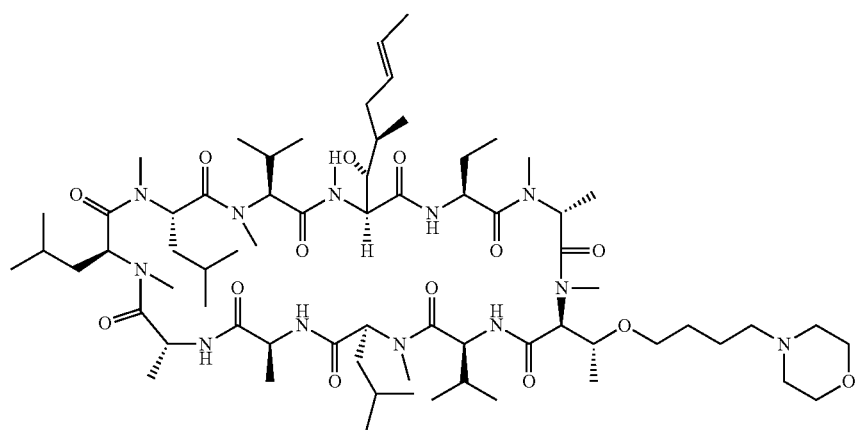 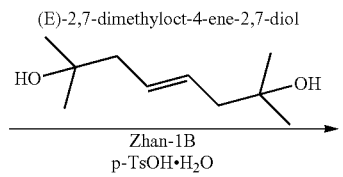

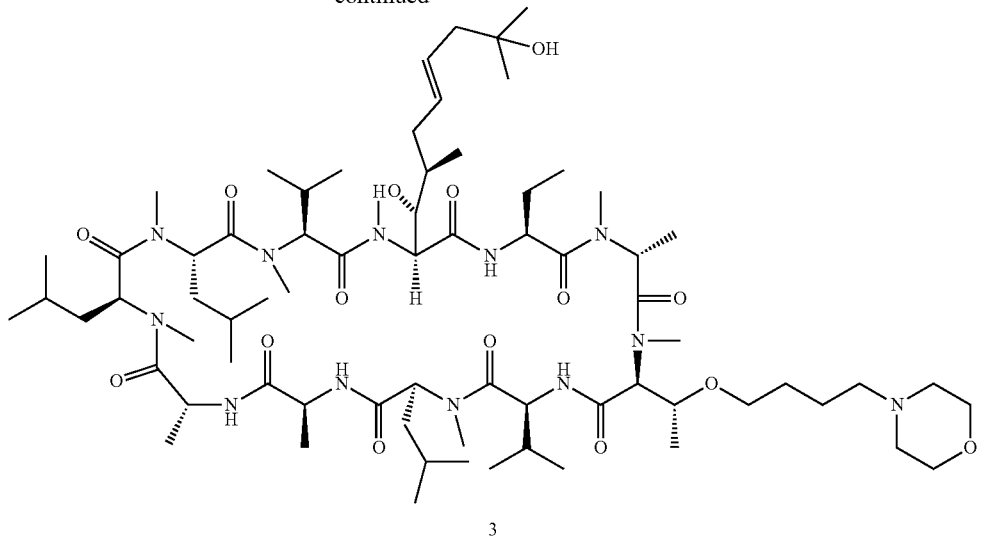

3

A mixture of compound 1 (1.0 g, 0.7431 mmol) and p-toluenesulfonic acid monohydrate (141 mg, 0.7431 mmol) in dry toluene (5.0 mL) was heated at 60° C. for 30 min, then cooled to <−40° C. (dry-ice/acetone bath) and degassed. It was added to a degassed mixture of (E)-2,7-dimethyloct-4-ene-2,7-diol (1.92 g, 22.31 mmol) and Zhan-1B catalyst (109 mg, 0.1487 mmol) in toluene (2.4 mL) under nitrogen at 60° C. The reaction mixture was stirred at 60° C. for 3 h. Then, N,N′-diisopropylethylamine (0.164 mL, 1.486 mmol), 2-mercaptonicotinic acid (35 mg, 0.223 mmol) and were added to the reaction and heated at 60° C. for 30 min. After cooling, the reaction mixture was diluted with ethyl acetate (100 mL), washed with saturated aqueous NaHCO₃ solution (2×30 mL), brine (10 mL), dried over Na₂SO₄, filtered and evaporated to dryness. The residue was purified by silica gel column chromatography with 0~100% acetone in hexane to afford the compound 3 (E/Z mixture, 0.86 g) as a white foam; E/Z ratio=7:3; MS: (ESI) m/z (M+H) 1404.46, (M+Na) 1426.48.

Step b

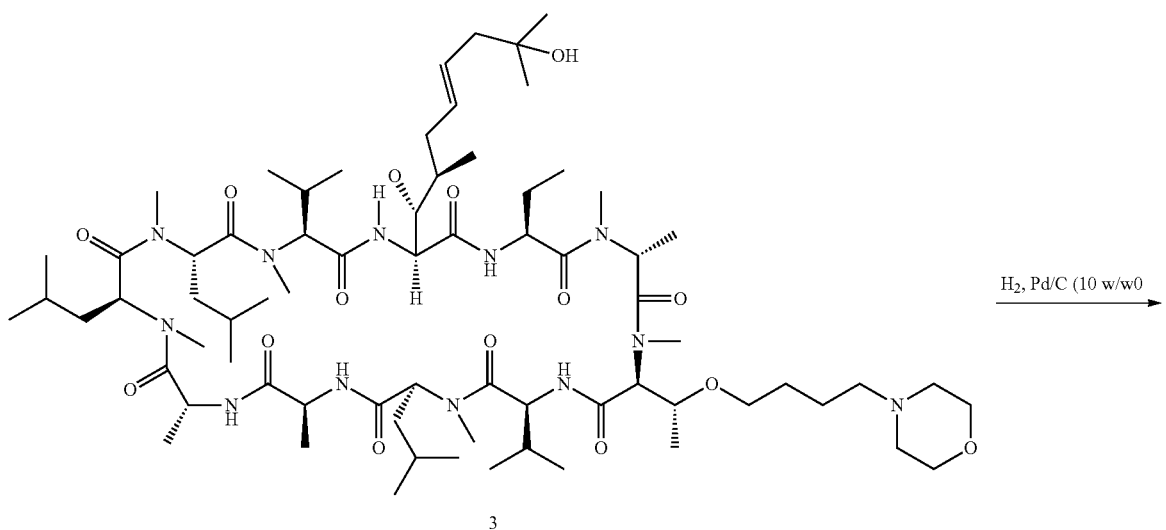

3

H₂, Pd/C (10 w/w0

-continued

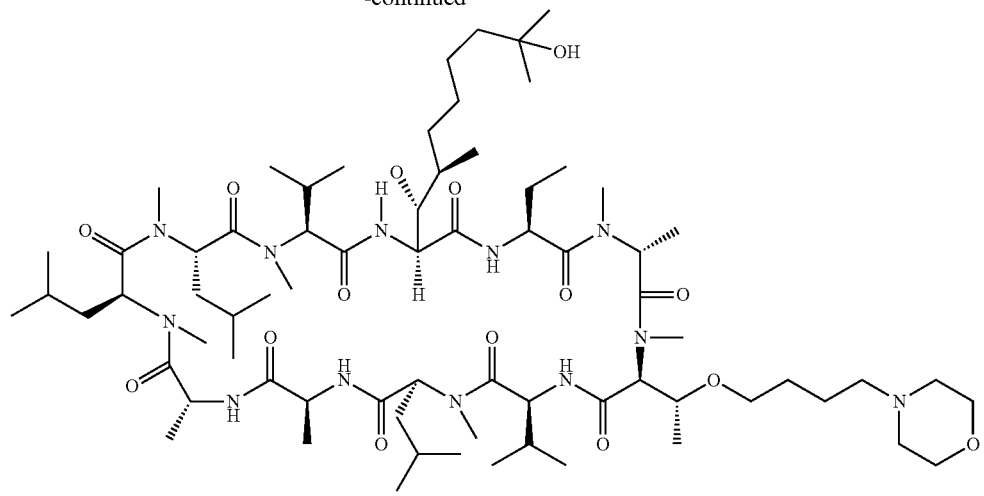

example 43

The compound 3 (1.60 g, 1.1401 mmol) and 10% Pd/C (0.32 g) in ethyl acetate (32 mL) was degassed with $H_2$ for 15 min and then stirred at room temperature overnight under balloon pressure of $H_2$. The reaction mixture was filtrated through a Celite pad and washed with ethyl acetate (30 mL×2). The crude mixture was treated with activated charcoal (80 mg, 5% w/w) by stirring in ethyl acetate at 40° C. for 1 h for decolorizing. The filtrate was collected and the solvent was evaporated to afford crude product as white solid form. The crude product was purified by silica gel column chromatography with 0~100% Acetone in Hexane to afford the the compound of example 43 (1.49 g) as a white foam; MS: (ESI) m/z (M+H) 1406.69, (M+Na) 1428.69.

Example 44

Compound of formula IV: A is

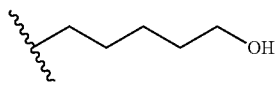 [SMILES: *CCCCCO]

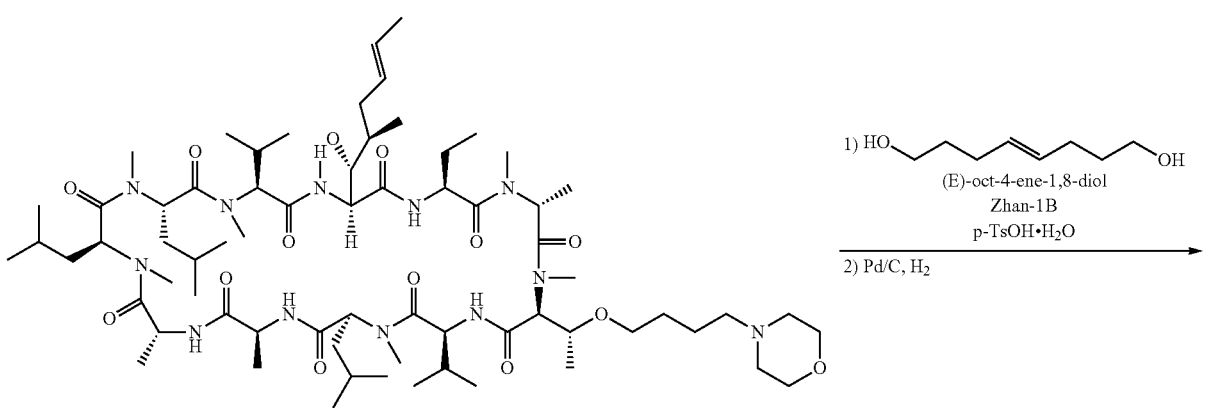

1) HO⟋⟍⟋⟍⟋⟍OH
(E)-oct-4-ene-1,8-diol
Zhan-1B
p-TsOH•$H_2O$

2) Pd/C, $H_2$

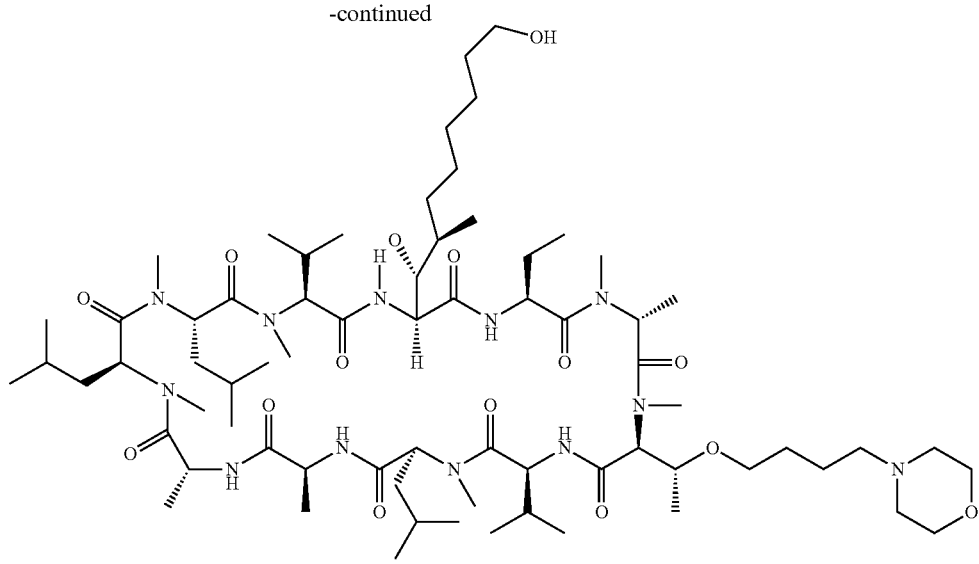
example 44
The compound of example 44 was prepared from compound 1 and (E)-oct-4ene-1,8-diol using the same procedure as described in the preparation of the compounds of example 40 and example 41. MS-ESI (m/z): 1392.12 (M+H)$^+$.
Example 45
Compound of formula IV: A is
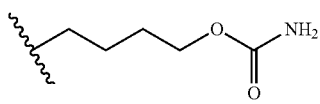 [SMILES: *CCCCOC(N)=O]
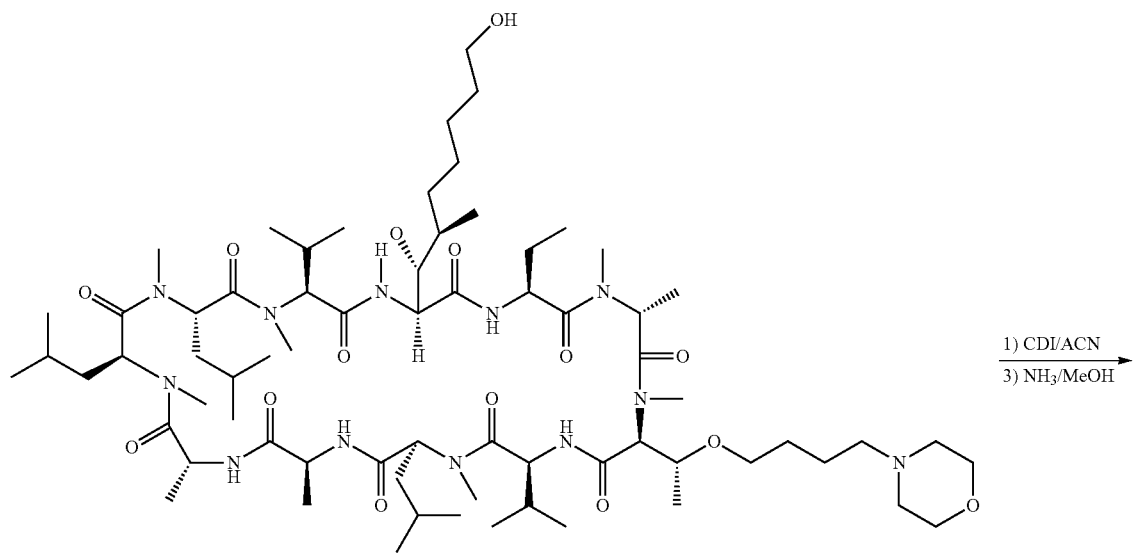
example 42

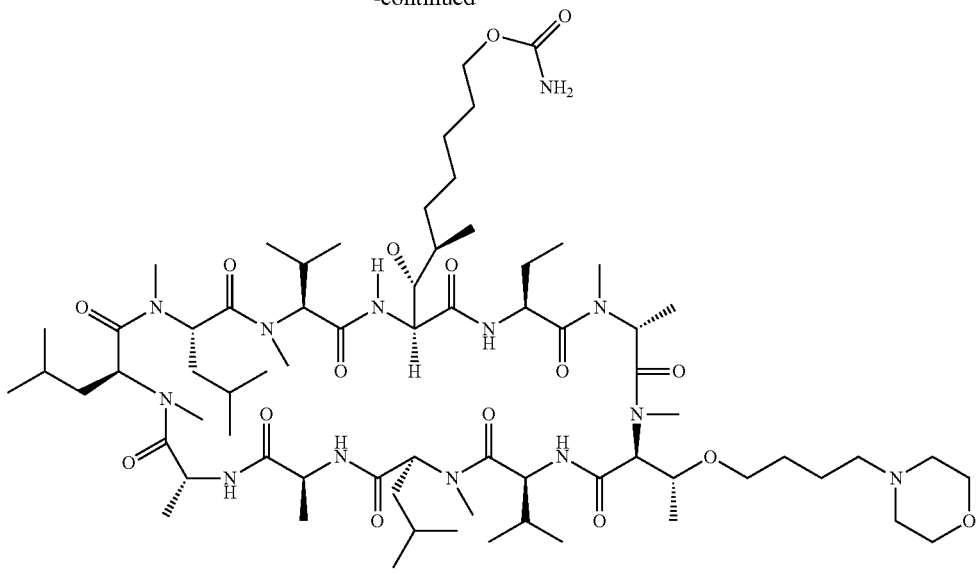

example 45

To a solution of compound of example 42 (20 mg, 0.015 mmol) in acetonitrile (1 mL) was added CDI (30 mg, 0.185 mmol, 12.3 equiv.) and the mixture was heated at 50° C. for 1 h. A 7N solution of $NH_3$ in MeOH (0.5 mL, 3.5 mmol) was added and the solution was heated at 70° C. for 30 min. The solvent was removed and the residue was purified by Prep HPLC (Acetonitrile: $H_2O$=40~95% over 30 min; Column temperature: 50° C.) to give the compound of example 45 (15 mg) as a white foam, MS-ESI (m/z): 1420.86 $(M+H)^+$.

Example 46

Compound of formula IV: A is

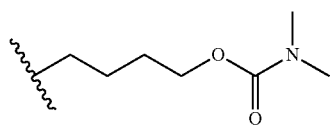 [SMILES: *CCCCOC(=O)N(C)C]

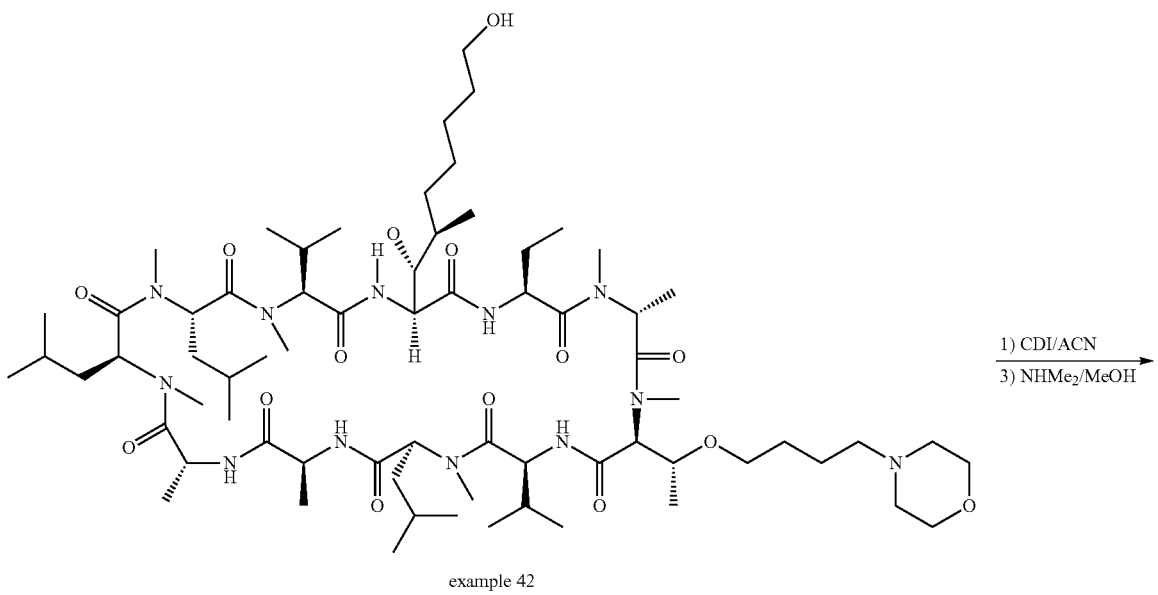

example 42

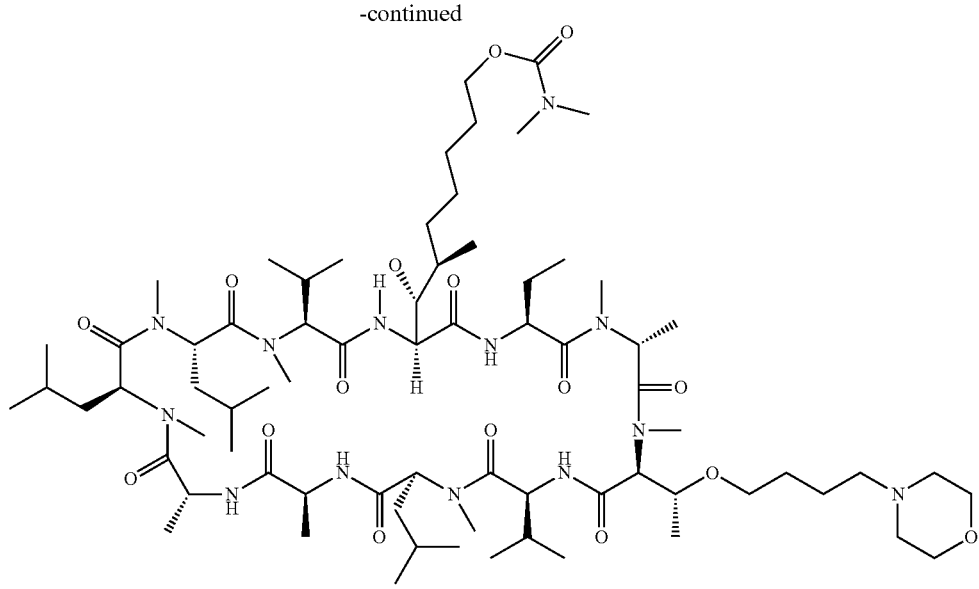
example 46
The compound of example 46 was prepared from example 42 using the same procedure as described in the preparation of the compounds of example 45. MS-ESI (m/z): 1449.12 (M+H)+.
Example 47
Compound of formula IV: A is
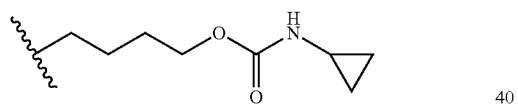
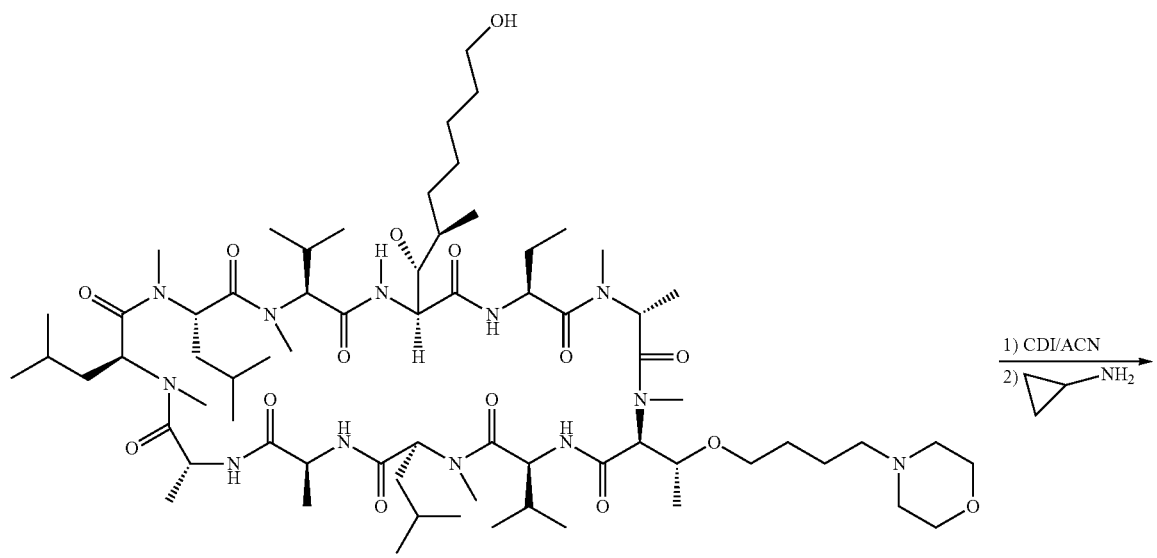
example 42

-continued
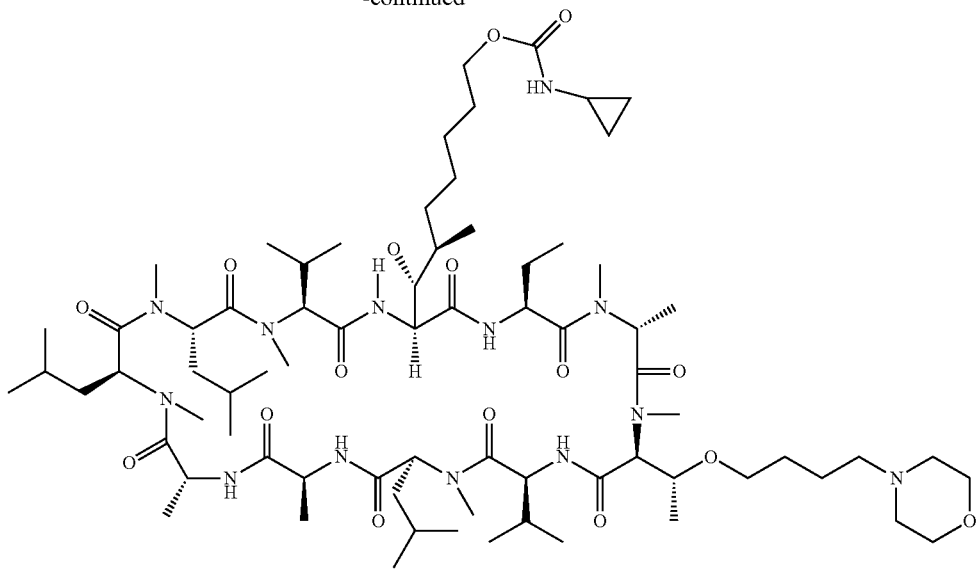
example 47
The compound of example 47 was prepared from example 42 using the same procedure as described in the preparation of the compounds of example 45. MS-ESI (m/z): 1461.12 (M+H)⁺.
Example 48
Compound of formula IV: A is
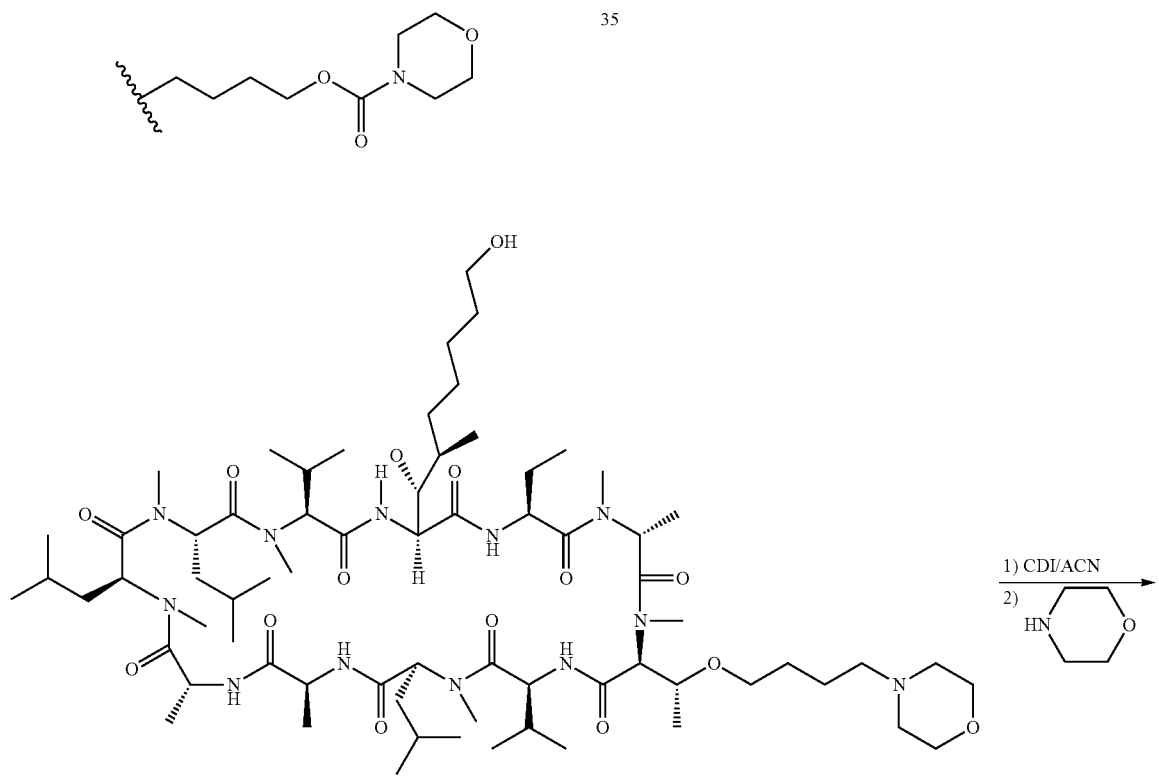
example 42

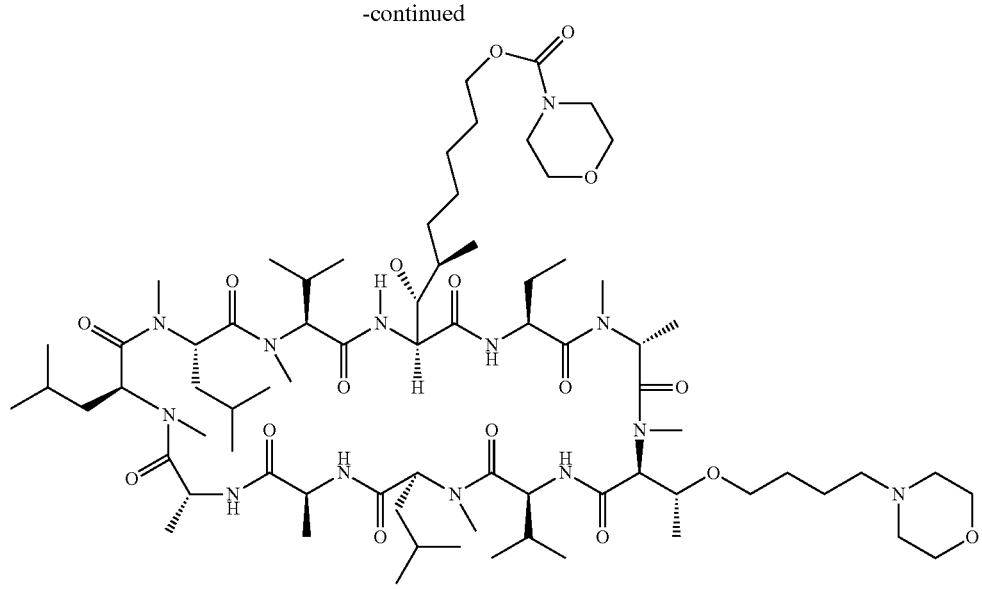
example 48
The compound of example 48 was prepared from example 42 using the same procedure as described in the preparation of the compounds of example 45. MS-ESI (m/z): 1491.12 (M+H)$^+$.
Example 49
Compound of formula IV: A is
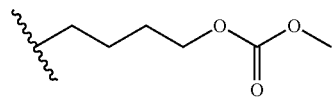 [SMILES: *CCCCOC(=O)OC]
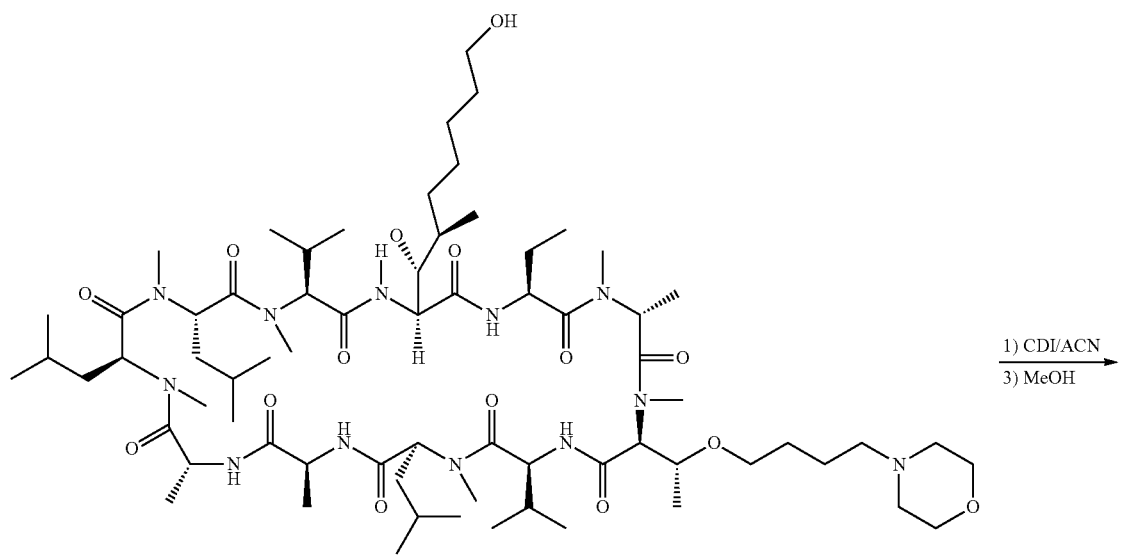
example 42
1) CDI/ACN
3) MeOH

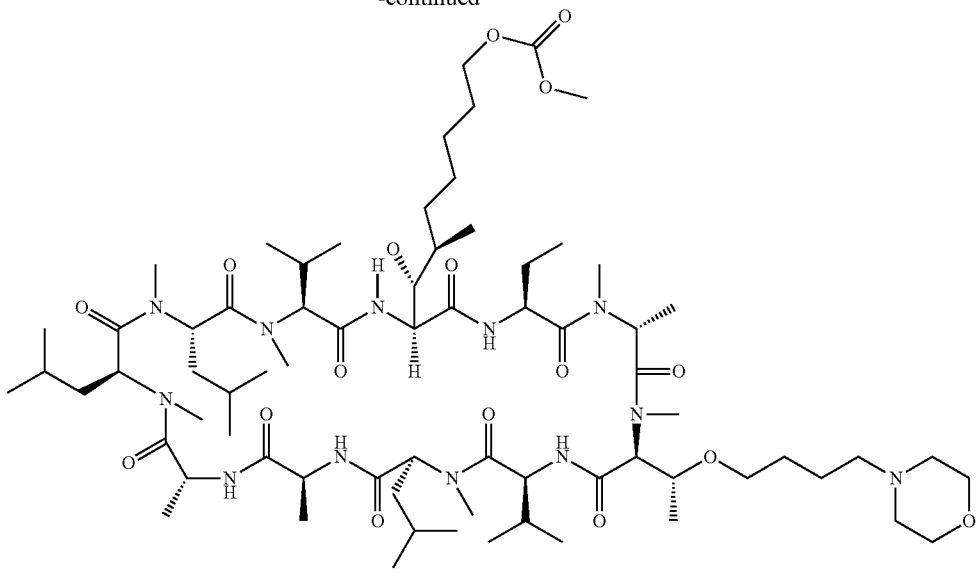
example 49
The compound of example 49 was prepared from example 42 using the same procedure as described in the preparation of the compounds of example 45. MS-ESI (m/z): 1436.02 (M+H)$^+$.
Example 50
Compound of formula IV: A is
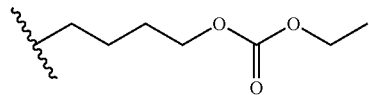 [SMILES: *CCCCOC(=O)OCC]
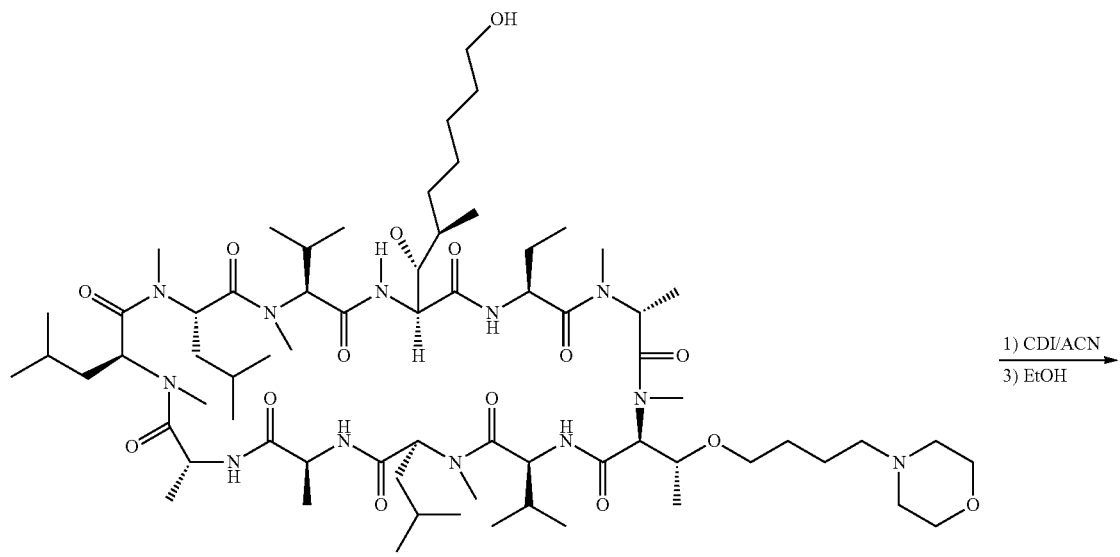
example 42

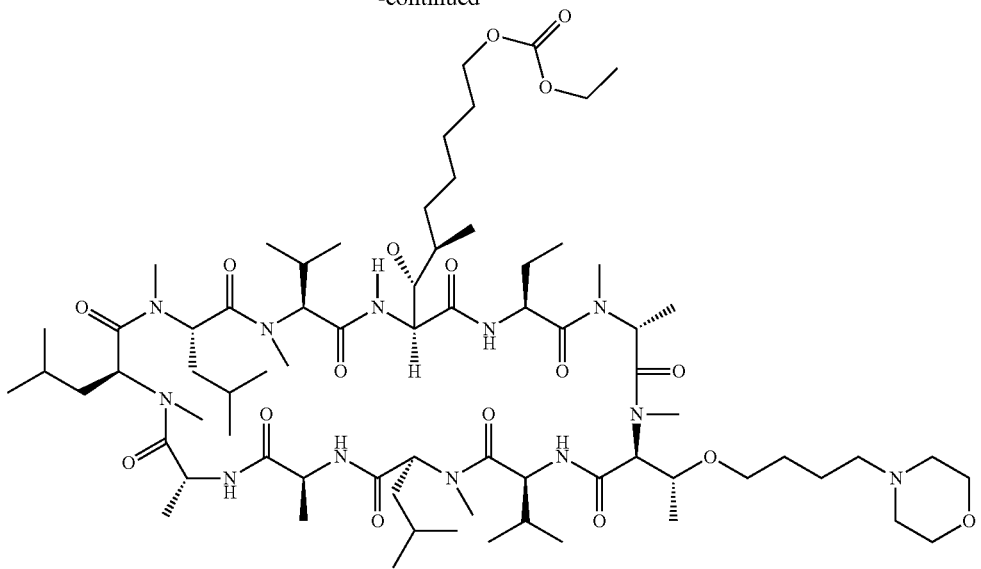
example 50
The compound of example 50 was prepared from example 42 using the same procedure as described in the preparation of the compounds of example 45. MS-ESI (m/z): 1450.04 (M+H)$^+$.
Example 51
Compound of formula IV: A is
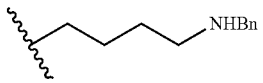
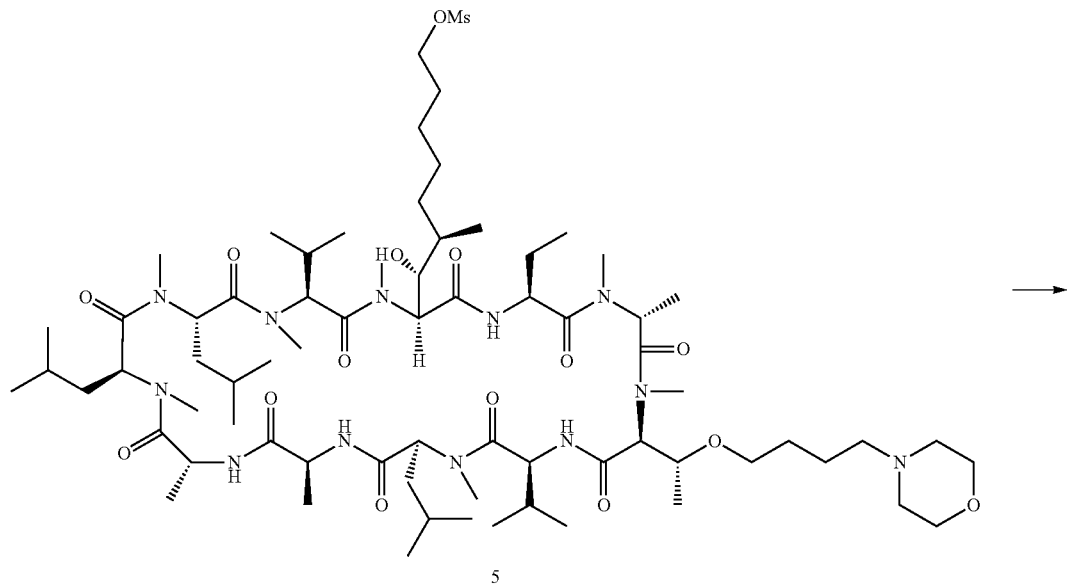

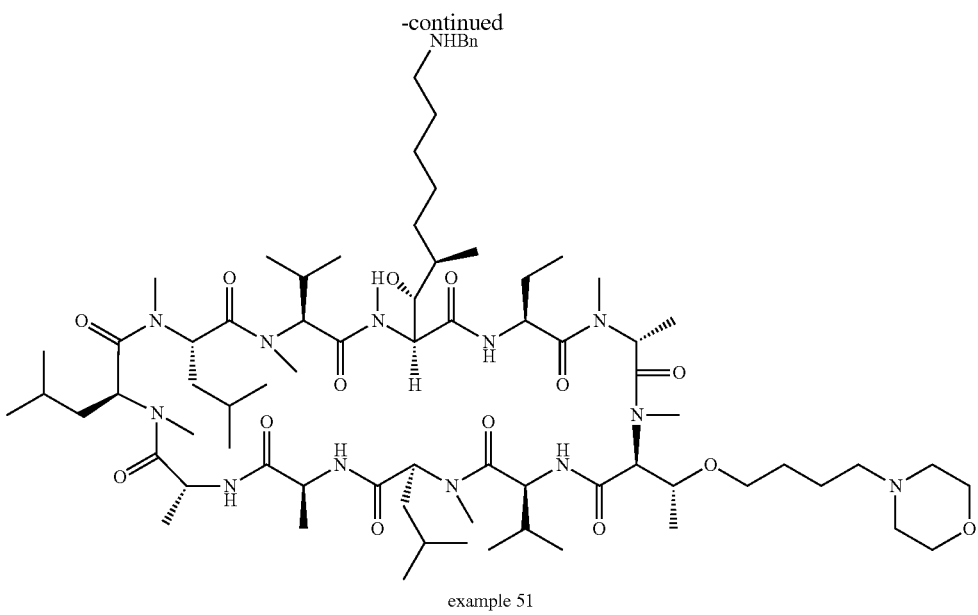
example 51
The compound of example 51 was prepared from compound 5 and benzyl amine using the same procedure as described in the preparation of the compounds of example 19. MS-ESI (m/z): 1467.04 (M+H)+.
Example 52
Compound of formula IV: A is
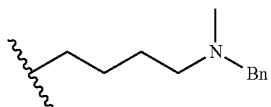 [SMILES: *CCCCN(C)Cc1ccccc1]
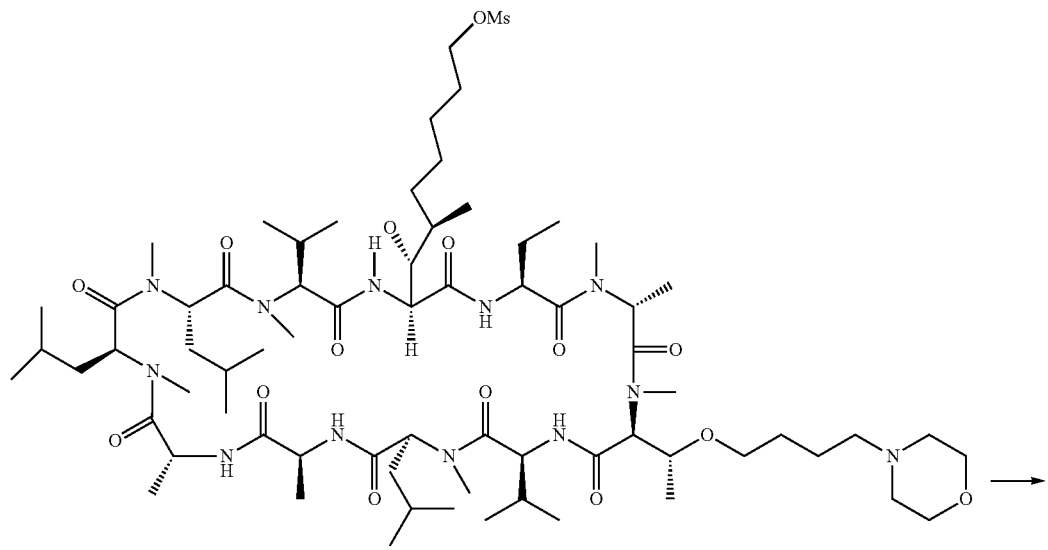

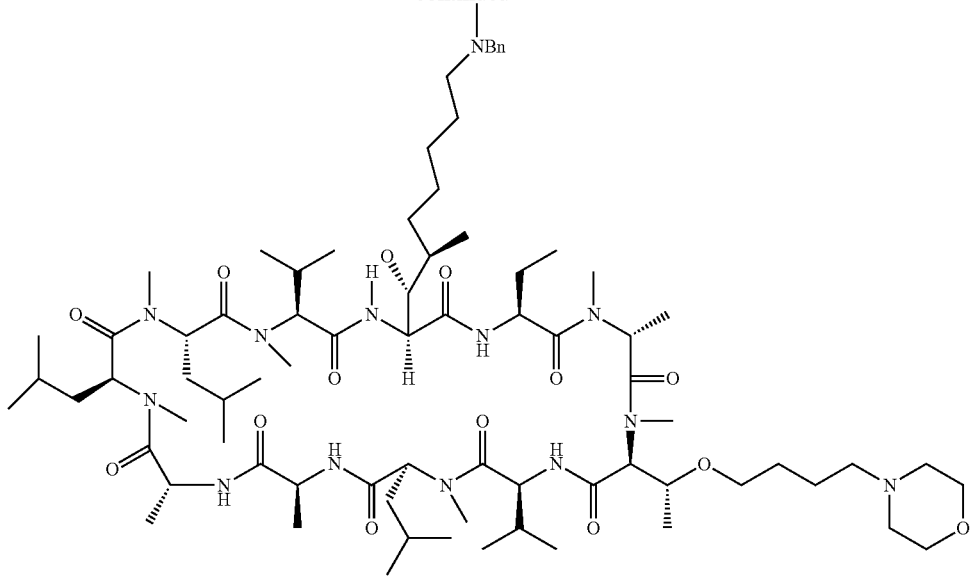
example 52
The compound of example 52 was prepared from compound 5 and benzyl methyl amine using the same procedure as described in the preparation of the compounds of example 19. MS-ESI (m/z): 1481.04 (M+H)+.
Example 53
Compound of formula IV: A is
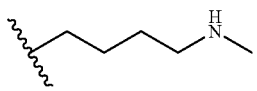
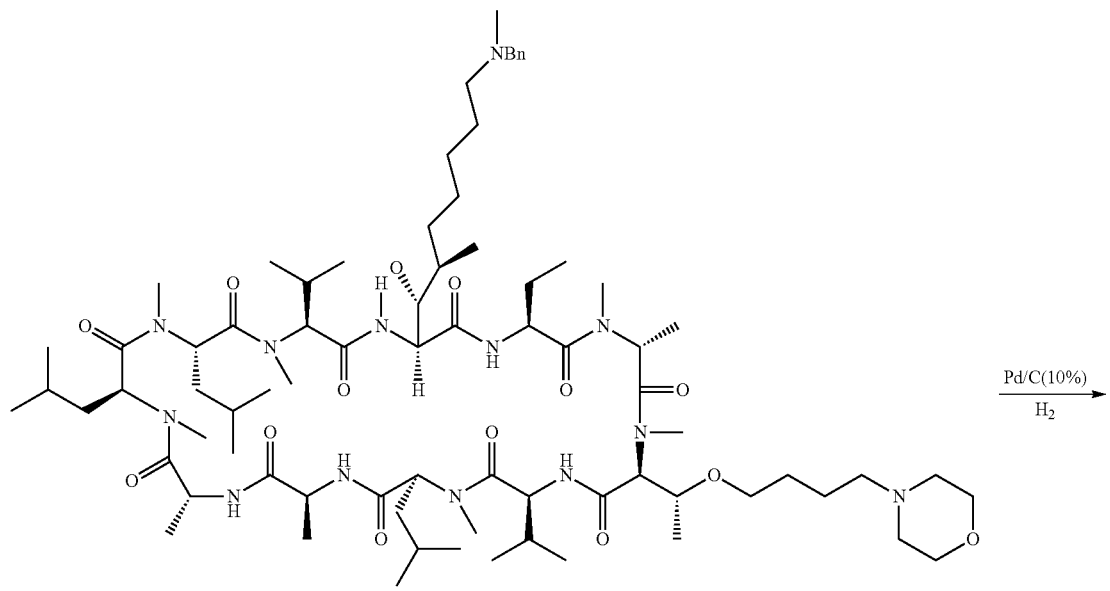
example 52

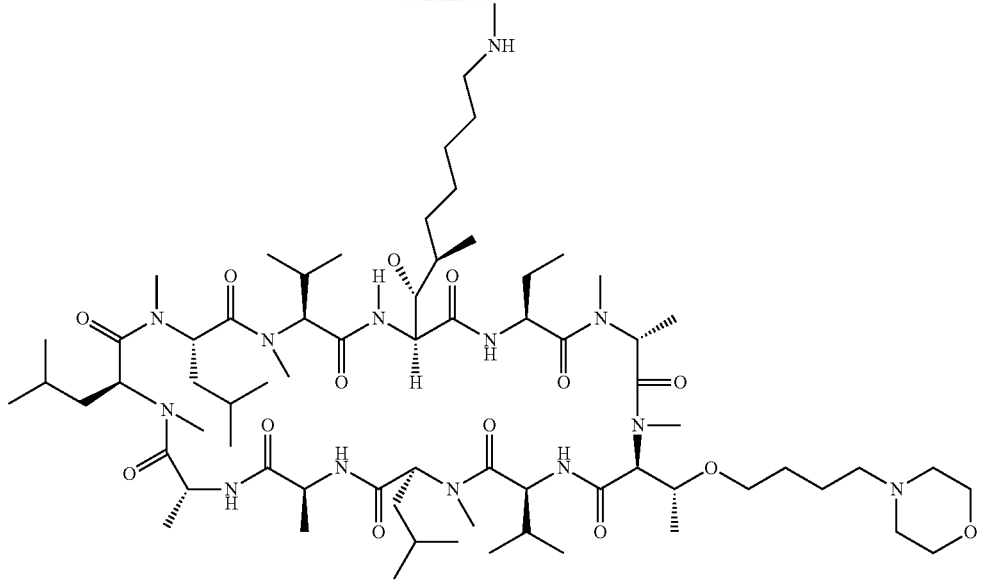
example 53
The compound of example 53 was prepared from compound of example 52 using palladium catalysed hydrogenation condition as described in the preparation of the compounds of example 40. MS-ESI (m/z): 1391.04 (M+H)$^+$.
Example 54
Compound of formula IV: A is
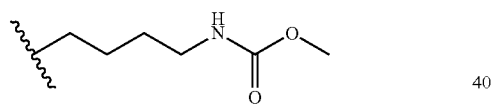
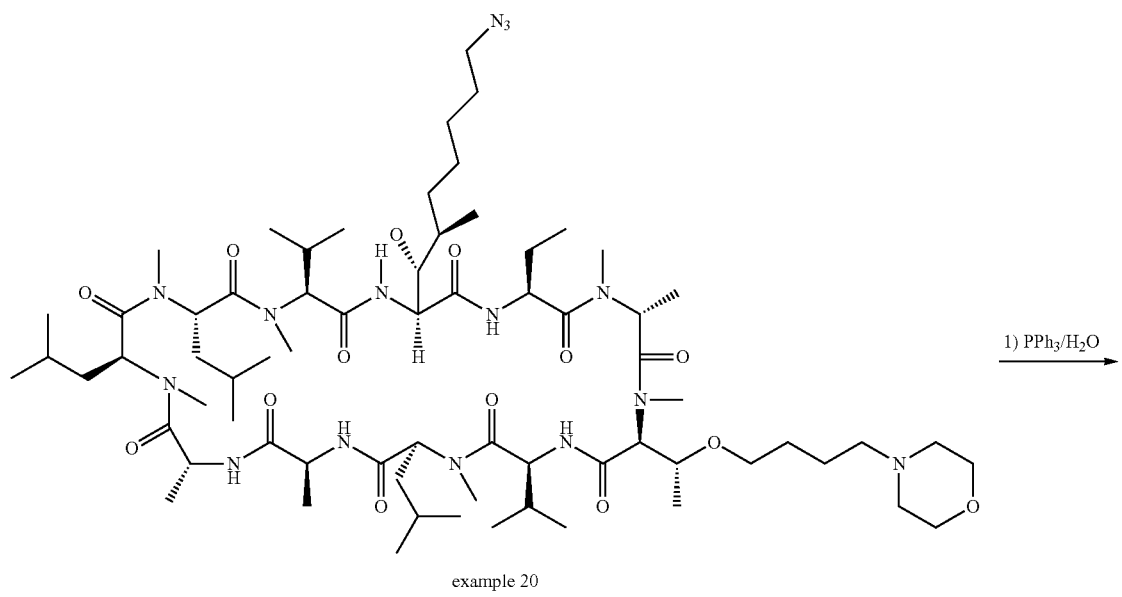
example 20

-continued

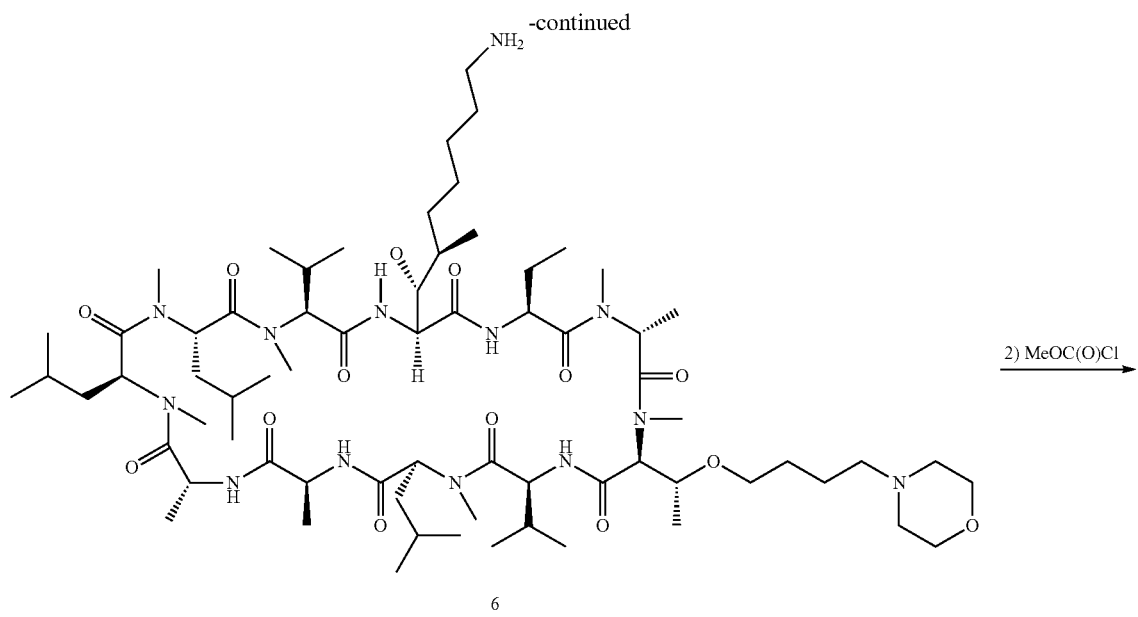

6

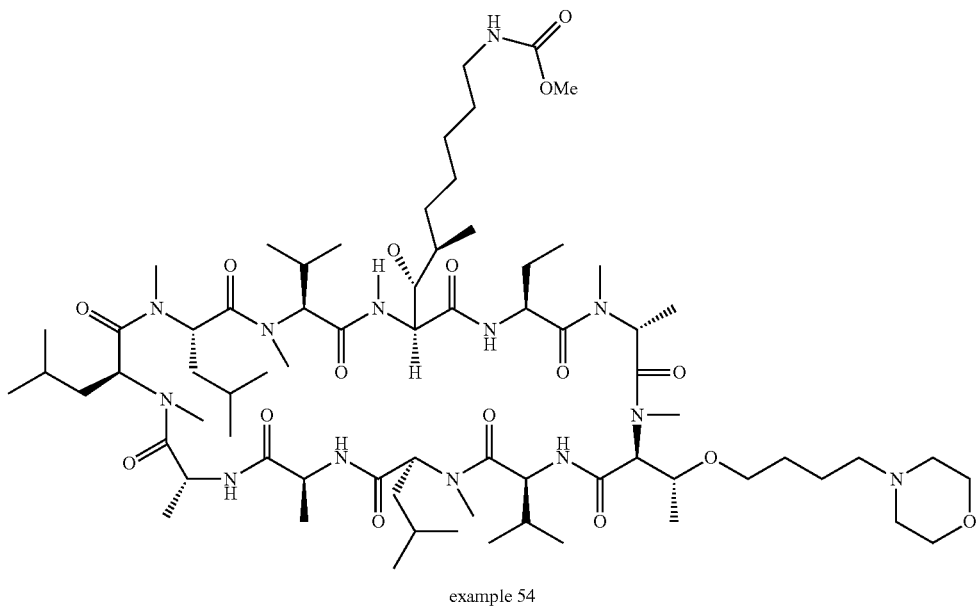

example 54

Step 54a:

A mixture of compound of example 20 (119 mg, 0.0856 mmol) and triphenylphosphine (67.3 mg) in dry THF was heated at 60° C. for 100 min. After evaporation, the residue was purified by silica gel column chromatography with 0~20% methanol containing 1N—NH$_3$ in dichloromethane to give the title compound 6 (95.7 mg) as a pale yellow foam; MS: (ESI) m/z (M+H) 1378.00, (M+Na) 1400.04.

Step 54b:

A mixture of compound 6 (34 mg) and 1,1'-carbonyldiimidazole (6 mg) in dry acetonitrile (0.4 mL) was stirred at room temperature for 2 hrs. After removal of the solvent, the residue was dissolved in methanol (0.6 mL) and DBU and heated at 70° C. for 1 hr. After evaporation, the residue was purified by preparative HPLC to give the pure title compound of example 54 as a white cotton after lyophilization (30 mg); MS: (ESI) m/z (M+H) 1435.05, (M+Na) 1457.07.

Example 55

Compound of formula IV: A is

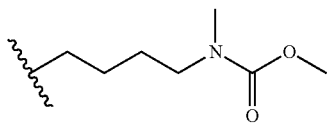 [SMILES: *CCCCN(C)C(=O)OC]

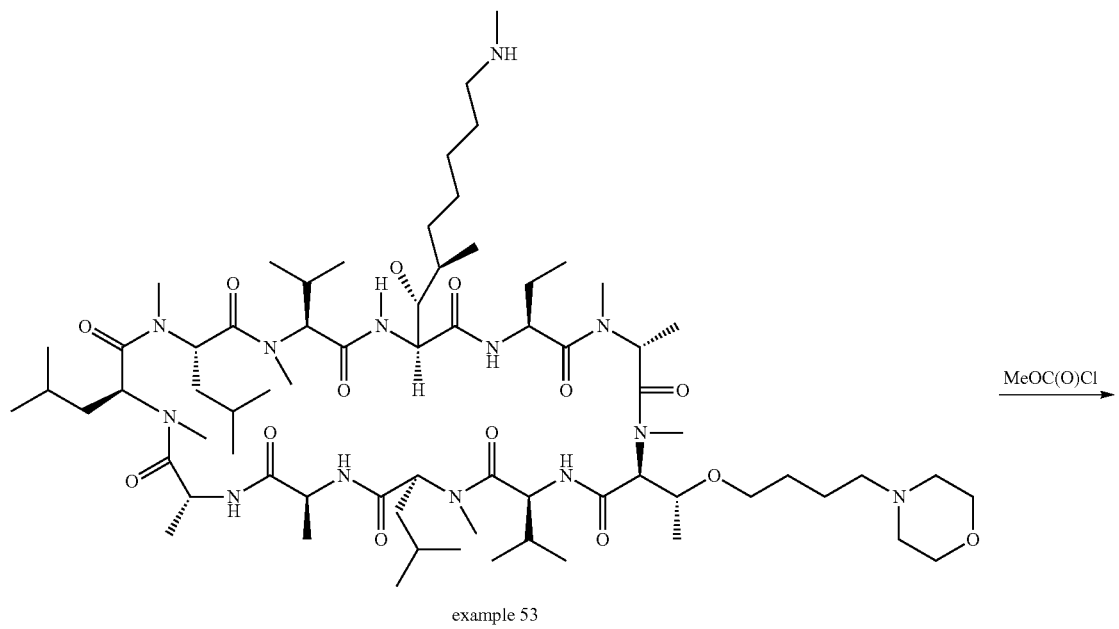
example 53
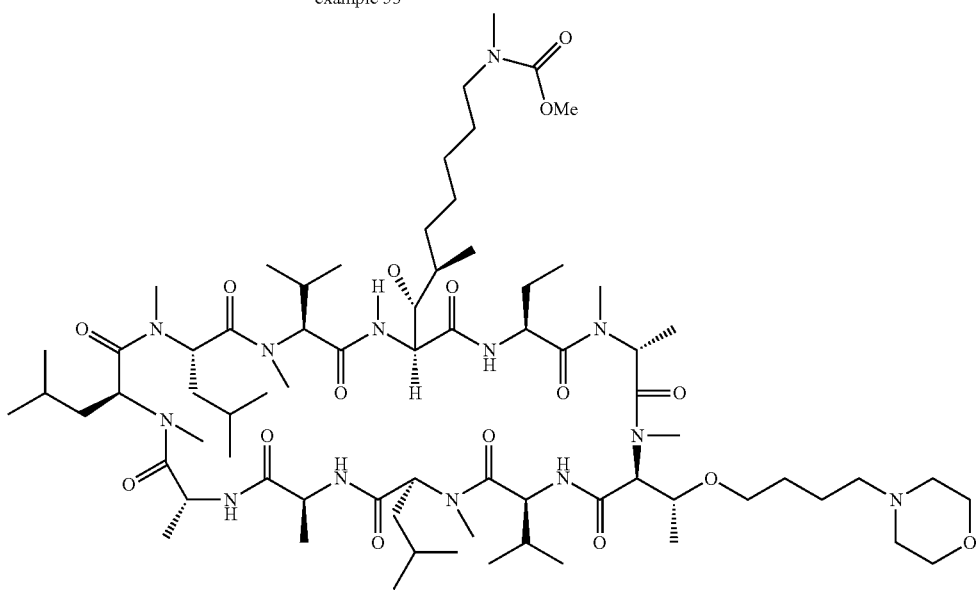
example 55
The compound of example 55 was prepared from compound of example 53 using the same condition as described in the preparation of the compounds of example 54 (step 54b). MS-ESI (m/z): 1449.04 (M+H)+.
Example 56
Compound of formula IV: A is
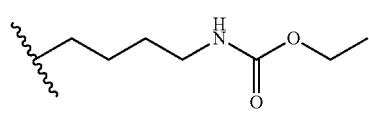 [SMILES: *CCCCNC(=O)OCC]

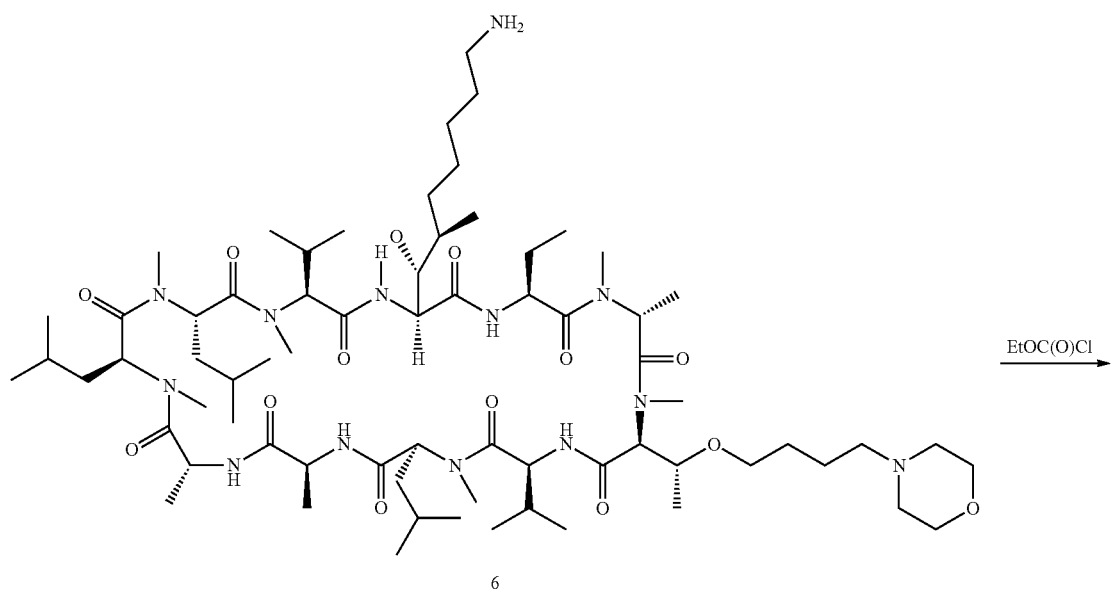
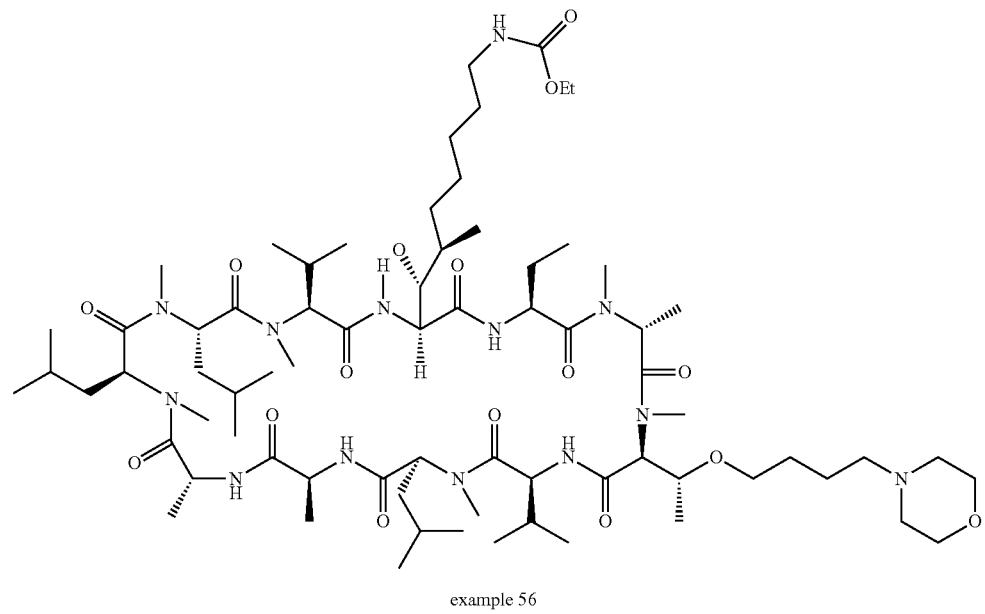
example 56
The compound of example 56 was prepared from compound 6 using the same condition as described in the preparation of the compounds of example 54 (step 54b). MS-ESI (m/z): 1449.04 (M+H)+.
Example 57
Compound of formula IV: A is
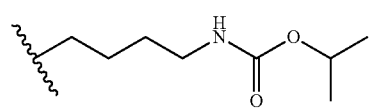 [SMILES: *CCCCNC(=O)OC(C)C]

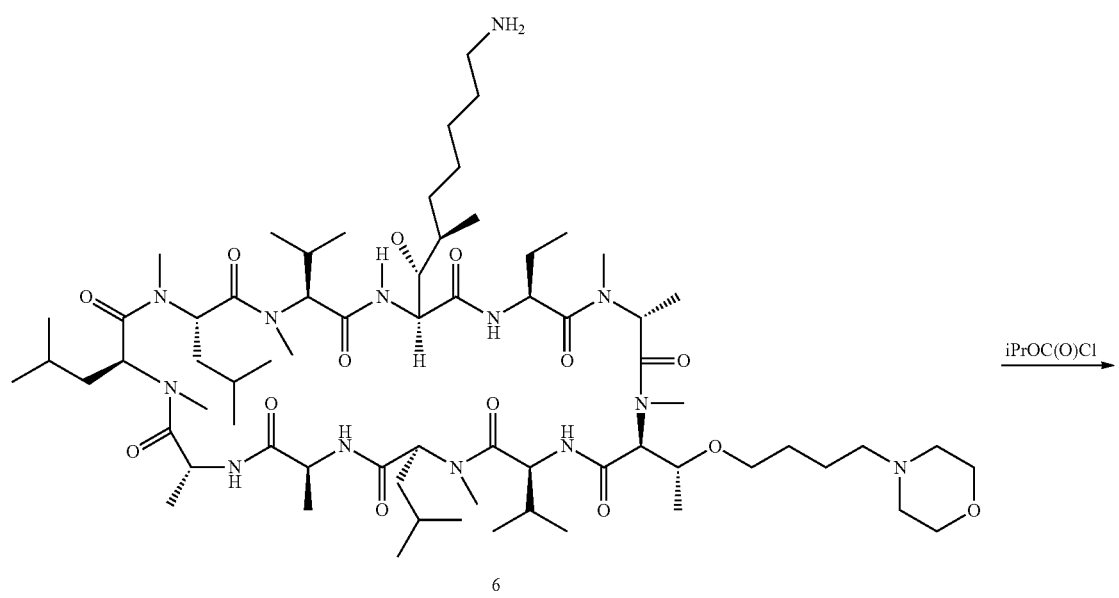
The compound of example 57 was prepared from compound 6 using the same condition as described in the preparation of the compounds of example 54 (step 54b). MS-ESI (m/z): 1463.04 (M+H)⁺.
Example 58
Compound of formula IV: A is
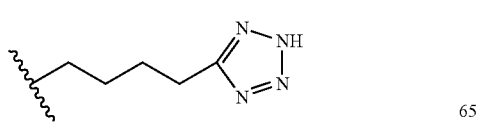

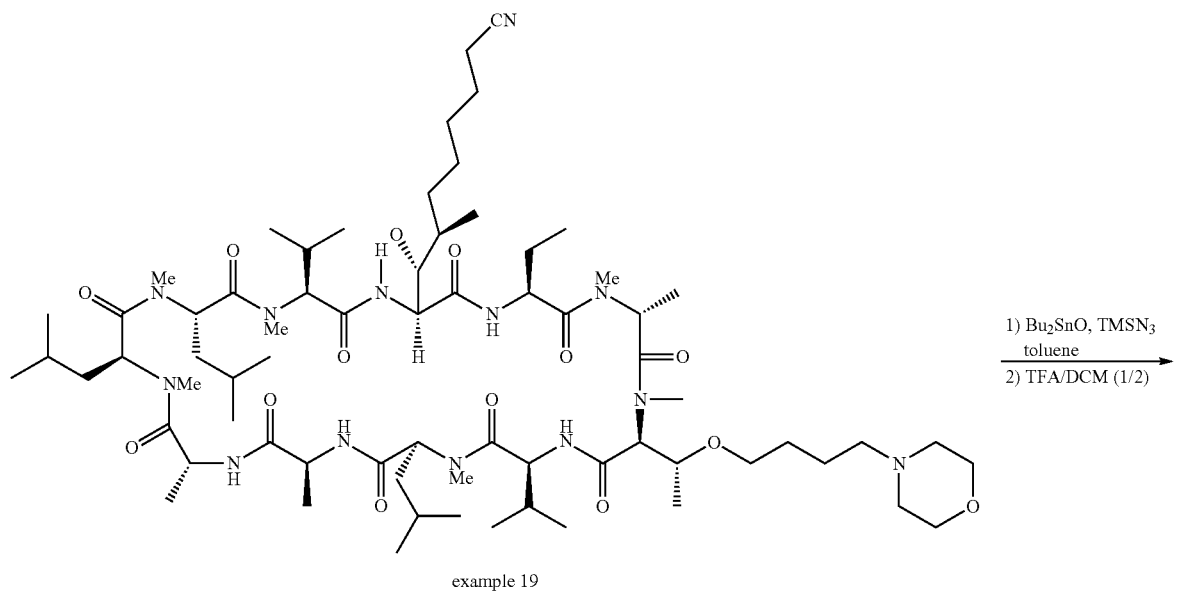

example 19

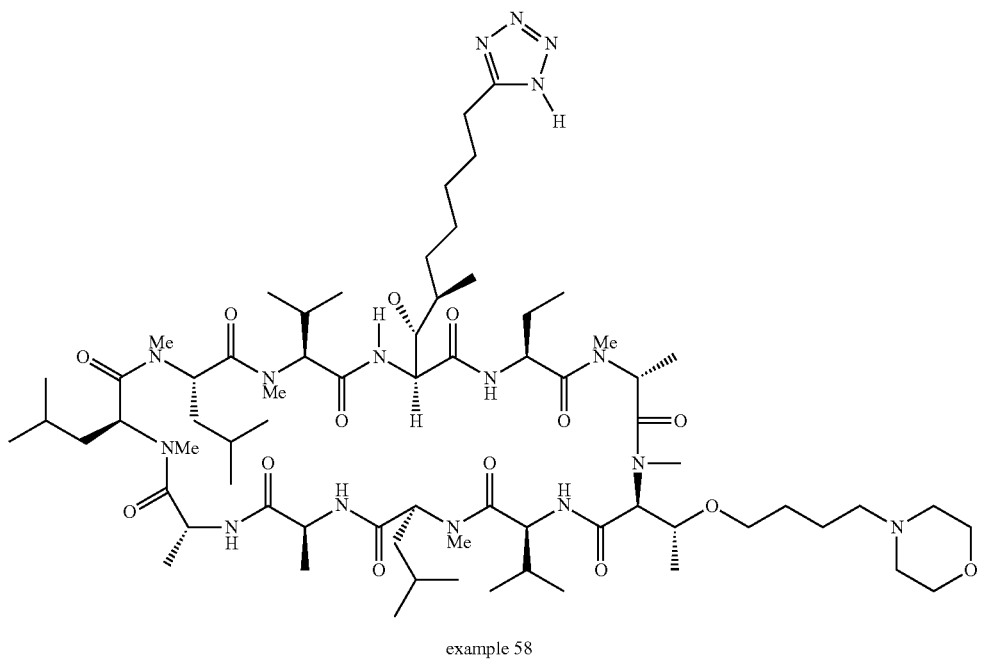

example 58

To a 5 mL vial were added compound of example 19 (38 mg, 0.027 mmol), Bu$_2$SnO (100.8 mg, 0.405 mmol, 15.0 equiv.), toluene (2.0 mL), TMSN$_3$ (1 mL) respectively and the mixture was irradiated with microwave at 170° C. for 20 min. Concentrated, dissolved into DCM (3 mL), and the solution was cooled to 0° C. followed by addition of TFA (1.5 mL). After stirred at 0° C. for 1 h, the mixture was diluted with DCM, washed with Sat. NaHCO$_3$ solution/Sat. Na$_2$CO$_3$ (5:1) and then brine. Dried, filtered, concentrated, purified by Combiflash (MeOH/DCM: 0~20%) to give the compound of example 58 as a white foam (21 mg). MS-ESI (m/z): 1429.70 (M+H)$^+$.

Example 59

Compound of formula IV: A is

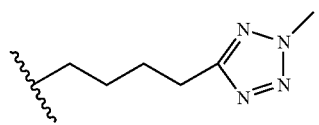 [SMILES: *CCCCc1nnn(C)n1]

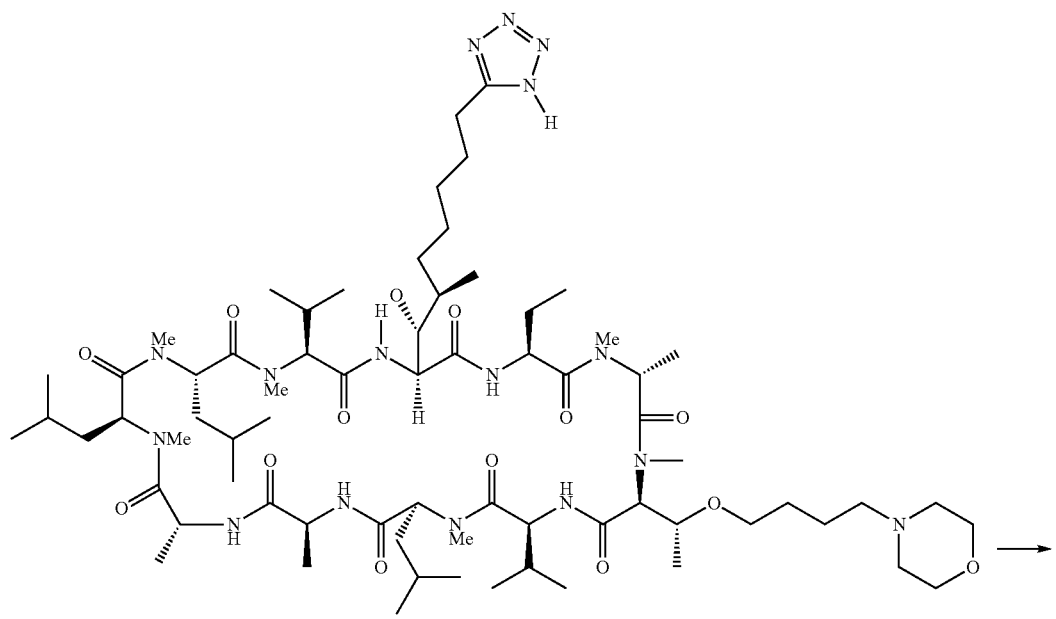
example 58
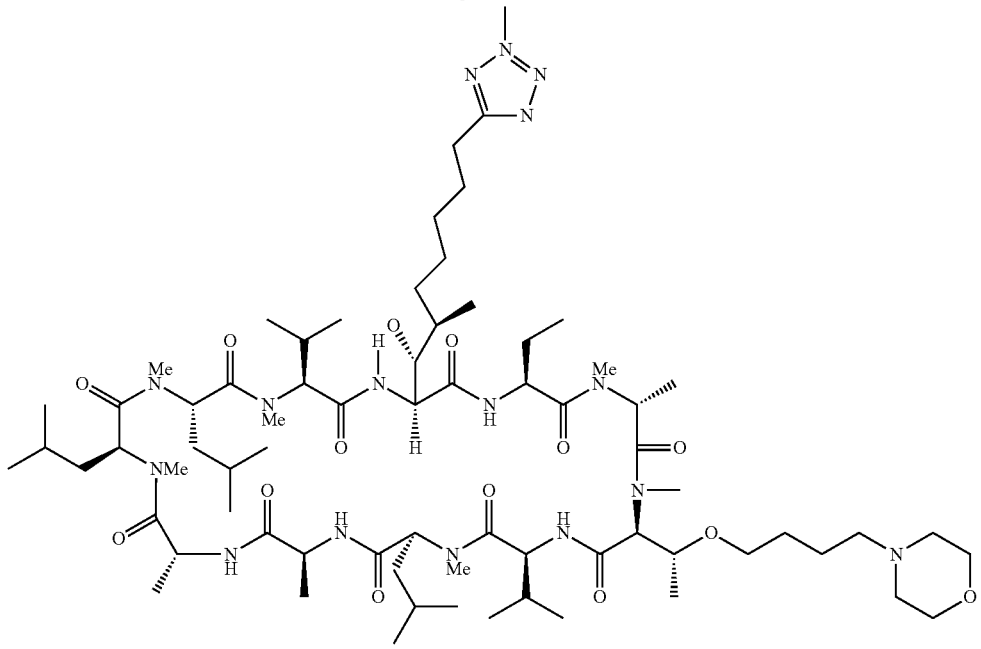
example 59
To a 5 ml vial were added compound of example 58 (18 mg, 0.013 mmol), MeOH (2 mL), TMSCHN$_2$ (200 μL, 2 M in THF) respectively, and the solution was stirred at rt for 45 min. Concentrated, purified by Prep HPLC (Acetonitrile:H$_2$O=40~95% over 30 min; Column temperature: 50° C.) to give the compound of example 59 as a white foam (2.4 mg), MS-ESI (m/z): 1443.98 (M+H)$^+$.
Example 60
Compound of formula IV: A is
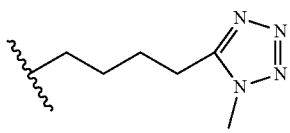 [SMILES: *CCCCc1nnnn1C]

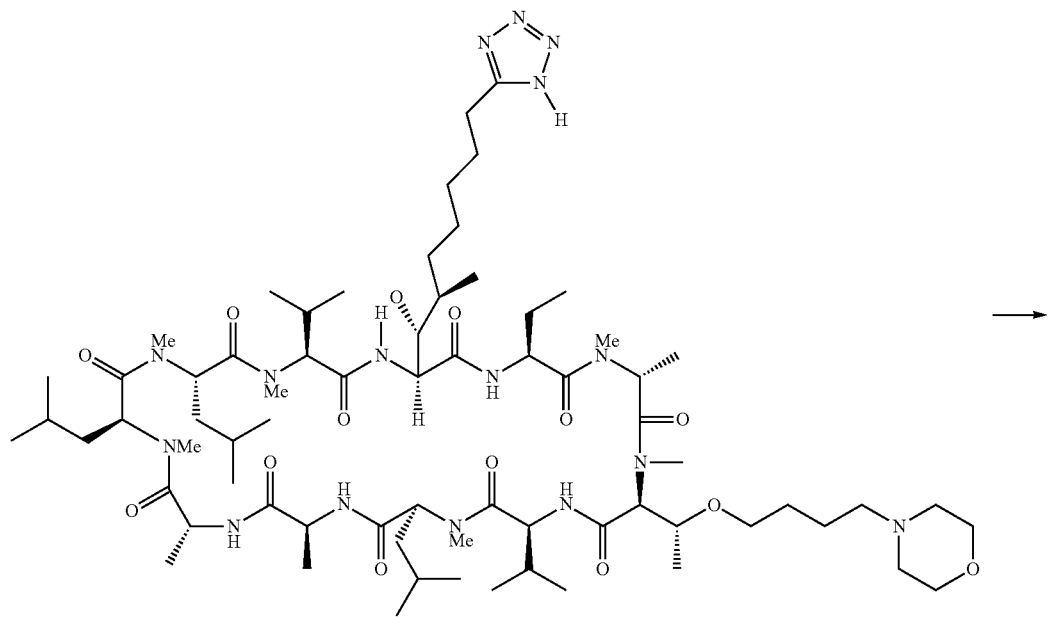
example 58
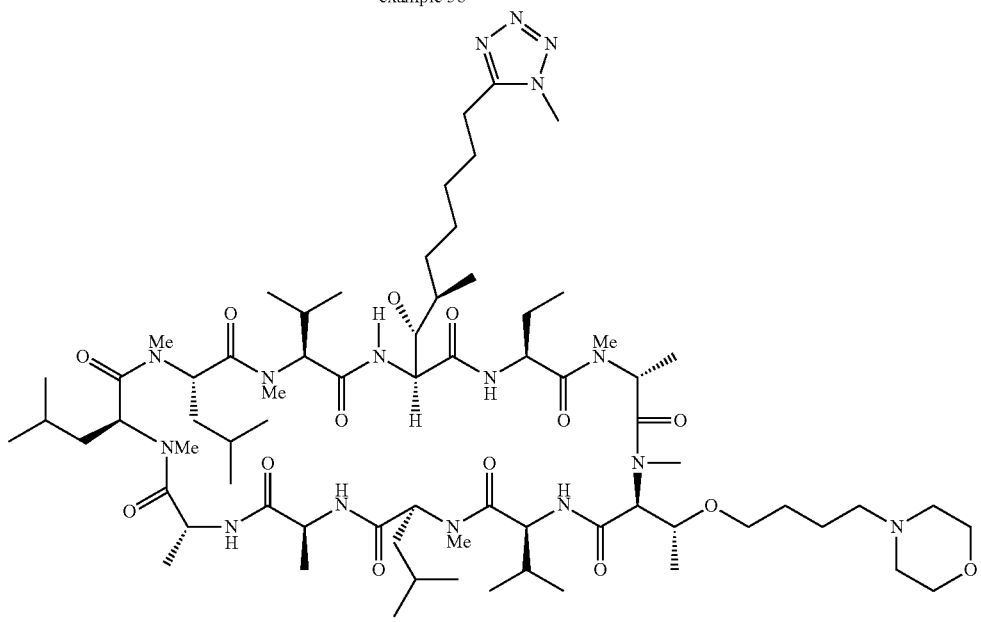
example 60
The compound of example 60 was prepared from compound of example 58 using the same condition as described in the preparation of the compounds of example 59. MS-ESI (m/z): 1443.98 (M+H)⁺.
Example 61
Compound of formula IV: A is
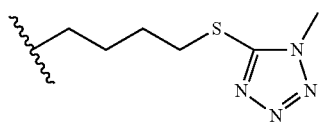 [SMILES: *CCCCSc1nnnn1C]

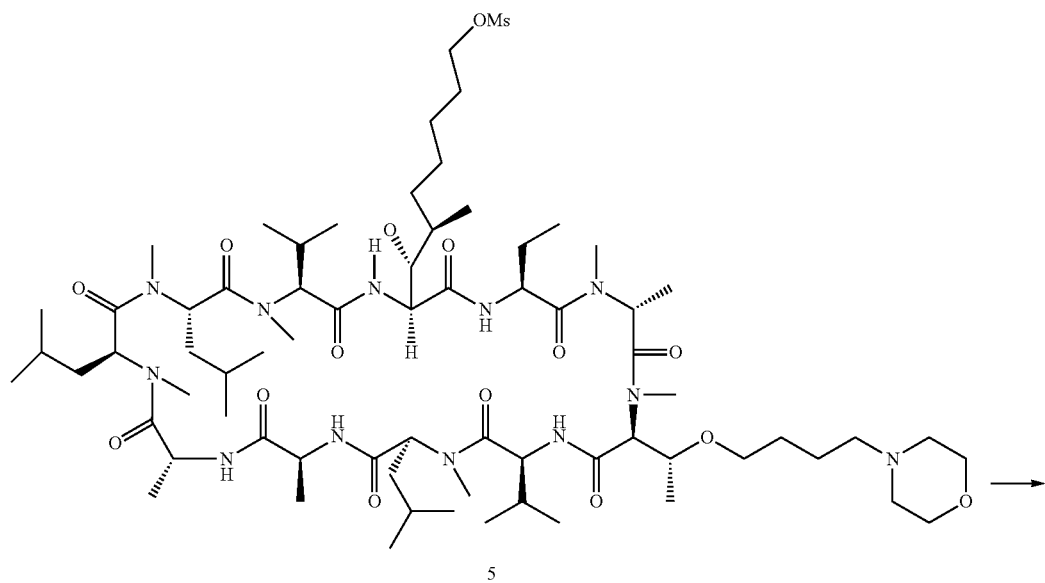

5

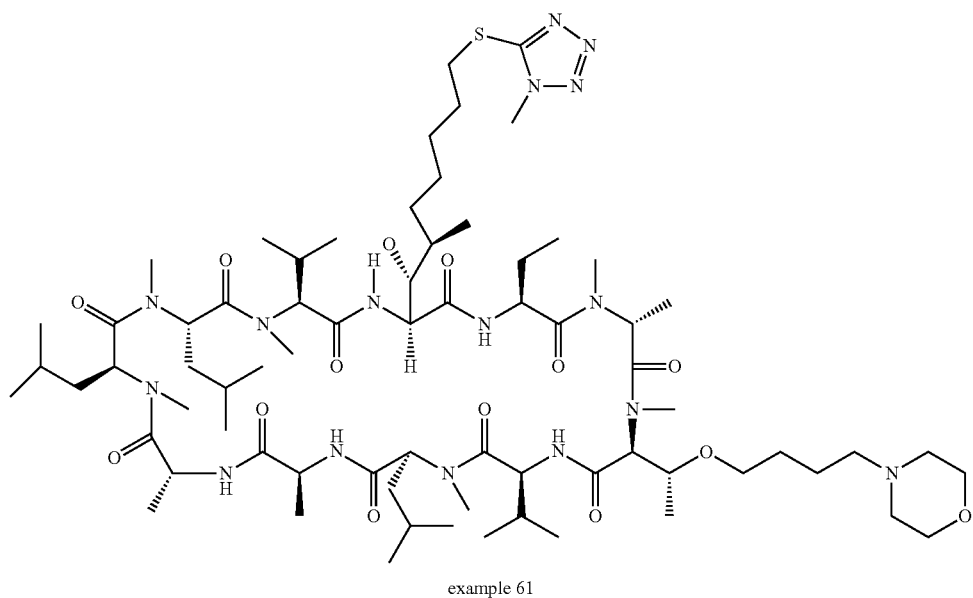

example 61

A mixture of compound 5 (46.8 mg, 0.032 mmol) and 1-methyl-5-mercaptoterazole sodium (13.3 mg, 0.0963 mmol) in dry DMF (0.4 mL) was heated at 60° C. for 2 hrs. After cooling to room temperature, the reaction was diluted with ethyl acetate (15 mL), washed with saturated aqueous NaHCO$_3$ sol'n (5 mL), H$_2$O (3×5 mL), brine (5 mL), dried over Na$_2$SO$_4$, filtered, evaporated to dryness. The residue was purified by preparative HPLC [HPLC condition: mobile phase A-20 mM NH$_4$HCO$_3$ in H$_2$O (HPLC grade); mobile phase B-acetonitrile (HPLC grade); Luna column (preheated at 55° C.), flow rate: 20 mL/min; 50-95% B for 40 min.] to give the pure title compound of example 61 (25 mg) as a white cotton after lyophilization; MS: (ESI) m/z (M+H) 1476.48, (M+Na) 1498.53.

Example 62

Compound of formula IV: A is

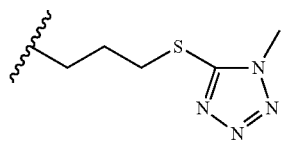 [SMILES: *CCCSc1nnnn1C]

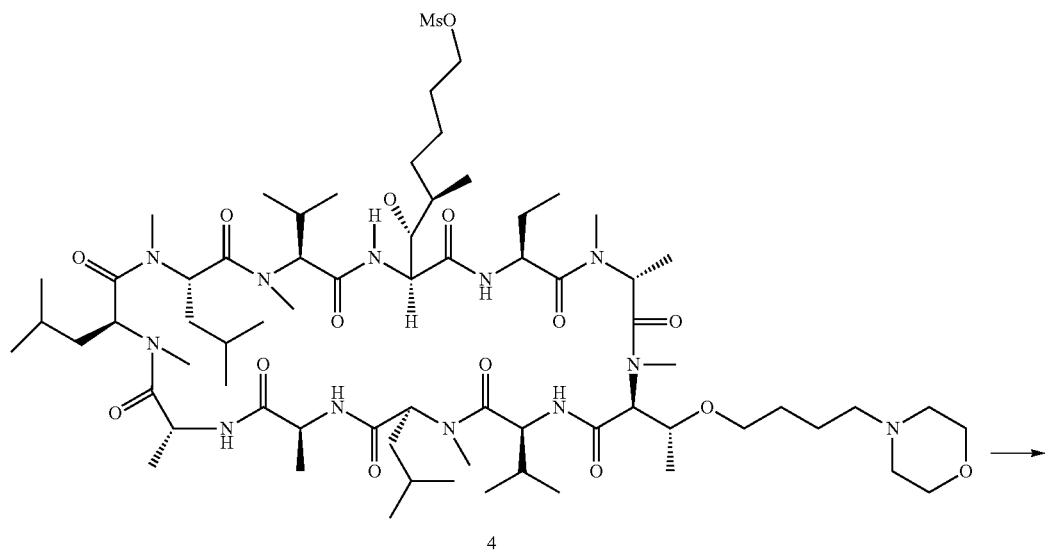

4

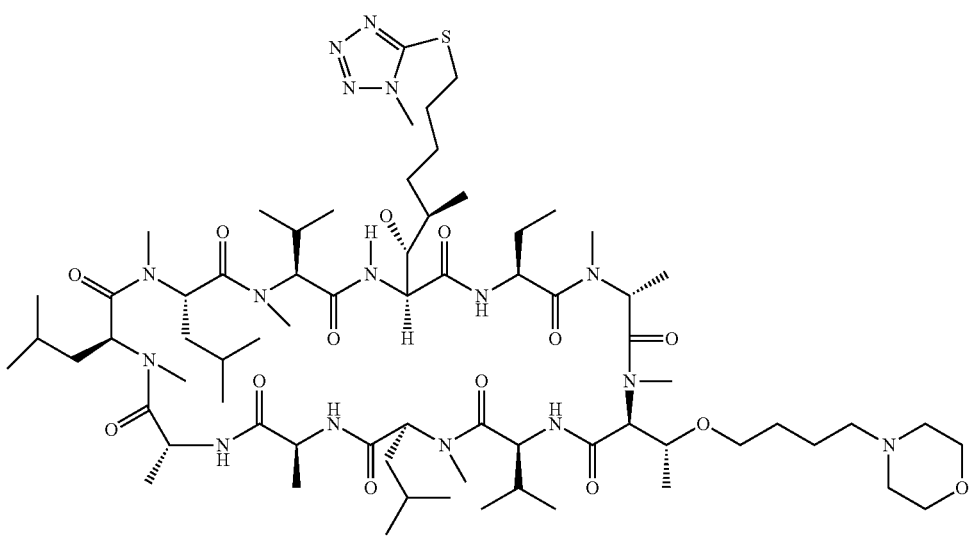

example 62

A mixture of compound 4 (42 mg, 0.0291 mmol) and 1-methyl-5-mercaptoterazole sodium (12 mg, 0.0873 mmol) in dry DMF (0.4 mL) was heated at 60° C. for 2 hrs and 65° C. for 30 min. After cooling to room temperature, the reaction was diluted with ethyl acetate (15 mL), washed with saturated aqueous $NaHCO_3$ sol'n (5 mL), $H_2O$ (3×5 mL), brine (5 mL), dried over $Na_2SO_4$, filtered, evaporated to dryness. The residue was purified by preparative HPLC [HPLC condition: mobile phase A-20 mM $NH_4HCO_3$ in $H_2O$ (HPLC grade); mobile phase B-acetonitrile (HPLC grade); Luna column (pre-heated at 55° C.), flow rate: 20 mL/min; 50-95% B for 40 min.] to give the pure title compound of example 62 (25 mg) as a white cotton after lyophilization; MS: (ESI) m/z (M+H) 1462.70, (M+Na) 1484.70.

Example 63

Compound of formula IV: A is

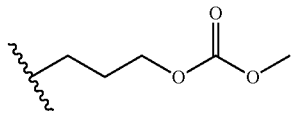 [SMILES: *CCCOC(=O)OC]

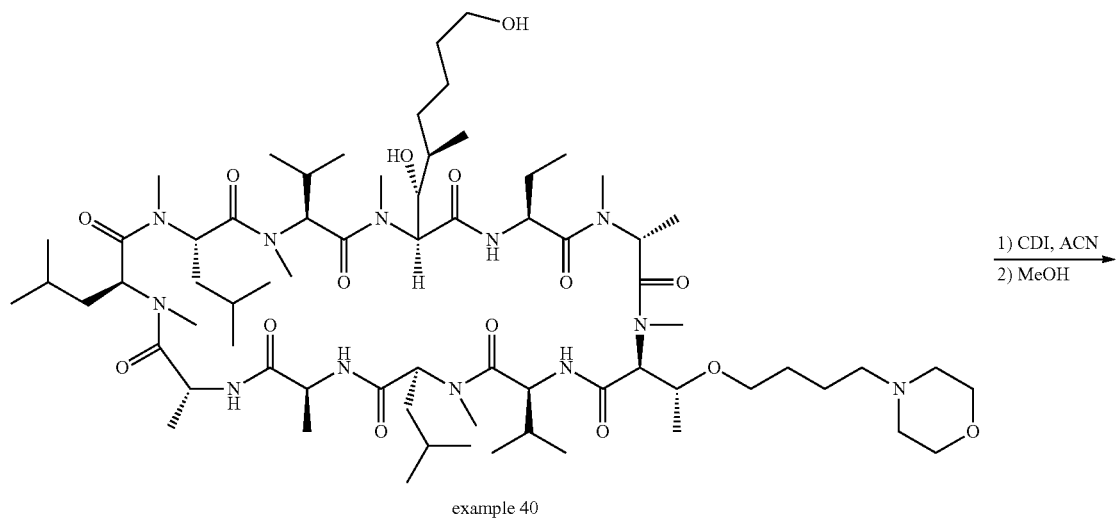
example 40
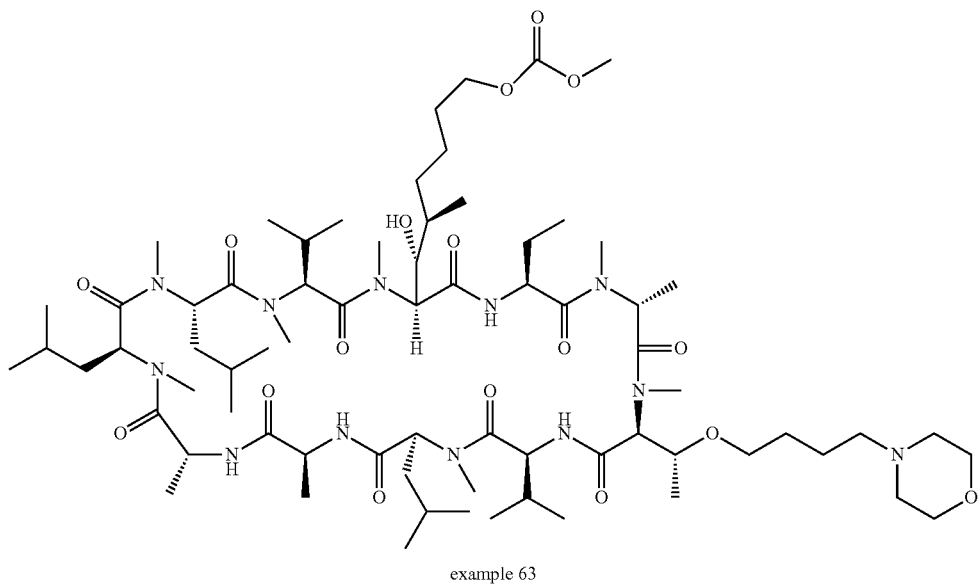
example 63
The compound of example 63 was prepared from example 40 using the same procedure as described in the preparation of the compounds of example 45. MS-ESI (m/z): 1422.02 (M+H)$^+$.
Example 64
Compound of formula IV: A is
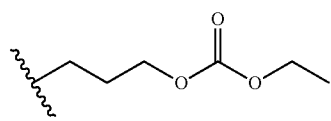 [SMILES: *CCCOC(=O)OCC]

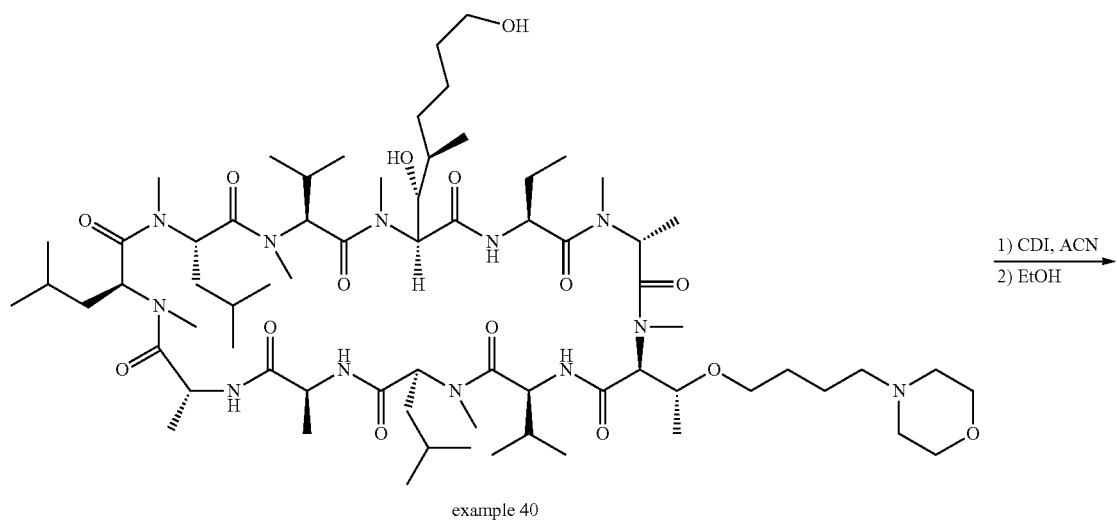
example 40
1) CDI, ACN
2) EtOH
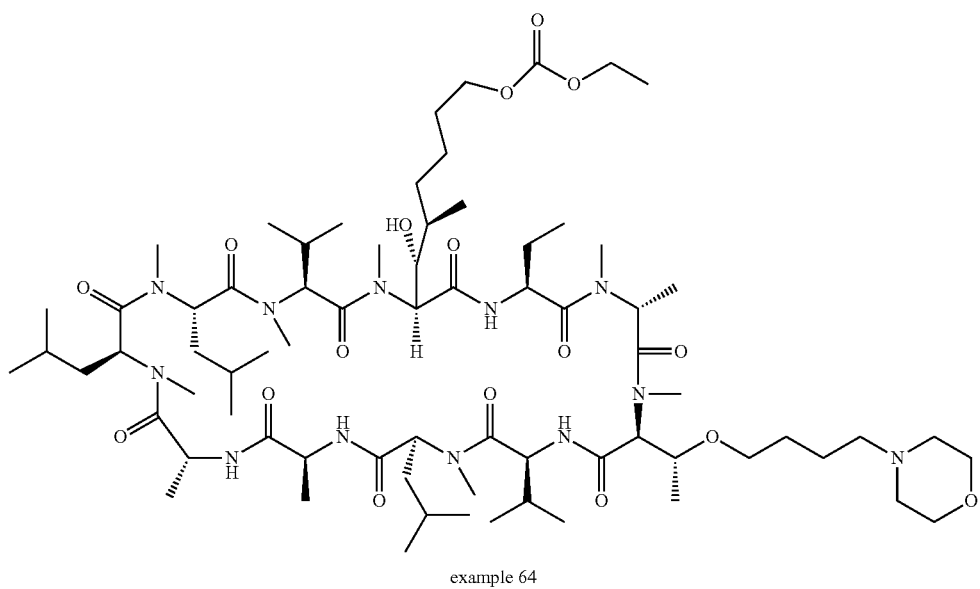
example 64
The compound of example 64 was prepared from example 40 using the same procedure as described in the preparation of the compounds of example 45. MS-ESI (m/z): 1436.02 (M+H)⁺.
Example 65
Compound of formula IV: A is
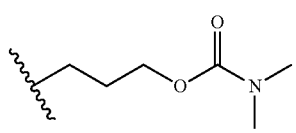 [SMILES: *CCCOC(=O)N(C)C]

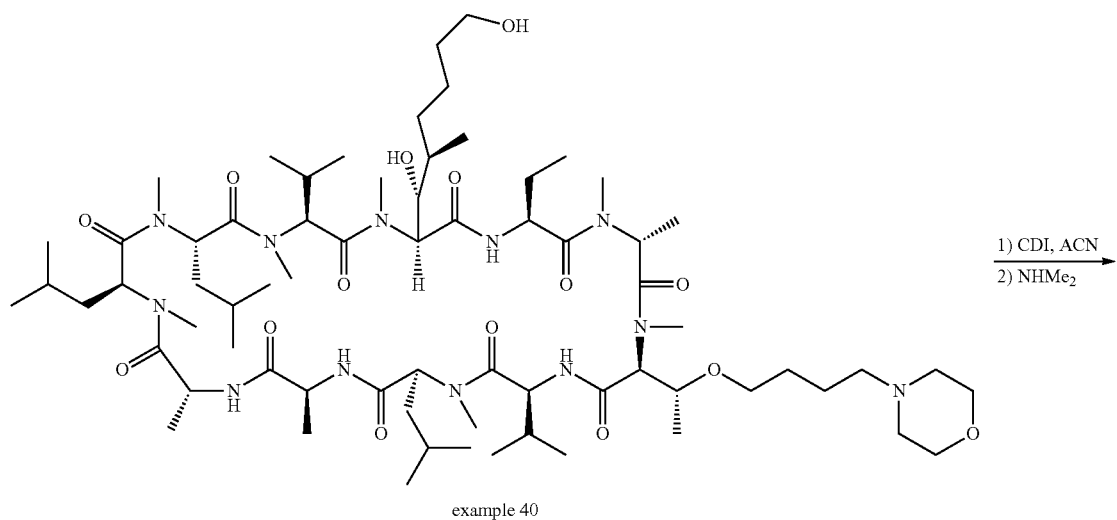
example 40
1) CDI, ACN
2) NHMe₂
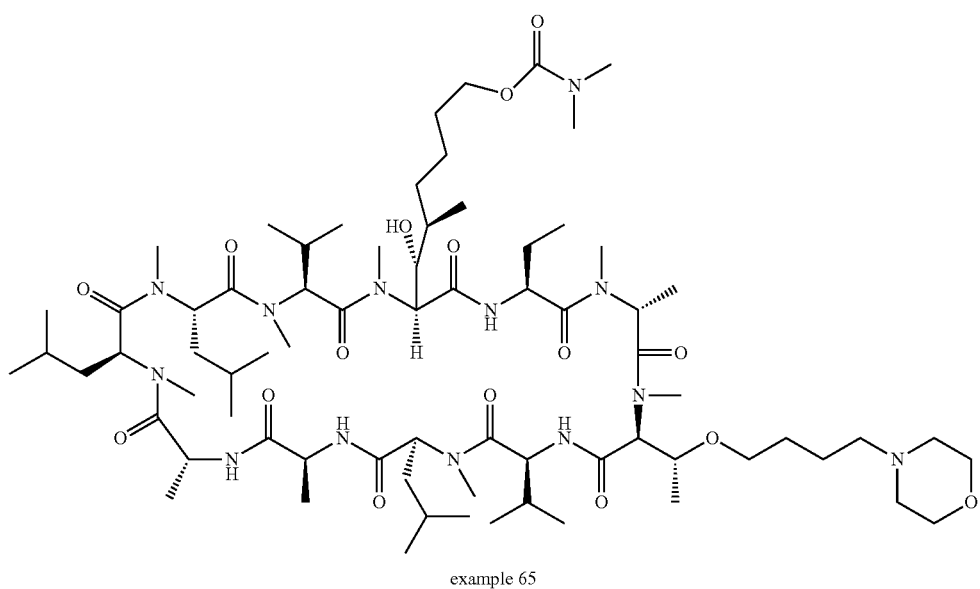
example 65
The compound of example 65 was prepared from example 40 using the same procedure as described in the preparation of the compounds of example 45. MS-ESI (m/z): 1435.02 (M+H)⁺.
Example 66
Compound of formula IV: A is
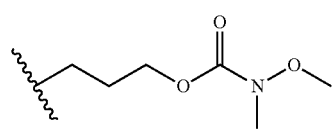 [SMILES: *CCCOC(=O)N(C)OC]

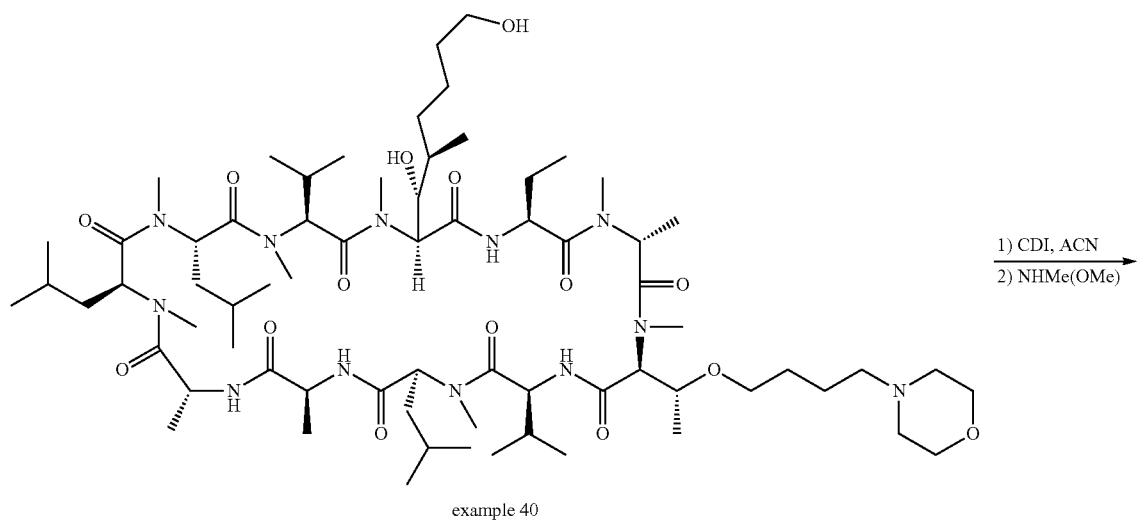
example 40
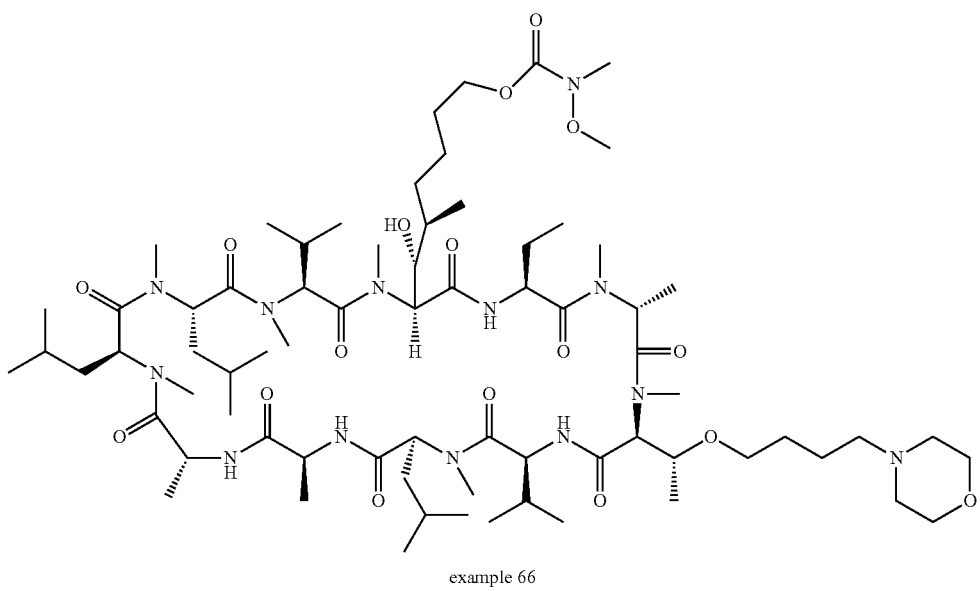
example 66
The compound of example 66 was prepared from example 40 using the same procedure as described in the preparation of the compounds of example 45. MS-ESI (m/z): 1451.02 (M+H)⁺.
Example 67
Compound of formula IV: A is
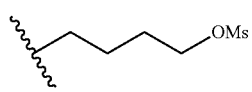 [SMILES: *CCCCOS(C)(=O)=O]

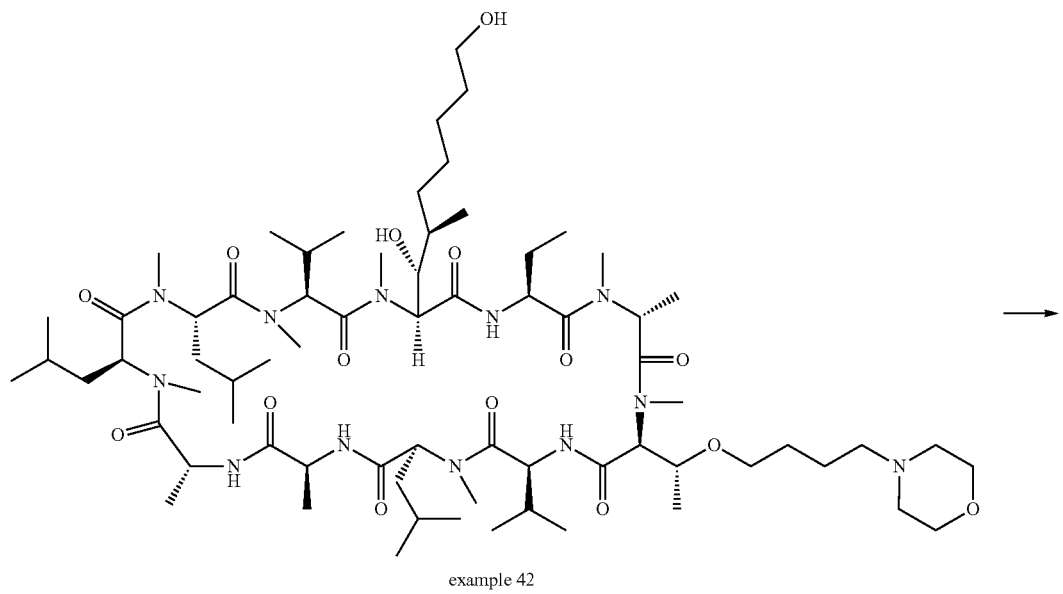

example 42

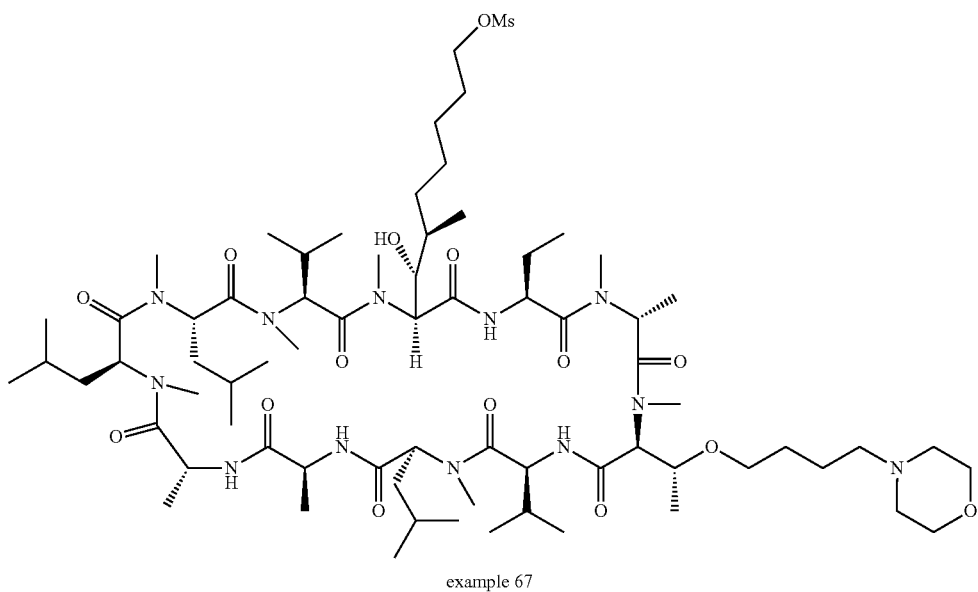

example 67

A mixture of compound of example 42 (411.7 mg, 0.2988 mmol) and triethylamine (0.17 mL, 1.2 mmol) in dichloromethane (5 mL) was cooled to 0° C., treated with methanesulfonyl chloride (0.046 mL, 0.60 mmol) at 0° C. and stirred for 30 min. The reaction was diluted with dichloromethane (20 mL), washed with saturated aqueous NaHCO$_3$ sol'n (5 mL), brine (5 mL), dried over Na$_2$SO$_4$, filtered, evaporated to dryness. The residue was further dried on the vacuum pump to give the intermediate compound of example 67 as a white foam (442 mg); MS: (ESI) m/z (M+H) 1456.40, (M+Na) 1478.42.

Example 68

Compound of formula IV: A is

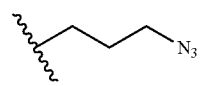 [SMILES: *CCCN=[N+]=[N-]]

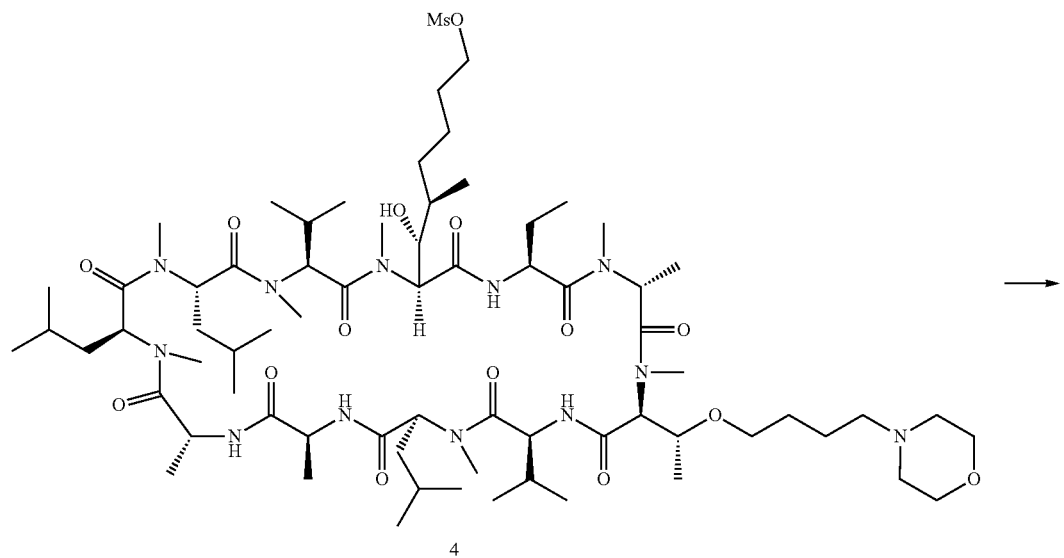
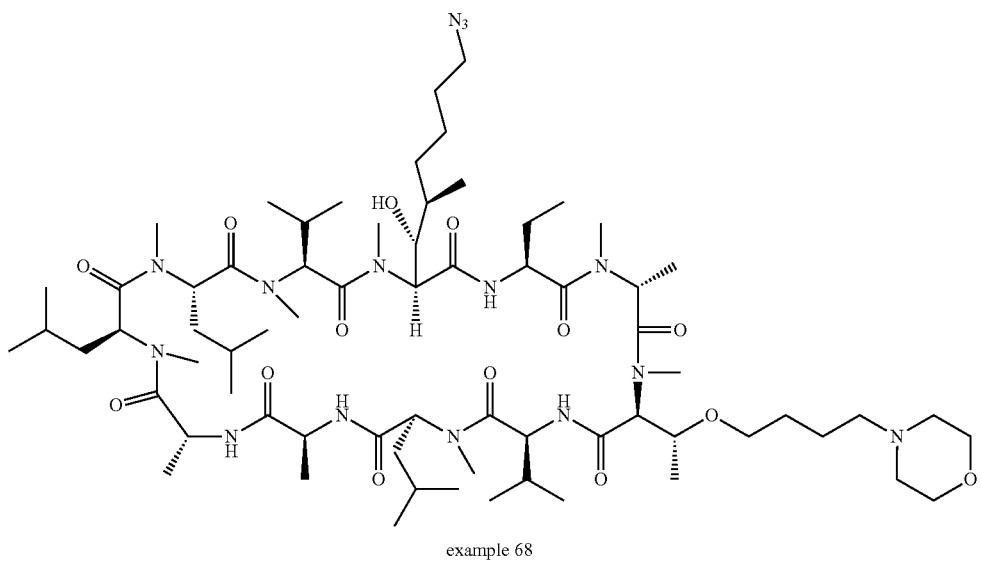
example 68
The compound of example 68 was prepared from compound 4 using the same procedure as described in the preparation of the compounds of example 20. MS-ESI (m/z): 1389.02 (M+H)⁺.
Example 69
Compound of formula IV: A is
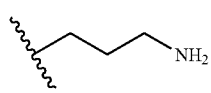

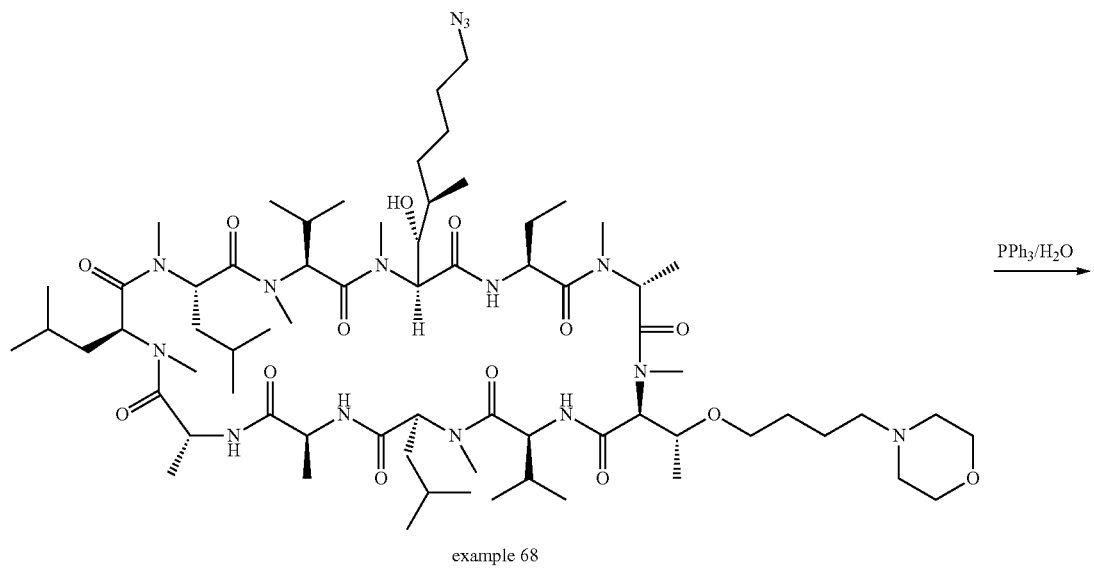

example 68

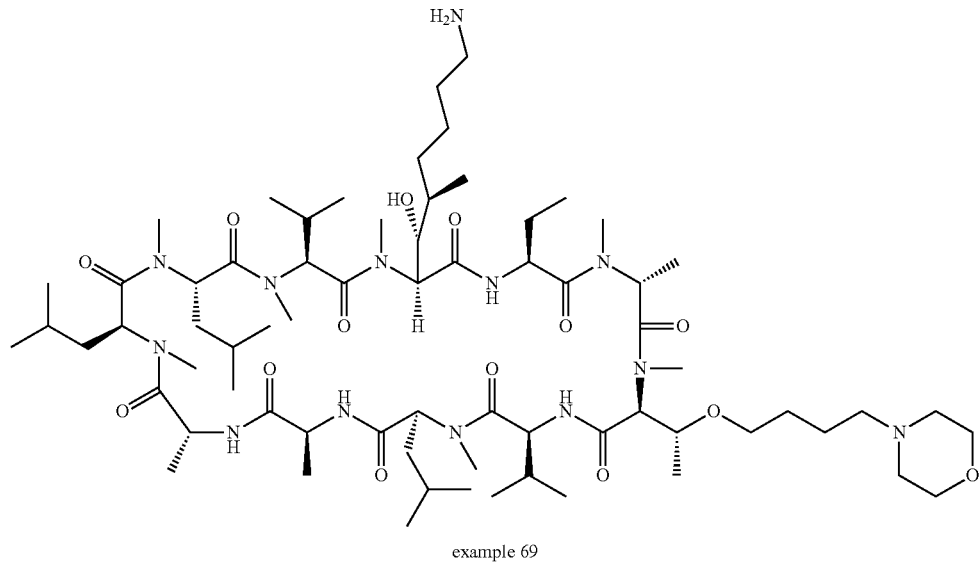

example 69

A mixture of azide compound of example 68 (119 mg, 0.0856 mmol) and triphenylphosphine (67.3 mg) in dry THF was heated at 60° C. for 100 min. After evaporation, the residue was purified by silica gel column chromatography with 0~20% methanol containing 1N—NH$_3$ in dichloromethane to give the title compound of example 69 (95.7 mg) as a pale yellow foam; MS-ESI (m/z): 1363.02 (M+H)$^+$.

Example 70

Compound of formula IV: A is

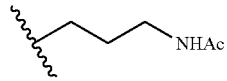

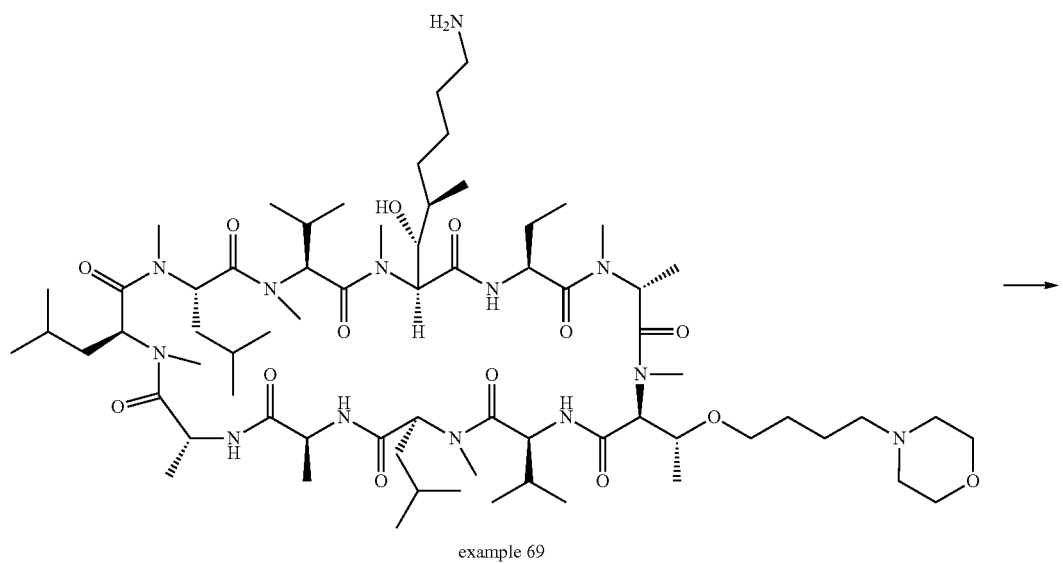
example 69
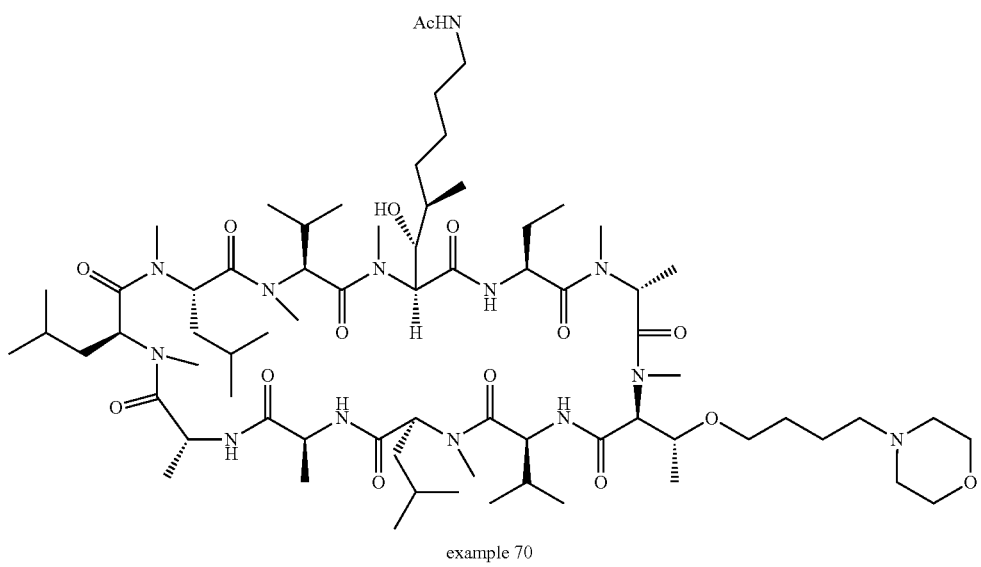
example 70
The compound example 70 was synthesized from the compound of example 69 (14.2 mg, 0.0104 mmol), acetic anhydride (1 eq.) and triethylamine (2 eq.) in dichloromethane (0.4 mL). The crude material after work-up was purified by preparative HPLC to give the pure title compound (12.6 mg) as a white cotton after lyophilization; MS: (ESI) m/z (M+H) 1405.09, (M+Na) 1427.03.
Example 71
Compound of formula IV: A is
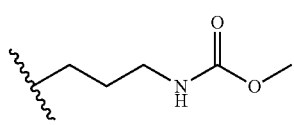 [SMILES: *CCCNC(=O)OC]

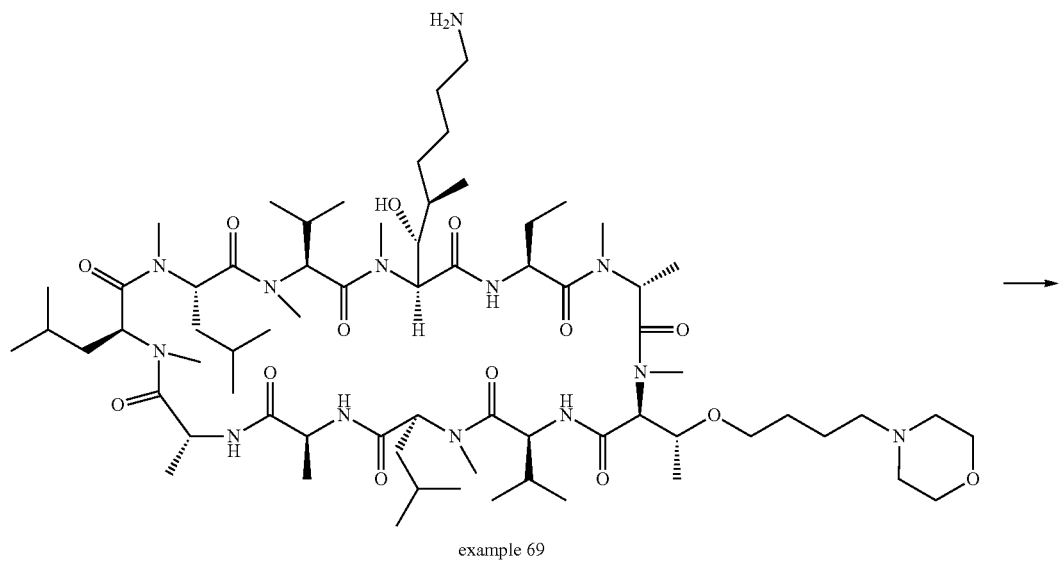
example 69
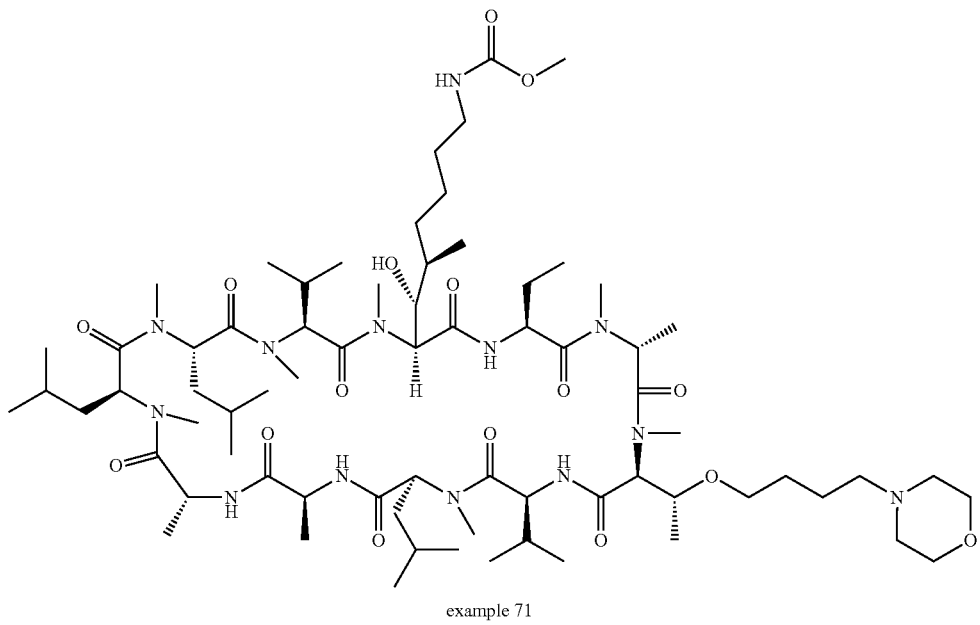
example 71
The compound of example 71 was prepared from compound of example 68 using the same procedure as described in the preparation of the compounds of example 71. MS-ESI (m/z): 1421.02 (M+H)$^+$.
Example 72
Compound of formula IV: A is
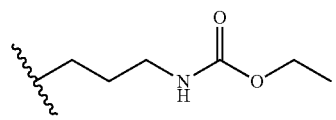 [SMILES: *CCCNC(=O)OCC]

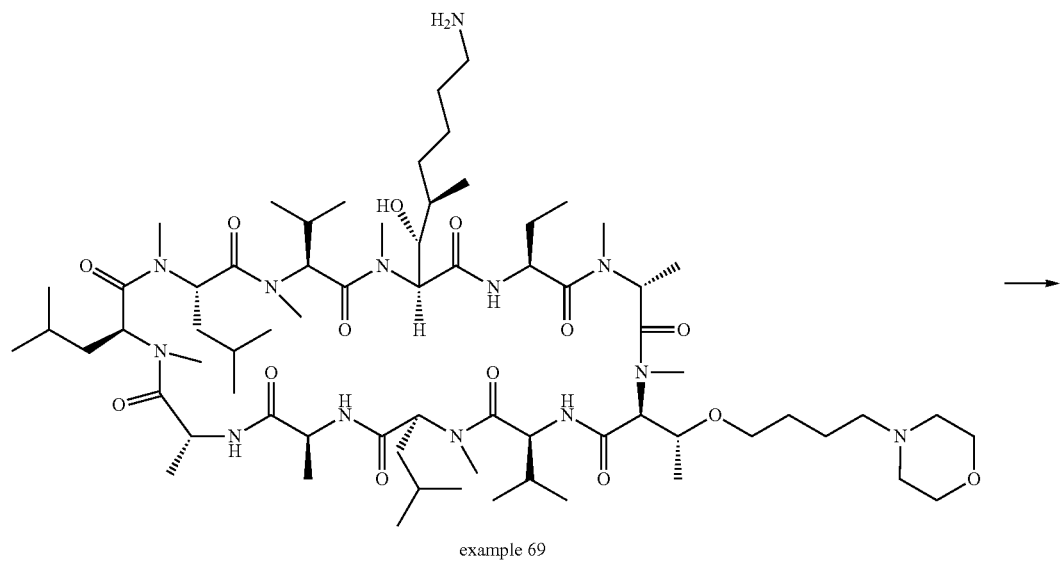
example 69
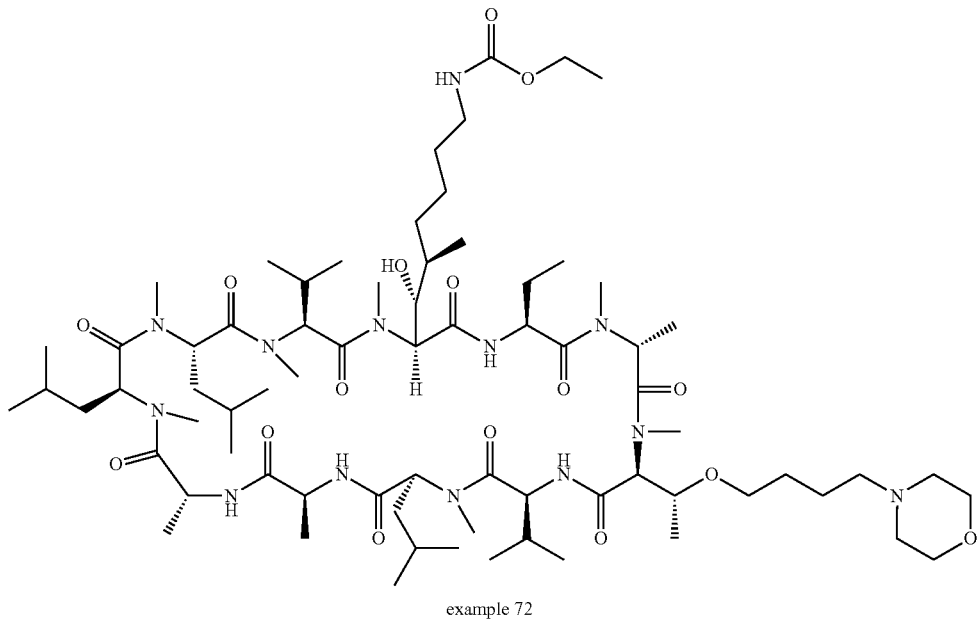
example 72
The compound of example 72 was prepared from compound of example 68 using the same procedure as described in the preparation of the compounds of example 71. MS-ESI (m/z): 1435.02 (M+H)$^+$.
Example 73
Compound of formula IV: A is
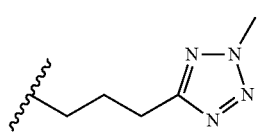 [SMILES: *CCCc1nnn(C)n1]

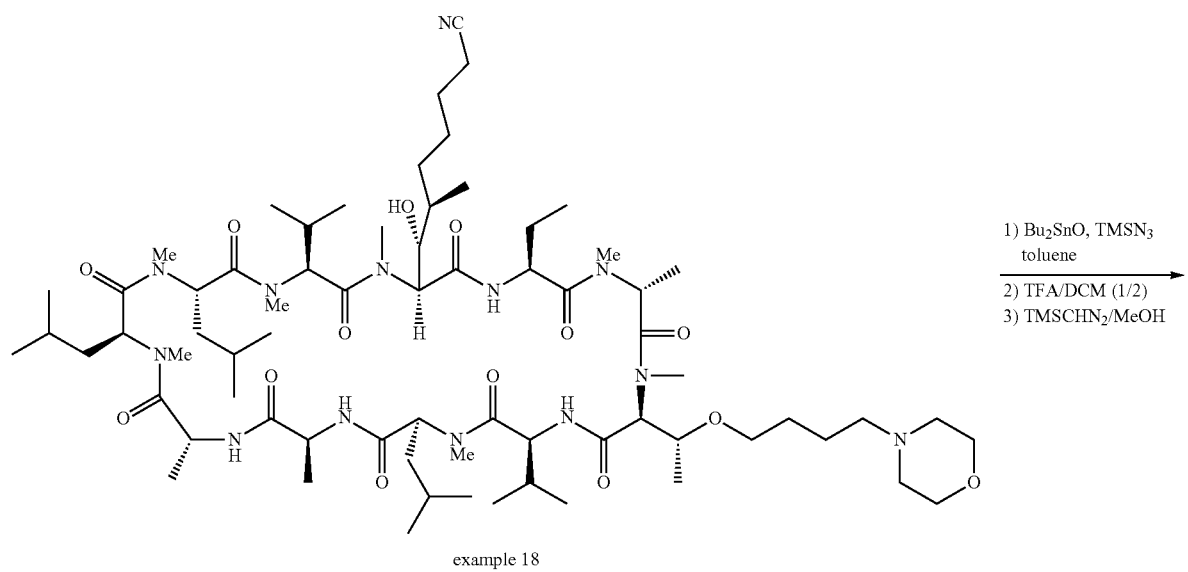
example 18
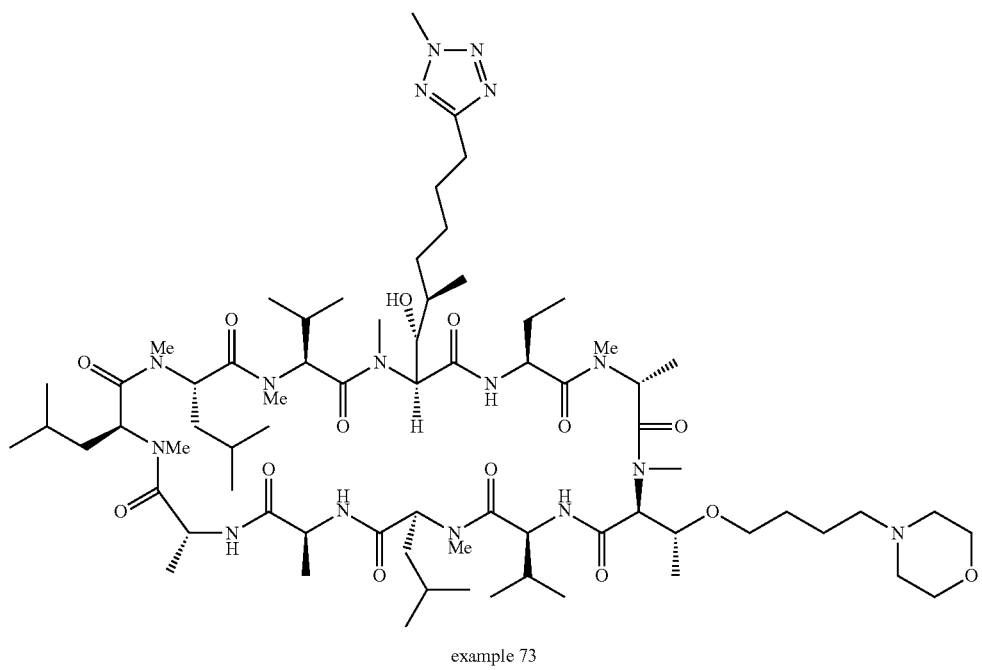
example 73
The compound of example 73 was prepared from compound of example 18 using the same procedure as described in the preparation of the compounds of example 58 and example 59. MS-ESI (m/z): 1430.02 (M+H)$^+$.
Example 74
Compound of formula IV: A is
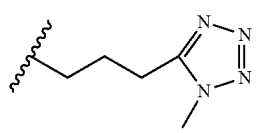 [SMILES: *CCCc1nnnn1C]

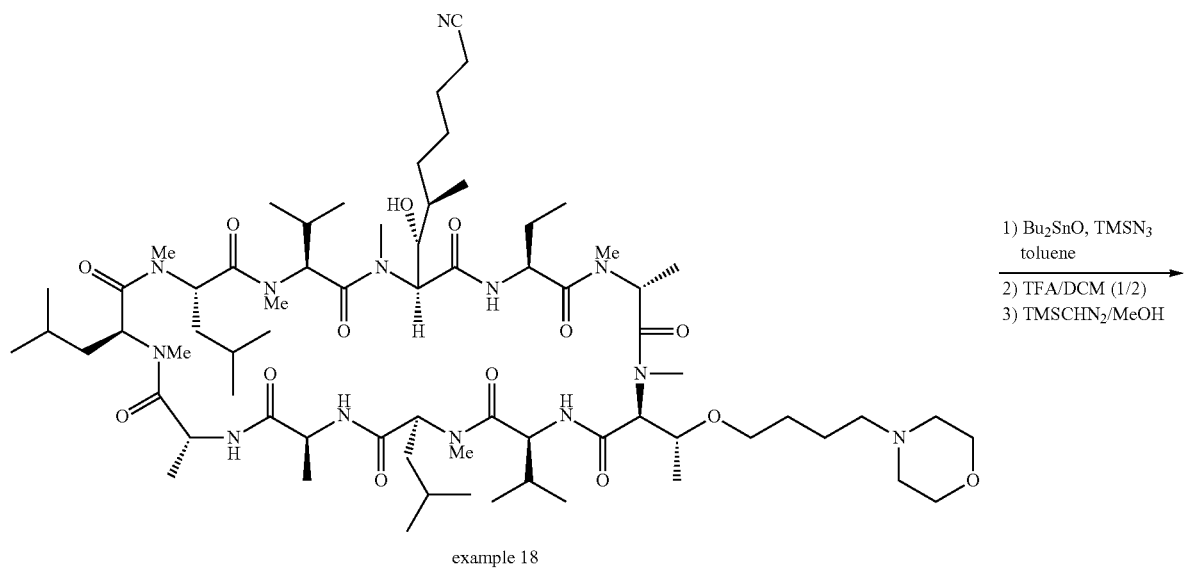
example 18
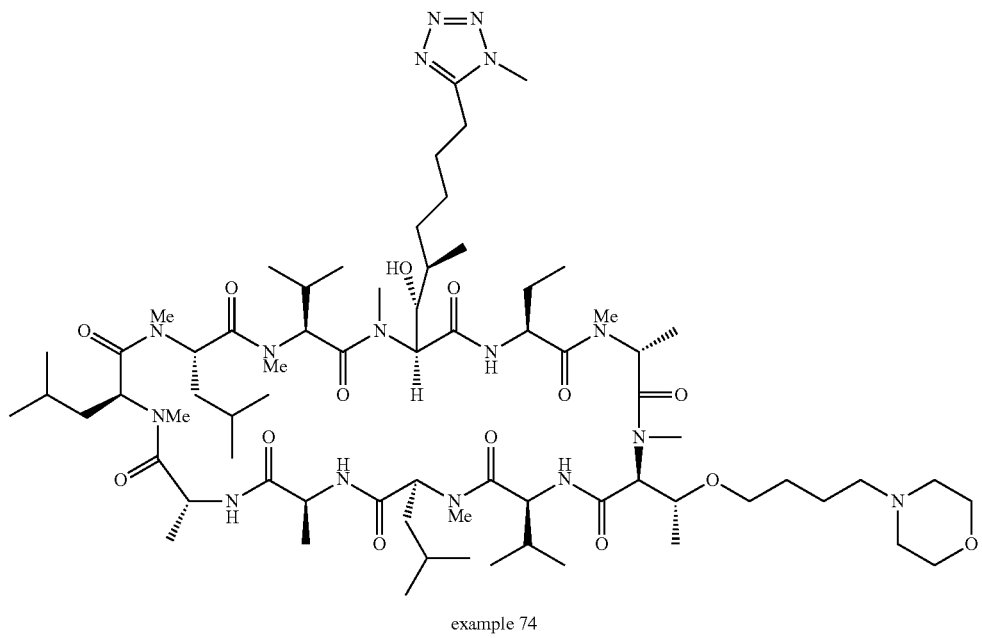
example 74
The compound of example 74 was prepared from compound of example 18 using the same procedure as described in the preparation of the compounds of example 58 and example 59. MS-ESI (m/z): 1430.02 (M+H)$^+$.
Example 75
Compound of formula IV: A is
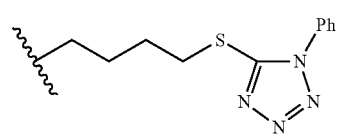

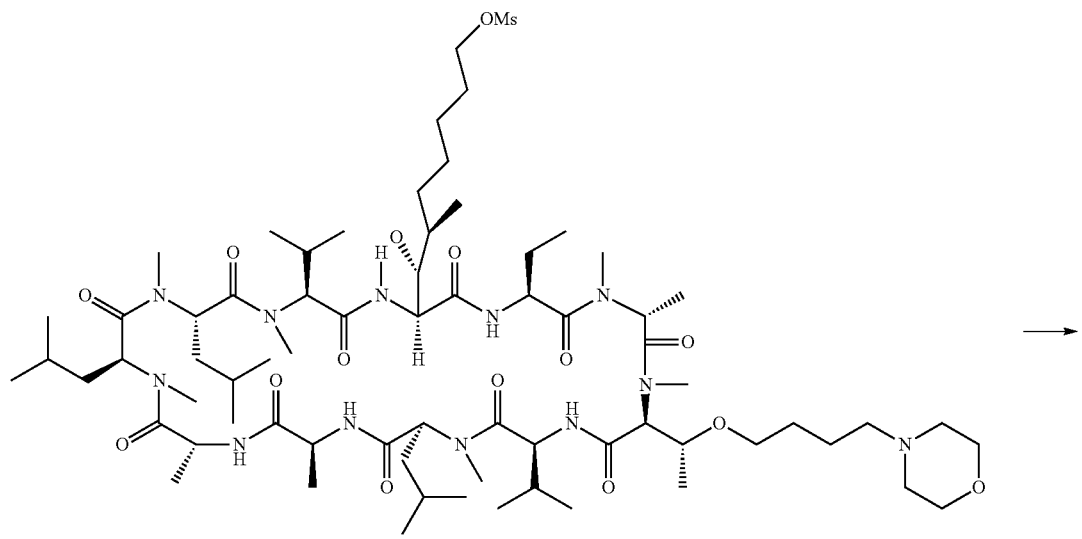
example 67
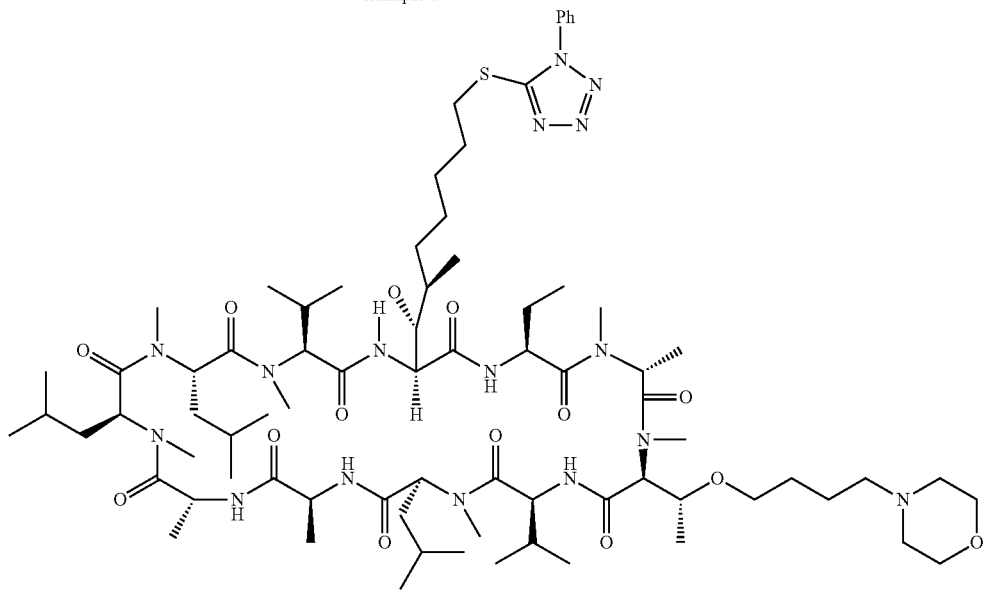
example 75
The compound of example 75 was prepared from compound of example 67 using the same procedure as described in the preparation of the compounds of example 61. MS: (ESI) m/z (M+H) 1538.04, (M+Na) 1560.08.
Example 76
Compound of formula IV: A is
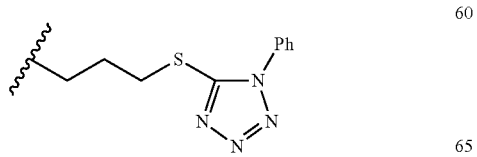

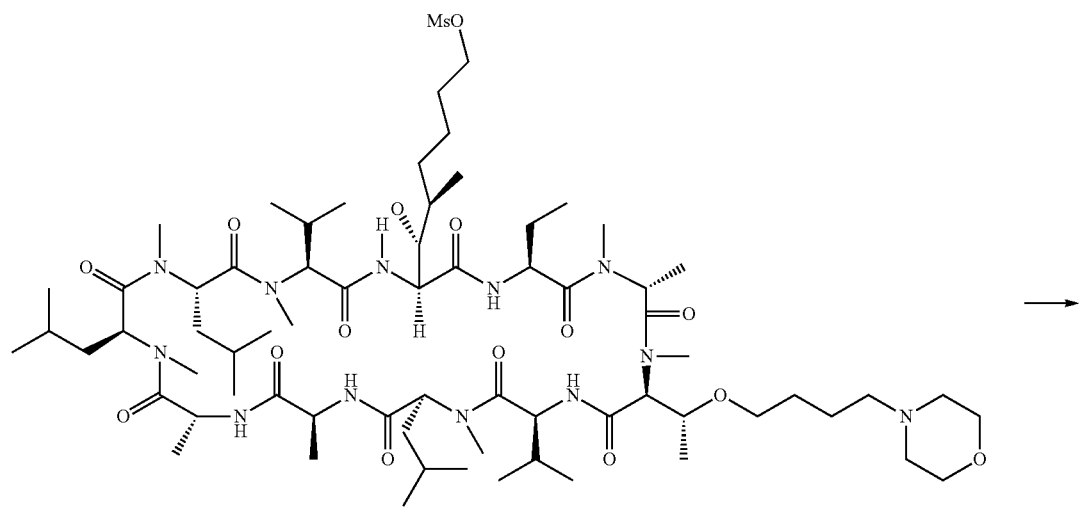
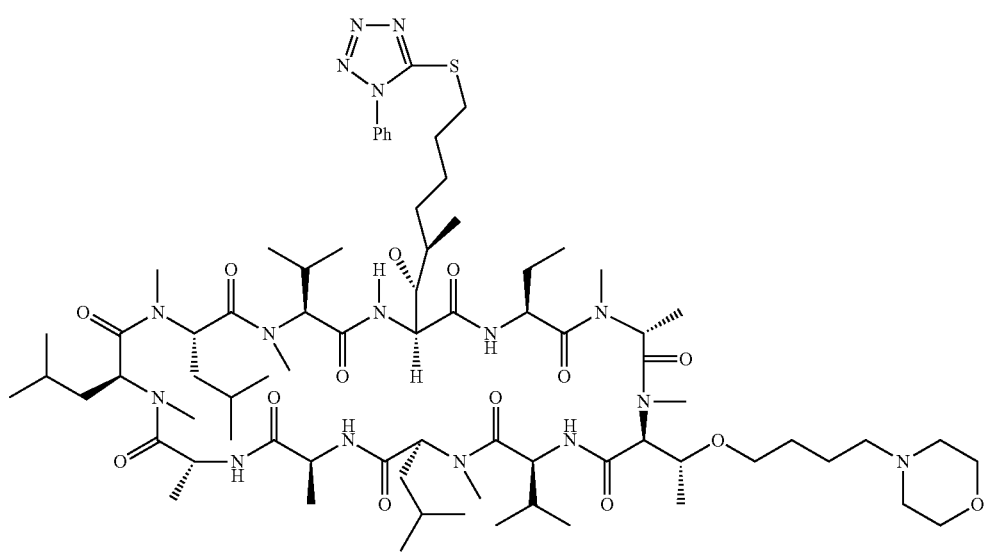
example 76
The compound of example 76 was prepared from compound 4 using the same procedure as described in the preparation of the compounds of example 58 and example 59. MS-ESI (m/z): 1524.02 (M+H)$^+$.
Example 77
Compound of formula IV: A is
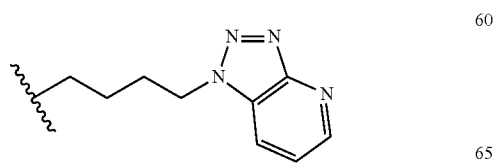

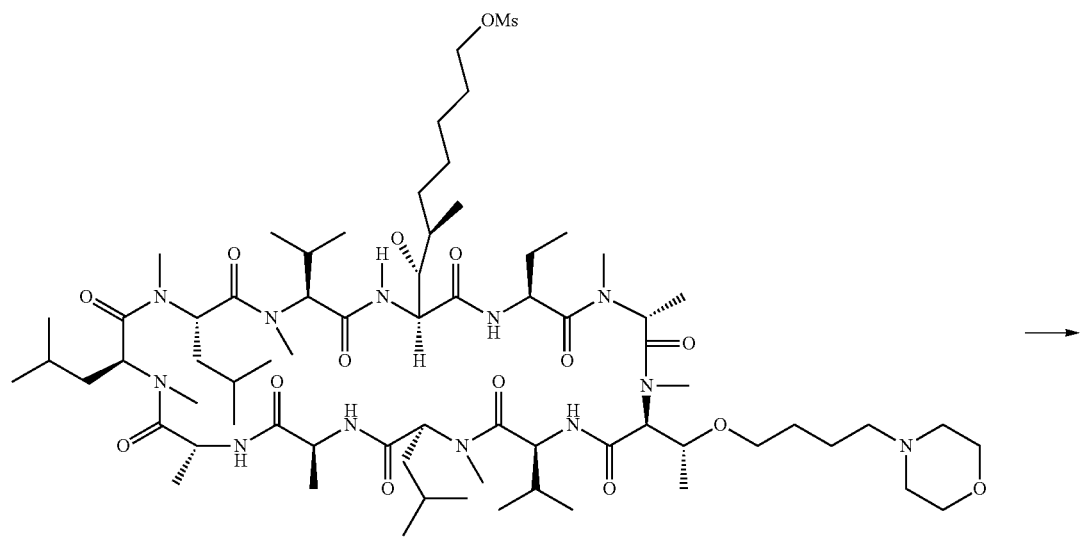
example 67
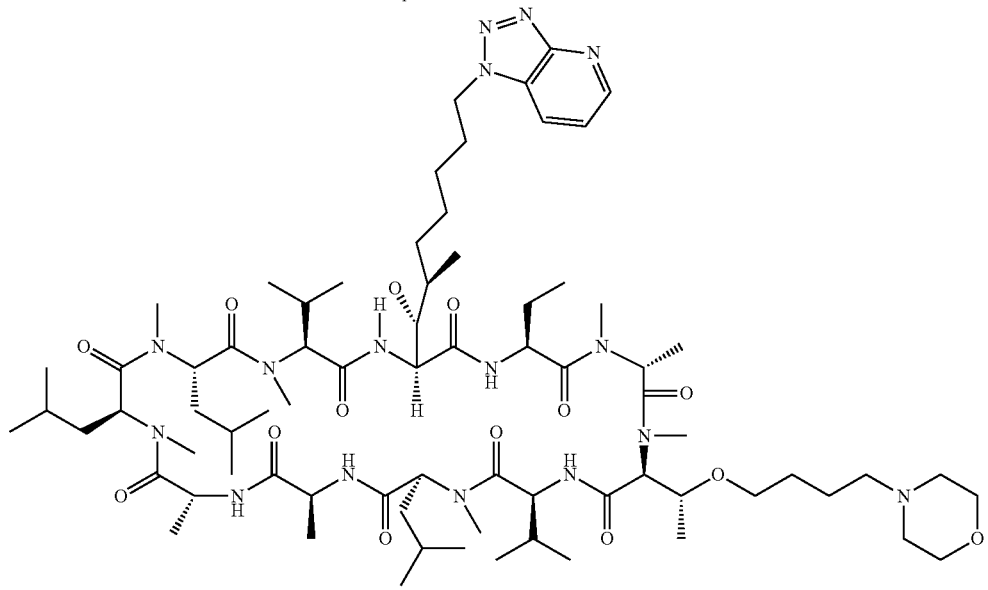
example 77
The compound of example 77 was prepared from compound of example 67 using the same procedure as described in the preparation of the compounds of example 61. MS-ESI (m/z): 1480.16 (M+H)$^+$.
Example 78
Compound of formula IV: A is
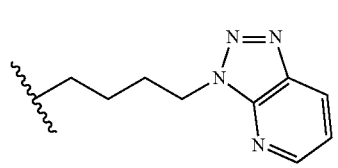 [SMILES: *CCCCn1nnc2cccnc21]

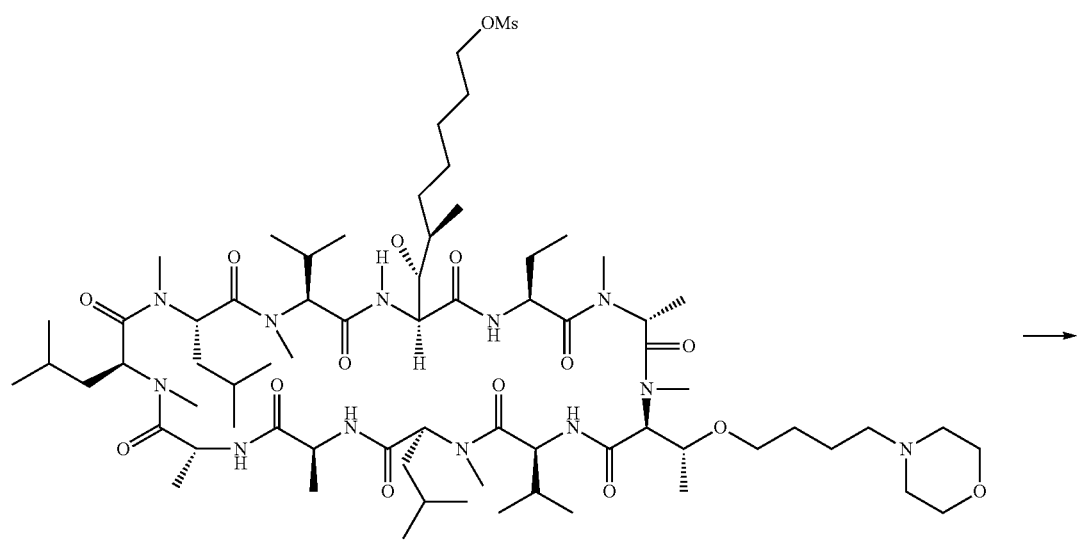
example 67
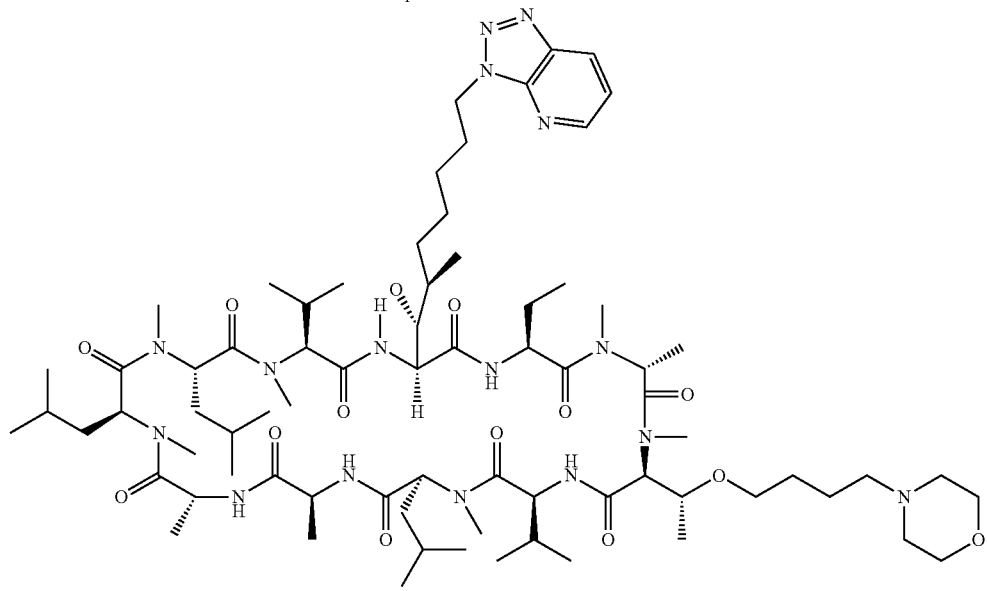
example 78
The compound of example 78 was prepared from compound of example 67 using the same procedure as described in the preparation of the compounds of example 61. MS-ESI (m/z): 1480.25 (M+H)⁺.
Example 79
Compound of formula IV: A is
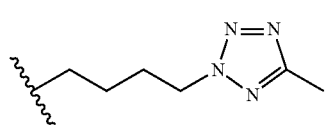 [SMILES: *CCCCn1nnc(C)n1]

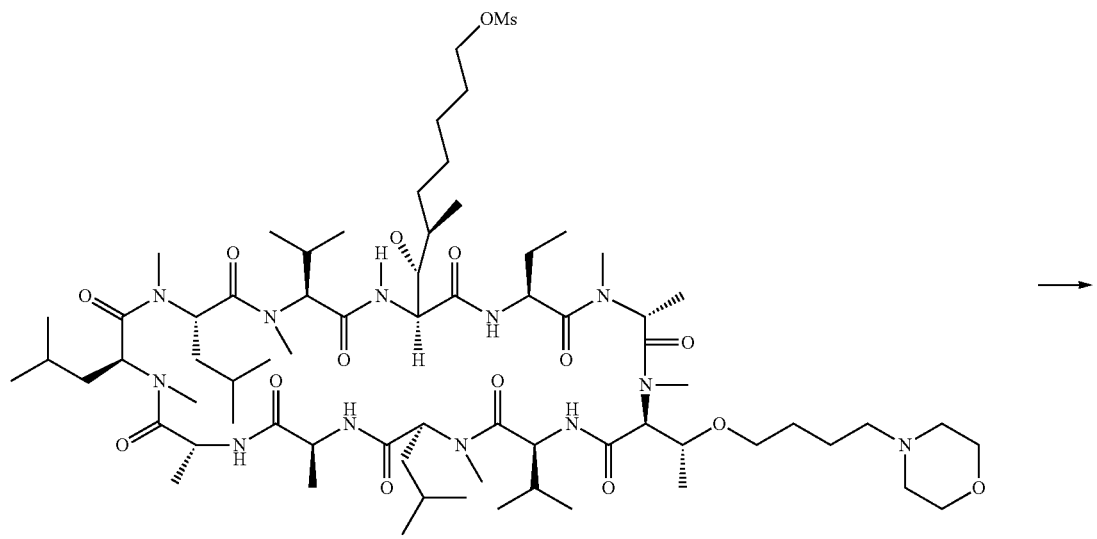
example 67
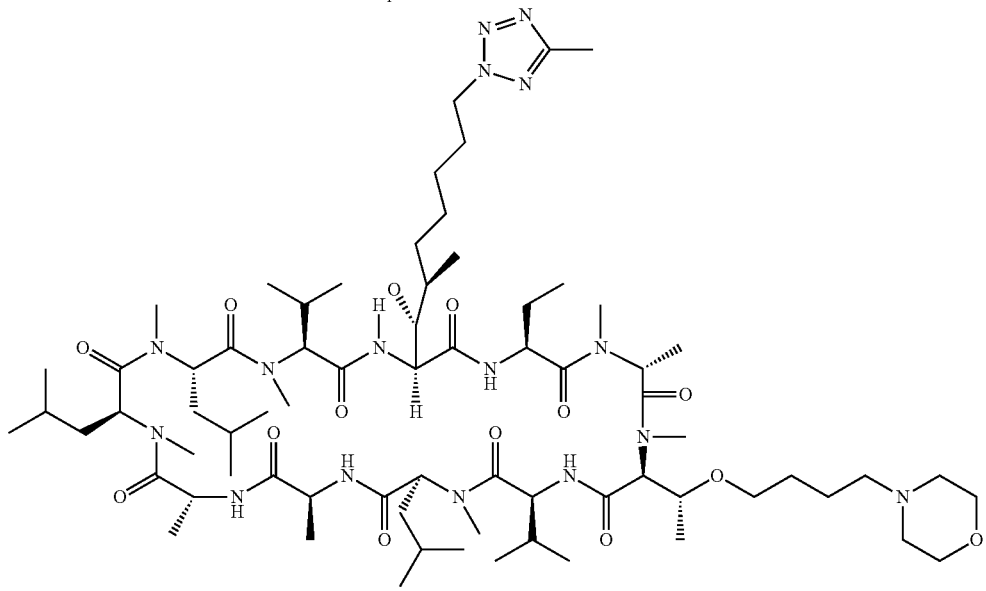
example 79
The compound of example 79 was prepared from compound of example 67 using the same procedure as described in the preparation of the compounds of example 61. MS-ESI (m/z): 1444.15 (M+H)$^+$.
Example 80
Compound of formula IV: A is
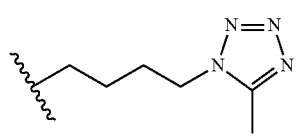 [SMILES: *CCCCn1nnnc1C]

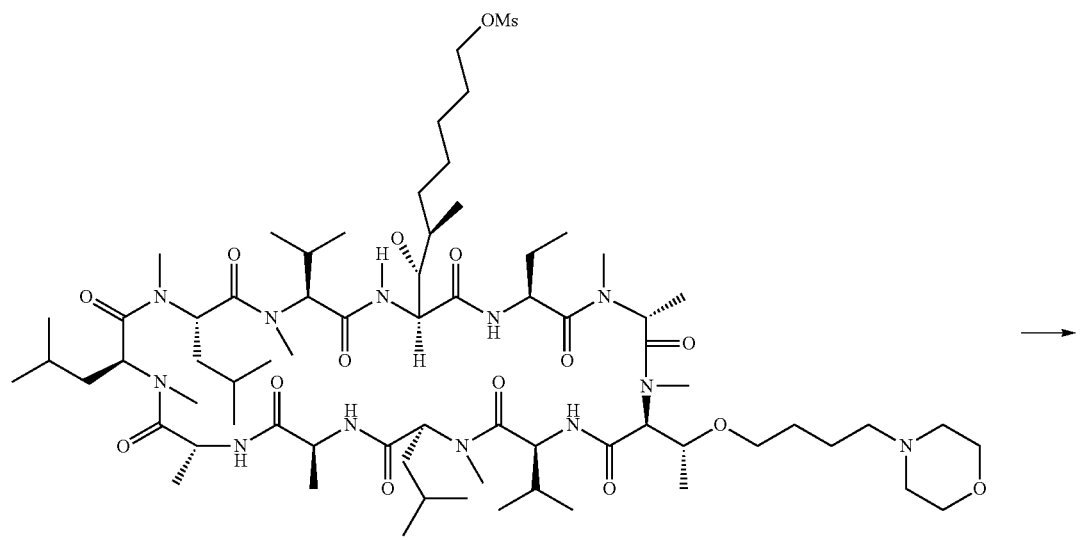
example 67
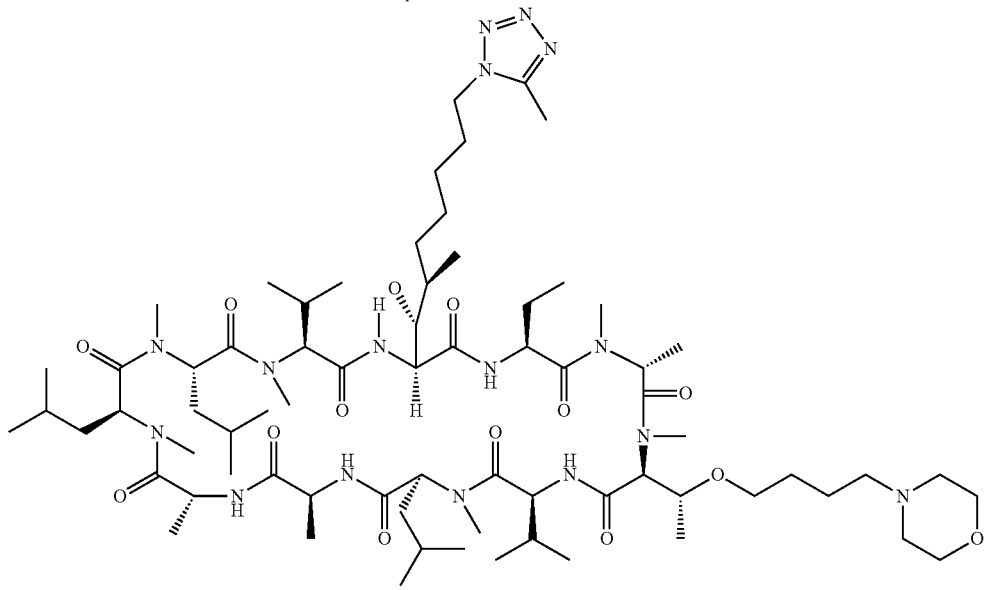
example 80
The compound of example 80 was prepared from compound of example 67 using the same procedure as described in the preparation of the compounds of example 61. MS-ESI (m/z): 1444.25 (M+H)⁺.
Example 81
Compound of formula IV: A is
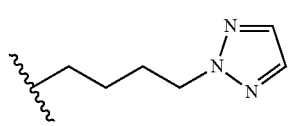 [SMILES: *CCCCn1nccn1]

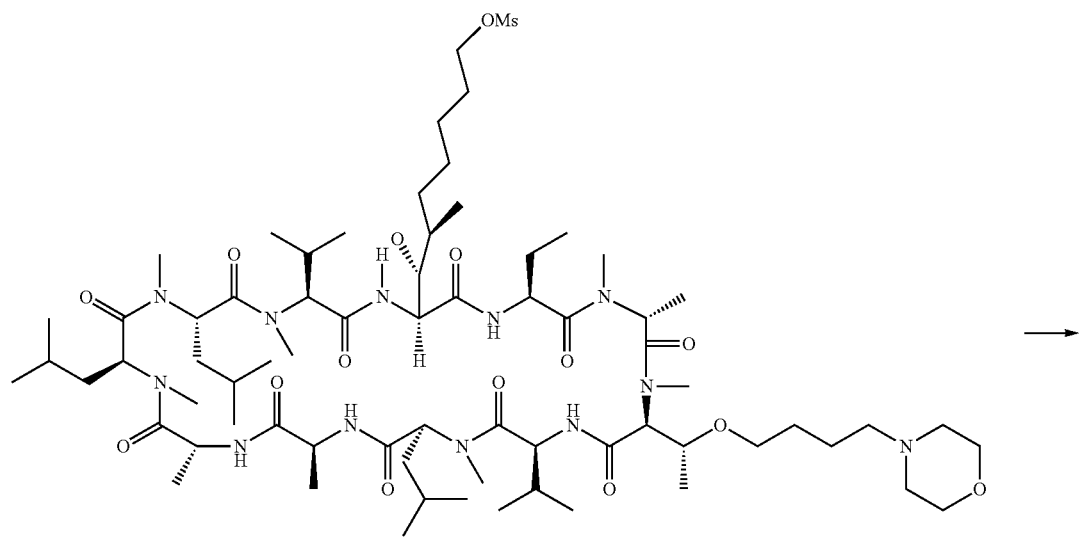
example 67
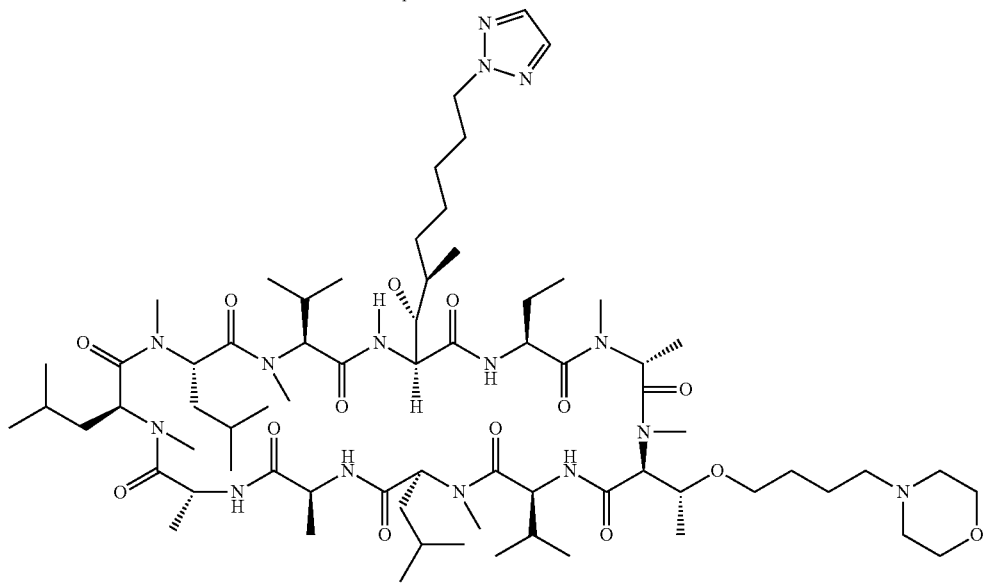
example 81
The compound of example 81 was prepared from compound of example 67 using the same procedure as described in the preparation of the compounds of example 61. MS-ESI (m/z): 1429.05 (M+H)$^+$.
Example 82
Compound of formula IV: A is
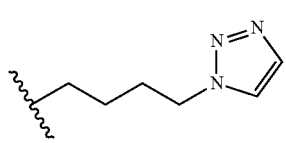 [SMILES: *CCCCn1ccnn1]

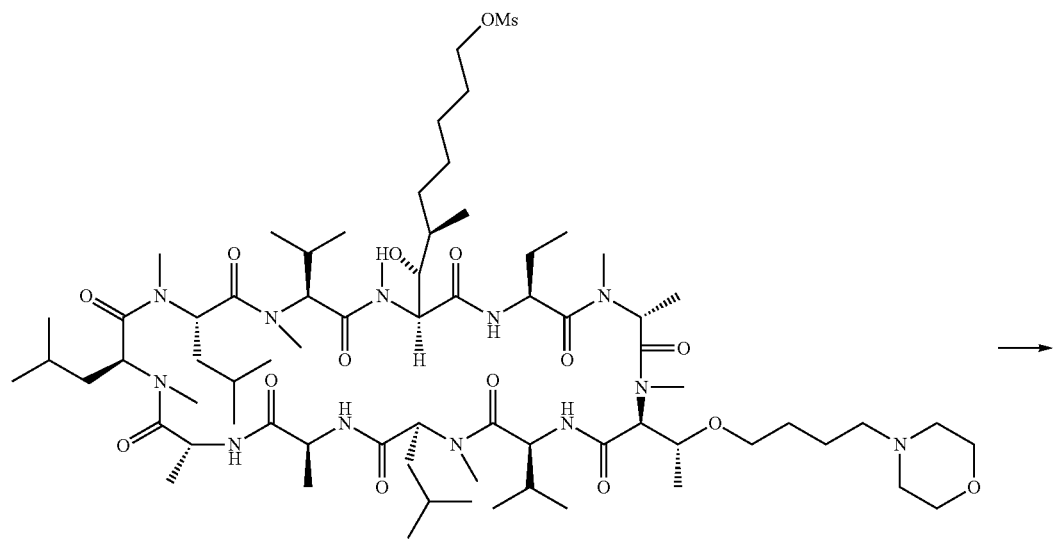
example 67
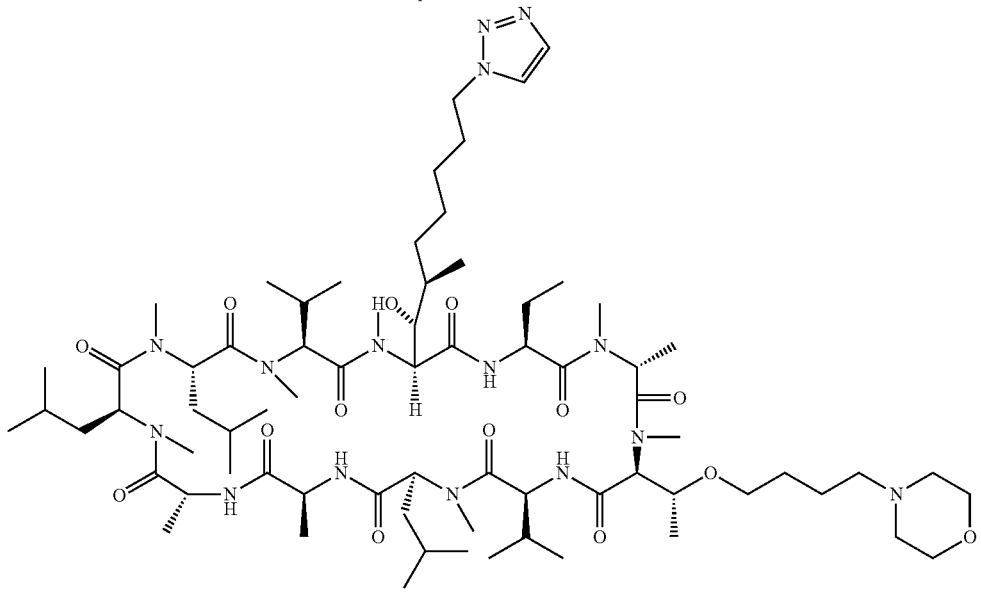
example 82
The compound of example 82 was prepared from compound of example 67 using the same procedure as described in the preparation of the compounds of example 61. MS-ESI (m/z): 1429.05 (M+H)$^+$.
Example 83
Compound of formula IV: A is
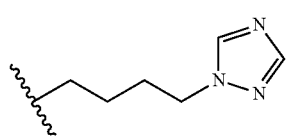 [SMILES: *CCCCn1cncn1]

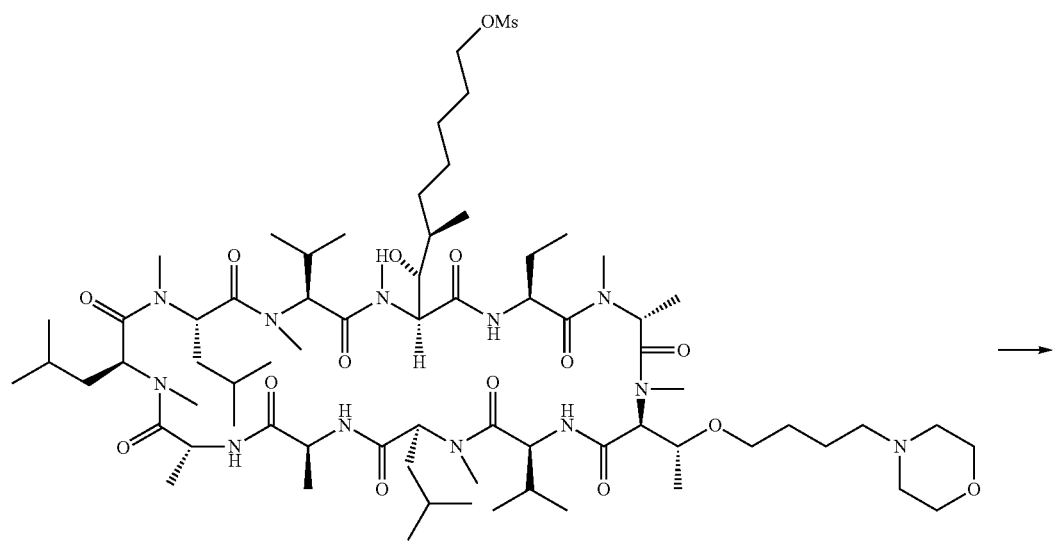
example 67
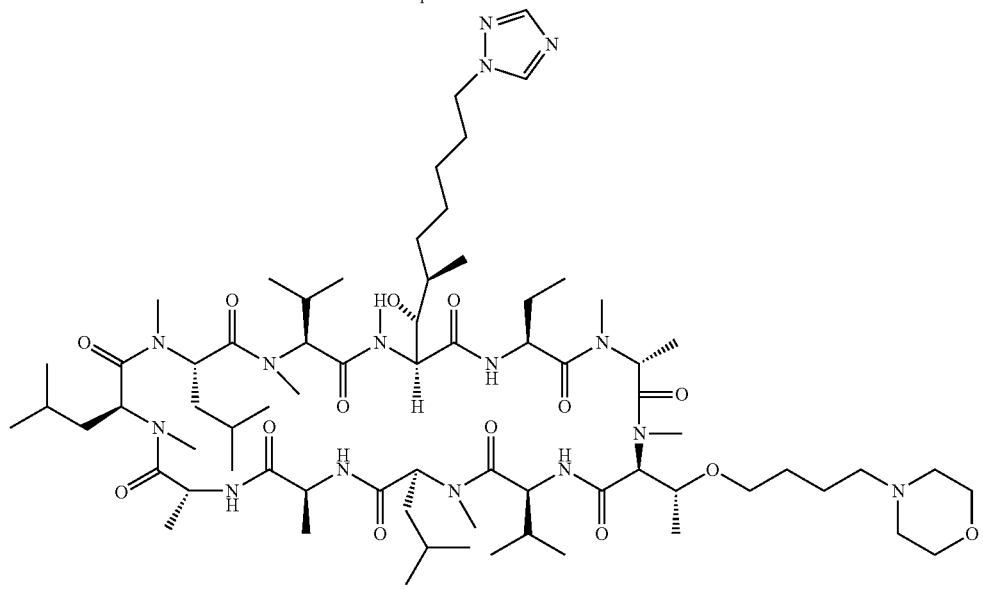
example 83
The compound of example 83 was prepared from compound of example 67 using the same procedure as described in the preparation of the compounds of example 61. MS-ESI (m/z): 1429.05 (M+H)$^+$.
Example 84
Compound of formula IV: A is
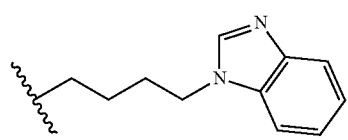 [SMILES: *CCCCn1cnc2ccccc21]

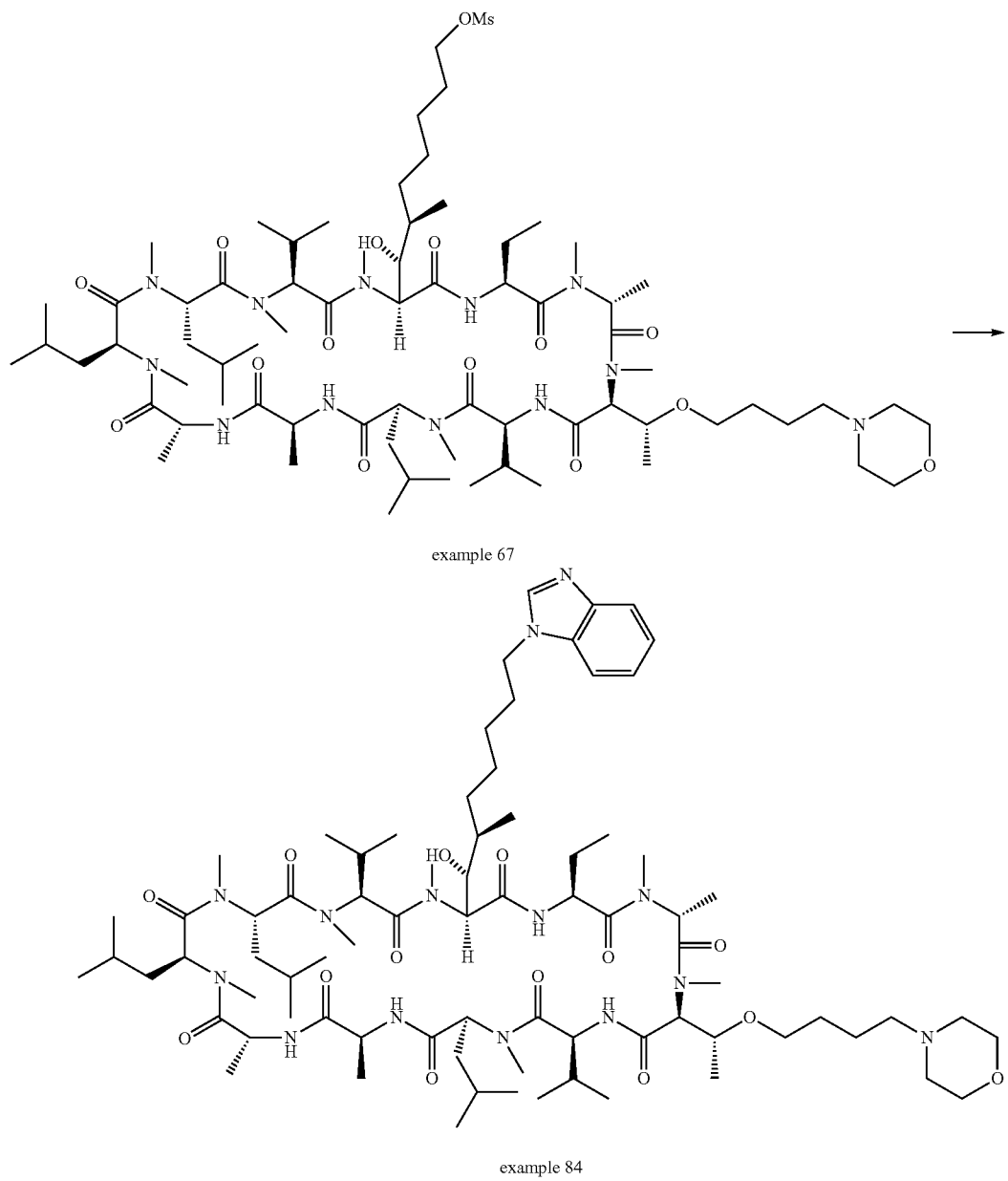
example 67
example 84
The compound of example 84 was prepared from compound of example 67 using the same procedure as described in the preparation of the compounds of example 61. MS-ESI (m/z): 1478.05 (M+H)$^+$.
Example 85
Compound of formula IV: A is
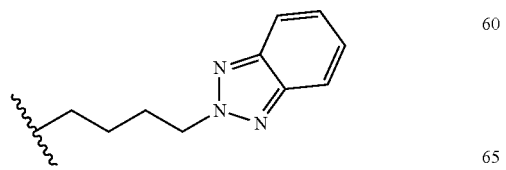

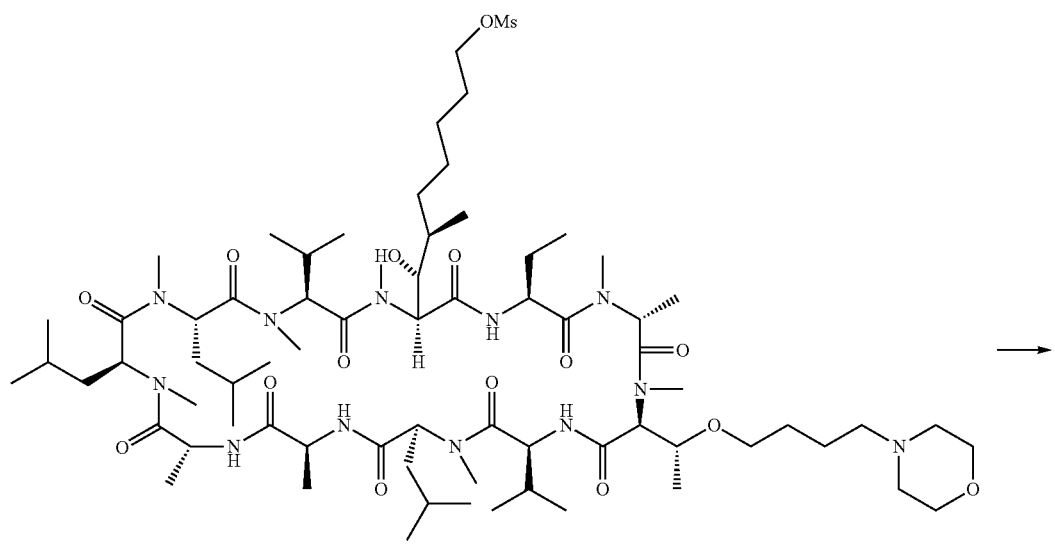
example 67
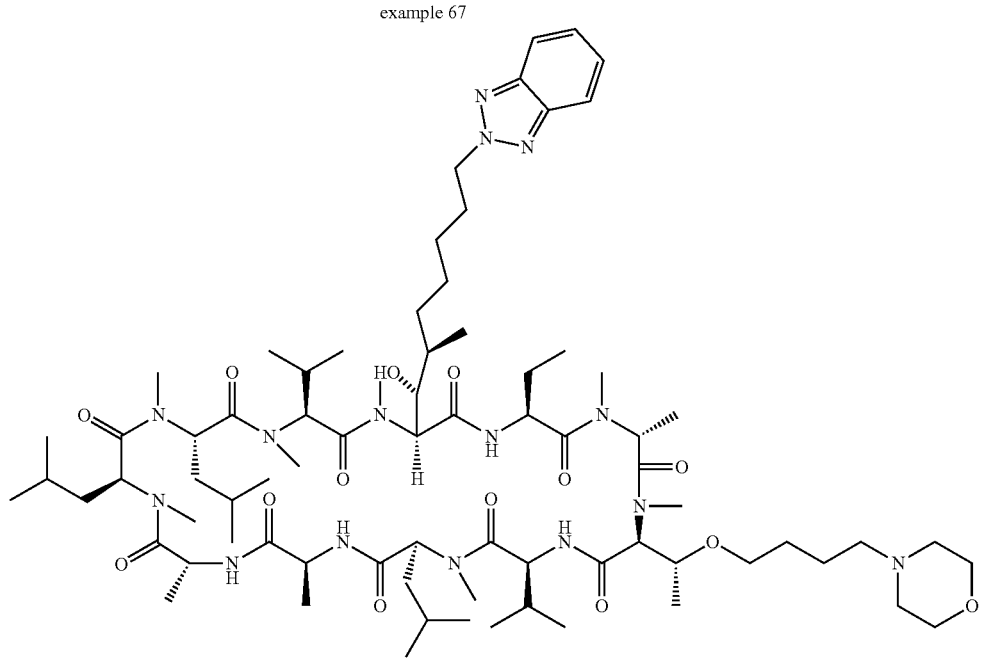
example 85
The compound of example 81 was prepared from compound of example 67 using the same procedure as described in the preparation of the compounds of example 61. MS-ESI (m/z): 1479.05 (M+H)+.
Example 86
Compound of formula IV: A is
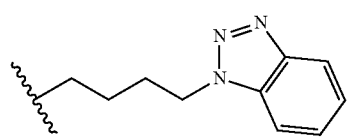

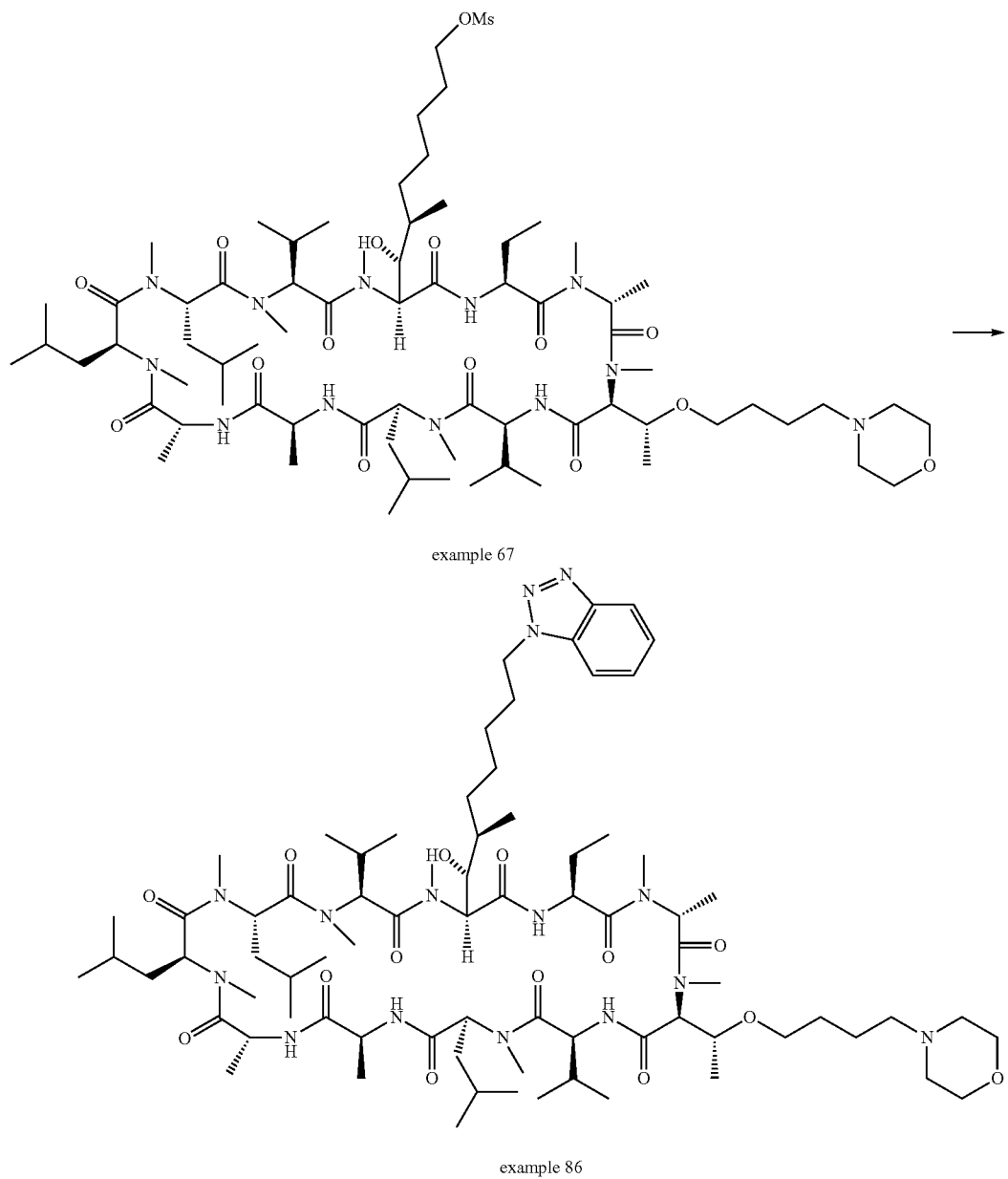

example 67 example 86

The compound of example 86 was prepared from compound of example 67 using the same procedure as described in the preparation of the compounds of example 61. MS-ESI (m/z): 1479.05 (M+H)$^+$.

The compound of examples 87~96 were prepared by similar methods as described above.

BIOLOGICAL ACTIVITY

1. HCV Replicon Cell Lines

HCV replicon cell lines (kindly provided by R. Bartenschlager) isolated from colonies as described by Lohman et al. (Lohman et al. (1999) Science 285: 110-113, expressly incorporated by reference in its entirety) and used for all experiments. The HCV replicon has the nucleic acid sequence set forth in EMBL Accession No.: AJ242651, the coding sequence of which is from nucleotides 1801 to 8406.

The coding sequence of the published HCV replicon was synthesized and subsequently assembled in a modified plasmid pBR322 (Promega, Madison, Wis.) using standard molecular biology techniques. One replicon cell line ("SGR 11-7") stably expresses HCV replicon RNA which consists of (i) the HCV 5'UTR fused to the first 12 amino acids of the capsid protein, (ii) the neomycin phosphotransferase gene (neo), (iii) the IRES from encephalomyocarditis virus (EMCV), and (iv) HCV NS2 to NS5B genes and the HCV 3'UTR. Another replicon cell line ("Huh-luc/neo-ET") described by Vrolijk et. al. (Vrolijk et. al. (2003) Journal of Virological Methods 110:201-209, expressly incorporated by reference in its entirety) stably expresses HCV replicon RNA which consists of (i) the HCV 5'UTR fused to the first 12 amino acids of the capsid protein, (ii) the firefly luciferase reporter gene, (iii) the ubiquitin gene, (iv) the neomycin phosphotransferase gene (neo), (v) the IRES from encephalomyocarditis virus (EMCV) and (vi) HCV NS3 to NS5B genes that harbor cell culture adaptive mutations (E1202G, T12801, K1846T) and the HCV 3'UTR.

These cell lines are maintained at 37° C., 5% $CO_2$, 100% relative humidity in DMEM (Cat#11965-084, Invitrogen), with 10% fetal calf serum ("FCS", Invitrogen), 1% non-essential amino acids (Invitrogen), 1% of Glutamax (Invitrogen), 1% of 100× penicillin/streptomycin (Cat #15140-122, Invitrogen) and Geneticin (Cat #10131-027, Invitrogen) at 0.75 mg/ml or 0.5 mg/ml for 11-7 and Huh-luc/neo-ET cells, respectively.

2. HCV Replicon Assay—qRT-PCR $EC_{50}$ values of single agent compounds were determined by HCV RNA detection using quantitative RT-PCR, according to the manufacturer's instructions, with a TAQMAN® One-Step RT-PCR Master Mix Reagents Kit (Cat #AB 4309169, Applied Biosystems) on an ABI Model 7500 thermocycler. $EC_{50}$ values of combinations are similarly determined by HCV RNA detection using quantitative RT-PCR. The TAQMAN primers to use for detecting and quantifying HCV RNA obtained from Integrated DNA Technologies. HCV RNA is normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat #AM1812). Chemical agent cytotoxicity is evaluated using an MTS assay according to the manufacturer's directions (Promega).

3. HCV Replicon Assay—Luciferase

Since clinical drug resistance often develops in viral infections following single agent therapies, there is a need to assess the additive, antagonistic, or synergistic properties of combination therapies. We use the HCV replicon system to assess the potential use of the compound of the present invention or in combination therapies with Interferon alpha, cyclosporine analogs and inhibitors targeting other HCV proteins. The acute effects of a single or combinations of drugs are studied in the "Huh-luc/neo-ET" replicon with each chemical agent titrated in an X or Y direction in a 6 point two-fold dilution curve centered around the EC50 of each drug. Briefly, replicon cells are seeded at 7,000 cells per well in 90 ul DMEM (without phenol red, Invitrogen Cat. #31053-036) per well with 10% FCS, 1% non-essential amino acids, 1% of Glutamax and 1% of 100× penicillin/streptomycin and incubated overnight at 37° C., 5% $CO_2$, 100% relative humidity. 16-20 h after seeding cells, test compounds previously solubilized and titrated in dimethyl sulfoxide ("DMSO") from each X plate and Y plate are diluted 1:100 in DMEM (without phenol red, Invitrogen Cat. #31053-036) with 10% FCS, 1% non-essential amino acids, 1% of Glutamax and 1% of 100× penicillin/streptomycin and added directly to the 96-well plate containing cells and growth medium at a 1:10 dilution for a final dilution of compound and DMSO of 1:1000 (0.2% DMSO final concentration). Drug treated cells are incubated at 37° C., 5% $CO_2$, 100% relative humidity for 72 hours before performing a luciferase assay using 100 ul per well BriteLite Plus (Perkin Elmer) according to the manufacturer's instructions. Data analysis utilizes the method published by Prichard and Shipman (Antiviral Research, 1990. 14:181-205). Using this method, the combination data are analyzed for antagonistic, additive, or synergistic combination effects across the entire combination surface created by the diluted compounds in combination.

The compounds of the present invention can be effective against the HCV 1a genotype. It should also be understood that the compounds of the present invention can inhibit multiple genotypes of HCV. In one embodiment, compounds of the present invention are active against the 1a, 1b, 2a, 2b, 3a, 4a, and 5a genotypes. Table 2 shows the $EC_{50}$ values of representative compounds of the present invention against the HCV 1a genotype from the above described Luciferase assay. $EC_{50}$ ranges against HCV 1a are as follows: A>1 μM; B 0.1-1 μM; C 0.01~0.1 μM; D<0.01 μM.

TABLE 2

Genotype-1a Replicon $EC_{50}$ for Compounds of Formula IV

| Compound | A | $EC_{50}$ (Ia) |
|---|---|---|
| 1 | (structure with two OH groups) | B |
| 2 | (structure with OAc) | C |
| 3 | (structure with OH) | B |
| 4 | (carbamate structure, N-methyl) | B |
| 5 | (carbamate structure, N-isopropyl) | A |
| 6 | (carbamate structure, N-cyclopropyl) | A |
| 7 | (branched alkyl structure) | C |
| 8 | (alkenyl structure) | C |
| 9 | (alkyl structure) | C |
| 10 | (styryl structure) | C |
| 11 | (benzyl structure) | C |

TABLE 2-continued

Genotype-1a Replicon EC$_{50}$ for Compounds of Formula IV

| Compound | A | EC$_{50}$ (Ia) |
|---|---|---|
| 12 | 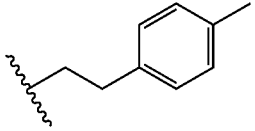 [SMILES: *CCc1ccc(C)cc1] 4-methylphenethyl | C |
| 13 | 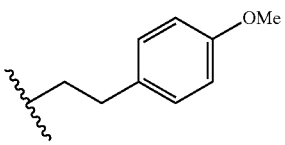 [SMILES: *CCc1ccc(OC)cc1] 4-methoxyphenethyl | C |
| 14 | 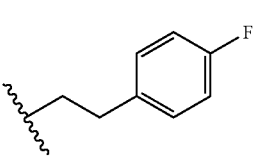 [SMILES: *CCc1ccc(F)cc1] 4-fluorophenethyl | C |
| 15 | 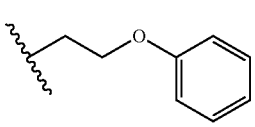 [SMILES: *CCOc1ccccc1] -(CH$_2$)$_3$-O-Ph | C |
| 16 | 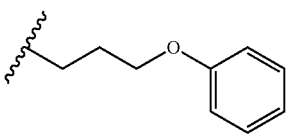 [SMILES: *CCCOc1ccccc1] -(CH$_2$)$_4$-O-Ph | C |
| 17 | 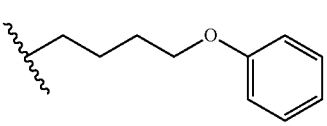 [SMILES: *CCCCOc1ccccc1] -(CH$_2$)$_5$-O-Ph | C |
| 18 | 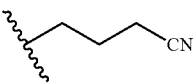 -(CH$_2$)$_3$-CN | C |
| 19 | 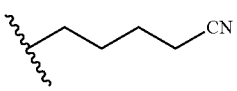 [SMILES: *CCCCC#N] -(CH$_2$)$_4$-CN | C |
| 20 | 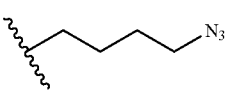 [SMILES: *CCCCN=[N+]=[N-]] -(CH$_2$)$_4$-N$_3$ | C |
| 21 | 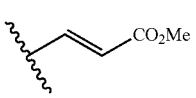 [SMILES: */C=C/C(=O)OC] -CH=CH-CO$_2$Me | C |
| 22 | 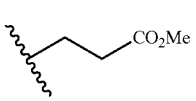 [SMILES: *CCC(=O)OC] -(CH$_2$)$_2$-CO$_2$Me | C |
| 23 | 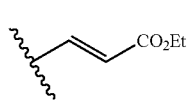 -CH=CH-CO$_2$Et | C |
| 24 | 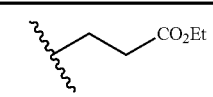 -(CH$_2$)$_2$-CO$_2$Et | C |
| 25 | 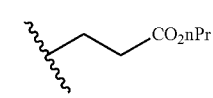 -(CH$_2$)$_2$-CO$_2$nPr | C |
| 26 | 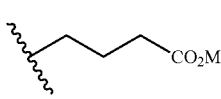 -(CH$_2$)$_3$-CO$_2$Me | D |
| 27 | 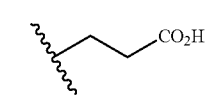 -(CH$_2$)$_2$-CO$_2$H | A |
| 28 | 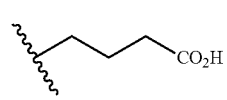 [SMILES: *CCCC(=O)O] -(CH$_2$)$_3$-CO$_2$H | A |
| 29 | 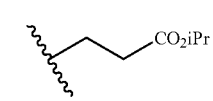 -(CH$_2$)$_2$-CO$_2$iPr | C |
| 30 | 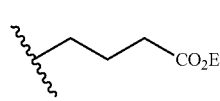 -(CH$_2$)$_3$-CO$_2$Et | D |
| 31 | 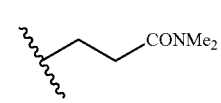 -(CH$_2$)$_2$-CONMe$_2$ | B |
| 32 | 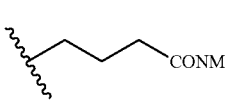 -(CH$_2$)$_3$-CONMe$_2$ | C |
| 33 | 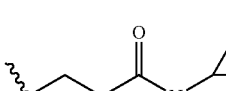 -(CH$_2$)$_2$-C(O)NH-cyclopropyl | B |
| 34 | 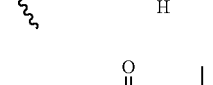 -(CH$_2$)$_2$-C(O)NH-iPr | B |
| 35 | 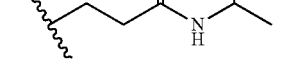 -(CH$_2$)$_2$-C(O)N(Me)(OMe) | C |
| 36 | 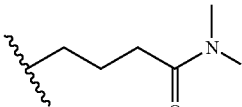 -(CH$_2$)$_3$-CONH$_2$ | B |
| 37 | 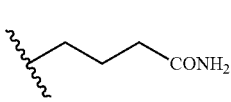 -CH=CH-CH$_2$-OAc | C |

TABLE 2-continued

Genotype-1a Replicon EC$_{50}$ for Compounds of Formula IV

| Compound | A | EC$_{50}$ (Ia) |
|---|---|---|
| 38 | (cis-CH=CH-CH$_2$OAc) | C |
| 39 | (trans-CH=CH-CH$_2$OH) | D |
| 40 | (CH$_2$)$_3$OH | C |
| 41 | (trans-CH=CH-CH$_2$CH$_2$OH) | C |
| 42 | (CH$_2$)$_4$OH | C |
| 43 | (CH$_2$)$_3$C(CH$_3$)$_2$OH | C |
| 44 | (CH$_2$)$_5$OH | C |
| 45 | (CH$_2$)$_4$OC(O)NH$_2$ | C |
| 46 | (CH$_2$)$_4$OC(O)N(CH$_3$)$_2$ | C |
| 47 | (CH$_2$)$_4$OC(O)NH-cyclopropyl | C |
| 48 | (CH$_2$)$_4$OC(O)-morpholinyl | C |
| 49 | (CH$_2$)$_4$OC(O)OCH$_3$ | D |
| 50 | (CH$_2$)$_4$OC(O)OCH$_2$CH$_3$ | C |
| 51 | (CH$_2$)$_4$NHBn | C |
| 52 | (CH$_2$)$_4$N(CH$_3$)Bn | C |
| 53 | (CH$_2$)$_4$NHCH$_3$ | C |
| 54 | (CH$_2$)$_4$NHC(O)OCH$_3$ | C |
| 55 | (CH$_2$)$_4$N(CH$_3$)C(O)OCH$_3$ | C |
| 56 | (CH$_2$)$_4$NHC(O)OCH$_2$CH$_3$ | C |
| 57 | (CH$_2$)$_4$NHC(O)OCH(CH$_3$)$_2$ | C |
| 58 | (CH$_2$)$_4$-(2H-tetrazol-5-yl) | A |
| 59 | (CH$_2$)$_4$-(2-methyl-tetrazol-5-yl) | C |
| 60 | (CH$_2$)$_4$-(1-methyl-tetrazol-5-yl) | C |
| 61 | (CH$_2$)$_4$S-(1-methyl-tetrazol-5-yl) | C |
| 62 | (CH$_2$)$_3$S-(1-methyl-tetrazol-5-yl) | C |

TABLE 2-continued

Genotype-1a Replicon EC$_{50}$ for Compounds of Formula IV

| Compound | A | EC$_{50}$ (Ia) |
|---|---|---|
| 63 | (structure) | C |
| 64 | (structure) | C |
| 65 | (structure) | C |
| 66 | (structure) | C |
| 67 | (structure) | C |
| 68 | (structure) | C |
| 69 | (structure) | B |
| 70 | (structure) | C |
| 71 | (structure) | C |
| 72 | (structure) | C |
| 73 | (structure) | C |
| 74 | (structure) | C |
| 75 | (structure) | C |
| 76 | (structure) | C |
| 77 | (structure) | C |
| 78 | (structure) | C |
| 79 | (structure) | C |
| 80 | (structure) | C |
| 81 | (structure) | C |
| 82 | (structure) | C |
| 83 | (structure) | C |
| 84 | (structure) | C |

TABLE 2-continued

Genotype-1a Replicon EC$_{50}$ for Compounds of Formula IV

| Compound | A | EC$_{50}$ (Ia) |
|---|---|---|
| 85 | [benzotriazole-2-yl-butyl] | C |
| 86 | [benzotriazole-1-yl-butyl] | C |
| 87 | [carbamate-PEG-OMe crown-ether-like structure] | A |
| 88 | [NH-tBu butyl] | B |
| 89 | [NH-adamantyl butyl] | C |
| 90 | [gem-dimethyl-N$_3$ butyl] | C |
| 91 | [gem-dimethyl-NH$_2$ butyl] | A |
| 92 | [gem-dimethyl-NHC(O)OMe butyl] | D |
| 93 | [gem-dimethyl-NHC(O)OEt butyl] | C |
| 94 | [gem-dimethyl-NHC(O)OiPr butyl] | C |
| 95 | [gem-dimethyl-NHC(O)OnPr butyl] | C |
| 96 | [S(O)-methyltetrazole butyl] | C |

4. IL-2 Suppression Assay

Cyclosporine A (CsA) is a known immunosuppressant that can bind simultaneously to both cyclophilin A (CypA) as well as calcineurin, a host cell phosphatase in immune cells. The interaction of CsA with calcineurin prevents calcineurin from dephosphorylating (and thereby activating) Oct and NF-AT, transcription factors required for stimulating the release of Interleukin 2 (IL-2) from various immune cells. HCV replication is dependent upon the host protein CypA which can be inhibited by treatment of replicon cells with CsA. While the anti-HCV effect of cyclosporine compounds is promising, the immunosuppressive property of these compounds is not desirable. Effective cyclosporine treatment of HCV will require that the compound not bind to calcineurin while retaining the ability to bind to CypA.

An IL-2 suppression assay can be conducted in order to determine the propensity of a compound to inhibit IL-2 production from stimulated immune cells, a measure of immunosuppression. Purified peripheral blood mononuclear cells (PBMCs) from a single human blood donor are stimulated in the presence of medium containing phorbol myristic acid (PMA) and ionomycin with or without test compounds. Compounds are titrated in a two-fold dilution curve in DMSO on a master plate. The master plate is diluted 40-fold into assay medium and a subsequent 8.3-fold onto each assay plate (final dilution of 333.3-fold), resulting in a final DMSO concentration of 0.3%. Compounds are added to each assay plate containing 2.0% (final) PBMCs/well in stimulation medium containing phorbol myristic acid (PMA) at 10 ng/mL (final concentration) and ionomycin (1.0 µM final). Plates are incubated at 37° C. 16-20 hrs before quantifying the levels of IL-2 in 5 µl of supernatant from each well using the AlphaLisa (Perkin-Elmer) human IL-2 detection kit. Table 3 shows suppression of IL-2 induction activity ($EC_{50}$) of CsA and representative compounds of the present invention.

TABLE 3

Suppression of IL-2 Induction Activity

| Compound | $EC_{50}$ (µM) (IL-2) |
|---|---|
| CsA | 0.0064 |
| Example 24 | >100 |
| Example 27 | >100 |
| Example 42 | >100 |
| Example 43 | >100 |
| Example 59 | >100 |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by the formula:

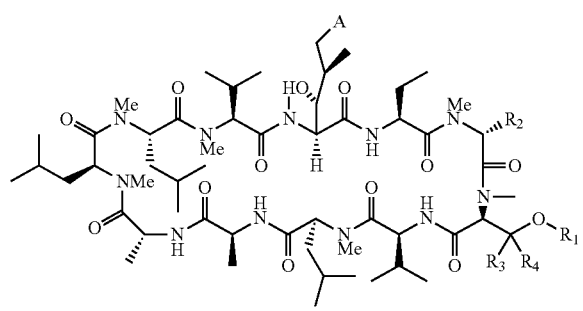

(I)

or a pharmaceutically acceptable salt thereof, wherein
$R_1$ is $C_1$-$C_5$-alkyl-Y or $C_2$-$C_5$-alkenyl-Y, where Y is H; optionally substituted aryl, optionally substituted heterocyclyl; —OC(O)$R_5$; $NR_5R_6$; OH; —O—$(CH_2)_n$—W, where n is 1 to 4 and W is heterocyclyl; —OC(O)$NR_5R_6$; —C(O)H; —CH=NOZ, where Z is H, or alkyl, aryl, arylalkyl, heteroaryl or heteroarylalkyl, each optionally substituted; —CH($OR_5$)$_2$; —SC(O)$R_5$; —SH; —$OSO_2R_5$; —C(O)OH; or —C(O)N($R_8$)OH, where $R_8$ is hydrogen or $C_1$-$C_4$-alkyl; $N_3$; —CN; or halogen;

A is (a) $C_3$-$C_4$-alkyl-X, where X is H; OH; optionally substituted phenyl; optionally substituted —O-phenyl; optionally substituted —S-phenyl; optionally substituted 5-membered heteroaryl; optionally substituted —O-5-membered heteroaryl; optionally substituted —S-5-membered heteroaryl; —OC(O)$NR_5R_6$, —NHC(O)$OR_5$, C(O)$OR_7$, —OC(O)$OR_7$, —CN, —$N_3$, —C(O)$NR_5R_6$, —C(O)$R_5$, optionally substituted —$OSO_2$-phenyl, —NHC(O)$R_5$ or —$NR_5R_6$; or (b) $C_3$-$C_4$-alkenyl-X', where X' is OH; optionally substituted phenyl; optionally substituted —O-phenyl; optionally substituted —S-phenyl; optionally substituted 5-membered heteroaryl; optionally substituted —O-5-membered heteroaryl; optionally substituted —S-5-membered heteroaryl; —OC(O)$NR_5R_6$, —NHC(O)$OR_5$, C(O)$OR_7$, —OC(O)$OR_7$, —CN, —$N_3$, —C(O)$NR_5R_6$, —C(O)$R_5$, optionally substituted —$OSO_2$-phenyl, —NHC(O)$R_5$, or —$NR_5R_6$;

each $R_5$ and $R_6$ is independently H; optionally substituted alkyl, optionally substituted alkenyl, optionally substituted aryl, optionally substituted heteroaryl, optionally substituted arylalkyl or optionally substituted heteroarylalkyl; alternatively, $R_5$, $R_6$ and the nitrogen atom to which they are attached form an optionally substituted heterocyclic; $R_7$ is optionally substituted alkyl, optionally substituted alkenyl, optionally substituted aryl, optionally substituted heteroaryl, optionally substituted arylalkyl or optionally substituted heteroarylalkyl; and $R_2$, $R_3$ and $R_4$ are independently selected from: hydrogen and methyl.

2. A compound according to claim 1, which is represented by the formula (II):

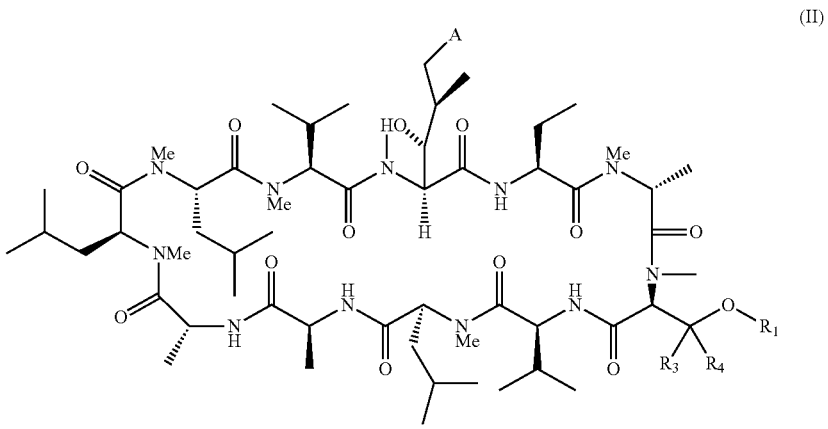

(II)

or a pharmaceutically acceptable salt thereof, wherein $R_1$, $R_3$, $R_4$ and A are as defined in claim 1.

3. A compound according to claim 1, which is represented by the formula (III):

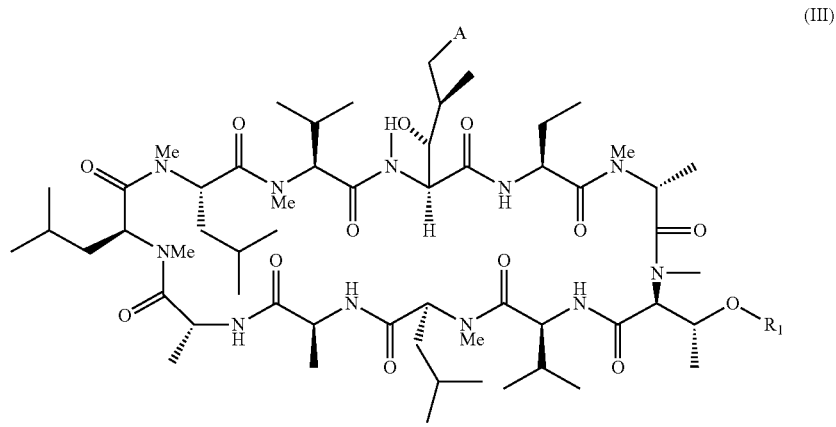

(III)

or a pharmaceutically acceptable salt thereof, wherein $R_1$ and A are as defined in claim 1.

4. A pharmaceutical composition comprising a therapeutically effective amount of a compound of claim 1, or a pharmaceutically-acceptable salt thereof, in combination with a pharmaceutically acceptable carrier.

5. A method of treating viral infection in a subject, wherein said viral infection is selected from HCV, HBV, HAV and HIV infection, comprising administering to said subject a therapeutically effective amount of the pharmaceutical composition according to claim 4.

6. The method of claim 5 further comprising coadministering one or more additional anti-viral agents.

7. The method of claim 5, wherein said additional antiviral agent is selected from peg-interferon, ribavirin, viral-enzyme targeted compounds, viral-genome-targeted therapies, immunomodulatory agents, Toll-receptor agonists and combinations thereof.

* * * * *